(12) United States Patent
Jansen et al.

(10) Patent No.: US 9,493,851 B2
(45) Date of Patent: Nov. 15, 2016

(54) METHODS FOR TREATING LIGNOCELLULOSIC MATERIALS

(71) Applicants:VIRDIA LTD, Herzelia (IL); VIRDIA, INC., Danville, VA (US)

(72) Inventors: Robert Jansen, Redwood City, CA (US); Claire Gregoire, Verrieres le Buisson (FR); Philip Travisano, Danville, VA (US); Lee Madsen, Manassas, VA (US); Neta Matis, Hod Hasharon (IL); Yael Har-Tal, Herzaliya (IL); Shay Eliahu, Ramat Efal (IL); James Alan Lawson, Ellsworth, ME (US); Noa Lapidot, Mevaseret Zion (IL); Aharon M. Eyal, Jerusalem (IL); Timothy Allen Bauer, Belleville, IL (US); Hagit Sade, Ramat Gan (IL); Paul McWilliams, Racine, WI (US); Michael Zviely, Haifa (IL); Adam Carden, Henderson, NC (US)

(73) Assignee: Virdia, Inc., Raceland, LA (US)

( * ) Notice: Subject to any disclaimer, the term of this patent is extended or adjusted under 35 U.S.C. 154(b) by 139 days.

(21) Appl. No.: 14/398,444

(22) PCT Filed: May 3, 2013

(86) PCT No.: PCT/US2013/039585
§ 371 (c)(1),
(2) Date: Oct. 31, 2014

(87) PCT Pub. No.: WO2013/166469
PCT Pub. Date: Nov. 7, 2013

(65) Prior Publication Data
US 2015/0087031 A1    Mar. 26, 2015

Related U.S. Application Data

(60) Provisional application No. 61/642,338, filed on May 3, 2012, provisional application No. 61/662,830, filed on Jun. 21, 2012, provisional application No. 61/672,719, filed on Jul. 17, 2012, provisional (Continued)

(51) Int. Cl.
*C13K 13/00* (2006.01)
*C13K 1/02* (2006.01)
(Continued)

(52) U.S. Cl.
CPC ............... *C13K 13/007* (2013.01); *C07G 1/00* (2013.01); *C10L 1/02* (2013.01); *C10L 1/023* (2013.01);
(Continued)

(58) Field of Classification Search
CPC .................................................. C13K 13/00
See application file for complete search history.

(56) References Cited

U.S. PATENT DOCUMENTS 2,752,270 A    6/1956    Specht
2,917,390 A   12/1959    Apel et al.

(Continued)

FOREIGN PATENT DOCUMENTS

CN    101691587 A    4/2010
EP      0018621 A1   11/1980

(Continued)

OTHER PUBLICATIONS

Grzenia et al, Membrane extraction for detoxification of biomass hydrolysates, Feb. 2012, Bioresource Technology 111, pp. 248-254.*

(Continued)

*Primary Examiner* — Melvin C Mayes
*Assistant Examiner* — Stefanie Cohen
(74) *Attorney, Agent, or Firm* — Wilson Sonsini Goodrich & Rosati

(57) ABSTRACT

The present invention relates to methods of processing lignocellulosic material to obtain hemicellulose sugars, cellulose sugars, lignin, cellulose and other high-value products. Also provided are hemicellulose sugars, cellulose sugars, lignin, cellulose, and other high-value products.

42 Claims, 53 Drawing Sheets

Related U.S. Application Data application No. 61/680,183, filed on Aug. 6, 2012, provisional application No. 61/680,661, filed on Aug. 7, 2012, provisional application No. 61/681,299, filed on Aug. 9, 2012, provisional application No. 61/693,637, filed on Aug. 27, 2012, provisional application No. 61/715,703, filed on Oct. 18, 2012, provisional application No. 61/720,325, filed on Oct. 30, 2012, provisional application No. 61/720,313, filed on Oct. 30, 2012, provisional application No. 61/785,891, filed on Mar. 14, 2013, provisional application No. 61/786,169, filed on Mar. 14, 2013, provisional application No. 61/680,181, filed on Aug. 6, 2012.

(51) Int. Cl.
| | |
|---|---|
| *C13K 1/04* | (2006.01) |
| *C07G 1/00* | (2011.01) |
| *C12P 19/14* | (2006.01) |
| *C12P 19/02* | (2006.01) |
| *C10L 1/02* | (2006.01) |
| *D21C 11/00* | (2006.01) |

(52) U.S. Cl.
CPC ............ *C10L 1/026* (2013.01); *C12P 19/02* (2013.01); *C12P 19/14* (2013.01); *C13K 1/02* (2013.01); *C13K 1/04* (2013.01); *C13K 13/002* (2013.01); *D21C 11/0007* (2013.01); *C12P 2201/00* (2013.01); *C12P 2203/00* (2013.01); *Y02E 50/13* (2013.01)

(56) References Cited

U.S. PATENT DOCUMENTS

| | | |
|---|---|---|
| 2,989,569 A | 6/1961 | Apel |
| 3,132,051 A | 5/1964 | Nobile et al. |
| 4,102,705 A | 7/1978 | Pfeiffer et al. |
| 4,174,976 A | 11/1979 | Tsao et al. |
| 4,332,623 A | 6/1982 | Ando et al. |
| 4,379,751 A | 4/1983 | Yoritomi et al. |
| 4,470,851 A | 9/1984 | Paszner et al. |
| 4,520,105 A | 5/1985 | Sinner et al. |
| 4,579,595 A | 4/1986 | Sachetto et al. |
| 4,608,245 A * | 8/1986 | Gaddy ............... C13K 1/04 127/37 |
| 4,615,742 A | 10/1986 | Wright |
| 4,970,002 A | 11/1990 | Ando et al. |
| 5,102,553 A | 4/1992 | Kearney et al. |
| 5,142,023 A | 8/1992 | Gruber et al. |
| 5,244,553 A | 9/1993 | Goldstein |
| 5,247,058 A | 9/1993 | Gruber et al. |
| 5,247,059 A | 9/1993 | Gruber et al. |
| 5,258,488 A | 11/1993 | Gruber et al. |
| 5,274,073 A | 12/1993 | Gruber et al. |
| 5,338,822 A | 8/1994 | Gruber et al. |
| 5,357,035 A | 10/1994 | Gruber et al. |
| 5,359,026 A | 10/1994 | Gruber et al. |
| 5,446,123 A | 8/1995 | Gruber et al. |
| 5,475,080 A | 12/1995 | Gruber et al. |
| 5,484,881 A | 1/1996 | Gruber et al. |
| 5,510,526 A | 4/1996 | Baniel et al. |
| 5,525,706 A | 6/1996 | Gruber et al. |
| 5,536,807 A | 7/1996 | Gruber et al. |
| 5,538,637 A | 7/1996 | Hester et al. |
| 5,539,081 A | 7/1996 | Gruber et al. |
| 5,580,389 A | 12/1996 | Farone et al. |
| 5,585,191 A | 12/1996 | Gruber et al. |
| 5,594,095 A | 1/1997 | Gruber et al. |
| 5,597,714 A | 1/1997 | Farone et al. |
| 5,602,286 A | 2/1997 | Muralidhara et al. |
| 5,726,046 A | 3/1998 | Farone et al. |
| 5,730,877 A | 3/1998 | Heikkila et al. |
| 5,780,678 A | 7/1998 | Baniel et al. |
| 5,782,982 A | 7/1998 | Farone et al. |
| 5,820,687 A | 10/1998 | Farone et al. |
| 5,847,238 A | 12/1998 | Muralidhara et al. |
| 5,859,270 A | 1/1999 | Kolstad et al. |
| 5,865,948 A | 2/1999 | Lora et al. |
| 5,876,505 A | 3/1999 | Klyosov et al. |
| 5,892,109 A | 4/1999 | Baniel et al. |
| 5,959,128 A | 9/1999 | Kolstad et al. |
| 6,007,636 A | 12/1999 | Lightner |
| 6,086,681 A | 7/2000 | Lindroos et al. |
| 6,087,532 A | 7/2000 | Baniel et al. |
| 6,093,326 A | 7/2000 | Heikkila et al. |
| 6,160,173 A | 12/2000 | Eyal et al. |
| 6,187,204 B1 | 2/2001 | Heikkila et al. |
| 6,187,951 B1 | 2/2001 | Baniel et al. |
| 6,207,209 B1 | 3/2001 | Jirjis et al. |
| 6,207,824 B1 | 3/2001 | Henkes et al. |
| 6,224,776 B1 | 5/2001 | Heikkila et al. |
| 6,229,046 B1 | 5/2001 | Eyal et al. |
| 6,239,274 B1 | 5/2001 | Heikkila et al. |
| 6,258,175 B1 | 7/2001 | Lightner |
| 6,320,077 B1 | 11/2001 | Eyal et al. |
| 6,361,990 B1 | 3/2002 | Porter et al. |
| 6,379,554 B1 | 4/2002 | Kearney et al. |
| 6,391,204 B1 | 5/2002 | Russo |
| 6,419,828 B1 | 7/2002 | Russo, Jr. |
| 6,451,123 B1 | 9/2002 | Saska et al. |
| 6,452,051 B1 | 9/2002 | Eyal et al. |
| 6,534,679 B2 | 3/2003 | Eyal et al. |
| 6,572,775 B2 | 6/2003 | Heikkila et al. |
| 6,610,867 B2 | 8/2003 | Jakel et al. |
| 6,620,292 B2 | 9/2003 | Wingerson |
| 6,685,781 B2 | 2/2004 | Hyoky et al. |
| 6,692,578 B2 | 2/2004 | Schmidt et al. |
| 6,693,188 B2 | 2/2004 | Bohlmann et al. |
| 6,699,457 B2 | 3/2004 | Cortright et al. |
| 6,752,902 B2 | 6/2004 | Heikkila et al. |
| 6,824,599 B2 | 11/2004 | Swatloski et al. |
| 6,833,149 B2 | 12/2004 | Jirjis et al. |
| 6,875,349 B2 | 4/2005 | Heikkila et al. |
| 6,896,811 B2 | 5/2005 | Heikkila et al. |
| 6,924,371 B2 | 8/2005 | Karki et al. |
| 6,953,873 B2 | 10/2005 | Cortright et al. |
| 6,964,757 B2 | 11/2005 | Cortright et al. |
| 6,964,758 B2 | 11/2005 | Cortright et al. |
| 7,019,170 B2 | 3/2006 | Eyal et al. |
| 7,022,239 B2 | 4/2006 | Heikkila et al. |
| 7,144,977 B2 | 12/2006 | Eyal et al. |
| 7,186,856 B2 | 3/2007 | Meng et al. |
| 7,198,925 B2 | 4/2007 | Foody |
| 7,229,558 B2 | 6/2007 | Heikkila et al. |
| 7,361,273 B2 | 4/2008 | Heikkila et al. |
| 7,465,791 B1 | 12/2008 | Hallberg et al. |
| 7,501,025 B2 | 3/2009 | Bakker et al. |
| 7,503,981 B2 | 3/2009 | Wyman et al. |
| 7,534,597 B2 | 5/2009 | Hause et al. |
| 7,618,612 B2 | 11/2009 | Cortright et al. |
| 7,629,010 B2 | 12/2009 | Passarelli et al. |
| 7,649,086 B2 | 1/2010 | Belanger et al. |
| 7,678,768 B2 | 3/2010 | Purpura et al. |
| 7,699,958 B2 | 4/2010 | Griffith et al. |
| 7,718,070 B2 | 5/2010 | Mahnon |
| 7,901,511 B2 | 3/2011 | Griffin et al. |
| 7,959,811 B2 | 6/2011 | Airaksinen et al. |
| 8,637,660 B2 | 1/2014 | Fanselow et al. |
| 8,637,661 B2 | 1/2014 | Fanselow et al. |
| 8,722,878 B2 | 5/2014 | Raines et al. |
| 8,999,065 B2 | 4/2015 | Kazachkin et al. |
| 9,200,337 B2 | 12/2015 | Colakyan et al. |
| 2002/0153317 A1 | 10/2002 | Heikkila et al. |
| 2003/0094416 A1 | 5/2003 | Heikkila et al. |
| 2004/0231661 A1 | 11/2004 | Griffin et al. |
| 2005/0034823 A1 | 2/2005 | Brelid et al. |
| 2008/0041366 A1 | 2/2008 | Wahnon |
| 2008/0057555 A1 | 3/2008 | Nguyen |
| 2008/0202504 A1 | 8/2008 | Hilst |
| 2009/0056707 A1 * | 3/2009 | Foody ............... B01J 39/04 127/46.2 |
| 2009/0142848 A1 | 6/2009 | Wyman et al. |

(56) References Cited

U.S. PATENT DOCUMENTS

| | | |
|---|---|---|
| 2009/0173339 A1 | 7/2009 | Heikkila et al. |
| 2009/0176286 A1 | 7/2009 | O'Connor et al. |
| 2009/0218055 A1 | 9/2009 | Unsitalo et al. |
| 2009/0226979 A1 | 9/2009 | Retsina et al. |
| 2010/0024807 A1 | 2/2010 | Burke et al. |
| 2010/0043782 A1 | 2/2010 | Kilambi et al. |
| 2010/0043784 A1 | 2/2010 | Jensen |
| 2010/0048884 A1 | 2/2010 | Kilambi |
| 2010/0048924 A1 | 2/2010 | Kilambi |
| 2010/0069626 A1 | 3/2010 | Kilambi |
| 2010/0086981 A1 | 4/2010 | Latouf et al. |
| 2010/0124772 A1 | 5/2010 | Sabesan |
| 2010/0184176 A1 | 7/2010 | Ishida et al. |
| 2010/0189706 A1 | 7/2010 | Chang et al. |
| 2010/0279361 A1 | 11/2010 | South et al. |
| 2010/0279372 A1 | 11/2010 | Cho et al. |
| 2011/0146138 A1 | 6/2011 | Berry et al. |
| 2011/0192560 A1 | 8/2011 | Heikkila et al. |
| 2011/0274612 A1 | 11/2011 | Wohlmann et al. |
| 2011/0318796 A1 | 12/2011 | Walther |
| 2012/0058526 A1 | 3/2012 | Jansen et al. |
| 2012/0104313 A1 | 5/2012 | Garbero et al. |
| 2013/0183227 A1 | 7/2013 | Wohlmann et al. |
| 2014/0011248 A1 | 1/2014 | Medoff et al. |
| 2014/0220651 A1 | 8/2014 | Raines et al. |
| 2014/0227161 A1 | 8/2014 | Manesh et al. |
| 2014/0309416 A1 | 10/2014 | Teixeira et al. |
| 2014/0316162 A1 | 10/2014 | Gao et al. |
| 2015/0136121 A1 | 5/2015 | Jansen et al. |
| 2015/0141628 A1 | 5/2015 | Jansen et al. |
| 2015/0144126 A1 | 5/2015 | Jansen et al. |
| 2015/0299738 A1 | 10/2015 | Wang et al. |

FOREIGN PATENT DOCUMENTS

| | | | |
|---|---|---|---|
| EP | 0112926 | A1 | 7/1984 |
| EP | 0317036 | A1 | 5/1989 |
| EP | 0690931 | B1 | 10/2001 |
| EP | 0697904 | B1 | 6/2002 |
| EP | 1458805 | B1 | 8/2011 |
| EP | 1733282 | B1 | 1/2012 |
| EP | 2325246 | B1 | 11/2013 |
| EP | 2781605 | A1 | 9/2014 |
| GB | 1562682 | A | 3/1980 |
| GB | 2240053 | A | 7/1991 |
| JP | S 60174743 | A | 9/1985 |
| WO | WO 82/01723 | A1 | 5/1982 |
| WO | WO 84/03304 | A1 | 8/1984 |
| WO | WO 94/17213 | A1 | 8/1994 |
| WO | WO 94/26380 | A1 | 11/1994 |
| WO | WO 99/06133 | A1 | 2/1999 |
| WO | WO 00/61276 | A1 | 10/2000 |
| WO | WO 01/32715 | A1 | 5/2001 |
| WO | WO 02/02826 | A1 | 1/2002 |
| WO | WO 03/010339 | A1 | 2/2003 |
| WO | WO 2004/050983 | A1 | 6/2004 |
| WO | WO 2006/086861 | A2 | 8/2006 |
| WO | WO 2006/086861 | A3 | 10/2006 |
| WO | WO 2007/019505 | A2 | 2/2007 |
| WO | WO 2007/019505 | A3 | 6/2007 |
| WO | WO 2007/075476 | A2 | 7/2007 |
| WO | WO 2007/120210 | A2 | 10/2007 |
| WO | WO 2008/017145 | A1 | 2/2008 |
| WO | WO 2008/019468 | A1 | 2/2008 |
| WO | WO 2008/111045 | A2 | 9/2008 |
| WO | WO 2008/131229 | A1 | 10/2008 |
| WO | WO 2008/144903 | A1 | 12/2008 |
| WO | WO 2009/015663 | A2 | 2/2009 |
| WO | WO 2009/116885 | A1 | 9/2009 |
| WO | WO 2009/117317 | A1 | 9/2009 |
| WO | WO 2009/125400 | A2 | 10/2009 |
| WO | WO 2009/015663 | A3 | 12/2009 |
| WO | WO 2009/155982 | A1 | 12/2009 |
| WO | WO 2010/009343 | A2 | 1/2010 |
| WO | WO 2010/015404 | A1 | 2/2010 |
| WO | WO 2010/026572 | A1 | 3/2010 |
| WO | WO 2010/009343 | A3 | 4/2010 |
| WO | WO 2010/038021 | A2 | 4/2010 |
| WO | WO 2010/043424 | A1 | 4/2010 |
| WO | WO 2010/045576 | A2 | 4/2010 |
| WO | WO 2010/046619 | A1 | 4/2010 |
| WO | WO 2010/081231 | A1 | 7/2010 |
| WO | WO 2010/038021 | A3 | 8/2010 |
| WO | WO 2010/113129 | A2 | 10/2010 |
| WO | WO 2010/113129 | A3 | 10/2010 |
| WO | WO 2010/113130 | A2 | 10/2010 |
| WO | WO 2010/128272 | A1 | 11/2010 |
| WO | WO 2010/146331 | A2 | 12/2010 |
| WO | WO 2010/113130 | A3 | 1/2011 |
| WO | WO 2011/002660 | A1 | 1/2011 |
| WO | WO 2011/017797 | A1 | 2/2011 |
| WO | WO 2011/070602 | A1 | 6/2011 |
| WO | WO 2011/080131 | A2 | 7/2011 |
| WO | WO 2011/089589 | A1 | 7/2011 |
| WO | WO 2011/080131 | A3 | 9/2011 |
| WO | WO 2011/111189 | A1 | 9/2011 |
| WO | WO 2011/111190 | A1 | 9/2011 |
| WO | WO 2011/151823 | A1 | 12/2011 |
| WO | WO 2011/154604 | A1 | 12/2011 |
| WO | WO 2011/161685 | A2 | 12/2011 |
| WO | WO 2012/018740 | A1 | 2/2012 |
| WO | WO 2012/031270 | A1 | 3/2012 |
| WO | WO 2012/061085 | A2 | 5/2012 |
| WO | WO 2012/106727 | A1 | 8/2012 |
| WO | WO 2013/026849 | A1 | 2/2013 |
| WO | WO 2013/040702 | A1 | 3/2013 |
| WO | WO 2013/071180 | A1 | 5/2013 |
| WO | WO 2013/083876 | A2 | 6/2013 |
| WO | WO 2013/192572 | A1 | 12/2013 |
| WO | WO 2014/044753 | A1 | 3/2014 |
| WO | WO 2014/106221 | A1 | 7/2014 |
| WO | WO 2014/138553 | A1 | 9/2014 |
| WO | WO 2014/169079 | A2 | 10/2014 |

OTHER PUBLICATIONS

European search report and opinion dated Nov. 18, 2015 for EP Application No. 137844221.
European search report and opinion dated May 4, 2015 for EP Application No. 14197793.4.
U.S. Appl. No. 14/537,445, filed Nov. 10, 2014, Jansen et al.
U.S. Appl. No. 14/537,494, filed Nov. 10, 2014, Jansen et al.
U.S. Appl. No. 14/537,530, filed Nov. 10, 2014, Jansen et al.
Aden, et al. Lignocellulosic Biomass to Ethanol Process Design and Economics Utilizing Co-Current Dilute Acid Prehydrolysis and Enzymatic Hydrolysis for Corn Stover. National Renewable Energy Laboratory, NREL is a U.S. Department of Energy LaboratoryOperated by Midwest Research Institute. Jun. 2002.
Ahring et al. Enzymatic hydrolysis and ethanol fermentation of high dry matter wet-exploded wheat straw at low enzyme loading. Applied biochemistry and biotechnology. 2008;148:35-44.
Amidon, et al. Biorefinery: Conversion of Woody Biomass to Chemicals, Energy and Materials. Journal of Biobased Materials and Bioenergy. 2008; 2:100-120.
Antonplis, et al. High pressure HCl conversion of cellulose to glucose. Lawrence Berkeley National Laboratory, University of California, Paper LBL,14221. Aug. 1981.
Badger. Ethanol from cellulose: a general review. Trends in new crops and new uses. 2002; 17-21.
Bergius. Conversion of wood to carbohydrates and problems in the industrial use of concentrated hydrochloric acid. Industrial and Engineering chemistry. 1937; 29(3):247-253.
Bergius. The utilisation of wood for the production of foodstuffs, alcohol and glucose. Chemical society institution. Nov. 15, 1933.
Bergius. Winslow Notes on Bergius Process. 1937.
Bergius. Wood Sugar Plants at Mannheim-Rheinau & Regensburg. 1945.
Bizzari, et al. CEH Marketing research report: Lignosulfonates (2009) pp. 14-16.

(56) References Cited

OTHER PUBLICATIONS

Bozell. The Use of Renewable Feedstocks for the Production of Chemicals and Materials—A Brief Overview of Concepts. National Renewable Energy Laboratory, 1617 Cole Boulevard, Golden, CO 80401. 2010.

Bunker. The Wartime Production of Food Yeast in Germany. 2010.

Campbell,et al. The Saccharification of Wood by the Bergius process at Suddeutschen Holzversucherung Werke A.G. Regensburg. Report on visit to Suddeutschen Holzversucherung Werke A.G. Regensburg.CIOS trip No. 764, this target was visited on Aug. 9, 1945.

Capanema, et al. Quantitative characterization of a hardwood milled wood lignin by nuclear magnetic resonance spectroscopy. J Agr. Food. Chem. 2005; 53(25): 9639-9649.

Carvalheiro, et al. Hemicellulose biorefineries: a review on biomass pretreatments. Journal of Scientific & Industrial Research, vol. 67, Nov. 2008, pp. 849-864.

Carvalho, et al. Comparison of different procedures for the detoxification of eucalyptus hemicellulosic hydrolysate for use in fermentative processes. J Chem Technol Biotechnol 2006; 81:152-157.

Chaow-U-Thai et al. Removal of ash from sugarcane leaves and tops. International Journal of Biosciences.2012; 2(5): 12-17.

Eyal, et al. Recovery and concentration of strong mineral acids from dilute solutions through LLX.I: review of parameters for adjusting extractant propert and analysis of process options. Solvent Extraction and ion exchange. 1991; 9(2):195-210.

Eyal, et al. Sulfuric acid recovery through solvent aided decomposition of ammonium sulfate. Solvent Extraction and ion exchange. 1986; 44:803-821.

Fahim, et al. Liquid-Liquid Equilibria of the Ternary System Water+Acetic Acid+1-Hexanol. J. Chem. Eng. Data. 1997; 42:183-186.

Gamez et al. Study of the hydrolysis of sugar cane bagasse using phosphoric acid. Journal of Food Engineering.2006; 74: 78-88.

Hagglund. The Decomposition of Wood by Acids wood Saccharification. Chemistry of Wood. New York: Academic Press, 1951. 631. Chapter IV. 390-413.

Hagglund. Wood Saccharification. A Modified Rheinau Process. 2011.

Hamelinck, et al. Production of advanced biofuels. International Sugar Journal. 2006; 108(1287):168-175.

Harris, et al. Hydrolysis of wood cellulose with hydrochloric acid and sulfur dioxide and the decomposition of its hydrolytic products. Journal of Physical and Colloid Chemistry. (1949), 53:344-51. Abstract only.

Harris, et al. The Madison Wood-Sugar Process. US Dept. of Agriculture. Jun. 1946; 1-21.

Harris. Derived products and chemical utilization of wood waste. Forest Products Laboratory; Forest Service US Department of Agriculture; Rept. No. R1666-10. Jun. 1949.

Hasegawa, et al. New Pretreatment Methods Combining a Hot Water Treatment and Water/Acetone Extraction for Thermo-Chemical Conversion of Biomass. Energy & Fuels. 2004; 18:755-760.

International search report and written opinion dated Mar. 25, 2015 for EP Application No. 14197798.3.

International search report and written opinion dated Dec. 13, 2013 for PCT Application No. US2013/039585.

International search report dated Mar. 27, 2015 for EP Application No. 14197787.6.

Jacobsen, et al. Xylose Monomer and Oligomer Yields for Uncatalyzed Hydrolysis of Sugarcane Bagasse Hemicellulose at Varying Solids Concentration, Industrial & Engineering Chemistry Research, 2002, 41, 1454-1461.

Johnson. Effects of Dilute Acid Hydrolyzate Components on Glucose Degradation. National Bioenergy Center, NREL, 1617 Cole Blvd., Golden, Colorado 80401, USA. 2011.

Kadam, et al. Generating Process and Economic Data Needed for Preliminary Design of PureVision Biorefineries. DOE Project No. DE-FG36-05GO85004, Final Nonproprietary Technical Report. Dec 28, 2007.

Kadla, et al. Lignin-based carbon fibers for composite fiber applications. Carbon. 2002; 40:2913-2920.

Kamm, et al. Chemical and biochemical generation of carbohydrates from lignocellulose-feedstock (*Lupinus nootkatensis*)—quantification of glucose. Chemosphere. 2006; 62:97-105.

Kim, et al. Continuous Countercurrent Extraction of Hemicellulose from Pretreated Wood Residues. Applied Biochemistry and Biotechnology. 2001; 91-93:253-267.

Kumar, et al. Effect of Enzyme Supplementation at Moderate Cellulase Loadings on Initial Glucose and Xylose Release From Corn Stover Solids Pretreated by Leading Technologies. Biotechnology and Bioengineering. Feb. 1, 2009; 102(2):457-567.

Kumar, et al. Methods for Pretreatment of Lignocellulosic Biomass for Efficient Hydrolysis and Biofuel Production. Ind. Eng. Chem. Res. 2009; 48:3713-3729.

Lavarack, et al. The acid hydrolysis of sugarcane bagasse hemicellulose to produce xylose, arabinose, glucose and other products. Biomass and Bioenergy. 2002; 23:367-380.

Lee, et al. Dilute-Acid Hydrolysis of Lignocellulosic Biomass. Advances in Biochemical Engineering/ Biotechnology. 1999; 65:93-115.

Li, et al. Acidolysis of Wood in Ionic Liquids. Ind. Eng. Chem. Res. 2010; 49(7):3126-3136.

Li, et al. Interaction of Supercritical Fluids with Lignocellulosic Materials. Ind. Eng. Chem. Res. 1988; 27:1301-1312.

Muurinen, E. Dissertation entitled: Organosolv pulping: A review and distillation study related to peroxyacid pulping. (2000) Department of Process Engineering, Oulu University, Finland.

Onda et al. Selective Hydrolysis of Cellulose and Polysaccharides into Sugars by Catalytic Hydrothermal Method Using Sulfonated Activated-carbon. Journal of Japan Petroleum Institue.2012; 55(2): 73-86.

Palmqvist, et al. Fermentation of lignocellulosic hydrolysates. II: inhibitors and mechanisms of inhibition. Bioresource Technology. 2000; 74:25-33.

Pessoa Jr, et al. Acid hydrolysis of hemicellulose from sugarcane bagasse. Braz. J. Chem. Eng. vol. 14 No. 3 São Paulo Sep. 1997.

Rabinovich. Wood hydrolysis industry in the Soviet Union and Russia: a mini-review. Cellulose Chem. Technol.2010; 44(4-6):173-186.

Radiotis, et al. Optimizing Production of Xylose and Xylooligomers from Wood Chips. 3rd NWBC, Stockholm, Sweden Mar. 23, 2011.

Ragauskas, et al. From wood to fuels Integrating biofuels and pulp production. Industrial biotechnology. 2006; 2(1):55-65.

Saddler et. al. Pretreatment of Lodgepole Pine Killed by Mountain Pine Beetle Using the Ethanol Organosolv Process: Fractionation and Process Optimization. Ind. Eng. Chem. Res. 2007;46: 2609-2617.

Saltberg, et al. Removal of metal ions from wood chips during acidic leaching 1:Comparison between Scandinavian softwood , birch and eucalyptus. Nordic Pulp and Paper Research J. 2006; 21(4):507-512.

Saltberg, et al. Removal of metal ions from wood chips during acidic leaching 2: Modeling leaching of calcium ions from softwood chips. Nordic Pulp and Paper Research J. 2006; 21(4):513-519.

Sannigrahi, et al. Effects of two-stage dilute acid pretreatment on the structure and composition of lignin and cellulose in loblolly pine. Bioenerg. Res 2008; 1 (3-4): 205-214.

Sannigrahi, et al. Lignin structural modifications resulting from ethanol organosolv treatment of loblolly pine. Energy Fuel 2010; 24(1): 683-689.

Sasaki, et al. Cellulose hydrolysis in subcritical and supercritical water. J. of Supercritical Fluids. 1998; 13:261-268.

Schoenemann. The New Rheinau Wood Saccharification Process. Institute of Chemical Technology. Jul. 27, 1953; 1-49.

Singh, et al. Visualization of Biomass Solubilization and Cellulose Regeneration During Ionic Liquid Pretreatment of Switchgrass. Biotechnology and Bioengineering. Sep. 1, 2009; 104(1):68-75.

Sluiter, et al. Determination of Ash in Biomass, Laboratory Analytical Procedure (LAP), Issue Date: Jul. 17, 2005. Technical Report, NREL/TP-510-42622, Jan. 1, 2008.

Sluiter, et al. Determination of Sugars, Byproducts, and Degradation Products in Liquid Fraction Process Samples, Laboratory Analytical

(56) References Cited

OTHER PUBLICATIONS

Procedure (LAP), Issue Date: Dec. 8, 2006. Technical Report, NREL/TP-510-42623, Jan. 1, 2008.

Sluiter, et al. Determination of Total Solids in Biomass and Total Dissolved Solids in Liquid Process Samples, Laboratory Analytical Procedure (LAP), Issue Date: Mar. 31, 2008. Technical Report, NREL/TP-510-42621, Revised Mar. 2008.

Steele. Recent breakthroughs in enzymes for biomass hydrolysis. Genecor. National Ethanol Conference, Feb. 23-25, 2009, San Antonio, Texas.

Suess. Interaction of organic compounds with calcium carbonate-I. Association phenomena and geochemical implications. Geochimia et Cosmochimic Acata. 1970; 34:157-168.

Taherzadeh, et al. Pretreatment of Lignocellulosic Wastes to Improve Ethanol and Biogas Production: A Review. Int. J. Mol. Sci. 2008; 9:1621-1651; DOI: 10.3390/ijms9091621.

Trickett. Utilization of Baggase for the production of C5 and C6 sugars. 1982. University of Natal, Durban, South Africa.

Van Dyke. Enzymatic Hydrolysis of Cellulose—A Kinetic Study. For the degree of Doctor of Science at the Massachusetts Institute of Technology, Sep. 1972.

Wyman. Potential Synergies and Challenges in Refining Cellulosic Biomass to Fuels, Chemicals, and Power. Biotechnol. Prog. 2003; 19:254-262.

Yankov, et al. Improvement of the lactic acid extraction. Extraction from aqueous solutions and simulated fermentation broth by means of mixed extractant and TOA, partially loaded with HCI. Chem. Biochem. Eng. Q. 2005; 19(1):17-24.

European search report and opinion dated Aug. 10, 2015 for EP Application No. 14197787.6.

Rasrendra, et al. Recovery of acetic acid from an aqueous pyrolysis oil phase by reactive extraction using tri-n-octylamine. Chemical Engineering Journal. Dec. 1, 2011; 176-177:244-252.

Grzenia, et al. Membrane extraction for removal of acetic acid from biomass hydrolysates. J Membr Sci 2008;322:189-195.

\* cited by examiner

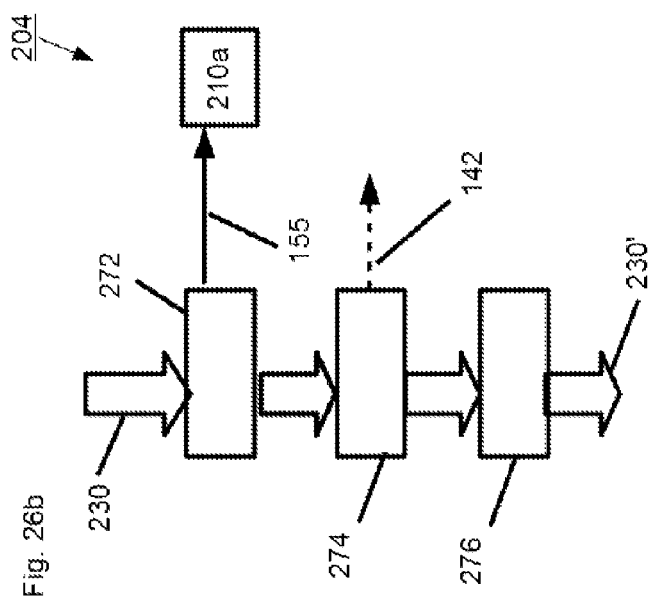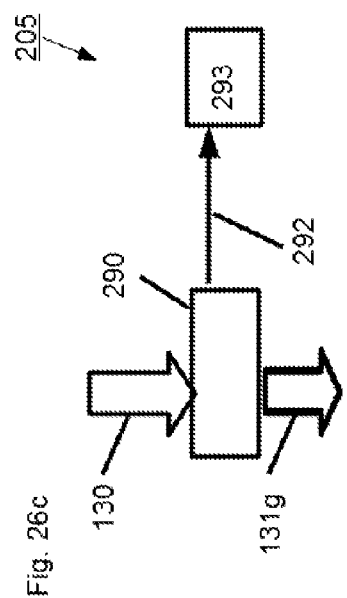

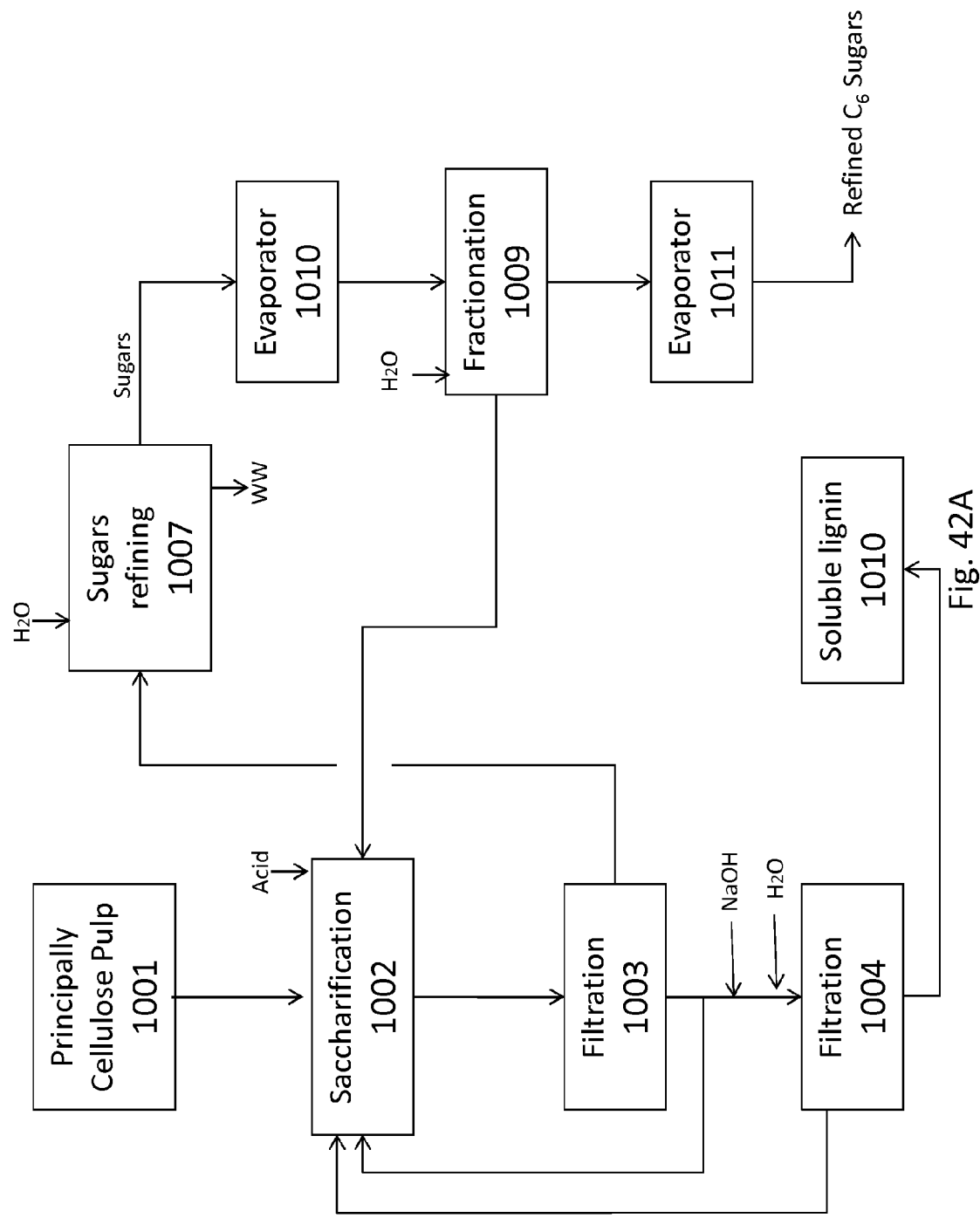

METHODS FOR TREATING LIGNOCELLULOSIC MATERIALS

CROSS-REFERENCE

This application is a national stage application of PCT/US2013/039585, filed May 3, 2013, which claims the benefit under 35 USC §119(e) of U.S. Provisional Application No. 61/642,338, filed on May 3, 2012, U.S. Provisional Application No. 61/662,830, filed on Jun. 21, 2012, U.S. Provisional Application No. 61/693,637, filed on Aug. 27, 2012, U.S. Provisional Application No. 61/672,719, filed on Jul. 17, 2012, U.S. Provisional Application No. 61/720,313, filed on Oct. 30, 2012, U.S. Provisional Application No. 61/680,183, filed on Aug. 6, 2012, U.S. Provisional Application No. 61/680,661, filed on Aug. 7, 2012, U.S. Provisional Application No. 61/720,325, filed on Oct. 30, 2012, U.S. Provisional Application No. 61/785,891, filed on Mar. 14, 2013, U.S. Provisional Application No. 61/680,181, filed on Aug. 6, 2012, U.S. Provisional Application No. 61/681,299, filed on Aug. 9, 2012, U.S. Provisional Application No. 61/715,703, filed on Oct. 18, 2012, and U.S. Provisional Application No. 61/786,169, filed on Mar. 14, 2013, each incorporated herein by reference in its entirety.

STATEMENT AS TO FEDERALLY SPONSORED RESEARCH

This invention was made with government support under Grant No. DE-EE0005003 awarded by the Department of Energy. The government has certain rights in the invention.

INCORPORATION BY REFERENCE

All publications, patents, and patent applications mentioned in this specification are herein incorporated by reference to the same extent as if each individual publication, patent, or patent application was specifically and individually indicated to be incorporated by reference.

FIELD OF THE INVENTION

The invention relates to processing of lignocellulosic biomass materials containing lignin, cellulose and hemicellulose polymers.

BACKGROUND OF THE INVENTION

Lignocellulosic biomass materials are renewable sources for production of amino acids for feed and food supplements, monomers and polymers for the plastic industry, and renewable sources for different types of fuels, polyol sugar substitutes (xylitol, sorbitol, manitols and the likes), and numerous other chemicals that can be synthesized from C5 and C6 sugars. Nonetheless, efficient and cost effective processes to extract C5 and C6 sugars from the biomass are still a challenge. Lignocellulosic biomass materials are composite materials that contains not only the lignocellulosic polymers, but also a wide variety of small amounts of lipophilic or amphiphilic compounds, e.g., fatty acids, rosin acids, phytosteroids, as well as proteins and ash element. When hydrolyzing the hemicellulose polymers, ester bonds on the sugar molecules can also be hydrolyzed, releasing the un-substituted sugar molecule along with a significant amount of methanol and acetic acid. Additional organic acids such as lactic acid, glucoronic acid, galacturonic acid, formic acid and levullinic acid are also typically found in cellulosic hydrolysate. In addition to these, the lignin polymer tends to release under mild hydrolyzing conditions some small chain aqueous soluble lignin molecules. Consequently, the typical hydrolysate is a very complex solution of multiple components. This poses a significant challenge in separation and refining of the sugars to obtain useful grades of the extracted sugars.

SUMMARY OF THE INVENTION

The invention provides methods of refining a sugar stream. The method involves (i) contacting the sugar stream with an amine extractant to form a mixture; and (ii) separating from the mixture a first stream comprising the amine extractant and an acid or an impurity; and a second stream comprising one or more sugars. Optionally, the first stream is an organic stream and the second stream is an aqueous stream. Optionally, the first stream comprises less than 0.5% w/w sugars. Optionally, the second stream comprises less than 0.5% w/w acid. Optionally, the second stream comprises less than 0.5% w/w amine. Optionally, the second stream comprises less than 0.5% w/w impurities. Optionally, impurities are extracted from the sugar stream into the amine extractant. In some embodiments, the method further involves, prior to step (i), contacting the sugar stream with a strong acid cation exchanger to remove residual cations. Optionally, the amine extractant comprises an amine and a diluent. Optionally, the ratio of the amine and the diluent is 3:7. Optionally, the ratio of the amine and the diluent is 5.5:4.55. Optionally, the ratio of the amine and the diluent is between 3:7 and 6:4. Optionally, the diluent comprises an alcohol. Optionally, the diluent comprises a C6, C8, C10, C12, C14, C16 alcohol or kerosene. Optionally, the diluent comprises hexanol. Optionally, the amine is an amine comprising at least 20 carbon atoms. Optionally, the amine is tri-laurylamine. In some embodiments, the method further involves removing diluent from the second stream using a packed distillation column. Optionally, at least 95% of diluent in the second stream is removed. In some embodiments, the method further involves contacting the sugar stream with a strong acid cation exchanger to remove residual amines, thereby forming an amine-removed hydrolysate. In some embodiments, the method further involves contacting the amine-removed hydrolysate with a weak base anion exchanger to form a neutralized hydrolysate. In some embodiments, the method further involves evaporating the hydrolysate to form a concentrated hydrolysate. In some embodiments, the method further involves fractionating the hydrolysate into a monomeric sugar stream and an oligomeric sugar stream. In some embodiments, the method further involves purifying or concentrating the monomeric sugar stream. In some embodiments, the method further involves, prior to contacting the sugar stream with an amine extractant to form a first mixture, allowing residual acid in the sugar stream hydrolyze at least some oligomeric sugars in the sugar stream into monomeric sugars. Optionally, the method further involves, prior to allowing, diluting the sugar stream to a lower sugar concentration. Optionally, the method further involves, prior to allowing, increasing the acid concentration in the sugar stream. Optionally, the acid concentration is increased to be more than 0.5%. In some embodiments, the method further involves combining the oligomeric sugar stream with the sugar stream before the sugar stream is contacted with the amine extract; wherein the residual acid in the sugar stream hydrolyzes at least some oligomeric sugars in the oligomeric sugar stream into monomeric sugars. Optionally, the method further involves contacting the first stream with a base solution to form a neutralized amine extractant. Optionally, the contacting is conducted at 70° C. Optionally, the method further involves prior to contacting the first stream with a base solution, further comprising washing the first stream with an aqueous stream to remove sugar from the first stream. Optionally, the washed first stream comprises less than 0.1% weight/weight sugar. Optionally, the method further involves washing at least a portion of the neutralized amine extractant with water, and recycling the washed amine extractant. Optionally, the method further involves treating part of the washed neutralized amine extractant stream by heating it with 10% lime. Optionally, the contacting is conducted at 80-90° C.

The invention further provides methods for removing acid from an acidic hemicellulose sugars stream. The method involves (i) contacting an acidic hemicellulose sugar stream comprising an acid and one or more hemicellulose sugars with an amine extractant to form an amine mixture; and (ii) separating from the amine mixture a first stream comprising the acid and the amine extractant, and a second stream comprising the hemicellulose sugar stream. In some embodiments, the method further involves prior to step (i), contacting a lignocellulosic feedstock with an acidic aqueous solution; and separating the acidic aqueous solution from the lignocellulosic feedstock thereby forming a lignocellulosic stream and the acidic hemicellulose sugar stream. Optionally, the first stream is an organic stream and the second stream is an aqueous stream. Optionally, the first stream comprises less than 0.5% w/w hemicellulose sugars. Optionally, the second stream comprises less than 0.5% w/w acid. Optionally, the second stream comprises less than 0.5% w/w amine. Optionally, the second stream comprises less than 0.5% w/w impurities. Optionally, impurities are extracted from the acidic hemicellulose sugar stream into the amine extractant. Optionally, the amine extractant comprises an amine and a diluent. Optionally, the ratio of the amine and the diluent is 3:7. Optionally, the ratio of the amine and the diluent is 5.5:4.55. Optionally, the ratio of the amine and the diluent is between 3:7 and 6:4. Optionally, the diluent comprises an alcohol. Optionally, the diluent comprises a C6, C8, C10, C12, C14, C16 alcohol or kerosene. Optionally, the diluent comprises hexanol. Optionally, the amine is an amine comprising at least 20 carbon atoms. Optionally, the amine is tri-laurylamine. Optionally, the acidic aqueous solution comprises 0.1-2% acid. Optionally, the acid comprises $H_2SO_4$ and/or $SO_2$ and/or $H_2SO_3$, and/or HCl. In some embodiments, the method further involves removing diluent from the second stream using a packed distillation column. Optionally, at least 95% of diluent in the second stream is removed. In some embodiments, the method further involves contacting the second stream with a strong acid cation exchanger to remove residual amines thereby forming an amine-removed sugar stream. In some embodiments, the method further involves contacting the amine-removed sugar stream with a weak base anion exchanger to form a neutralized sugar stream. In some embodiments, the method further involves evaporating the sugar stream thereby forming a concentrated sugar solution. In some embodiments, the method further involves fractionating the sugar stream into a xylose-enriched stream and a mixed sugar stream. Optionally, the sugars are fractionated using an ion-exchange resin. Optionally, the ion-exchange column is an anion exchange resin. Optionally, the anion exchange resin has a particle size in the range of 200-400 µm. Optionally, the anion exchange resin has a particle size in the range of 280-320 µm. Optionally, the fractionation is carried out in a simulated moving bed mode. Optionally, the fractionation is carried out in a sequential simulated moving bed mode. Optionally, the sequential simulated moving bed chromatography system comprises steps 1-3; a feed stream in passed into an adsorbent and a first raffinate stream is flushed from the adsorbent during step 1; a second raffinate stream is flushed from the adsorbent with a desorbent stream during step 2; and the desorbent is recycled back to the adsorbent during step 3; wherein the xylose-enriched stream is extracted in both step 1 and step 2. Optionally, the desorbent flow rate of the chromatography system is equal to the sum of the extract flow rate and the raffinate flow rate. In some embodiments, the method further involves crystallizing xylose from the xylose-enriched stream. In some embodiments, the method further involves contacting the first stream with a base solution to form a neutralized extractant. In some embodiments, the method further involves, prior to contacting the first stream with a base solution, further comprising washing the first stream with an aqueous stream to remove hemicellulose sugar from the first stream. Optionally, the washed first stream comprises less than 0.1% weight/weight sugar. In some embodiments, the method further involves washing the neutralized extractant with water, and recycling the washed amine extractant. In some embodiments, the method further involves treating part of the washed neutralized extractant by heating it with 10% lime. Optionally, the lignocellulosic stream is used to make bioenergy pellets.

The invention further provides methods for fractionating a liquid sample comprising a mixture of a first fraction and a second fraction. The method involves (i) fractionating the liquid sample with a sequential simulated moving bed chromatography system; wherein the sequential simulated moving bed chromatography system comprises steps 1-3; a feed stream in passed into an adsorbent and a first raffinate stream is flushed from the adsorbent during step 1; a second raffinate stream is flushed from the adsorbent with a desorbent stream during step 2; and the desorbent is recycled back to the adsorbent during step 3; (ii) recovering one or more product stream from the chromatography system; wherein the product stream is extracted in both step 1 and step 2. Optionally, the liquid sample further comprises a third fraction. Optionally, desorbent flow rate of the chromatography system is equal to the sum of the extract flow rate and the raffinate flow rate. Optionally, the chromatography system comprises an ion-exchange resin. Optionally, the ion-exchange resin is an anion exchange resin. Optionally, the ion-exchange resin has a particle size in the range of 200-400 µm. Optionally, the ion-exchange resin has a particle size in the range of 280-320 µm.

The invention further provides a hemicellulose sugar mixture. The mixture comprises one or more, two or more, three or more, four or more, five or more, or six or seven or eight or more of the following characteristics: (i) monosaccharides in a ratio to total dissolved sugars >0.50 weight/weight; (ii) glucose in a ratio to total monosaccharides <0.25 weight/weight; (iii) xylose in a ratio to total monosaccharides >0.18 weight/weight; (iv) fructose in a ratio to total monosaccharides <0.10 weight/weight; (v) fructose in a ratio to total monosaccharides >0.01 weight/weight; (vi) furfurals in an amount up to 0.01% weight/weight; and (vii) one or more phenols in an amount up to 500 ppm; and (viii) hexanol in an amount up to 0.1% weight/weight. Optionally, the monosaccharides to total dry solid ratio is >0.70 weight/weight. Optionally, the monosaccharides to total dry solid ratio is >0.90 weight/weight. Optionally, the glucose to total monosaccharides ratio is <0.15 weight/weight. Optionally, the glucose to total monosaccharides ratio is <0.13 weight/ weight. Optionally, the glucose to total monosaccharides ratio is <0.06 weight/weight. Optionally, the xylose to total monosaccharides ratio is >0.20 weight/weight. Optionally, the xylose to total monosaccharides ratio is >0.50 weight/weight. Optionally, the xylose to total monosaccharides ratio is >0.70 weight/weight. Optionally, the fructose to total monosaccharides ratio is >0.02 weight/weight. Optionally, the fructose to total monosaccharides ratio is <0.08 weight/weight. Optionally, the mixture contains furfurals in an amount up to 0.005% weight/weight. Optionally, the mixture contains furfurals in an amount up to 0.001% weight/weight. Optionally, the mixture contains phenols in an amount up to 400 ppm. Optionally, the mixture contains phenols in an amount up to 300 ppm.

The invention further provides a xylose-enriched stream hemicellulose sugar mixture. The mixture comprises one or more, two or more, three or more, four or more, five or more, six or more, seven or more, eight or more, nine or more, or ten or more of the following characteristics: (i) oligosaccharides in a ratio to total dissolved sugars <0.10 weight/weight; (ii) xylose in a ratio to total dissolved sugars >0.50 weight/weight; (iii) arabinose in a ratio to total dissolved sugars <0.10 weight/weight; (iv) galactose in a ratio to total dissolved sugars <0.05 weight/weight; (v) the sum of glucose and fructose in a ratio to total dissolved sugars <0.10 weight/weight; (vi) mannose in a ratio to total dissolved sugars <0.02 weight/weight; (vii) fructose in a ratio to total dissolved sugars <0.05 weight/weight; (viii) furfurals in an amount up to 0.01% weight/weight; (ix) phenols in an amount up to 500 ppm; and (x) hexanol in an amount up to 0.1% weight/weight. Optionally, the oligosaccharides to total dissolved sugars ratio is <0.07. Optionally, the oligosaccharides to total dissolved sugars ratio is <0.05. Optionally, the xylose to total dissolved sugars ratio is >0.40 weight/weight. Optionally, the xylose to total dissolved sugars ratio is >0.70 weight/weight. Optionally, the xylose to total dissolved sugars ratio is >0.80 weight/weight. Optionally, the sum of glucose and fructose to total dissolved sugars ratio is <0.09. Optionally, the sum of glucose and fructose to total dissolved sugars ratio is <0.05. Optionally, the mixture contains furfurals in an amount up to 0.005% weight/weight. Optionally, the mixture contains furfurals in an amount up to 0.001% weight/weight. Optionally, the mixture contains phenols in an amount up to 60 ppm. Optionally, the mixture contains phenols in an amount up to 0.05 ppm.

The invention further provides a xylose-removed hemicellulose sugar mixture. The mixture comprises one or more, two or more, three or more, four or more, five or more, six or more, seven or more, eight or more, nine or more, or ten or more of the following characteristics: (i) oligosaccharides in a ratio to total dissolved sugars >0.15 weight/weight; (ii) the sum of glucose and fructose in a ratio to total dissolved sugars >0.20 weight/weight; (iii) arabinose in a ratio to total dissolved sugars >0.02 weight/weight; (iv) galactose in a ratio to total dissolved sugars >0.02 weight/weight; (v) xylose in a ratio to total dissolved sugars <0.20; (vi) mannose in a ratio to total dissolved sugars >0.01; (vii) fructose in a ratio to total dissolved sugars <0.05; (viii) furfurals in an amount up to 0.01% weight/weight; (ix) phenols in an amount up to 500 ppm; and (x) hexanol in an amount up to 0.1% weight/weight. Optionally, the oligosaccharides to total dissolved sugars ratio is >0.20 weight/weight. Optionally, the oligosaccharides to total dissolved sugars ratio is >0.23 weight/weight. Optionally, the oligosaccharides to total dissolved sugars ratio is >0.25 weight/weight. Optionally, the sum of glucose and fructose to total dissolved sugars ratio is >0.10 weight/weight. Optionally, the sum of glucose and fructose to total dissolved sugars ratio is >0.25 weight/weight. Optionally, the sum of glucose and fructose to total dissolved sugars ratio is >0.35 weight/weight. Optionally, the mixture contains furfurals in an amount up to 0.005% weight/weight. Optionally, the mixture contains furfurals in an amount up to 0.001% weight/weight. Optionally, the mixture contains phenols in an amount up to 60 ppm. Optionally, the mixture contains phenols in an amount up to 0.05 ppm. Optionally, the xylose to total dissolved sugars ratio is <0.30 weight/weight. Optionally, the xylose to total dissolved sugars ratio is <0.15 weight/weight. Optionally, the xylose to total dissolved sugars ratio is <0.10 weight/weight.

The invention further provides a mother liquor hemicellulose sugar mixture. The mixture comprises one or more, two or more, three or more, four or more, five or more, six or more, seven or more, eight or more, nine or more, or ten or more of the following characteristics: (i) oligosaccharides in a ratio to total dissolved sugars <0.15 weight/weight; (ii) xylose in a ratio to total dissolved sugars >0.40 weight/weight; (iii) arabinose in a ratio to total dissolved sugars <0.15 weight/weight; (iv) galactose in a ratio to total dissolved sugars <0.06 weight/weight; (v) the sum of glucose and fructose in a ratio to total dissolved sugars <0.20 weight/weight; (vi) mannose in a ratio to total dissolved sugars <0.03; (vii) fructose in a ratio to total dissolved sugars <0.04; (viii) furfurals in an amount up to 0.01% weight/weight; (ix) phenols in an amount up to 500 ppm; and (x) hexanol in an amount up to 0.1% weight/weight. Optionally, the oligosaccharides to total dissolved sugars ratio is <0.12. Optionally, the oligosaccharides to total dissolved sugars ratio is <0.10. Optionally, the oligosaccharides to total dissolved sugars ratio is <0.20. Optionally, the xylose to total dissolved sugars ratio is >0.50 weight/weight. Optionally, the xylose to total dissolved sugars ratio is >0.60 weight/weight. Optionally, the xylose to total dissolved sugars ratio is >0.70 weight/weight. Optionally, the sum of glucose and fructose to total dissolved sugars ratio is <0.30. Optionally, the sum of glucose and fructose to total dissolved sugars ratio is <0.20. Optionally, the sum of glucose and fructose to total dissolved sugars ratio is <0.10. Optionally, the mixture contains furfurals in an amount up to 0.005% weight/weight. Optionally, the mixture contains furfurals in an amount up to 0.001% weight/weight. Optionally, the mixture contains phenols in an amount up to 60 ppm. Optionally, the mixture contains phenols in an amount up to 0.05 ppm.

The invention further provides a method of producing a cellulose sugar stream. The method involves (i) moving a lignocellulosic stream and an acid stream counter-currently through a plurality of stirred tank reactors to produce an acidic hydrolysate stream and an acidic lignin stream; and (ii) separating the acidic hydrolysate stream from the acidic lignin stream; wherein the plurality of stirred tank reactors includes a first reactor, a last reactor, and one or more intermediate reactors; wherein the lignocellulosic stream enters the first reactor, the acid stream enters the last reactor, the acidic hydrolysate stream exits from the first reactor, and the lignin stream exits from the last reactor. In some embodiments, the method further involves, prior to step (i), contacting a lignocellulosic feedstock with an acidic aqueous solution; and separating the acidic aqueous solution from the lignocellulosic feedstock thereby forming an acidic hemicellulose sugar stream and the lignocellulosic stream. In some embodiments, the method further involves, prior to step (i), reducing particle size in the lignocellulosic stream to 400 to 5000 microns. Optionally, the acidic hydrolysate stream comprises one or more cellulose sugars. Optionally, the acidic hydrolysate stream further comprises one or more hemicellulose sugars. In some embodiments, the method further involves (iii) contacting the acidic hydrolysate stream comprising an acid and one or more cellulose sugars with a S1 solvent extractant to form a first mixture; and (iv) separating from the first mixture a first stream comprising the acid and the S1 solvent extractant and a second stream comprising the one or more cellulose sugars; wherein the acid is extracted from the acidic hydrolysate stream into the S1 solvent extractant. Optionally, the contacting is conducted at 50° C. In some embodiments, the method further involves (v) evaporating the second stream comprising the one or more cellulose sugars to form a concentrated second stream; and (vi) repeating step (iii) and (iv) above to form a stream comprising the acid and the S1 solvent extractant and a stream comprising the one or more cellulose sugars. Optionally, the acidic hydrolysate stream is evaporated before the acidic hydrolysate stream is contacted with the S1 solvent extractant, thereby reducing the acid concentration in the acidic hydrolysate stream to azeotrope. Optionally, the first stream is an organic stream and the second stream is an aqueous stream. In some embodiments, the method further involves (v) contacting the second stream with an amine extractant to form a second mixture; and (vi) separating from the second mixture a third stream comprising the acid and the amine extractant and a fourth stream comprising the one or more cellulose sugars. In some embodiments, the method further involves, prior to contacting the second stream with an amine extractant to form a second mixture, allowing the residual acid in the second stream hydrolyze at least some oligomeric sugars in the sugar stream into monomeric sugars thereby forming a cellulose sugar stream. In some embodiments, the method further involves, prior to allowing, diluting the second stream to a lower sugar concentration. Optionally, an oligomeric sugar stream is added to the second stream before the second stream is contacted with the amine extract; wherein the residual acid in the second stream hydrolyzes at least some oligomeric sugars in the mixture of the oligomeric sugar stream and the second stream into monomeric sugars. Optionally, the third stream is an organic stream and the fourth stream is an aqueous stream. Optionally, the acidic hydrolysate stream is separated from the lignin stream using a filter, membrane, or hydroclone. Optionally, the acid stream comprise at least 40% weight/weight acid. Optionally, the S1 solvent extractant comprises an alcohol. Optionally, the S1 solvent extractant comprises a C6, C8, C10, C12, C14, C16 alcohol or kerosene or a mixture thereof. Optionally, the S1 solvent extractant comprises hexanol. Optionally, the amine extractant comprises an amine and a diluent. Optionally, the ratio of the amine and the diluent is 3:7. Optionally, the ratio of the amine and the diluent is 5.5:4.55. Optionally, the ratio of the amine and the diluent is between 3:7 and 6:4. Optionally, the diluent comprises an alcohol. Optionally, the diluent comprises a C6, C8, C10, C12, C14, C16 alcohol or kerosene. Optionally, the diluent comprises hexanol. Optionally, the amine is an amine comprising at least 20 carbon atoms. Optionally, the amine is tri-laurylamine. Optionally, the lignocellulosic feedstock comprises mainly cellulose and lignin. Optionally, at least a portion of the acidic hydrolysate stream leaving one or more intermediate tank is added to the lignocellulosic stream before the lignocellulosic stream enters the first reactor. Optionally, the lignocellulosic stream is heated. Optionally, the acid hydrolysate stream contains 22-33% acid weight/weight. In some embodiments, the method further involves removing diluent from the fourth stream using a packed distillation column. Optionally, at least 95% of diluent in the fourth stream is removed. In some embodiments, the method further involves contacting the fourth stream with a strong acid cation exchanger to remove residual amines, thereby forming an amine-removed hydrolysate. In some embodiments, the method further involves contacting the amine-removed hydrolysate with a weak base anion exchanger to form a neutralized hydrolysate. In some embodiments, the method further involves evaporating the hydrolysate to form a concentrated hydrolysate. In some embodiments, the method further involves fractionating the hydrolysate into a monomeric sugar stream and an oligomeric sugar stream. In some embodiments, the method further involves purifying or concentrating the monomeric sugar stream. In some embodiments, the method further involves combining the oligomeric sugar stream with the second stream before the second stream is contacted with the amine extract; wherein the residual acid in the second stream hydrolyzes at least some oligomeric sugars in the oligomeric sugar stream into monomeric sugars. In some embodiments, the method further involves contacting the first stream comprising the acid and the S1 solvent extractant with an aqueous solution to form a deacidified extractant and an aqueous back-extract; wherein the acid is extracted from the first stream into the aqueous back-extract. Optionally, the contacting is conducted at 50° C. In some embodiments, the method further involves, prior to contacting the first stream with an aqueous solution to form a deacidified extractant and an aqueous back-extract, contacting the first stream with an azeotropic or higher concentration acid solution to recover sugars from the first stream. Optionally, the aqueous back-extract comprising 15-20% acid and is used in a downstream process. In some embodiments, the method further involves evaporating the aqueous back-extract under a first pressure, thereby generates a super-azeotropic acid solution having an acid concentration higher than that of the aqueous back-extract prior to the evaporation. In some embodiments, the method further involves evaporating the super-azeotropic acid solution under a second pressure to generate a super-azeotropic gaseous acid, wherein the second pressure is higher than the first pressure. In some embodiments, the method further involves absorbing the super-azeotropic gaseous acid in an aqueous solution to produce a concentrated acid solution. In some embodiments, the method further involves contacting the third stream with a base solution to form a neutralized amine extractant. Optionally, the contacting is conducted at 70° C. In some embodiments, the method further involves, prior to contacting the third stream with a base solution, further comprising washing the third stream with an aqueous stream to remove cellulose sugar from the third stream. Optionally, the washed third stream comprises less than 0.1% weight/weight cellulose sugar. In some embodiments, the method further involves washing at least a portion of the neutralized amine extractant with water, and recycling the washed amine extractant. In some embodiments, the method further involves treating part of the washed neutralized amine extractant stream by heating it with 10% lime. Optionally, the contacting is conducted at 80-90° C.

The invention further provides a method of hydrolyzing oligomeric sugars. The method involves (i) contacting an acidic hydrolysate stream comprising an acid and one or more cellulose sugars with a S1 solvent extractant to form a first mixture; (ii) separating from the first mixture a first stream comprising the acid and the S1 solvent extractant and a second stream comprising the one or more cellulose sugars; wherein the acid is extracted from the acidic hydrolysate stream into the S1 solvent extractant; (iii) allowing the residual acid in the second stream hydrolyze at least some oligomeric sugars in the sugar stream into monomeric sugars thereby forming a cellulose sugar stream; and (iv) fractionating the cellulose sugar stream into a monomeric sugar stream and an oligomeric sugar stream. In some embodiments, the method further involves, prior to fractionating, adding an oligomeric sugar stream into the second stream, wherein the residual acid in the second stream hydrolyzes at least some oligomeric sugars in the mixture of the second stream and the oligomeric sugar stream into monomeric sugars thereby forming a cellulose sugar stream. In some embodiments, the method further involves, prior to allowing, diluting the second stream to a lower sugar concentration. In some embodiments, the method further involves, prior to allowing, increasing the acid concentration in the second stream. Optionally, the acid concentration is increased to be more than 0.5%. Optionally, the acidic hydrolysate stream is evaporated before the input stream is contacted with the S1 solvent extractant, thereby reducing the acid concentration in the acidic hydrolysate stream to azeotrope. In some embodiments, the method further involves contacting the cellulose sugar stream with an anion exchanger to remove acid from the stream. Optionally, the hydrolyzing is catalyzed by HCl at a concentration of not more than 1.2% weight/weight. Optionally, the hydrolyzing is catalyzed by HCl at a concentration of not more than 0.7% weight/weight. Optionally, the hydrolyzing is performed at a temperature in the range between 60° C. and 150° C. Optionally, the secondary hydrolysate contains at least 70% monomeric sugars out of total sugars weight/weight. Optionally, the total sugar content of said secondary hydrolysate is at least 90% weight/weight of the sugar content of said aqueous, low acid mixture.

The invention further provides a high concentration C6 sugar mixture. The mixture comprises one or more, two or more, three or more, or four or more, five or more, or six or more of the following characteristics: (i) monosaccharides in a ratio to total dissolved sugars >0.85 weight/weight; (ii) glucose in a ratio to total dissolved sugars in the range of 0.40-0.70 weight/weight; (iii) 1-200 ppm chloride; (iv) furfurals in an amount up to 0.01% weight/weight; (v) phenols in an amount up to 500 ppm; and (vi) hexanol in an amount up to 0.1% weight/weight. Optionally, the monosaccharides to total dissolved sugars ratio is >0.90 weight/weight. Optionally, the monosaccharides to total dissolved sugars ratio is >0.95 weight/weight. Optionally, the glucose to total dissolved sugars ratio is in the range of 0.40-0.60 weight/weight. Optionally, the glucose to total dissolved sugars ratio is in the range of 0.50-0.60 weight/weight. Optionally, the chloride concentration is in the range of 10-100 ppm. Optionally, the chloride concentration is in the range of 10-50 ppm. Optionally, the mixture contains furfurals in an amount up to 0.005% weight/weight. Optionally, the mixture contains furfurals in an amount up to 0.001% weight/weight. Optionally, the mixture contains phenols in an amount up to 400 ppm. Optionally, the mixture contains phenols in an amount up to 100 ppm. Optionally, xylose to total dissolved sugars ratio is in the range of 0.03-0.12 weight/weight. Optionally, xylose to total dissolved sugars ratio is in the range of 0.05-0.10 weight/weight. Optionally, arabinose to total dissolved sugars ratio is in the range of 0.005-0.015 weight/weight. Optionally, galactose to total dissolved sugars ratio is in the range of 0.025-0.035 weight/weight. Optionally, mannose to total dissolved sugars ratio is in the range of 0.14-0.18 weight/weight.

The invention further provides a method of producing a high purity lignin. The method involves (i) adjusting the pH of an aqueous solution comprising lignin to an acidic pH; (ii) contacting the acidic aqueous lignin solution with a lignin extraction solution comprising a limited-solubility solvent thereby forming a first stream comprising the lignin and the lignin extraction solution, and a second stream comprising water soluble impurities; (iii) contacting the first stream with a strong acid cation exchanger to remove residual cations thereby obtaining a purified first stream; and (iv) separating the limited-solubility solvent from the lignin thereby obtaining a high purity lignin composition. Optionally, the separating step comprises precipitating the lignin by contacting the purified first stream with water. Optionally, the purified first stream is contacted with hot water thereby flash evaporating the limited-solubility solvent. Optionally, the separating step comprises evaporating the limited-solubility solvent from the lignin. Optionally, the evaporating comprises spray drying. In some embodiments, the method further involves filtering the lignin particles from the water. Optionally, the aqueous solution comprising lignin is generated by dissolving a lignin material in an alkaline solution. Optionally, the aqueous solution comprising lignin is generated by a process selected from a pulping, a milling, a biorefining, kraft pulping, sulfite pulping, caustic pulping, hydro-mechanical pulping, mild acid hydrolysis of lignocellulose feedstock, concentrated acid hydrolysis of lignocellulose feedstock, supercritical water or sub-supercritical water hydrolysis of lignocellulose feedstock, ammonia extraction of lignocellulose feedstock. Optionally, the lignin material is a deacidified lignin; the method further comprising, prior to step (i), contacting an acidic lignin with a hydrocarbon solvent to form a mixture; heating the hydrocarbon solvent to remove acid from the mixture thereby obtaining a deacidified lignin. Optionally, the pH of the aqueous lignin solution is adjusted to 3.5-4. Optionally, the first stream is an organic stream and the second stream is an aqueous stream. Optionally, the lignin material is an acidic lignin obtained by extracting hemicellulose sugar from a lignocellulosic feedstock followed by cellulose hydrolysis using an acid. Optionally, the lignin material is a deacidified lignin. Optionally, the aqueous solution is water. Optionally, the aqueous solution is an acidulant.

The invention further provides a method of producing a deacidified lignin. The method involves contacting an acidic lignin with a hydrocarbon solvent; and heating the hydrocarbon solvent to remove an acid from the acidic lignin thereby obtaining a deacidified lignin. Optionally, the acidic lignin is obtained by removing hemicellulose and cellulose material from a lignocellulosic feedstock. Optionally, the hydrocarbon is ISOPARK. Optionally, the limited-solubility solvent is methylethylketone. Optionally, the acidic lignin is washed with an aqueous wash solution to remove residual sugars and acid before the acidic lignin is contacted with the hydrocarbon solvent. Optionally, the aqueous wash solution is an aqueous back-extract according to certain embodiments of the present invention. Optionally, the lignin material is washed with the aqueous solution counter-currently. Optionally, the lignin material is washed in multiple stages. Optionally, the high purity lignin is characterized by at least one, two, three, four, five, six, seven, eight, nine, ten, eleven, twelve or thirteen characteristic selected from the group consisting of: (i) lignin aliphatic hydroxyl group in an amount up to 2 mmole/g; (ii) at least 2.5 mmole/g lignin phenolic hydroxyl group; (iii) at least 0.4 mmole/g lignin carboxylic hydroxyl group; (iv) sulfur in an amount up to 1% weight/weight; (v) nitrogen in an amount up to 0.05% weight/weight; (vi) chloride in an amount up to 0.1% weight/weight; (vii) 5% degradation temperature higher than 250° C.; (viii) 10% degradation temperature higher than 300° C.; (ix) low ash content; (x) a formula of CaHbOc; wherein a is 9, b is less than 10 and c is less than 3; (xi) a degree of condensation of at least 0.9; (xii) a methoxyl content of less than 1.0; and (xiii) an O/C weight ratio of less than 0.4.

The invention further provides a lignin composition characterized by at least one, two, three, four, five, six, seven, eight, nine, ten, eleven, twelve or thirteen characteristic selected from the group consisting of: (i) lignin aliphatic hydroxyl group in an amount up to 2 mmole/g; (ii) at least 2.5 mmole/g lignin phenolic hydroxyl group; (iii) at least 0.4 mmole/g lignin carboxylic hydroxyl group; (iv) sulfur in an amount up to 1% weight/weight; (v) nitrogen in an amount up to 0.05% weight/weight; (vi) chloride in an amount up to 0.1% weight/weight; (vii) 5% degradation temperature higher than 250° C.; (viii) 10% degradation temperature higher than 300° C.; (ix) low ash content; (x) a formula of CaHbOc; wherein a is 9, b is less than 10 and c is less than 3; (xi) a degree of condensation of at least 0.9; (xii) a methoxyl content of less than 1.0; and (xiii) an O/C weight ratio of less than 0.4. Optionally, the lignin composition comprises lignin aliphatic hydroxyl group in an amount up to 1 mmole/g. Optionally, the lignin composition comprises lignin aliphatic hydroxyl group in an amount up to 0.5 mmole/g. Optionally, the lignin composition comprises at least 2.7 mmole/g lignin phenolic hydroxyl group. Optionally, the lignin composition comprises at least 3.0 mmole/g lignin phenolic hydroxyl group. Optionally, the lignin composition comprises at least 0.4 mmole/g lignin carboxylic hydroxyl group. Optionally, the lignin composition comprises at least 0.9 mmole/g lignin carboxylic hydroxyl group.

The invention further provides a lignin composition characterized by at least one, two, three, or four characteristic selected from the group consisting of: (i) at least 97% lignin on a dry matter basis; (ii) an ash content in an amount up to 0.1% weight/weight; (iii) a total carbohydrate content in an amount up to 0.05% weight/weight; and (iv) a volatiles content in an amount up to 5% weight/weight at 200° C. Optionally, the mixture has a non-melting particulate content in an amount up to 0.05% weight/weight.

The invention further provides a method of producing high purity lignin from a biomass. The method involves (i) removing hemicellulose sugars from the biomass thereby obtaining a lignin-containing remainder; wherein the lignin-containing remainder comprises lignin and cellulose; (ii) contacting the lignin-containing remainder with a lignin extraction solution to produce a lignin extract and a cellulosic remainder; wherein the lignin extraction solution comprises a limited-solubility solvent, an organic acid, and water, wherein the limited-solubility solvent and water form an organic phase and an aqueous phase; and (iii) separating the lignin extract from the cellulosic remainder; wherein the lignin extract comprises lignin dissolved in the limited-solubility solvent. Optionally, the removal of the hemicellulose sugars does not remove a substantial amount of the cellulosic sugars. Optionally, the limited-solubility solvent and the water in the lignin extraction solution is in a ratio of about 1:1. In some embodiments, the method further involves purifying the cellulosic remainder to obtain cellulose pulp. Optionally, the cellulose pulp comprises lignin in an amount up to 10% weight/weight. Optionally, the cellulose pulp comprises lignin in an amount up to 7% weight/weight. In some embodiments, the method further involves contacting the lignin extract with a strong acid cation exchanger to remove residual cations thereby obtaining a purified lignin extract. In some embodiments, the method further involves separating the limited-solubility solvent from the lignin extract thereby obtaining high purity lignin. In some embodiments, the method further involves evaporating the limited-solubility solvent from the lignin. Optionally, the evaporating comprises spray drying. In some embodiments, the method further involves washing the cellulose remainder with the limited-solubility solvent and with water thereby obtaining cellulose pulp. In some embodiments, the method further involves contacting the cellulose pulp with an acid to produce an acidic hydrolysate stream comprising cellulose sugars. In some embodiments, the method further involves (i) contacting the acidic hydrolysate stream comprising an acid and one or more cellulose sugars with a S1 solvent extractant to form a first mixture; and (ii) separating from the first mixture a first stream comprising the acid and the S1 solvent extractant and a second stream comprising the one or more cellulose sugars; wherein the acid is extracted from the acidic hydrolysate stream into the S1 solvent extractant. In some embodiments, the method further involves (iii) evaporating the second stream comprising the one or more cellulose sugars to form a concentrated second stream; and (vi) repeating step (iii) and (iv) above to form a stream comprising the acid and the S1 solvent extractant and a stream comprising the one or more cellulose sugars. In some embodiments, the method further involves (v) contacting the second stream with an amine extractant to form a second mixture; and (vi) separating from the second mixture a third stream comprising the acid and the amine extractant and a fourth stream comprising the one or more cellulose sugars. In some embodiments, the method further involves hydrolyzing the cellulose pulp in an aqueous suspension comprising hydrolytic enzymes. In some embodiments, the method further involves (i) agitating or stirring of the suspension comprising the cellulose pulp, the hydrolytic enzymes and an acidulating agent in a temperature controlled tank; (ii) separating from the suspension a first stream comprising cellulose pulp and a second stream comprising hydrolyzed cellulose sugars; (iii) returning the first stream to the temperature controlled tank for further hydrolysis. Optionally, the separating is carried out using a separation device selected from a filter, a membrane, a centrifuge, a hydrocylone. Optionally, the concentration of dissolved glucose in the aqueous suspension is controlled below the inhibition level of the hydrolytic enzymes. In some embodiments, the method further involves (i) contacting the second stream with an amine extractant to form a first mixture; and (ii) separating from the first mixture a third stream comprising the acid and the amine extractant and a fourth stream comprising the one or more cellulose sugars. In some embodiments, the method further involves allowing the residual acid in the fourth stream hydrolyze at least some oligomeric sugars in the sugar stream into monomeric sugars thereby forming a cellulose sugar stream. In some embodiments, the method further involves, prior to allowing, diluting the second stream to a lower sugar concentration. In some embodiments, the method further involves, prior to allowing, increasing the acid concentration in the second stream. Optionally, the acid concentration is increased to be more than 0.5%. In some embodiments, the method further involves contacting the fourth stream with a strong acid cation exchanger to remove residual amines, thereby forming an amine-removed hydrolysate. In some embodiments, the method further involves contacting the amine-removed hydrolysate with a weak base anion exchanger to form a neutralized hydrolysate. In some embodiments, the method further involves evaporating the hydrolysate to form a concentrated hydrolysate. In some embodiments, the method further involves fractionating the hydrolysate into a monomeric sugar stream and an oligomeric sugar stream. In some embodiments, the method further involves purifying or concentrating the monomeric sugar stream. In some embodiments, the method further involves (iv) contacting the first stream with an alkaline solution thereby dissolving residual solid lignin in the cellulose pulp; (v) separating the remainder cellulose pulp from the dissolved lignin thereby forming an aqueous solution comprising lignin; (vi) adjusting the pH of an aqueous solution comprising lignin to an acidic pH; (vii) contacting the acidic aqueous lignin solution with a lignin extraction solution comprising a limited-solubility solvent thereby forming a third stream comprising the lignin and the lignin extraction solution, and a fourth stream comprising water soluble impurities; (viii) contacting the third stream with a strong acid cation exchanger to remove residual cations thereby obtaining a purified third stream; and (ix) separating the limited-solubility solvent from the lignin thereby obtaining a high purity lignin composition. Optionally, the separating is carried out by filtering. Optionally, the separating step comprises precipitating the lignin by contacting the purified first stream with water. Optionally, the purified third stream is contacted with hot water thereby flash evaporating the limited-solubility solvent. Optionally, the separating step comprises evaporating the limited-solubility solvent from the lignin. Optionally, the evaporating comprises spray drying.

The invention further provides a method for producing a conversion product. The method involves (i) providing a fermentor; and (ii) fermenting a medium comprising at least one member selected from the group consisting of a hemicellulose sugar mixture according to certain embodiments of the invention; a xylose-enriched stream hemicellulose sugar mixture according to certain embodiments of the invention; a xylose stream according to certain embodiments of the invention (e.g., a crystallized xylose stream or a re-dissolved xylose stream); a xylose-removed hemicellulose sugar mixture according to certain embodiments of the invention; a mother liquor hemicellulose sugar mixture according to certain embodiments of the invention; a high concentration C6 sugar mixture according to certain embodiments of the present invention, in the fermentor to produce a conversion product. The invention further provides a method for producing a conversion product (i) providing at least one member selected from the group consisting of a hemicellulose sugar mixture according to certain embodiments of the invention; a xylose-enriched stream hemicellulose sugar mixture according to certain embodiments of the invention; a xylose stream according to certain embodiments of the invention (e.g., a crystallized xylose stream or a re-dissolved xylose stream); a xylose-removed hemicellulose sugar mixture according to certain embodiments of the invention; a mother liquor hemicellulose sugar mixture according to certain embodiments of the invention; a high concentration C6 sugar mixture according to certain embodiments of the invention; and (ii) converting sugars in the at least one member to a conversion product using a chemical process. In some embodiments, the methods further involve processing the conversion product to produce a consumer product selected from the group consisting of detergent, polyethylene-based products, polypropylene-based products, polyolefin-based products, polylactic acid (polylactide)-based products, polyhydroxyalkanoate-based products and polyacrylic-based products. Optionally, the conversion product includes at least one member selected from the group consisting of alcohols, carboxylic acids, amino acids, monomers for the polymer industry and proteins. Optionally, the detergent comprises a sugar-based surfactant, a fatty acid-based surfactant, a fatty alcohol-based surfactant, or a cell-culture derived enzyme. Optionally, the polyacrylic-based products are selected the group consisting of plastics, floor polishes, carpets, paints, coatings, adhesives, dispersions, flocculants, elastomers, acrylic glass, absorbent articles, incontinence pads, sanitary napkins, feminine hygiene products and diapers. Optionally, the polyole fin-based products are selected from the group consisting of milk jugs, detergent bottles, margarine tubs, garbage containers, water pipes, absorbent articles, diapers, non-wovens, HDPE toys and HDPE detergent packagings. Optionally, the polypropylene-based products are selected from the group consisting of absorbent articles, diapers, and non-wovens. Optionally, the polylactic acid-based products are selected from the group consisting of packaging of agriculture products and of dairy products, plastic bottles, biodegradable products and disposables. Optionally, the polyhydroxyalkanoate-based products are selected from the group consisting of packaging of agriculture products, plastic bottles, coated papers, molded or extruded articles, feminine hygiene products, tampon applicators, absorbent articles, disposable non-wovens, wipes, medical surgical garments, adhesives, elastomers, films, coatings, aqueous dispersants, fibers, intermediates of pharmaceuticals and binders. Optionally, the conversion product includes at least one member selected from the group consisting of ethanol, butanol, isobutanol, a fatty acid, a fatty acid ester, a fatty alcohol and biodiesel. In some embodiments, the methods further involve processing of the conversion product to produce at least one product selected from the group consisting of an isobutene condensation product, jet fuel, gasoline, gasohol, diesel fuel, drop-in fuel, diesel fuel additive and a precursor thereof. Optionally, the gasohol is ethanol-enriched gasoline or butanol-enriched gasoline. Optionally, the product is selected from the group consisting of diesel fuel, gasoline, jet fuel and drop-in fuels.

The invention further provides a consumer product, a precursor of a consumer product, or an ingredient of a consumer product produced from a conversion product according to methods for producing a conversion product described herein. The invention further provides a consumer product, a precursor of a consumer product, or an ingredient of a consumer product comprising at least one conversion product produced by methods for producing a conversion product described herein, wherein the conversion product is selected from the group consisting of carboxylic and fatty acids, dicarboxylic acids, hydroxylcarboxylic acids, hydroxyl di-carboxylic acids, hydroxyl-fatty acids, methylglyoxal, mono-, di-, or poly-alcohols, alkanes, alkenes, aromatics, aldehydes, ketones, esters, biopolymers, proteins, peptides, amino acids, vitamins, antibiotics and pharmaceuticals. Optionally, the product is ethanol-enriched gasoline, jet fuel, or biodiesel. Optionally, the consumer product has a ratio of carbon-14 to carbon-12 of about $2.0 \times 10^{-13}$ or greater. Optionally, the consumer product comprising an ingredient according to certain embodiments of the present invention and an additional ingredient produced from a raw material other than lignocellulosic material. Optionally, the ingredient and the additional ingredient produced from a raw material other than lignocellulosic material are essentially of the same chemical composition. Optionally, the consumer product, the precursor of a consumer product, or the ingredient of a consumer product further comprises a marker molecule at a concentration of at least 100 ppb. Optionally, the marker molecule is selected from the group consisting of furfural, hydroxymethylfurfural, products of furfural or hydroxymethylfurfural condensation, color compounds derived from sugar caramelization, levulinic acid, acetic acid, methanol, galacturonic acid and glycerol.

The invention further provides a method of converting lignin into a conversion product. The method involves (i) providing a composition according to certain embodiments of the present invention, and (ii) converting at least a portion of lignin in the composition to a conversion product. Optionally, the converting comprises treating with hydrogen. In some embodiments, the method further involves producing hydrogen from lignin. Optionally, the conversion product comprises at least one item selected from the group consisting of bio-oil, carboxylic and fatty acids, dicarboxylic acids, hydroxyl-carboxylic, hydroxyl di-carboxylic acids and hydroxyl-fatty acids, methylglyoxal, mono-, di- or poly-alcohols, alkanes, alkenes, aromatics, aldehydes, ketones, esters, phenols, toluenes, and xylenes. Optionally, the conversion product comprises a fuel or a fuel ingredient. Optionally, the conversion product comprises para-xylene. Optionally, a consumer product produced from the conversion product or a consumer product containing the conversion product as an ingredient or component. Optionally, the product contains at least one chemical selected from the group consisting of lignosulfonates, bio-oil, carboxylic and fatty acids, dicarboxylic acids, hydroxyl-carboxylic, hydroxyl di-carboxylic acids and hydroxyl-fatty acids, methylglyoxal, mono-, di- or poly-alcohols, alkanes, alkenes, aromatics, aldehydes, ketones, esters, biopolymers, proteins, peptides, amino acids, vitamins, antibiotics, para-xylene and pharmaceuticals. Optionally, the product contains para-xylene. Optionally, the product is selected from the group consisting of dispersants, emulsifiers, complexants, flocculants, agglomerants, pelletizing additives, resins, carbon fibers, active carbon, antioxidants, flame retardant, liquid fuel, aromatic chemicals, vanillin, adhesives, binders, absorbents, toxin binders, foams, coatings, films, rubbers and elastomers, sequestrants, fuels, and expanders. Optionally, the product is used in an area selected from the group consisting of food, feed, materials, agriculture, transportation and construction. Optionally, the product has a ratio of carbon-14 to carbon-12 of about $2.0 \times 10^{-13}$ or greater. Optionally, the product contains an ingredient according to certain embodiments of the present invention and an ingredient produced from a raw material other than lignocellulosic material. Optionally, the ingredient according to certain embodiments of the present invention and the ingredient produced from a raw material other than lignocellulosic material are essentially of the same chemical composition. Optionally, the product contains a marker molecule at a concentration of at least 100 ppb. Optionally, the marker molecule is selected from the group consisting of furfural and hydroxy-methyl furfural, products of their condensation, color compounds, acetic acid, methanol, galcturonic acid, glycerol, fatty acids and resin acids.

DESCRIPTION OF THE FIGURES

FIG. 26b is a schematic overview of an optional solvent and/or water removal system according to some exemplary cellulose sugar refining embodiments of the invention.

FIG. 26c is a schematic overview of an optional pre-evaporation module according to some exemplary cellulose sugar refining embodiments of the invention.

FIG. 42A is a simplified flow schemes of method for treating cellulose pulp and residual lignin according to some embodiments of the invention.

DETAILED DESCRIPTION OF THE INVENTION

Introduction

The present invention relates to lignocellulosic biomass processing and refining to produce hemicelluose sugars, cellulose sugars, lignin, cellulose and other high-value products.

Figure 17:
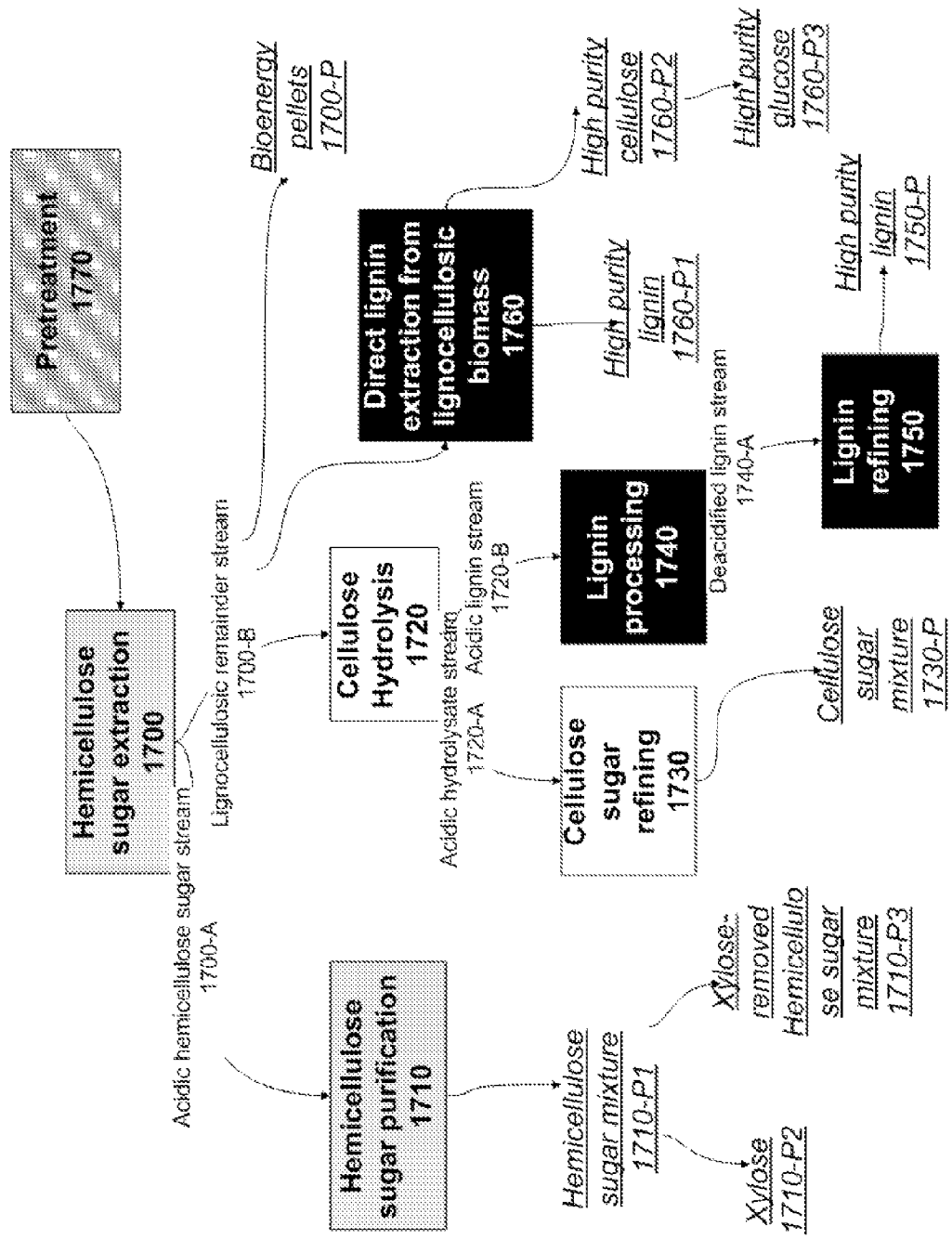
FIG. 17 is a schematic representation of an exemplary method of treating lignocellulosic biomass material according to some embodiments of the present invention.

An overview of the lignocellulosic biomass processing and refining according to embodiments disclosed herein is provided in FIG. 17. In general, the lignocellulosic biomass processing and refining processes include: (1) pretreatment 1770; (2) hemicellulose sugar extraction 1700 and purification 1710; (3) cellulose hydrolysis 1720 and cellulose sugar refining 1730; (4) lignin processing 1740 and refining 1750; and (5) direct lignin extraction 1760.

Various products can be made using these processes. For example, hemicellulose sugar extraction 1700 and purification 1710 produce a hemicellulose sugar mixture, xylose, and a xylose-removed hemicellulose sugar mixture, as well as bioenergy pellets. Cellulose hydrolysis 1720 and cellulose sugar refining 1730 processes produce a cellulose sugar mixture. Lignin processing 1740 and refining 1750 processes produce a high purity lignin and a high purity cellulose. Direct lignin extraction 1760 process produces a high purity lignin.

The lignocellulosic biomass processing and refining begins with pretreatment 1770, during which the lignocellulosic biomass can be, for example, debarked, chipped, shredded, dried, or grinded to particles.

During hemicellulose sugar extraction 1700, the hemicellulose sugars are extracted from the lignocellulosic biomass, forming an acidic hemicellulose sugar stream 1700A and a lignocellulosic remainder stream 1700B. The lignocellulosic remainder stream 1700B consists of mostly cellulose and lignin. It was surprisingly discovered in the present invention that hemicellulose sugars can be effectively extracted and converted into monomeric sugars (e.g., >90% of the total sugar) by treating biomass under mild conditions, e.g., with an acid in low concentrations, heat, and optionally pressure.

Figure 18:
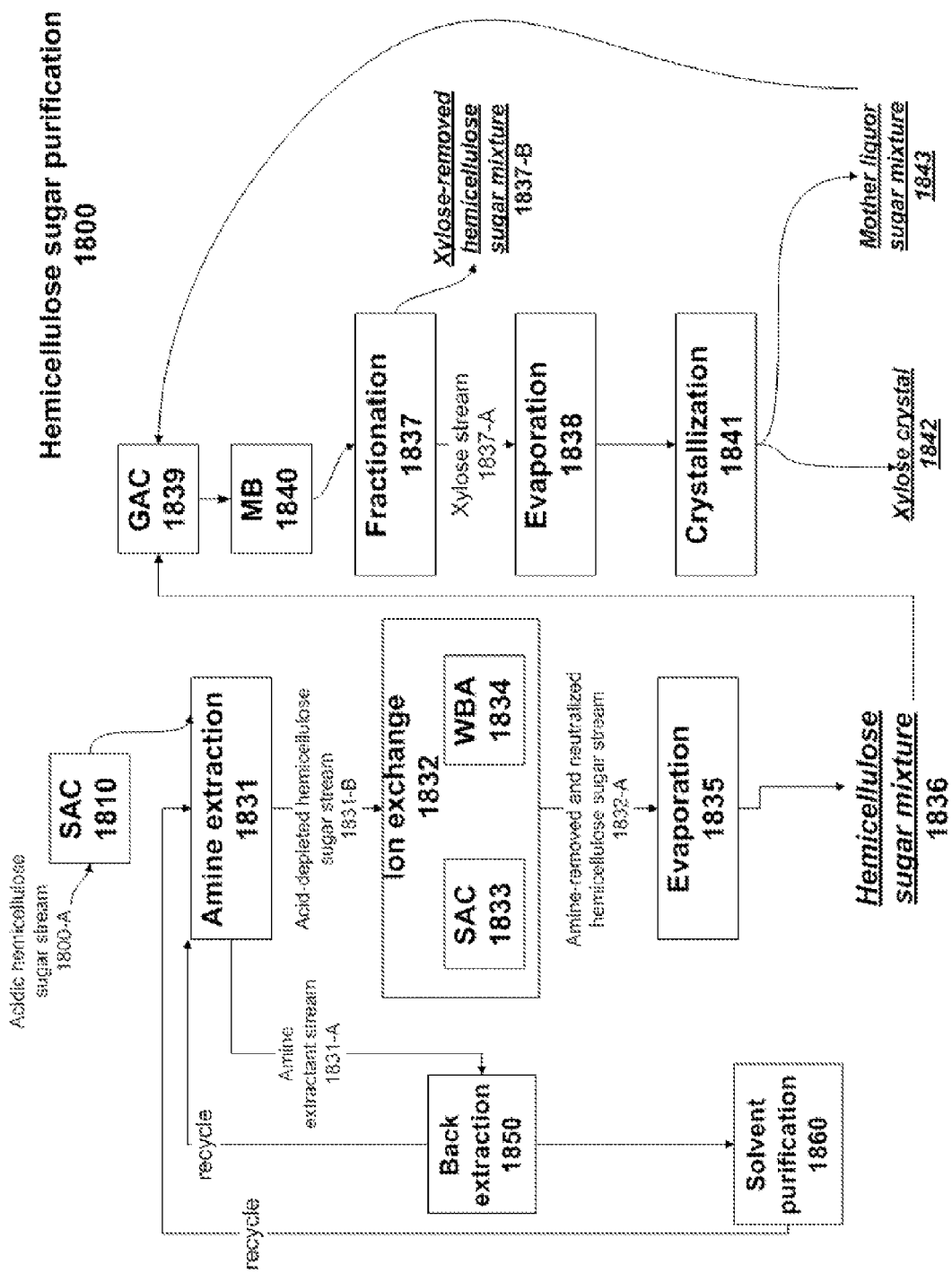
FIG. 18 is a schematic representation of an exemplary method of hemicellulose sugar extraction and purification according to some embodiments of the present invention. GAC stands for granulated activated carbon. MB stands for mixed bed (e.g., mixed bed cation/anion resin).

The acidic hemicellulose sugar stream 1700-A is purified in hemicellulose sugar purification 1710, acids and impurities co-extracted with hemicellulose sugars can be easily removed from the hemicellulose sugar stream by solvent extraction (see FIG. 18 for more details, e.g., amine extraction 1831 in FIG. 18). Once acids and impurities are removed from the hemicellulose sugar stream, the stream is neutralized and optionally evaporated to a higher concentration. A high purity hemicellulose sugar mixture 1710-P1 is obtained, which can be fractionated to obtain xylose and xylose-removed hemicellulose sugar mixture 1710-P3. Xylose is then crystallized to obtain xylose 1710-P2.

The lignocellulosic remainder 1700-B contains mostly cellulose and lignin. In some methods, the lignocellulosic remainder 1700-B can be processed to make bioenergy pellets 1700-P, which can be burnt as fuels.

In some methods, the lignocellulosic remainder 1700-B can be directly processed to extract lignin. This process produces a high purity lignin 1760-P1 and a high purity cellulose 1760-P2. The novel lignin purification process of the invention utilizes a limited-solubility solvent, and can produce a lignin having a purity greater than 99%.

In some methods, the lignocellulosic remainder 1700-B can be subject to cellulose hydrolysis 1720 to obtain cellulose sugar mixture 1730-P containing mostly C6 sugars. The novel cellulose hydrolysis process described herein allows cellulose hydrolysis of different lignocellulosic materials using a same set of equipment. Cellulose hydrolysis 1720 of the lignocellulosic remainder 1700-B results in an acidic hydrolysate stream 1720-A and an acidic lignin stream 1720-B.

Figure 19:
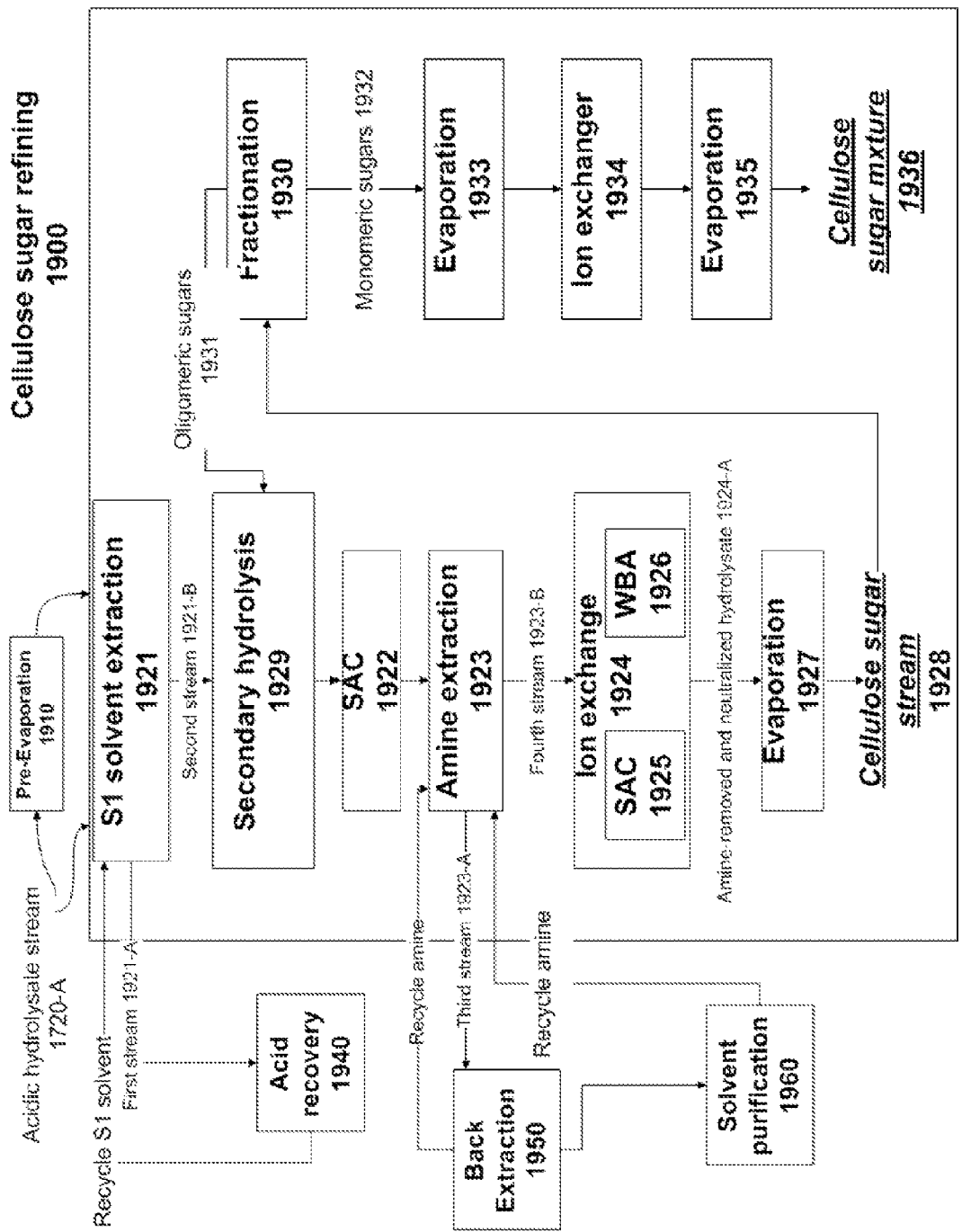
FIG. 19 is a schematic representation of an exemplary method of cellulose hydrolysis and main sugar refining according to some embodiments of the present invention.

The acidic hydrolysate stream 1720-A is then subject to cellulose sugar refining 1730 (see FIG. 19 for more details, e.g., cellulose sugar refining 1920 in FIG. 19). The acids in the acidic hydrolysate stream 1720-A can be removed using a novel solve extraction system. The deacidified main sugar stream is further fractionated to remove oligosaccharides from monosaccharides. The acid can be recovered and the solvents can be purified and recycled. The resulting cellulose sugar mixture 1730-P has unusually high monomeric sugar contents, particularly a high glucose content.

Figure 20:
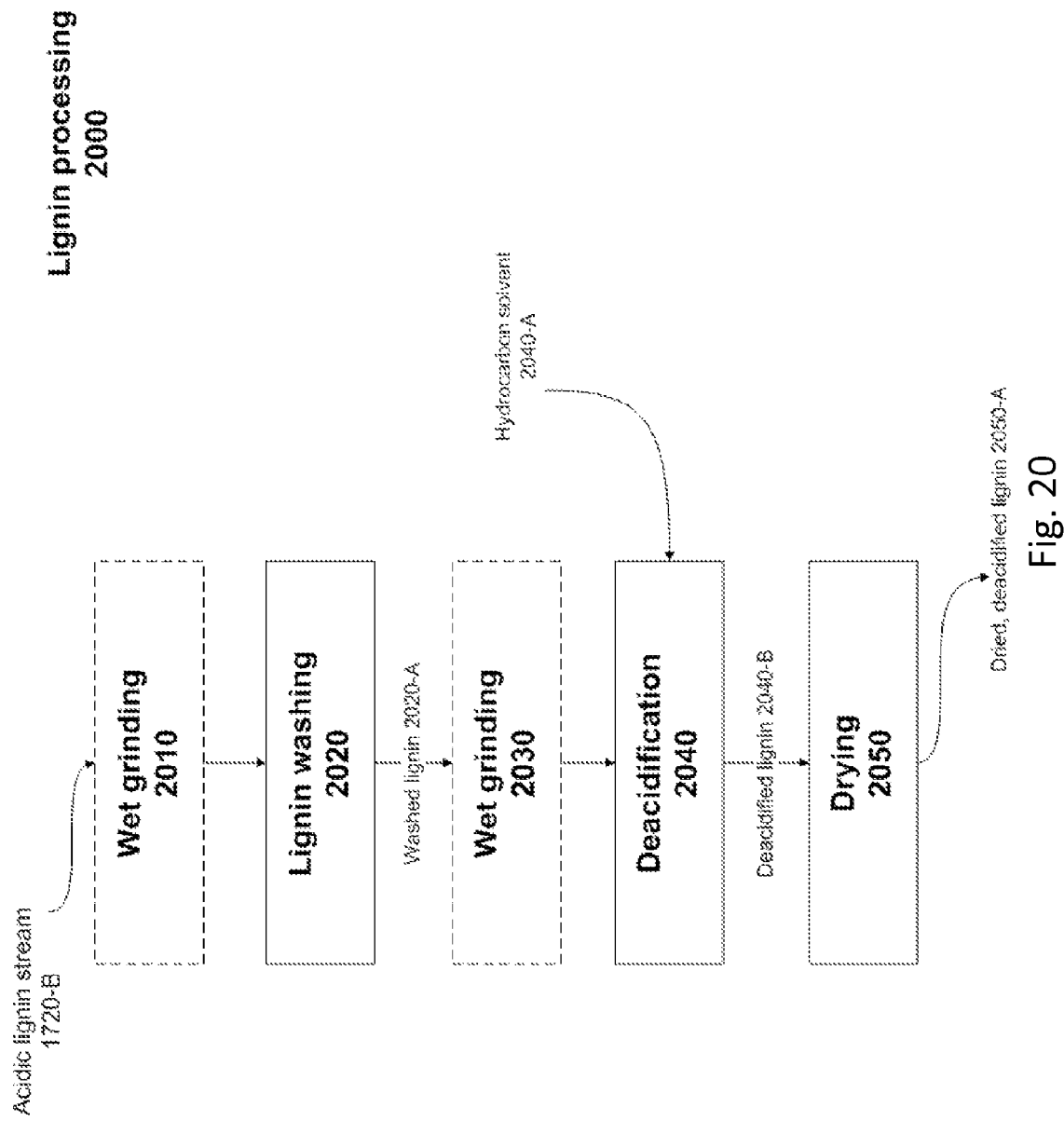
FIG. 20 is a schematic representation of an exemplary method of lignin processing according to some embodiments of the present invention.
Figure 21:
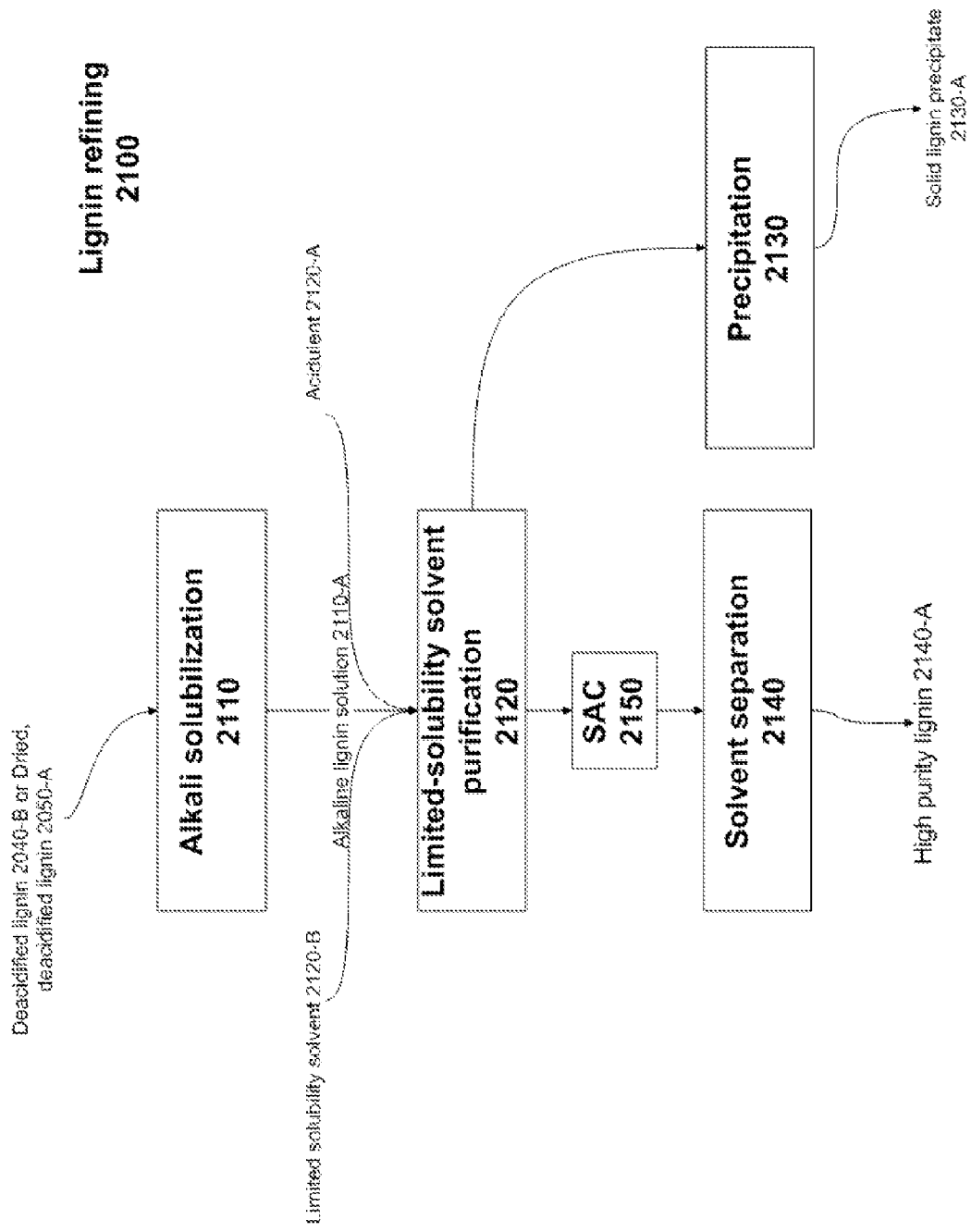
FIG. 21 is a schematic representation of an exemplary method of lignin refining according to some embodiments of the present invention.

Acidic lignin stream 1720-B is subject to lignin processing 1740 and lignin refining 1750 to obtain high purity lignin 1750-P (see FIGS. 20-21 for more details). Raw lignin stream 1720-B is first processed to remove any residual sugar and acids during lignin processing 1740. The deacidified lignin 1740-A is purified to obtain high purity lignin (lignin refining 1750). The novel lignin purification process of the invention utilizes a limited-solubility solvent, and can produce a lignin having a purity greater than 99%.

The sections I-VIII below illustrate lignocellulosic biomass processing and refining according to some embodiments disclosed herein. Section I discusses pretreatment 1770. Sections II and III discuss hemicellulose sugar extraction 1700 and purification 1710. Sections IV and V discuss cellulose hydrolysis 1720 and cellulose sugar refining 1730. Section VI and VII discuss lignin processing 1740 and refining 1750. Section VIII discusses direct lignin extraction 1760.

I. Pretreatment

Prior to hemicellulose sugar extraction 1700, lignocellulosic biomass can be optionally pre-treated. Pretreatment refers to the reduction in biomass size (e.g., mechanical breakdown or evaporation), which does not substantially affect the lignin, cellulose and hemicellulose compositions of the biomass. Pretreatment facilitates more efficient and economical processing of a downstream process (e.g., hemicellulose sugar extraction). Preferably, lignocellulosic biomass is debarked, chipped, shredded and/or dried to obtain pre-treated lignocellulosic biomass. Pretreatment can also utilize, for example, ultrasonic energy or hydrothermal treatments including water, heat, steam or pressurized steam. Pretreatment can occur or be deployed in various types of containers, reactors, pipes, flow through cells and the like. In some methods, it is preferred to have the lignocellulosic biomass pre-treated before hemicellulose sugar extraction 1700. In some methods, no pre-treatment is required, i.e., lignocellulosic biomass can be used directly in the hemicellulose sugar extraction 1700.

Optionally, lignocellulosic biomass can be milled or grinded to reduce particle size. In some embodiments, the lignocellulosic biomass is grinded such that the average size of the particles is in the range of 100-10,000 micron, preferably 400-5,000, e.g., 100-400, 400-1,000, 1,000-3,000, 3,000-5,000, or 5,000-10,000 microns. In some embodiments, the lignocellulosic biomass is grinded such that the average size of the particles is less than 10,000, 9,000, 8,000, 7,000, 6,000, 5,000, 4,000, 3,000, 1,000, or 400.

II. Hemicellulose Sugar Extraction

The present invention provides an advantageous method of extracting hemicellulose sugars from lignocellulosic biomass (hemicellulose sugar extraction 1700). Preferably, an aqueous acidic solution is used to extract lignocellulose biomass. The aqueous acidic solution can contain any acids, inorganic or organic. Preferably, an inorganic acid is used. For example, the solution can be an acidic aqueous solution containing an inorganic or organic acid such as $H_2SO_4$, $H_2SO_3$ (which can be introduced as dissolved acid or as $SO_2$ gas), HCl, and acetic acid. The acidic aqueous solution can contain an acid in an amount of 0 to 2% acid or more, e.g., 0-0.2%, 0.2-0.4%, 0.4-0.6%, 0.6-0.8%, 0.8-1.0%, 1.0-1.2%, 1.2-1.4%, 1.4-1.6%, 1.6-1.8%, 1.8-2.0% or more weight/weight. Preferably, the aqueous solution for the extraction includes 0.2-0.7% $H_2SO_4$ and 0-3,000 ppm $SO_2$. The pH of the acidic aqueous solution can be, for example, in the range of 1-5, preferably 1-3.5.

In some embodiments, an elevated temperature or pressure is preferred in the extraction. For example, a temperature in the range of 100-200° C., or more than 50° C., 60° C., 70° C., 80° C., 90° C., 100° C., 110° C., 120° C., 130° C., 140° C., 150° C., 160° C., 170° C., 180° C., 190° C., or 200° C. can be used. Preferably, the temperature is in the range of 110-160° C., or 120-150° C. The pressure can be in the range of 1-10 mPa, preferably, 1-5 mPa. The solution can be heated for 0.5-5 hours, preferably 0.5-3 hours, 0.5-1 hour, 1-2 hours, or 2-3 hours, optionally with a cooling down period of one hour.

Impurities such as ash, acid soluble lignin, fatty acids, organic acids such as acetic acid and formic acid, methanol, proteins and/or amino acids, glycerol, sterols, rosin acid and waxy materials can be extracted together with the hemicellulose sugars under the same conditions. These impurities can be separated from the aqueous phase by solvent extraction (e.g., using a solvent containing amine and alcohol).

After the hemicellulose sugar extraction 1700, the lignocellulosic remainder stream 1700-B can be separated from the acidic hemicellulose sugar steam 1700-A by any relevant means, including, filtration, centrifugation or sedimentation to form a liquid stream and a solid stream. The acidic hemicellulose sugar steam 1700-A contains hemicellulose sugars and impurities. The lignocellulosic remainder stream 1700-B contains predominantly cellulose and lignin.

The lignocellulosic remainder stream 1700-B can be further washed to recover additional hemicellulose sugars and acidic catalyst trapped inside the biomass pores. The recovered solution can be recycled back to the acidic hemicellulose sugar stream 1700-A, or recycled back to the hemicellulose sugar extraction 1700 reactor. The remaining lignocellulosic remainder stream 1700-B can be pressed mechanically to increase solid contents (e.g., dry solid contents 40-60%). Filtrate from the pressing step can be recycled back to the acidic hemicellulose sugar stream 1700-A, or recycled back to the hemicellulose sugar extraction 1700 reactor. Optionally, the remaining lignocellulosic remainder 1700-B is grinded to reduce particle sizes. Optionally, the pressed lignocellulosic remainder is then dried to lower the moisture content, e.g., less than 15%. The dried matter can be further processed to extract lignin and cellulose sugars (processes 1720 and 1760 in FIG. 17). Alternatively, the dried matter can be pelletized into pellets 1700-P, which can be burnt as energy source for heat and electricity production or can be used as feedstock for conversion to bio oil.

Alternatively, the lignocellulosic remainder stream 1700-B can be further processed to extract lignin (process 1760 in FIG. 17). Prior to the lignin extraction, the lignocellulosic remainder stream 1700-B can be separated, washed, and pressed as described above.

It was surprisingly found that hemicellulose sugar extraction 1700 can produce, in one single extraction process, a hemicellulose sugar stream containing at least 80-95% monomeric sugars. For example, the hemicellulose sugar stream can contain more than 80%, 85%, 90%, 91%, 92%, 93%, 94%, 95%, 96%, 97%, 98%, or 99% monomeric sugars. In addition, the present method produces minimal amounts of lignocellulose degradation products such as furfural, levulinic acid, and formic acid. In addition, a xylose yield greater than 93% of theoretical value can be achieved. Overall, 18-27% of total sugars and at least 70%, 75%, or 80% or more of the hemicellulose sugars can be extracted using the present method.

The acidic hemicellulose sugar stream 1700-A is then subject to hemicellulose sugar purification 1710. Various hemicellulose sugar products can be obtained from the purification. Exemplary purified products include hemicellulose sugar mixture 1710-P1, xylose 1710-P2, and xylose-removed hemicellulose sugar mixture 1710-P3.

III. Hemicellulose Sugar Purification

Prior to hemicellulose sugar purification 1710, the acidic hemicellulose sugar stream 1700-A from the hemicellulose sugar extraction 1700 can be optionally filtered, centrifuged, or concentrated by evaporation. For example, the hemicellulose sugar stream can be contacted with strong acid cation exchanger (e.g., in $H^+$ form) to convert all salts to their respective acids.

The hemicellulose sugar purification is illustrated in greater details according to an exemplary embodiment of the present invention as shown in FIG. 18. As illustrated in FIG. 18, the acidic hemicellulose sugar stream 1800-A is first subject to a strong cation exchange resin and then amine extraction 1831, during which acids and impurities are extracted from the hemicellulose sugar stream into the amine extractant. The acids-depleted hemicellulose sugar stream 1831-A is then purified by ion exchange 1832, including a strong acid cation exchanger 1833 and optionally followed by a weak base anion exchanger 1834. The amine-removed and neutralized hemicellulose sugar stream 1832-A is optionally evaporated 1835 to form a hemicellulose sugar mixture 1836. Optionally, the amine removed and neutralized hemicelluloses sugar stream 1832-A may also be refined by contact with granulated activated carbon prior to evaporation 1835.

The hemicellulose sugar mixture 1836 can be optionally fractionated (process 1837 in FIG. 18) to obtain high purity C5 sugars such as xylose. Fractionation can be carried out by any means, preferably using a simulated moving bed (SMB) or sequential simulated moving bed (SSMB). Examples of simulated moving bed processes are disclosed, for instance, in U.S. Pat. No. 6,379,554, U.S. Pat. No. 5,102,553, U.S. Pat. No. 6,093,326, and U.S. Pat. No. 6,187,204, examples of sequential simulated moving bed processes can be found in GB 2 240 053 and U.S. Pat. No. 4,332,623 as well as U.S. Pat. Nos. 4,379,751 and 4,970,002, each of the contents of the entirety of which is incorporated herein by this reference. In an exemplary SMB or SSMB setup, resin bed is divided into a series of discrete vessels, each of which sequence through a series of 4 zones (feed, separation, feed/separation/raffinate and safety) and connected by a recirculation loop. A manifold system connects the vessels and directs, in appropriate sequence to (or from) each vessel, each of the four media accommodated by the process. Those media are generally referred to as feed, eluent, extract and raffinate. For example, a feed can be hemicellulose sugar mixture 1836, the eluent can be water, the extract is an enriched solution of xylose and the raffinate is an aqueous solution containing high molecular weight sugars and other monomeric sugars i.e. arabinose, galactose and glucose. Optionally, the eluent can be an aqueous solution comprising low concentration of hydroxide ion to maintain the resin in hydroxyl form, or the eluent can be an aqueous solution comprising low concentration of acid to maintain the resin in a protonated form. For example, a feed comprising 30% sugar mix where xylose is about 65-70% of the mix can be fractionated using a SSMB to obtain an extract comprising about 16-20% sugars where xylose is about 82% or more and a raffinate comprising 5-7% sugar mix with only 15-18% xylose.

When a SSMB is used for fractionation, xylose exits from the extract flow and the higher sugars as well as glucose, galactose and arabinose exit from the raffinate flow. The xylose stream 1837-A can optionally be refined by contacting with granulated activated carbon and refined with mixed bed prior to evaporation to higher concentration (process 1838 in FIG. 18). The refined xylose stream 1839-A is then optionally evaporated again and crystallized (see, e.g., processes denoted in FIG. 18 by the number 1841). The products are xylose crystal 1842 and xylose-removed hemicellulose sugar mixture 1843.

The amine extractant stream 1831-A can be back-extracted with an aqueous solution containing a base (e.g., sodium hydroxide, sodium carbonate, and magnesium hydroxide) (see, e.g., process denoted in FIG. 18 by the number 1850). A portion of the solvent can be further purified using a lime solution (e.g. calcium oxide, calcium hydroxide, calcium carbonate, or a combination thereof) (see, e.g., process denoted in FIG. 18 by the number 1860) and the purified solvent can be recycled back to the amine extraction 1831.

Specific Embodiments of Hemicellulose Sugar Purification (FIGS. 1-7)

Figure 1:
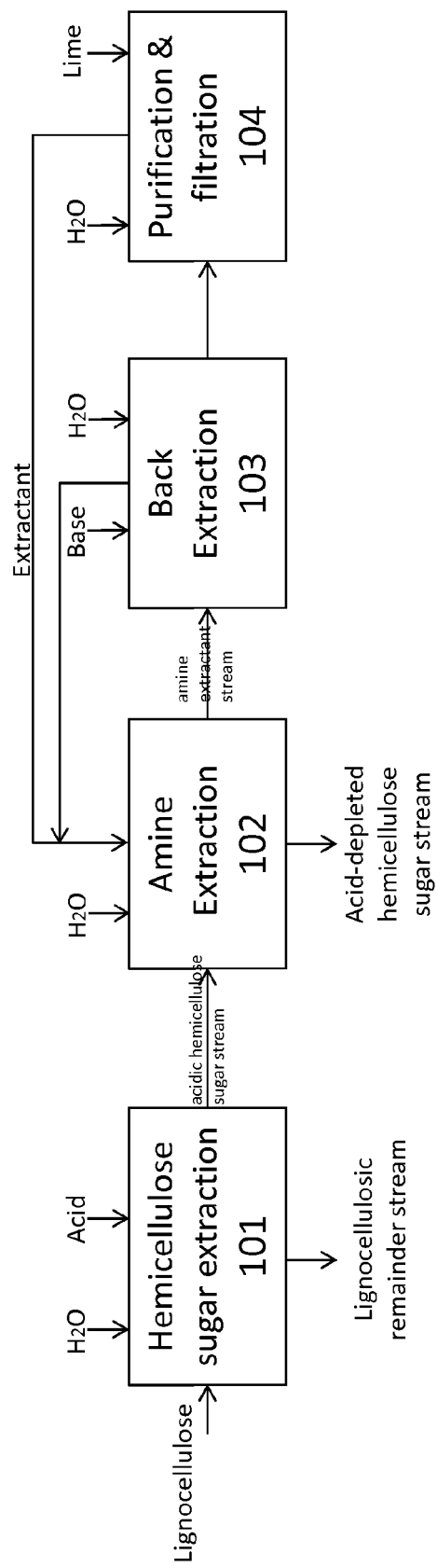
FIGS. 1-6 are simplified flow schemes of methods for treating lignocellulose material according to some embodiments of the invention.

Several preferred embodiments of hemicellulose sugar purification are illustrated in FIGS. 1-7. In FIG. 1, during hemicellulose sugar extraction 101, at least portion of the hemicellulose and impurities are extracted from lignocellulosic biomass by liquid extracting (e.g., using an acidic aqueous solution) to produce an acidic hemicellulose sugar stream and a lignocellulosic remainder stream. In some embodiments, hemicellulose sugar extraction 101 employs pressure cooking (e.g., 120-150° C., 1-5 mPa). The acidic hemicellulose sugar stream is subjected to amine extraction 102 using an amine extractant containing an amine having at least 20 carbon atoms, resulting in an acid-depleted hemicellulose sugar stream and an amine extractant stream. In one example, the amine extractant stream is subjected to a water wash followed by back extraction 103 with a base. At least a portion of the amine extractant stream is then subject to purification and filtration 104 before it is recycled back to amine extraction 102. The other part of the stream may be returned directly for reuse in amine extraction 102.

Figure 2:
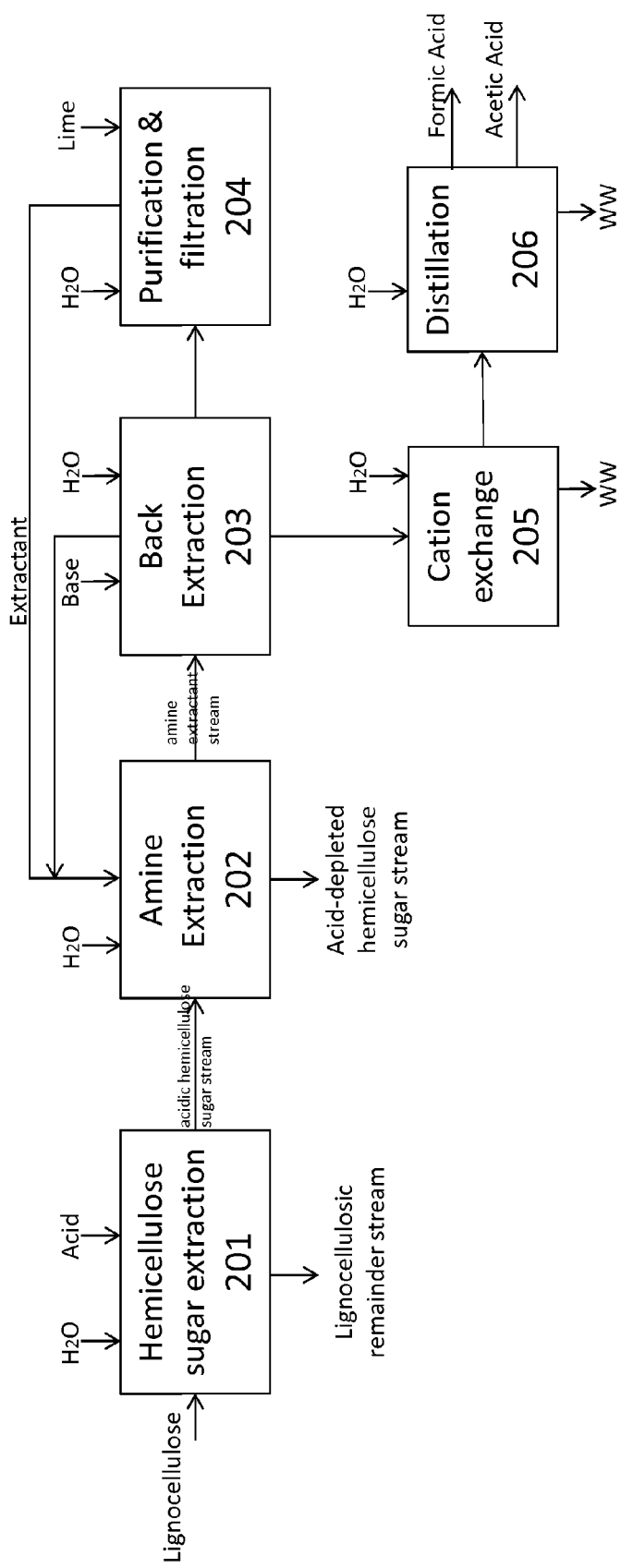

In FIG. 2, at least a portion of the hemicellulose and impurities are extracted in hemicellulose sugar extraction 201 by liquid extracting (e.g., using an acidic aqueous solution). In some embodiments, hemicellulose sugar extraction 201 produces an acidic hemicellulose sugar stream and a lignocellulosic remainder stream. In some embodiments, hemicellulose sugar extraction 201 employs pressure cooking. In some embodiments, the acidic hemicellulose sugar stream is subjected to amine extraction 202 using an amine extractant containing an amine having at least 20 carbon atoms, resulting in an acid-depleted hemicellulose sugar stream and an amine extractant stream. The amine extractant stream is subjected to a water wash followed by a back extraction 203 with a base. At least a portion of the amine extractant stream is then subject to purification and filtration 204 before it is recycled for reuse in amine extraction 202. The other part of the stream may be returned directly for reuse in the amine extraction 202. The aqueous stream resulting from the back extraction 203 is subjected to a cation exchange 205 and then to a distillation 206. In some embodiments distillation 206 produces acids.

Figure 3:
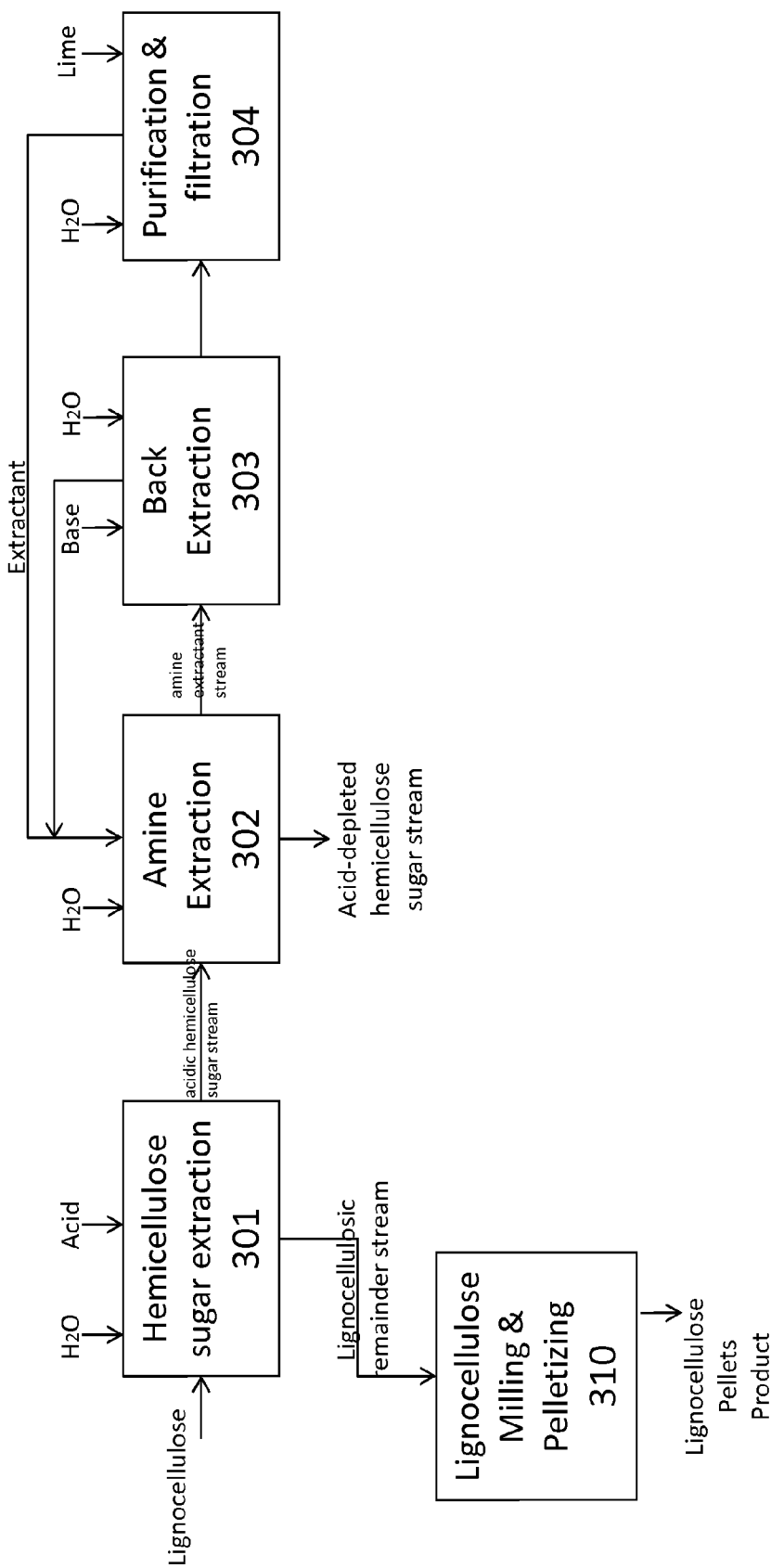

In FIG. 3, at least portion of the hemicellulose and impurities are extracted in hemicellulose sugar extraction 301 by liquid extracting (e.g., using an acidic aqueous solution) to produce an acidic hemicellulose sugar stream and a lignocellulosic remainder stream. In some embodiments, hemicellulose sugar extraction 301 employs pressure cooking. In some embodiments, the acidic hemicellulose sugar stream is subjected to amine extraction 302 using an amine extractant containing an amine having at least 20 carbon atoms, resulting in an acid-depleted hemicellulose sugar stream and an amine extractant stream. In some embodiments, the amine extractant stream is subjected to a water wash followed by back extraction 303 with a base. At least a portion of the amine extractant stream is then subject to purification and filtration 304 before reuse in amine extraction 302. The other part of the stream may be returned directly to reuse in amine extraction 302. The lignocellulose remainder stream is dried, milled if required and pelletized to produce lignocellulose pellets (process 310 in FIG. 3).

Figure 4:
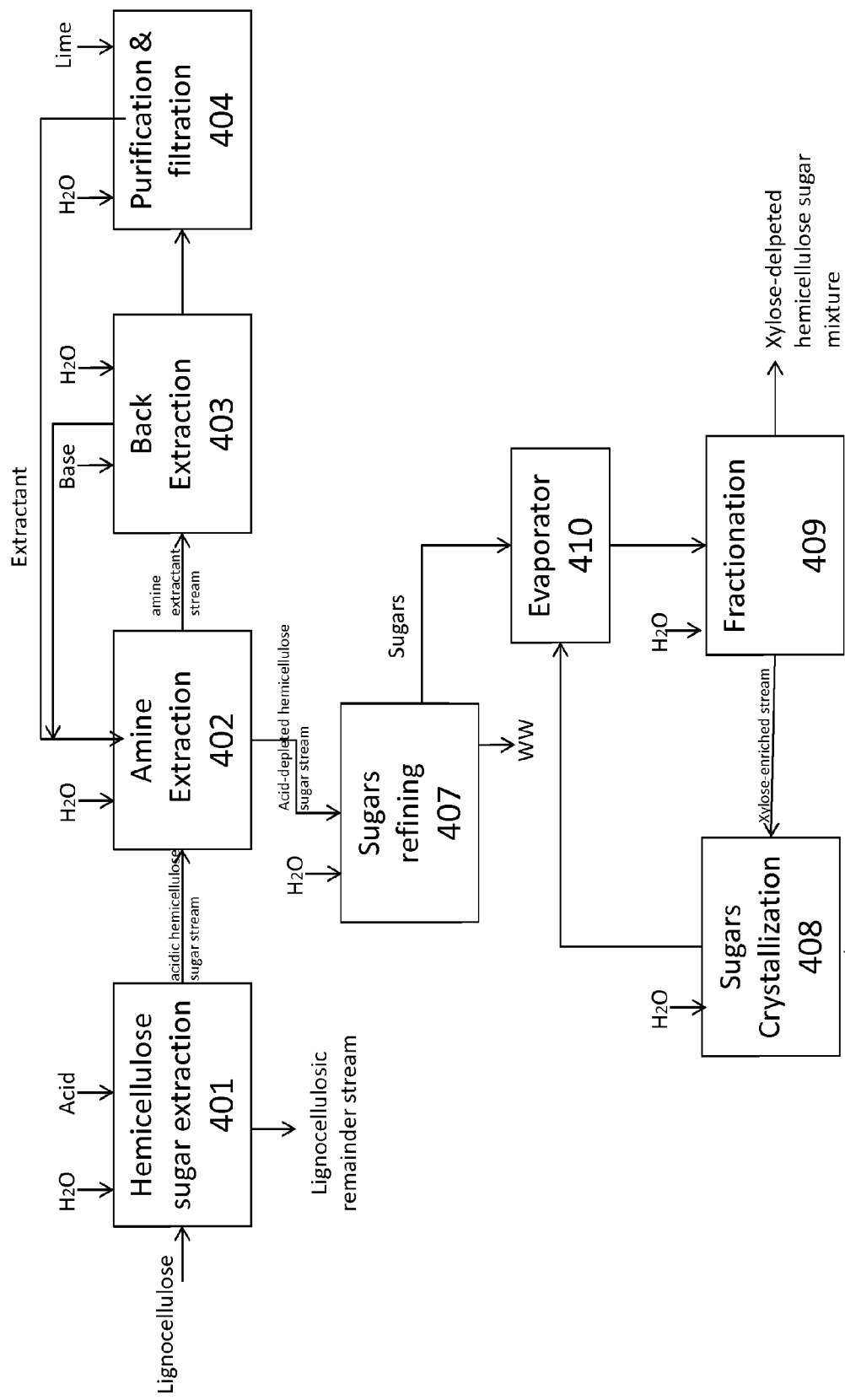

In FIG. 4, at least portion of the hemicellulose and impurities are extracted in hemicellulose sugar extraction 401 by liquid extracting (e.g., using an acidic aqueous solution) to produce an acidic hemicellulose sugar stream and a lignocellulosic remainder stream. In some embodiments, hemicellulose sugar extraction 401 employs pressure cooking. In some examples, the acidic hemicellulose sugar stream is subjected to amine extraction 402 using an amine extractant containing an amine having at least 20 carbon atoms, resulting in an acid-depleted hemicellulose sugar stream and an amine extractant stream. In some embodiments, the amine extractant stream is subjected to a water wash followed by back extraction 403 with a base. At least a portion of the amine extractant stream is then subject to purification and filtration 404 before reuse in amine extraction 402. The other part of the stream may be returned directly to reuse in amine extraction 402. Acid-depleted hemicellulose sugar stream is then subject to refining 407. In the depicted example, the refined sugar stream is then concentrated in evaporator 410, followed by fractionation at 409 to yield a stream containing xylose at high concentration and a xylose-depleted hemicellulose sugar stream. The stream containing xylose at high concentration is then crystallized 408 to make crystal sugar product. The resulting mother liquor is recycled to evaporator 410.

Figure 5:
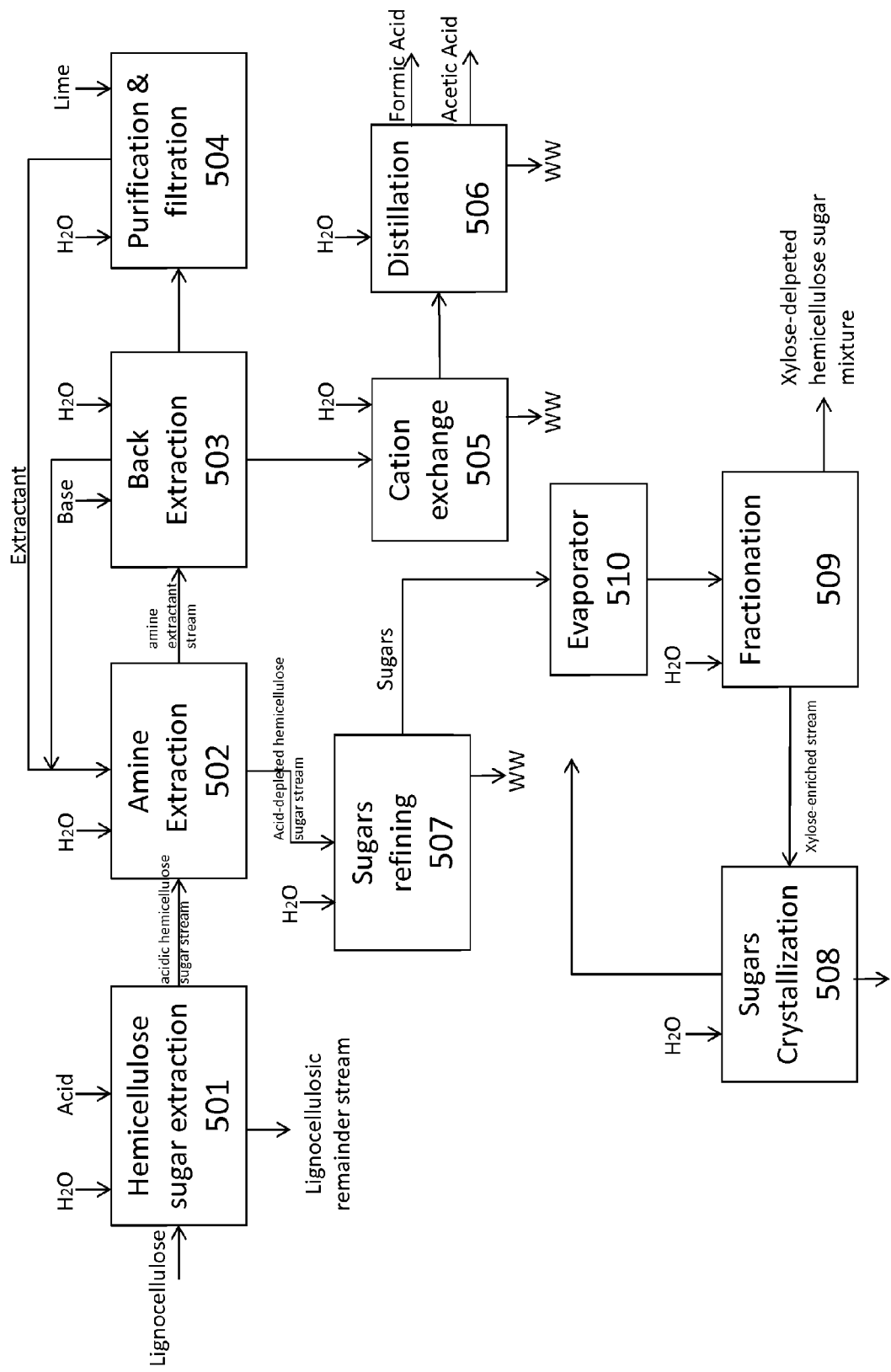

In FIG. 5, at least portion of the hemicellulose and impurities are extracted in hemicellulose sugar extraction 501 by liquid extracting (e.g., using an acidic aqueous solution) to produce an acidic hemicellulose sugar stream and a lignocellulosic remainder stream. In some embodiments, hemicellulose sugar extraction 501 employs pressure cooking. In some embodiments, the acidic hemicellulose sugar stream is subjected to amine extraction 502 using an amine extractant containing an amine having at least 20 carbon atoms, resulting in an acid-depleted hemicellulose sugar stream and an amine extractant stream. In some embodiments, the amine extractant stream is subjected to a water wash followed by back extraction 503 with a base. At least a portion of the amine extractant stream is then subject to purification and filtration 504 before reuse in amine extraction 502. The other part of the stream may be returned directly to reuse in amine extraction 502. Acid-depleted hemicellulose sugar stream is then subject to refining 507. In the depicted example, the refined sugar stream is then concentrated in evaporator 510, followed by fractionation at 509 to yield a stream containing xylose at high concentration and a xylose-depleted hemicellulose sugar stream. The stream containing xylose at high concentration is then crystallized (process 508) to make crystal sugar product. The resulting mother liquor is recycled to evaporator 510.

Figure 6:
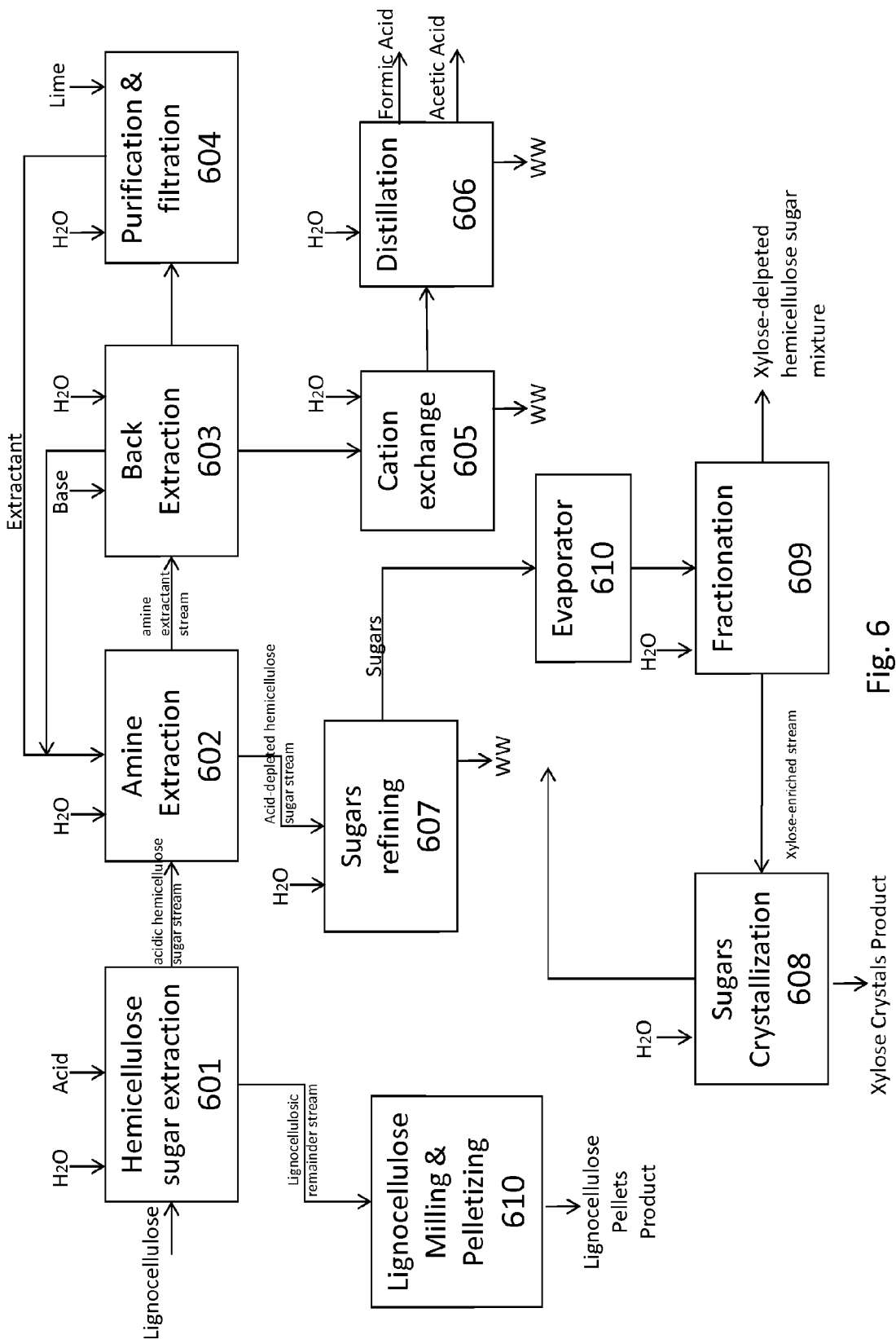

In FIG. 6, at least portion of the hemicellulose and impurities are extracted in hemicellulose sugar extraction 601 by liquid extracting (e.g., using an acidic aqueous solution) to produce an acidic hemicellulose sugar stream and a lignocellulosic remainder stream. In some embodiments, hemicellulose sugar extraction 601 employs pressure cooking. In some embodiments, the acidic hemicellulose sugar stream is subjected to amine extraction 602 using an amine extractant containing an amine having at least 20 carbon atoms, resulting in an acid-depleted hemicellulose sugar stream and an amine extractant stream. In some embodiments, the amine extractant stream is subjected to a water wash followed by back extraction 603 with a base. At least a portion of the amine extractant stream is then subject to purification and filtration 604 before reuse in amine extraction 602. The lignocellulosic remainder stream is milled and pelletized (process 610) to produce lignocellulose pellets. Acid-depleted hemicellulose sugar stream is then subject to refining 607. In the depicted example, the refined sugar stream is then concentrated in evaporator 610, followed by fractionation at 609 to yield a stream containing xylose at high concentration and a xylose-depleted hemicellulose sugar stream. The stream containing xylose at high concentration is then crystallized 608 to make crystal sugar product. The resulting mother liquor is recycled to evaporator 610.

Figure 7:
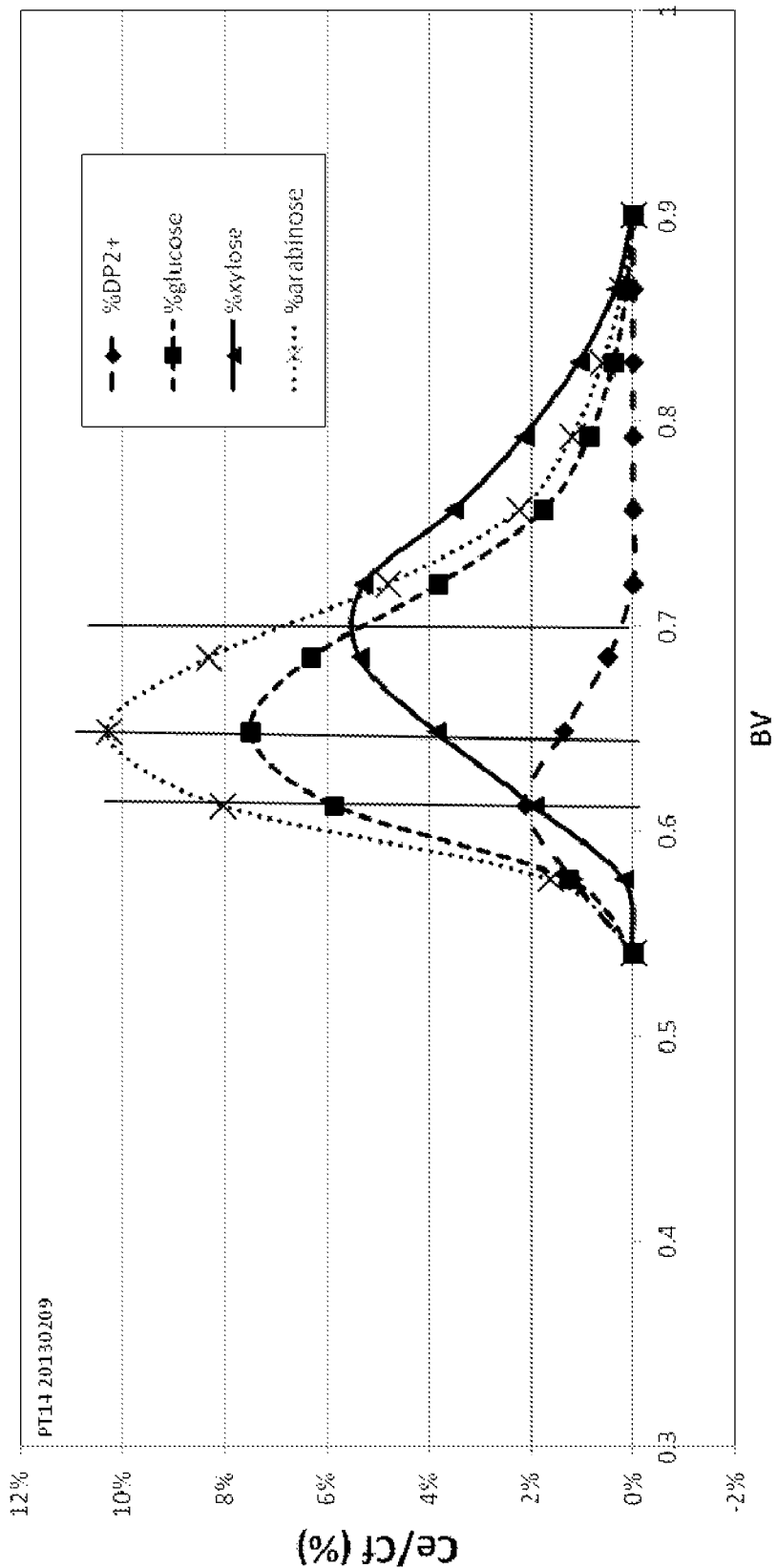
FIG. 7 depicts a chromatographic fractionation of a refined sugar mix to obtain an enriched xylose fraction and a mix sugar solution containing glucose, arabinose and a variety of DP2+ components.

FIG. 7 depicts a chromatographic fractionation of a refined sugar mix to obtain an enriched xylose fraction and a mix sugar solution containing glucose, arabinose and a variety of DP2+ components.

A more detailed description of these exemplary hemicellulose sugar purification embodiments is provided below.

1. Amine Extraction

As discussed above, the hemicellulose sugar stream 1800-A can be extracted with an amine extractant containing an amine base and a diluent, to remove mineral acid(s), organic acids, furfurals, acid soluble lignins (see, e.g., the processes denoted in FIGS. 1-6 by the number X02, where X is 1, 2, 3, 4, 5, or 6 depending on the figures; process 1831 in FIG. 18). The extraction can be carried out by any method suitable for extracting acids. Preferably, the hemicellulose sugar stream 1800-A is extracted with an amine extractant counter-currently, e.g., the hemicellulose sugar stream 1800-A flows in an opposite direction to the flow of the amine extractant. The counter-current extraction can be carried out in any suitable device, e.g., a mixer-settler device, stirred tanks, columns, or any other equipment suitable for this mode of extraction. Preferably, the amine extraction is conducted in a mixer-settler designed to minimize emulsion formation and reduce phase separation time. A mixer-settler has a first stage that mixes the phases together followed by a quiescent settling stage that allows the phases to separate by gravity. Various mixer-settlers known in the art can be used. In some methods, phase separation may be enhanced by incorporating a suitable centrifuge with the mixer-settler.

Typically, the vast majority of the sugars remain in the acid-depleted hemicellulose sugar stream 1831-B, whereas much of the organic or inorganic acids (e.g., the acids used in hemicellulose sugar extraction) and impurities are extracted into the amine extractant stream 1831-A. The amine extractant stream 1831-A can be contacted with an aqueous stream in a counter current mode, to recover any residual sugars absorbed into the amine extractant stream. In some embodiments, the amine extractant stream 1831-A contains less than 5, 4, 3, 2, 1, 0.8, 0.6, 0.5, 0.4, 0.2, 0.1% w/w hemicellulose sugars. In some embodiments, the acid-depleted hemicellulose sugar stream 1831-B contains less than 5, 4, 3, 2, 1, 0.8, 0.6, 0.5, 0.4, 0.2, 0.1% w/w acid. In some embodiments, the acid-depleted hemicellulose sugar stream 1831-B contains less than 5, 4, 3, 2, 1, 0.8, 0.6, 0.5, 0.4, 0.2, 0.1% w/w amine. In some embodiments, the acid-depleted hemicellulose sugar stream 1831-B contains less than 5, 4, 3, 2, 1, 0.8, 0.6, 0.5, 0.4, 0.2, 0.1% w/w impurities.

The amine extractant can contain 10-90% or preferably 20-60% weight/weight of one or a plurality of amines having at least 20 carbon atoms. Such amine(s) can be primary, secondary, and tertiary amines. Examples of tertiary amines include tri-laurylamine (TLA; e.g. COGNIS ALAMINE 304 from Cognis Corporation; Tucson Ariz.; USA), tri-octylamine, tri-isooctylamine, tri-caprylylamine and tri-decylamine.

Diluents suitable for use in the amine extraction include an alcohol such as butanol, isobutanol, hexanol, octanol, decanol, dodecanol, tetradecanol, pentadecanol, hexadecanol, octadecanol, eicosanol, docosanol, tetracosanol, and triacontanol. Preferably, the diluent is a long chain alcohol (e.g. C6, C8, C10, C12, C14, C16 alcohol), or kerosene. The diluent can have additional components. More preferably, the diluent comprises n-hexanol or 2-ethyl-hexanol. Most preferably, the diluent comprises n-hexanol. In some embodiments, the diluent consists essentially of, or consists of, n-hexanol.

Optionally, the diluent contains one or more additional components. In some methods, the diluent contains one or more ketones, one or more aldehydes having at least 5 carbon atoms, or another alcohol.

Preferably, the amine is tri-laurylamine and the diluent is hexanol. The ratio of amine and diluent can be any ratio, e.g., between 3:7 and 6:4 weight/weight. In some methods, the amine extraction solution contains tri-laurylamine and hexanol in a ratio of 1:7, 2:7, 3:7, 6:4, 5.5:4.55, 4:7, 5:7, 6:7, 7:7, 5:4, 3:4, 2:4, or 1:4 weight/weight. Preferably, the amine extraction solution contains tri-laurylamine and hexanol in a ratio of 3:7 weight/weight.

The amine extraction can be conducted at any temperature at which the amine is soluble, preferably at 50-70° C. Optionally, more than one extraction steps (e.g., 2, 3, or 4 steps) can be used. The ratio of the amine extractant stream (organic phase) to the hemicellulose sugar stream 1800-A (aqueous phase) can be 0.5-5:1, 1-2.5:1, or preferably, 1.5-3.0:1 weight/weight.

2. Back Extraction

The amine extractant stream 1831-A contains mineral and organic acid, as well as impurities extracted from biomass and sugar degradation products. The acids can be extracted from the amine extractant stream 1831-A in a back extraction step (see, e.g., the processes denoted in FIGS. 1-6 by the number X03, where X is 1, 2, 3, 4, 5, or 6 respectively; process 1850 in FIG. 18).

Optionally, prior to the back extraction 1850, the amine extractant stream 1831-A can be washed with an aqueous solution to recover any sugars in the stream. Typically, after the washing, the amine extractant stream 1831-A has less than 5%, 2%, 1%, 0.5%, 0.2%, 0.1%, 0.05% sugars.

The back extraction medium is an aqueous solution containing a base. For example, the extraction medium can be a solution containing $NaOH$, $Na_2CO_3$, $Mg(OH)_2$, $MgO$, or $NH_4OH$. The concentration of the base can be 1-20% by weight/weight, preferably 4-10% by weight/weight. Preferably, the base of choice produces a soluble salt when reacted with the acids in the acid-loaded organic stream. Preferably, the amount of the base in the back extraction medium is 2-10% excess over the stoichiometric equivalent of acids in the organic stream.

Back extraction 1850 can be carried out in any device, e.g., a mixer-settler device, stirred tanks, columns, or any other equipment suitable for this mode of back extraction. Preferably, the back extraction is conducted in a mixer-settler designed to minimize emulsion formation and reduce phase separation time, e.g., a mixer-settler equipped with low emulsifying mixers for high rate separation, or in tandem with a centrifuge to enhance separation. Back extraction can result in removal of at least 93% of the mineral acid and at least 85% of the organic acid from the organic phase.

Back extraction 1850 can be carried out in multiple reactors. In one example, back extraction 1850 is carried out in 4 reactors. In the first reactor, the amount of base is equivalent to that of carboxylic acid and only the carboxylic acids is back-extracted to produce a solution of their salt(s) (e.g. sodium salt). In the second reactor, the mineral acid is back-extracted. The streams coming out of each reactor is treated separately to allow recovering of the organic acids. Optionally, the aqueous streams coming out of the back extraction steps can be combined. Typically, the combined stream contains at least 3% of the anion of the mineral acid (e.g. sulfate ion if sulfuric and/or sulfurous acids where used in hemicellulose sugar extraction 1700), and 0.2-3% acetic acid as well as lower concentrations of other organic acids. The aqueous stream can contain low concentration of the organic phase diluent, typically less than 0.5%, depending on the solubility of the diluent used in water. Preferably, the aqueous stream coming out of back extraction is kept to allow segregation of chemicals present in these streams. In one example, $Ca^{2+}$ and $SO_4^{2-}$, which are deleterious to anaerobic digestion, is routed separately to aerobic treatment.

The organic phase diluent may be removed from the aqueous phase by distillation, where in many cases these diluents may form a heterogeneous azeotrope with water that has a lower boiling point than the diluent solvent alone, thus the energy required to distill off the diluent is significantly reduced due to the vast excess of water over the diluent. The distilled solvent can be recovered and recycled back into the solvent reservoir for further use. The diluent-stripped aqueous phase may be directed to the waste treatment unit of the plant.

3. Solvent Purification

The amine extractant stream, now neutralized after acid removal, can be washed with water to remove salts remaining from the back extraction. It is particularly preferred for certain blended extractants that can partially saturate with water (as is the case of certain alcohols for example). The wash stream may be combined with the back extraction aqueous stream. A fraction of the washed amine extractant, typically 5-15% of the total weight of the amine extractant stream, can be diverted to the purification and filtration step denoted as X04 in FIGS. 1-6 (see, also, process 1860 in FIG. 18). The remaining amine extractant is recycled to amine extraction denoted as X02 in FIGS. 1-6.

The fraction diverted to purification step (X04 in FIGS. 1-6; process 1860 in FIG. 18) can be treated with a lime suspension (e.g., a 5%, 10%, 15%, 20%, 25% weight/weight lime solution). The solvent to lime suspension ratio can be in the range 4-10, 4-5, 5-6, 6-7, 7-8, 8-9, or 9-10. Treatment may be conducted in any suitable device, e.g., a thermostatic mixed tank. The solution can be heated for at least 1 hour at 80-90° C. Lime reacts with residual organic acids and esters of organic acids and adsorbs effectively organic impurities present in the organic phase such as acid soluble lignin and furfurals, as visualized by change of color from dark to light. The contaminated lime and impurities can be filtered or centrifuged to recover the purified organic phase, which is washed with water and recycled back to the amine extraction step (X02 in FIGS. 1-6; process 1831 in FIG. 18). The aqueous stream may be diverted to other aqueous waste streams. Any solid cake that may be formed by the lime reaction may be used in the waste water treatment plant as a neutralization salt for residual acids from ion exchange regenerations for example.

The back extraction aqueous stream contains salts of the organic acids. This stream can be contacted with a cation exchanger to convert all salts to their respective organic acids (see, e.g., the processes denoted in FIGS. 2, 5 and 6 by the number X05 where X is 2, 5, or 6 respectively). Alternatively the organic acids can be converted to the acid form by acidifying the solution with a strong mineral acid. The acidified stream can be distilled to harvest formic acid and acetic acid (see, e.g., the processes denoted in FIGS. 2, 5 and 6 by the number X06 where X is 2, 5, or 6 respectively). Remaining aqueous streams are diverted to waste.

4. Sugar Purification

The acid-depleted hemicellulose sugar stream can be further purified (see, e.g., FIGS. 4-6). For example, the diluent in the acid-depleted hemicellulose sugar stream can be removed using a packed distillation column. The distillation can remove at least 70%, 80%, 90%, or 95% of the diluent in the acid-depleted hemicellulose sugar stream. With or without diluent distillation step, the acid-depleted hemicellulose sugar stream can also be contacted with a strong acid cation (SAC) exchanger to remove any residual metallic cations and any residual amines. Preferably, the acid-depleted hemicellulose sugar stream is purified using a packed distillation column followed by a strong acid cation exchanger.

Preferably, the acid-depleted hemicellulose sugar stream can then be contacted with a weak base anion (WBA) exchanger to remove excess protons. The amine-removed and neutralized hemicellulose sugar stream can be pH adjusted and evaporated to 25-65% and preferably 30-40% weight/weight dissolved sugars in any conventional evaporator, e.g., a multiple effect evaporator or a mechanical vapor recompression (MVR) evaporator.

Any residual solvent present in the hemicellulose sugar stream can also be removed by evaporation. For example, the solvent that forms a heterogeneous azeotrope with water can be separated and returned to the solvent cycle. Optionally the concentrated sugar solution can be contacted with activated carbon to remove residual organic impurities. The concentrated sugar solution may also be contacted with mixed bed resin system to remove any residual ions or color bodies. Optionally, the now refined sugar solution can be concentrated further by and conventional evaporator or MVR.

The resulting stream is a highly purified hemicellulose sugar mixture (e.g., 1836 in FIG. 18) comprising, e.g., 85-95% weight/weight monosaccharides out of the total dissolved sugars. The composition of the sugars depends on the composition of the starting biomass. A hemicellulose sugar mixture produced from softwood biomass can have 65-75% (weight/weight) C6 saccharides in the sugar solution out of total sugars. In contrast, a hemicellulose sugar mixture produced from hardwood biomass can contain 80-85% weight/weight C6 sugars out of total sugars. The purity of the stream in all cases may be sufficient for fermentation processes and/or catalytic processes utilizing these sugars.

The highly purified hemicellulose sugar mixture 1836 is characterized by one or more, two or more, three or more, four or more, five or more, six or more characteristics including (i) monosaccharides in a ratio to total dissolved sugars >0.50 weight/weight; (ii) glucose in a ratio to total monosaccharides <0.25 weight/weight; (iii) xylose in a ratio to total monosaccharides >0.18 weight/weight; (iv) fructose in a ratio to total monosaccharides <0.10 weight/weight; (v) fructose in a ratio to total monosaccharides >0.01 weight/weight; (vi) furfurals in amount up to 0.01% weight/weight; (vii) phenols in amounts up to 500 ppm; and (viii) a trace amount of hexanol. For example, the sugar mixture can be a mixture having a high monosaccharides to total dissolved sugars ratio, a low glucose content, and a high xylose content. In some embodiments, the sugar mixture is a mixture having a high monosaccharides to total dissolved sugars ratio, a low glucose content, a high xylose content, and a low impurity contents (e.g., low furfurals and phenols). In some embodiments, the mixture is characterized by a high monosaccharides to total dissolved sugars ratio, a low glucose content, a high xylose content, a low impurity contents (e.g., low furfurals and phenols), and a trace amount of hexanol.

In some embodiments, the resulting stream is a sugar mixture with a high monomeric ratio. In some sugar mixture, monosaccharides to total dissolved sugars ratio is larger than 0.50, 0.60, 0.70, 0.75, 0.80, 0.85, 0.90, or 0.95 weight/weight. In some embodiments, the resulting stream is a sugar mixture having a low glucose content. In some sugar mixture, the glucose to total monosaccharides ratio is less than 0.25, 0.20, 0.15, 0.13, 0.10, 0.06, 0.05, 0.03, or 0.02 weight/weight. In some embodiments, the resulting stream is a sugar mixture with a high xylose content. In some sugar mixture, the xylose to total monosaccharides ratio is larger than 0.10, 0.15, 0.18, 0.20, 0.30, 0.40, 0.50, 0.60, 0.70, 0.80 or 0.85 weight/weight.

In some sugar mixtures 1836, the fructose to total dissolved sugars ratio is less than 0.02, 0.03, 0.04, 0.05, 0.06, 0.07, 0.08, 0.09, 0.10, 0.15, 0.20, 0.25 or 0.30 weight/weight. In some sugar mixtures 1836, the fructose to total dissolved sugars ratio is larger than 0.001, 0.002, 0.005, 0.006, 0.007, 0.008, 0.009, 0.01, 0.02, 0.03, 0.04, 0.05, 0.06, 0.07, 0.08, or 0.09 weight/weight.

The above hemicellulose sugar mixture includes a very low concentration of impurities (e.g., furfurals and phenols). In some resulting stream, the sugar mixture has furfurals in an amount up to 0.1%, 0.05%, 0.04%, 0.03%, 0.04%, 0.01%, 0.075%, 0.005%, 0.004%, 0.002%, or 0.001% weight/weight. In some resulting stream, the sugar mixture has phenols in an amount up to 500 ppm, 400 ppm, 300 ppm, 200 ppm, 100 ppm, 60 ppm, 50 ppm, 40 ppm, 30 ppm, 20 ppm, 10 ppm, 5 ppm, 1 ppm, 0.1 ppm, 0.05 ppm, 0.02 ppm, or 0.01 ppm. The hemicellulose sugar mixture is further characterized by a trace amount of hexanol, e.g., 0.01-0.02%, 0.02-0.05%, 0.05-0.1%, 0.1%-0.2%, 0.2-0.5%, 0.5-1%, or less than 1, 0.5, 0.2, 0.1, 0.05, 0.02, 0.01, 0.005, 0.002, 0.001%, weight/weight hexanol.

This high purity sugar solution can be used to produce industrial products and consumer products as described in PCT/IL2011/00509 (incorporated herein by reference for all purposes). Furthermore, the softwood sugar product containing 65-75% weight/weight C6 sugars can be used as fermentation feed to species that are only able to utilize C6 sugars, and the resulting mix of C5 and product may be separated, the C5 can then be refined to obtain a C5 product, as described in PCT/US2011/50435 (incorporated herein by reference for all purposes).

Fermentation product includes at least one member selected from the group consisting of alcohols, carboxylic acids, amino acids, monomers for the polymer industry and proteins and wherein the method further comprises processing said fermentation product to produce a product selected from the group consisting of detergent, polyethylene-based products, polypropylene-based products, polyolefin-based products, polylactic acid (polylactide)-based products, polyhydroxyalkanoate-based products and polyacrylic-based products.

These fermentation products may be used alone or with other components as food or feed, pharmaceuticals, nutraceuticals, plastic parts or components to make various consumer products, fuel, gasoline, chemical additive or surfactant.

The high purity sugar solution products are suitable for chemical catalytic conversions since catalysts are usually sensitive to impurities associated with biomass and sugar degradation products. Typically, the purity is greater than 95, 96, 97, 98%, preferably greater than 99, 99.5, or 99.9%. This product contains small amounts of marker molecules including for example residual diluent, e.g. hexanol, 1-ethyl hexanol, kerosene or any other diluents used, as well as furfural, hydroxymethylfurfural, products of furfural or hydroxymethylfurfural condensation, color compounds derived from sugar caramelization, levulinic acid, acetic acid, methanol, galacturonic acid or glycerol.

5. Sugar Fractionation

Some biomass materials contain a high concentration of a single sugar as part of their hemicellulosic sugar composition. For example, *eucalyptus* and bagasse contain high concentration of xylose. A single sugar such as xylose has specific application and much greater industrial value as compared to a sugar mixture. Therefore, it is highly beneficial to fractionate the sugar stream to obtain a high concentration of the single sugar to facilitate sugar crystallization and production of high purity single sugar product.

The hemicellulose sugar mixture 1836 can be optionally concentrated by evaporation, and fractionated 1837 (e.g., by chromatographic separation) to produce a xylose-enriched stream 1837-A having more than 75, 78, 80, 82, 84, 85, 86, 88, 90% xylose, and a xylose-removed hemicellulose sugar mixture 1837-B. The xylose-removed hemicellulose sugar mixture 1837-B can be used as substrate for fermentation processes that are capable of fermenting C5/C6 sugar mixtures, as substrate for chemical conversion, or as substrate for anaerobic digestion to produce energy.

The chromatographic fractionation to achieve enrichment of xylose concentration can be carried out with ion exchange resins (e.g., a cation exchange resin and an anion exchange resin) as the column filling material. The cation exchange resins include strong acid cation exchange resins and weak acid cation exchange resins. The strong acid cation exchange resins can be in a monovalent or multivalent metal cation form, e.g., in $H^+$, $Mg^{2+}$, $Ca^{2+}$ or $Zn^{2+}$ form. Preferably, the resins are in $Na^+$ form. The strong acid cation exchange resins typically have a styrene skeleton, which is preferably cross-linked with 3 to 8%, preferably 5 to 6.5% of divinylbenzene. The weak acid cation exchange resins may be in a monovalent or multivalent metal cation form, e.g., $H^+$, $Mg^{2+}$ or $Ca^{2+}$ form, preferably in $Na^+$ form.

The chromatographic fractionation can be carried out in a batch mode or a simulated moving bed (SMB) mode or a sequential simulated moving bed (SSMB) mode. The temperature of the chromatographic fractionation is typically in the range of 20 to 90° C., preferably 40 to 65° C. The pH of the solution to be fractionated can be acidic or adjusted to a range of 2.5-7, preferably 3.5-6.5 and most preferably 4-5.5. Typically, the fractionation can be carried out with a linear flow rate of about 1 m/h-10 m/h in the separation column.

Anion exchange resins have usually been used in the past for demineralization of solutions, i.e., for ion exchange, or for decolorization, i.e., for adsorption. In some embodiments of the invention, there can be little or no net ion exchange or adsorption between the resin and the solution. In that case, an anion-type ion exchange resin is used for its properties as a chromatographic substrate, rather than in a column intended primarily for net exchange of ions.

Chromatographic separation differs from other column-based separations (e.g., ion-exchange or adsorption) in that no major component in the feed mixture is retained by the sorbent so strongly as to require that additional reagents be routinely used between cycles to regenerate the column by removing strongly retained components before the next separation cycle. In general, a chromatographic column can be re-used for multiple cycles before regeneration before the columns require some degree of periodic cleansing or regeneration. The function of an ion-exchange or adsorption column is to bind components tightly, necessarily requiring frequent regeneration for the resin to be reused. By contrast, the function of a chromatographic column is to provide differential mobility for components moving through the column to effect a separation, but not to bind too tightly to the principal components. Regeneration of a chromatographic column may be needed from time to time due to incidental binding of minor components or impurities to the resin. The minimal quantity of reagents needed for resin regeneration is a major advantage of chromatographic separations over ion-exchange separations. The operational cost of chromatographic separations is due primarily to the energy needed to evaporate water (or other solvent) from dilute products, and to a lesser extent to the infrequent replacement or regeneration of resin.

A preferred method for large-scale chromatographic separations is the sequential simulated moving bed (SSMB), or alternatively a simulated moving bed (SMB). Both methods use a number of columns packed with a suitable sorbent and connected in series. There are inlet ports for feed and solvent (which may include recycled solvent), and outlet ports for two or more products (or other separated fractions). The injection of the mixture solution to be separated is periodically switched between the columns along the direction of the liquid flow, thereby simulating continuous motion of the sorbent relative to the ports and to the liquid. The SMB is a continuous counter current type operation. SSMB is a more advance method, requiring a sequential operation. Its advantages over SMB and over other older methods include: fewer number of columns is needed in the SSMB method versus the SMB, hence less resin is required and hence associated cost of installation is significantly reduced in large system; the pressure profile is better controlled, facilitating the use of more sensitive resins; achievable recovery/purity is higher than obtained with SMB systems.

Fractionation of xylose from the refined mix sugar solution X09 (X denotes 4, 5, or 6 in FIGS. 4-6; process 1837 in FIG. 18) can be preferably achieved using a strong base anion (SBA) exchanger having a particle size of ~280-320 µm. This larger particle size is advantageous over much smaller particles sizes used in U.S. Pat. No. 6,451,123. A larger particle size reduces the back pressure of the column to industrially practical range. Suitable commercial SBA resins can be purchased from Finex (AS 510 GC Type I, Strong Base Anion, gel form), similar grades can be purchased from other manufacturers including Lanxess AG, Purolite, Dow Chemicals Ltd. or Rohm & Haas. The SBA resin may be in the sulfate or chloride form, preferably in the sulfate form. The SBA is partially impregnated with hydroxyl groups by low concentration NaOH, the range of base to sulfate is 3-12% to 97-88% respectively. To maintain this level of OH groups on the resin, a low level of NaOH, sufficient to replace the hydroxyl removed by sugar adsorption, may be included in the desorption pulse, thus making the xylose retain longer than other sugars on this resin. Fractionation may be conducted in the SSMB mode at about 40-50° C., resulting in a xylose rich stream, containing at least 79%, at least 80%, at least 83%, preferably at least 85% xylose out of total sugars, and a mix sugar stream, at a recovery of at least 80%, at least 85% xylose.

In some methods, the SSMB sequence includes three steps. In the first step, a product stream is extracted by exposing and flushing the adsorbent with a desorbent stream ("desorbent to extract" step). Concurrently, a feed stream in passed into the adsorbent and a raffinate stream is flushed from the adsorbent ("feed to raffinate" step). In the second step, a raffinate stream is extracted by exposing and flushing the adsorbent with a desorbent stream ("desorbent to raffinate" step). In the third step, the desorbent is recycled back to the adsorbent ("recycle" step).

Typically, the product is extracted in such a manner that the raffinate flow equals the desorbent flow but it results in a high desorbent consumption to reach the target product recovery. Preferably, in some SSMB sequences, the product is extracted in more than one step (e.g., not only in step 1, but also in step 2). In some methods, the product stream is not only extracted in the first step, but also extracted in the second step (i.e., the "desorbent to raffinate" step). When the product is extracted in more than one step, the desorbent flow rate is equal to the sum of the extract flow rate and the raffinate flow rate. In some embodiments, the desorbent flow rate is about the same as the sum of the extract flow rate and the raffinate flow rate. In some embodiments, the desorbent flow rate is within 50-150%, 60-140%, 70-130%, 80-120%, 90-110%, 95-105%, 96-104%, 97-103%, 98-102%, 99-101%, or 99.5-100.5%, of the sum of the extract flow rate and the raffinate flow rate. This change in the SSMB sequence decreases the required desorbent, resulting in the target product recovery with much less desorbent volume while maintaining the SSMB chromatographic profiles in the four (4) zones and six (6) columns and purity.

Following fractionation X09 the sugar streams can optionally be contacted with a weak acid cation (WAC) exchange resin in the H+ form to neutralize the sugar stream. This acidification allows evaporation of the sugar stream while maintaining sugar stability. The WAC resin can be regenerated by a mineral acid or preferably by contacting with the waste acid stream of the SAC resin used at the sugar refining step X07 (X denotes 4, 5, or 6 in FIGS. 4-6). Following the WAC neutralization step, the mix sugar stream can optionally be directed to evaporator X10 (X denotes 4, 5, or 6 in FIGS. 4-6), while the xylose rich stream is directed to the sugar crystallizer X08 (X denotes 4, 5, or 6 in FIGS. 4-6).

The xylose-enriched stream 1837-A is characterized by one or more, two or more, three or more, four or more, five or more, six or more, seven or more, eight or more, nine or more, ten or more characteristics including (i) oligosaccharides in a ratio to total dissolved sugars <0.10 weight/weight; (ii) xylose in a ratio to total dissolved sugars >0.50 weight/weight; (iii) arabinose in a ratio to total dissolved sugars <0.10 weight/weight; (iv) galactose in a ratio to total dissolved sugars <0.05 weight/weight; (v) the sum of glucose and fructose in a ratio to total dissolved sugars <0.10 weight/weight; (vi) mannose in a ratio to total dissolved sugars <0.02 weight/weight; (vii) fructose in a ratio to total dissolved sugars <0.05 weight/weight; (viii) furfurals in an amount up to 0.01% weight/weight; (ix) phenols in an amount up to 500 ppm; and (x) a trace amount of hexanol. For example, the sugar mixture 1837-A is a mixture characterized a low oligosaccharides to total dissolved sugars ratio and a high xylose to total dissolved sugars ratio. In some embodiments, the sugar mixture 1837-A is a mixture characterized by a low oligosaccharides to total dissolved sugars ratio, a high xylose to total dissolved sugars ratio, and a low impurity contents (e.g., low furfurals and phenols). In some embodiments, the sugar mixture 1837-A is a mixture characterized by a low oligosaccharides to total dissolved sugars ratio, a high xylose to total dissolved sugars ratio, a low impurity contents (e.g., low furfurals and phenols), and a trace amount of hexanol. In some embodiments, the sugar mixture 1837-A is a mixture characterized by a low oligosaccharides to total dissolved sugars ratio, a high xylose to total dissolved sugars ratio, a low ratio of the sum of glucose and fructose to total dissolved sugars ratio, a low impurity contents (e.g., low furfurals and phenols), and a trace amount of hexanol.

In some embodiments, the xylose-enriched stream 1837-A is a sugar mixture characterized by a high xylose to total dissolved sugars ratio. In some sugar mixtures, the xylose to total dissolved sugars ratio is larger than 0.40, 0.45, 0.50, 0.55, 0.60, 0.65, 0.70, 0.75, 0.80, 0.85, or 0.90 weight/weight. In some embodiments, the xylose-enriched stream 1837-A is a sugar mixture characterized by a low oligosaccharides to total dissolved sugars ratio. In some sugar mixtures, the oligosaccharides to total dissolved sugars ratio is less than 0.002, 0.005, 0.007, 0.01, 0.02, 0.03, 0.04, 0.05, 0.06, 0.07, 0.08, 0.09, 0.10, 0.20, or 0.30 weight/weight. In some embodiments, the xylose-enriched stream 1837-A is a sugar mixture with a low glucose/fructose content. In some sugar mixtures, the ratio of the sum of glucose and fructose to total dissolved sugars is less than 0.005, 0.01, 0.02, 0.03, 0.04, 0.05, 0.06, 0.07, 0.08, 0.09, 0.10, 0.20, 0.25, or 0.30 weight/weight. In some embodiments, the xylose-enriched stream 1837-A is a sugar mixture with a high xylose to total sugars ratio, a low oligosaccharides to total dissolved sugars ratio, and a low glucose and fructose contents.

In some sugar mixtures 1837-A, the arabinose to total dissolved sugars ratio is less than 0.001, 0.002, 0.003, 0.004, 0.005, 0.01, 0.02, 0.03, 0.04, 0.05, 0.06, 0.07, 0.08, 0.09, 0.10, 0.20 or 0.30 weight/weight. In some sugar mixtures 1837-A, the galactose to total dissolved sugars ratio is less than 0.0005, 0.001, 0.002, 0.003, 0.004, 0.005, 0.01, 0.02, 0.03, 0.04, 0.05, 0.06, 0.07, 0.08, 0.09, or 0.10 weight/weight. In some sugar mixtures 1837-A, the mannose to total dissolved sugars ratio is less than 0.001, 0.002, 0.003, 0.004, 0.005, 0.01, 0.02, 0.03, 0.04, 0.05, 0.06, 0.07, 0.08, 0.09, 0.10, 0.20 or 0.30 weight/weight. In some sugar mixtures 1837-A, the fructose to total dissolved sugars ratio is less than 0.001, 0.002, 0.003, 0.004, 0.005, 0.01, 0.02, 0.03, 0.04, 0.05, 0.06, 0.07, 0.08, 0.09, 0.10, 0.20 or 0.30 weight/weight.

The sugar mixture 1837-A includes a very low concentration of impurities (e.g., furfurals and phenols). In some sugar mixtures 1837-A, the sugar mixture has furfurals in an amount up to 0.1%, 0.05%, 0.04%, 0.03%, 0.04%, 0.01%, 0.075%, 0.005%, 0.004%, 0.002%, or 0.001% weight/weight. In some sugar mixtures 1837-A, the sugar mixture has phenols in an amount up to 500 ppm, 400 ppm, 300 ppm, 200 ppm, 100 ppm, 60 ppm, 50 ppm, 40 ppm, 30 ppm, 20 ppm, 10 ppm, 5 ppm, 1 ppm, 0.1 ppm, 0.05 ppm, 0.02 ppm, or 0.01 ppm. The sugar mixture is further characterized by a trace amount of hexanol, e.g., 0.01-0.02%, 0.02-0.05%, 0.05-0.1%, 0.1%-0.2%, 0.2-0.5%, 0.5-1%, or less than 1, 0.5, 0.2, 0.1, 0.05, 0.02, 0.01, 0.005, 0.002, 0.001%, weight/weight hexanol.

The xylose-removed hemicellulose sugar mixture 1837-B is characterized by one or more, two or more, three or more, four or more, five or more, six or more, seven or more, eight or more, nine or more, ten or more characteristics including (i) oligosaccharides in a ratio to total dissolved sugars >0.15 weight/weight; (ii) the sum of glucose and fructose in a ratio to total dissolved sugars >0.10 weight/weight; (iii) arabinose in a ratio to total dissolved sugars >0.02 weight/weight; (iv) galactose in a ratio to total dissolved sugars >0.02 weight/weight; (v) xylose in a ratio to total dissolved sugars <0.20; (vi) mannose in a ratio to total dissolved sugars >0.01; (vii) fructose in a ratio to total dissolved sugars <0.05; (viii) furfurals in an amount up to 0.01% weight/weight; (ix) phenols in an amount up to 500 ppm; and (x) a trace amount of hexanol. For example, the sugar mixture can be a mixture characterized by a high oligosaccharides to total dissolved sugars ratio, and a high glucose/fructose to total dissolved sugars ratio. In some embodiments, the sugar mixture 1837-B is a mixture characterized by a high oligosaccharides to total dissolved sugars ratio, a high glucose/fructose to total dissolved sugars ratio, and a low impurity contents (e.g., low furfurals and phenols). In some embodiments, the sugar mixture is a mixture characterized by a high oligosaccharides to total dissolved sugars ratio, a high glucose/fructose to total dissolved sugars ratio, a low impurity contents (e.g., low furfurals and phenols), and a trace amount of hexanol. In some embodiments, the sugar mixture is a mixture characterized by a high xylose concentration, a high oligosaccharides to total dissolved sugars ratio, a high ratio of the sum of glucose and fructose to total dissolved sugars ratio, and a low impurity contents (e.g., low furfurals and phenols).

In some embodiments, the xylose-removed hemicellulose sugar mixture 1837-B is a sugar mixture characterized by a high oligosaccharides to total dissolved sugars ratio. In some sugar mixtures, the oligosaccharides to total dissolved sugars ratio is larger than 0.15, 0.20, 0.25, 0.30, 0.35, 0.40, 0.45, 0.50, 0.55, or 0.65 weight/weight. In some embodiments, the xylose-removed hemicellulose sugar mixture 1837-B is a sugar mixture with a high glucose/fructose content. In some sugar mixtures, the ratio of the sum of glucose and fructose to total dissolved sugars is larger than 0.05, 0.10, 0.13, 0.15, 0.20, 0.25, 0.30, 0.35, 0.40, 0.45, 0.50, or 0.55 weight/weight. In some embodiments, the xylose-depleted liquor is a sugar mixture with a high oligosaccharides to total dissolved sugars ratio, and a high glucose and fructose contents.

In some sugar mixtures 1837-B, the arabinose to total dissolved sugars ratio is larger than 0.02, 0.03, 0.04, 0.05, 0.06, 0.08, 0.10, 0.12, 0.20, or 0.30 weight/weight. In some sugar mixtures 1837-B, the galactose to total dissolved sugars ratio is larger than 0.02, 0.03, 0.04, 0.05, 0.06, 0.08, 0.10, 0.12, 0.20, or 0.30 weight/weight. In some sugar mixtures 1837-B, the xylose to total dissolved sugars ratio is less than 0.30, 0.20, 0.18, 0.17, 0.16, 0.15, 0.12, 0.10, or 0.05 weight/weight. In some sugar mixtures 1837-B, the mannose to total dissolved sugars ratio is larger than 0.005, 0.006, 0.007, 0.008, 0.010, 0.015, or 0.020 weight/weight. In some sugar mixtures 1837-B, the fructose to total dissolved sugars ratio is less than 0.005, 0.01, 0.02, 0.03, 0.04, 0.05, 0.06, 0.07, 0.08, 0.09, 0.10, or 0.20 weight/weight.

The sugar mixture 1837-B includes a very low concentration of impurities (e.g., furfurals and phenols). In some resulting stream, the sugar mixture has furfurals in an amount up to 0.1%, 0.05%, 0.04%, 0.03%, 0.04%, 0.01%, 0.075%, 0.005%, 0.004%, 0.002%, or 0.001% weight/weight. In sugar mixtures 1837-B, the sugar mixture has phenols in an amount up to 500 ppm, 400 ppm, 300 ppm, 200 ppm, 100 ppm, 60 ppm, 50 ppm, 40 ppm, 30 ppm, 20 ppm, 10 ppm, 5 ppm, 1 ppm, 0.1 ppm, 0.05 ppm, 0.02 ppm, or 0.01 ppm. The sugar mixture is further characterized by a trace amount of hexanol, e.g., 0.01-0.02%, 0.02-0.05%, 0.05-0.1%, 0.1%-0.2%, 0.2-0.5%, 0.5-1%, or less than 1, 0.5, 0.2, 0.1, 0.05, 0.02, 0.01, 0.005, 0.002, 0.001%, weight/weight hexanol.

6. Sugar Crystallization

This exemplary description is related to the processes denoted in FIGS. 4, 5 and 6 by the number X08, where X is 4, 5, or 6 respectively (process 1841 in FIG. 18). Pure xylose is known to crystallize out of supersaturated mixed sugar solutions. To achieve that, the sugar solution stream resulting from the sugar refining of X07 is concentrated by evaporation X10, and fractionated by chromatographic separation at X09 to produce a xylose-enriched stream (corresponding to 1837-A in FIG. 18) having more than 75, 78, 80, 82, 84, 85, 86, 88, 90% xylose, and a xylose-removed hemicellulose sugar mixture (corresponding to 1837-B in FIG. 18). The xylose-enriched stream (corresponding to 1837-A in FIG. 18) coming out of fractionation X09 is fed into a crystallization module X08 (process 1841 in FIG. 18) to produce xylose crystals.

In some methods, the xylose-enriched stream 1837-A is optionally further evaporated before it is fed into a crystallization module 1841 to produce xylose crystals. The crystals can be harvested from the mother liquor by any suitable means, e.g., centrifugation. Depending on the crystallization technique, the crystals can be washed with the appropriate solution, e.g., an aqueous solution or solvent. The crystals can be either dried or re-dissolved in water to make xylose syrup. Typically a yield of 45-60% of the potential xylose can be crystallized in a 20-35, preferably 24-28 hour cycle.

After crystallization, the mother liquor hemicellulose sugar mixture 1843 can be recycled back to the fractionation step as it contains a very high content of xylose, e.g., >57% xylose, >65% and more typically >75% xylose. Alternatively, the mother liquor hemicellulose sugar mixture 1843 can be sent to anaerobic digestion to harvest the energy attainable from this fraction.

In some embodiments, the mother liquor hemicellulose sugar mixture 1843 is a sugar mixture characterized by a high xylose concentration. In some sugar mixtures, the sugar mixture has more than 65, 67, 69, 70, 71, 72, 73, 74, 75, 76, 77, 78, 79, 80, or 85% weight/weight xylose.

Sugar solution stream originating from some hardwood and specific grasses such as bagasse can contain at least 60% xylose and more typically 60-80% or 66-73% weight/weight xylose. Xylose can be used as a raw material for bacterial and chemical production of furfural and tetrahydrofuran. Xylose can also be used as the starting material for preparing xylitol, a low calorie alternative sweetener that has beneficial properties for dental care and diabetes management, and has been shown to contribute to clearing ear and upper respiratory tract infections. Given these beneficial properties, xylitol is incorporated in food and beverages, toothpastes and mouth wash products, chewing gums and confectionary products. World xylitol market is limited due to its high price compared to other non-reducing polyol sugars (ca. sorbitol, mannitol). The method of the present invention provides a cost-effective production method for xylose and xylitol.

The mother liquor hemicellulose sugar mixture 1843 is characterized by one or more, two or more, three or more, four or more, five or more, six or more, seven or more, eight or more, nine or more, ten or more characteristics including (i) oligosaccharides in a ratio to total dissolved sugars <0.15 weight/weight; (ii) xylose in a ratio to total dissolved sugars >0.40 weight/weight; (iii) arabinose in a ratio to total dissolved sugars <0.15 weight/weight; (iv) galactose in a ratio to total dissolved sugars <0.06 weight/weight; (v) the sum of glucose and fructose in a ratio to total dissolved sugars <0.20 weight/weight; (vi) mannose in a ratio to total dissolved sugars <0.03; (vii) fructose in a ratio to total dissolved sugars <0.04; (viii) furfurals in an amount up to 0.01% weight/weight; (ix) phenols in an amount up to 500 ppm; and (x) a trace amount of hexanol. For example, the sugar mixture 1843 is a mixture characterized a low oligosaccharides to total dissolved sugars ratio and a high xylose to total dissolved sugars ratio. In some embodiments, the sugar mixture 1843 is a mixture characterized by a low oligosaccharides to total dissolved sugars ratio, a high xylose to total dissolved sugars ratio, and a low impurity contents (e.g., low furfurals and phenols). In some embodiments, the sugar mixture 1843 is a mixture characterized by a low oligosaccharides to total dissolved sugars ratio, a high xylose to total dissolved sugars ratio, a low impurity contents (e.g., low furfurals and phenols), and a trace amount of hexanol. In some embodiments, the sugar mixture 1843 is a mixture characterized by a low oligosaccharides to total dissolved sugars ratio, a high xylose to total dissolved sugars ratio, a low ratio of the sum of glucose and fructose to total dissolved sugars ratio, a low impurity contents (e.g., low furfurals and phenols), and a trace amount of hexanol.

In some embodiments, the mother liquor hemicellulose sugar mixture 1843 is a sugar mixture characterized by a high xylose to total dissolved sugars ratio. In some sugar mixtures, the xylose to total dissolved sugars ratio is larger than 0.35, 0.40, 0.45, 0.50, 0.55, 0.60, 0.65, 0.70, 0.75, 0.80, or 0.85 weight/weight. In some embodiments, the mother liquor hemicellulose sugar mixture 1843 is a sugar mixture characterized by a low oligosaccharides to total dissolved sugars ratio. In some sugar mixtures, the oligosaccharides to total dissolved sugars ratio is less than 0.005, 0.007, 0.01, 0.02, 0.03, 0.04, 0.05, 0.06, 0.07, 0.08, 0.09, 0.10, 0.20, 0.30, or 0.35 weight/weight. In some embodiments, the mother liquor hemicellulose sugar mixture 1843 is a sugar mixture with a low glucose/fructose content. In some sugar mixtures, the ratio of the sum of glucose and fructose to total dissolved sugars is less than 0.01, 0.02, 0.03, 0.04, 0.05, 0.06, 0.07, 0.08, 0.09, 0.10, 0.20, 0.25, 0.30, or 0.35 weight/weight. In some embodiments, the mother liquor hemicellulose sugar mixture 1843 is a sugar mixture with a high xylose to total sugars ratio, a low oligosaccharides to total dissolved sugars ratio, and a low glucose and fructose contents.

In some sugar mixtures 1843, the arabinose to total dissolved sugars ratio is less than 0.002, 0.003, 0.004, 0.005, 0.01, 0.02, 0.03, 0.04, 0.05, 0.06, 0.07, 0.08, 0.09, 0.10, 0.15, 0.20, 0.25, 0.30 or 0.35 weight/weight. In some sugar mixtures 1843, the galactose to total dissolved sugars ratio is less than 0.001, 0.002, 0.003, 0.004, 0.005, 0.010, 0.015, 0.020, 0.025, 0.030, 0.035, 0.040, 0.05, 0.06, 0.065, 0.07, 0.08, 0.09, or 0.10 weight/weight. In some sugar mixtures 1843, the mannose to total dissolved sugars ratio is less than 0.001, 0.002, 0.003, 0.004, 0.005, 0.01, 0.02, 0.03, 0.04, 0.05, 0.06, 0.07, 0.08, 0.09, 0.10, 0.20 or 0.30 weight/weight. In some sugar mixtures 1843, the fructose to total dissolved sugars ratio is less than 0.001, 0.002, 0.003, 0.004, 0.005, 0.01, 0.02, 0.03, 0.04, 0.05, 0.06, 0.07, 0.08, 0.09, 0.10, 0.20 or 0.30 weight/weight.

The sugar mixture 1843 includes a very low concentration of impurities (e.g., furfurals and phenols). In some sugar mixtures 1843, the sugar mixture has furfurals in an amount up to 0.1%, 0.05%, 0.04%, 0.03%, 0.04%, 0.01%, 0.075%, 0.005%, 0.004%, 0.002%, or 0.001% weight/weight. In some sugar mixtures 1843, the sugar mixture has phenols in an amount up to 500 ppm, 400 ppm, 300 ppm, 200 ppm, 100 ppm, 60 ppm, 50 ppm, 40 ppm, 30 ppm, 20 ppm, 10 ppm, 5 ppm, 1 ppm, 0.1 ppm, 0.05 ppm, 0.02 ppm, or 0.01 ppm. The sugar mixture is further characterized by a trace amount of hexanol, e.g., 0.01-0.02%, 0.02-0.05%, 0.05-0.1%, 0.1%-0.2%, 0.2-0.5%, 0.5-1%, or less than 1, 0.5, 0.2, 0.1, 0.05, 0.02, 0.01, 0.005, 0.002, 0.001%, weight/weight hexanol.

7. Hemicellulose Sugar Product

This section relates to the use of the mixed sugars streams produced at the sugar refining step X07, or fractionated from the xylose-enrich stream at step X09, wherein X is 4, 5 or 6 in FIGS. 4, 5, and 6, respectively. This high purity mixed sugar product can be used in a fermentation process. Such fermentation process may employ a microorganism or genetically modified microorganism (GMO) from the genera *Clostridium, Escherichia* (e.g., *Escherichia coli*), *Salmonella, Zymomonas, Rhodococcus, Pseudomonas, Bacillus, Enterococcus, Alcaligenes, Lactobacillus, Klebsiella, Paenibacillus, Corynebacterium, Brevibacterium, Pichia, Candida, Hansenula* and *Saccharomyces*. Hosts that may be particularly of interest include *Oligotropha carboxidovorans, Escherichia coli, Bacillus licheniformis, Paenibacillus macerans, Rhodococcus erythropolis, Pseudomonas* putida, Lactobacillus plantarum, Enterococcus faecium, Cupriavidus necator, Enterococcus gallinarium, Enterococcus faecalis, Bacillus subtilis and Saccharomyces cerevisiae. Also, any of the known strains of these species may be utilized as a starting microorganism. Optionally, the microorganism may be an actinomycete selected from Streptomyces coelicolor, Streptomyces lividans, Streptomyces hygroscopicus, or Saccharopolyspora erytraea. In various exemplary embodiments, the microorganism can be a eubacterium selected from Pseudomonas fluorescens, Pseudomonas aeruginosa, Bacillus subtilis or Bacillus cereus. In some examples, the microorganism or genetically modified microorganism is a gram-negative bacterium.

Conversion product made through fermentation can be, for example, an alcohol, carboxylic acid, amino acid, monomer for the polymer industry or protein. A particular example is lactic acid, which is the monomer building polylactic acid, a polymer with numerous uses.

The conversion product can be processed to produce a consumer product selected from the group consisting of a detergent, a polyethylene-based product, a polypropylene-based product, a polyolefin-based product, a polylactic acid (polylactide)-based product, a polyhydroxyalkanoate-based product and a polyacrylic-based product. The detergent can include a sugar-based surfactant, a fatty acid-based surfactant, a fatty alcohol-based surfactant or a cell-culture derived enzyme.

The polyacrylic-based product can be a plastic, a floor polish, a carpet, a paint, a coating, an adhesive, a dispersion, a flocculant, an elastomer, an acrylic glass, an absorbent article, an incontinence pad, a sanitary napkin, a feminine hygiene product and a diaper. The polyolefin-based products can be a milk jug, a detergent bottle, a margarine tub, a garbage container, a plumbing pipe, an absorbent article, a diaper, a non-woven, an HDPE toy or an HDPE detergent packaging. The polypropylene based product can be an absorbent article, a diaper or a non-woven. The polylactic acid based product can be a packaging of an agriculture product or of a dairy product, a plastic bottle, a biodegradable product or a disposable. The polyhydroxyalkanoate based products can be packaging of an agriculture product, a plastic bottle, a coated paper, a molded or extruded article, a feminine hygiene product, a tampon applicator, an absorbent article, a disposable non-woven or wipe, a medical surgical garment, an adhesive, an elastomer, a film, a coating, an aqueous dispersant, a fiber, an intermediate of a pharmaceutical or a binder. The conversion product can be ethanol, butanol, isobutanol, a fatty acid, a fatty acid ester, a fatty alcohol or biodiesel.

Xylose can be reacted with chlorambucil to obtain benzenebutanoic acid, 4-[bis(2-chloroethyl)amino]-, 2-β-D-xylopyranosylhydrazide, a glycosylated chlorambucil analog which is useful as antitumor and/or anti-metastatic agent. Xylose may be reacted with phenethyl bromide and 1-bromo-3,3-dimethoxypropane to obtain (2S,3S,4S)-2H-Pyrrole, 3,4-dihydro-3,4-bis(phenyl-methoxy)-2-[(phenyl-methoxy)methyl]-, 1-oxide, used as α-glucosidase inhibitor for preventing and/or treating diabetes mellitus, hyperlipidemia, neoplasm, and viral infection.

The sugar mix product can be converted to fuel products, for example, an isobutene condensation product, jet fuel, gasoline, gasohol, diesel fuel, drop-in fuel, diesel fuel additive or a precursor thereof. This conversion may be done through fermentation or by catalyzed chemical conversion. The gasohol may be ethanol-enriched gasoline and/or butanol-enriched gasoline.

Consumer products, precursor of a consumer product, or ingredient of a consumer product can be made from the conversion product or include at least one conversion product such as, for example, a carboxylic or fatty acid, a dicarboxylic acid, a hydroxylcarboxylic acid, a hydroxyldicarboxylic acid, a hydroxyl-fatty acid, methylglyoxal, mono-, di-, or poly-alcohol, an alkane, an alkene, an aromatic, an aldehyde, a ketone, an ester, a biopolymer, a protein, a peptide, an amino acid, a vitamin, an antibiotics and a pharmaceutical. For example, the product may be ethanol-enriched gasoline, jet fuel, or biodiesel.

The consumer product may have a ratio of carbon-14 to carbon-12 of about $2.0 \times 10^{-13}$ or greater. The consumer product can include an ingredient of a consumer product as described above and an additional ingredient produced from a raw material other than lignocellulosic material. In some cases, ingredient and the additional ingredient produced from a raw material other than lignocellulosic material are essentially of the same chemical composition. The consumer product can include a marker molecule at a concentration of at least 100 ppb. The marker molecule can be, for example, hexanol, 1-ethyl hexanol, furfural or hydroxymethylfurfural, products of furfural or hydroxymethylfurfural condensation, color compounds derived from sugar caramelization, levulinic acid, acetic acid, methanol, galacturonic acid or glycerol.

IV. Cellulose Hydrolysis

Once hemicellulose sugars are extracted, lignocellulosic remainder stream 1700-B can be subject to cellulose hydrolysis 1720 to obtain an acidic hydrolysate stream 1720-A and acidic lignin stream 1720-B (see, FIG. 17). Preferably, prior to the cellulose hydrolysis, biomass is milled or grinded to reduce particle size (see, e.g., FIG. 3 and FIG. 6, number 310 and 610). Once hemicellulose sugar is extracted, it is much easier to mill or grind the lignocellulosic remainder. Therefore, it is preferred to mill or grind biomass at this stage as it consumes less energy.

Compared to ungrounded particles such as chips, ground particles can be suspended in the hydrolysis liquid, and can be circulated from container to container. Ground particles from different lignocellulosic biomass materials can be processed by the same set of equipments using similar or same operating parameters. Reduced particle size greatly accelerates the downstream cellulose hydrolysis process. Preferably, the lignocellulosic biomass is grinded such that the average size of the particles is in the range of 100-10,000 micron, preferably 400-5,000, e.g., 100-400, 400-1,000, 1,000-3,000, 3,000-5,000, or 5,000-10,000 microns. Preferably, the lignocellulosic biomass is grinded such that the average size of the particles is less than 10,000, 9,000, 8,000, 7,000, 6,000, 5,000, 4,000, 3,000, 1,000, or 400.

Any hydrolysis methods and systems can be used for cellulose hydrolysis, including enzymatic means and chemical methods. For example, simulated moving bed systems can be used for cellulose hydrolysis as disclosed in WO2012061085 (incorporated herein by reference for all purposes). In one embodiment, the present invention contemplates a method of extracting cellulose sugars using the stirred tank hydrolysis system (see, FIG. 8A). This counter current system is advantageous for acid hydrolysis of cellulose sugars. When multiple tanks are used, the system enables separate temperature control for each individual tank. The system can be adapted for various lignocellulosic biomass materials.

Figure 8A:
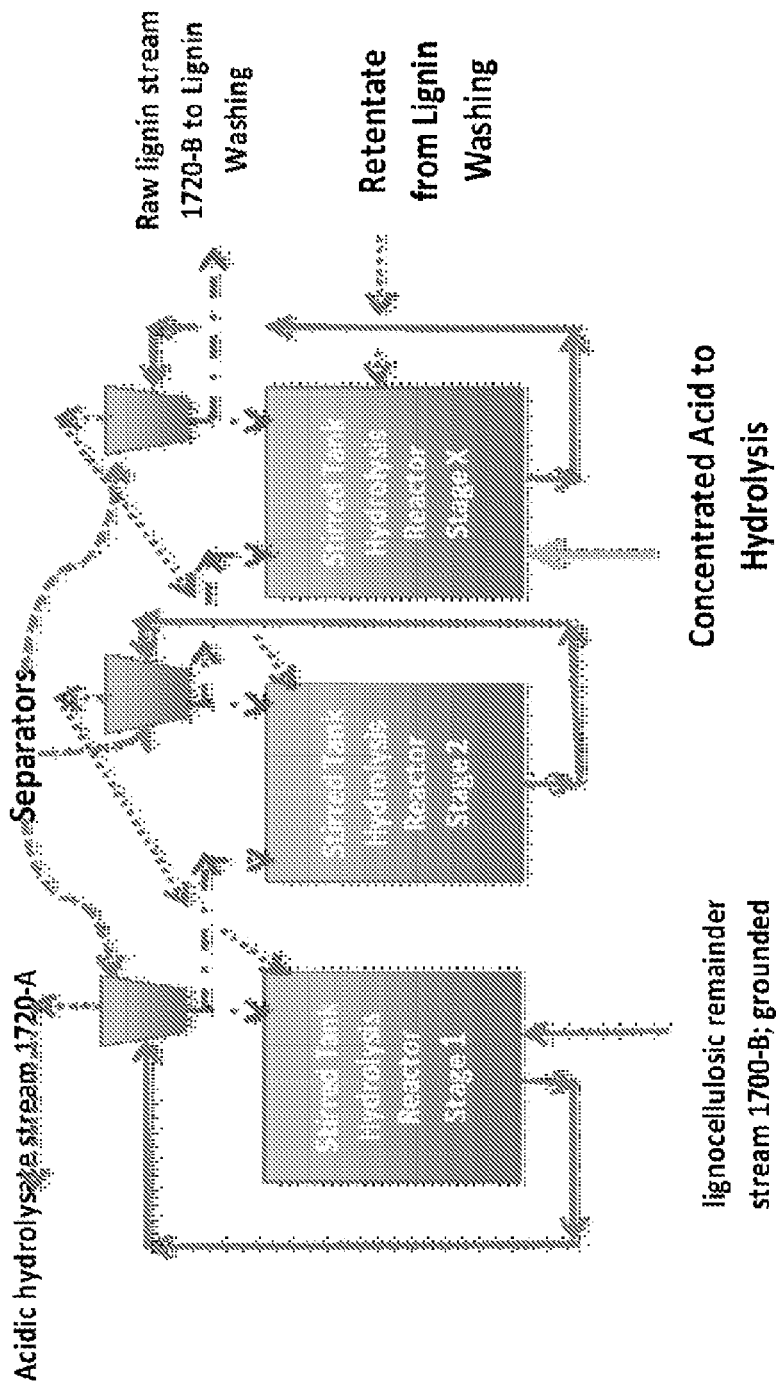
FIG. 8A is a simplified scheme of a counter current stirred reactor system for hydrolysis of cellulose in an aqueous solution containing HCl.

As exemplified in FIG. 8A, lignocellulosic remainder stream 1700-B at moisture content of 5 to 85% weight/weight is milled or grinded to particle size of 400-5000 micron (preferably 1400 micron) by any industrial mill including hammer mill and pin mill. If moisture content is higher than 15%, the ground lignocellulosic remainder is dried to have moisture 0.15%. The hydrolysis system includes a number of n stirred tanks (e.g., n=1-9, preferably 4) connected in series as depicted in FIG. 8A. The aqueous liquid in the tank, containing acid, dissolved sugar and suspended biomass is recycled by a high pressure high flow rate pump causing stirring of the solution in each tank. The flow line is also fitted with a solid/liquid separation device (e.g., a filter, a membrane, or a hydrocylone) that allows at least some of the liquid and dissolved molecules, i.e. acid and sugars, to permeate thereby producing a permeate (or filtrate) stream. At least some of the feed liquid is retained by the solid/liquid separation device to produce retentate stream thus producing stirring of the liquid in the reactor. Super azeotropic HCl solution with acid concentration of at least 41% is fed into tank n. The permeate of the separation unit of tank n is fed into reactor n−1 while at least part of the retentate is recycled back into tank n. The permeate of tank n−1 is fed into tank n−2 while the retentate is recycled back into tank n−1 and so on. The permeate exiting tank 1 of the series is the acidic hydrolysate stream 1720-A. The solids concentration in each stirred tank reactor can be maintained between 3-15%, 3-5%, 5-10%, or 10-15% weight/weight. Overall, the biomass is retained in the system over 10 to 48 hours. The temperature of each reactor is controlled separately at the range 5 to 40° C.

In some embodiments, the ground lignocellulosic remainder stream 1700-B is added to the first stage of a series of stirred tank reactors (e.g., 1 to 9 reactors, preferably 4 reactors). The slurry is mixed though agitation or recirculation of the liquor inside the reactors. At least some of the retentate of tank 1 is fed into tank 2; at least some of the retentate of tank 2 is fed into tank 3 and so on. Eventually acidic lignin stream 1720-B exits tank n to the lignin wash system.

In some embodiments, concentrated hydrochloric acid (>35%, 36%, 37%, 38%, 39%, 40%, 41%, or preferably 42%) is added into the last reactor in the series, and less concentrated hydrochloric acid (~25%, 26%, 27%, 28%, 29%, 30%, or preferably 31%) exits from the first reactor in the series.

In some embodiments, hydrolyzed sugars exit from the first reactor in the series. The acidic hydrolysate stream 1720-A containing the acid and cellulose sugars is transferred from the last reactor to the second to the last reactor and so on until the hydrolysate leaves the first reactor for additional purification. In an exemplary reactor system, the hydrolysate leaving the first reactor has between 8-16% sugars and hydrochloric acid. In some embodiments, the acidic hydrolysate stream 1720-A can contain more than 8%, 9%, 10%, 11%, 12%, 13%, 14%, dissolved sugars. In some embodiments, the acidic hydrolysate stream 1720-A can contain more than 22%, 24%, 26%, 28%, 30%, 32% 34%, or 36% HCl. In some embodiments, the acidic hydrolysate stream 1720-A can contain less than 32%, 30%, 28%, 26%, 24%, 22%, or 20% HCl.

The temperature in all the reactors is maintained in the range of 5-80° C., e.g., 15-60° C., preferably 10-40° C. Total retention time of the biomass in all reactors can range from 1 to 5 days, e.g., 1 to 3 days, preferably 10 to 48 hours.

Preferably, when multiple stirred tank reactors are used, at least a portion of the aqueous acid hydrolysate stream leaving an intermediate reactor (e.g., reactor 2 or 3) is mixed with the lignocellulosic remainder stream 1700-B before 1700-B stream is introduced into the first reactor. The 1700-B stream is pre-hydrolyzed by the aqueous acid hydrolysate stream from the intermediate reactor before it is contacted with the strong acid in the first reactor. Preferably, the pre-hydrolysis mixture is heated to a temperature in the range of 15 to 60° C., preferably 25 to 40° C., most preferably 40° C. for 5 minutes to 1 day, preferably 15-20 minutes. In one example, *eucalyptus* is hydrolyzed using stirred tank reactors. Upon initial introduction of the *eucalyptus* wood into the acid, viscosity initially increases as a result of fast dissolution of oligomers of cellulosic sugars, the high viscosity hinders the ability to pump and recirculate the aqueous solution through the system; the short stirring of ground lignocellulosic remainder stream 1700-B with intermediate reactor hydrolysate at elevated temperature accelerates further hydrolysis of the dissolved oligomers to monomer, accompanied with decrease in viscosity. In another example, *eucalyptus* is first contacted with acid solution coming out of stage 2 (i.e. concentration ~33%) at 35-50° C. for 15-20 minutes. The pre-hydrolyzed *eucalyptus* can be fed into the system much faster and is further hydrolyzed in the stirred tank reactors.

Stirred tank reactors can be used for various materials including hardwood, softwood, and bagasse. Exemplary results using a 4-reactor stirred tank system is provided in FIG. 8B.

After the cellulose hydrolysis, the remaining residues in the lignocellulosic biomass form acidic lignin stream 1720-B. Acidic lignin stream 1720-B can be further processed and refined to produce novel lignin compositions as described in more detail herein. The acidic hydrolysate stream 1720-A produced by cellulose hydrolysis is further refined as described below.

V. Cellulose Sugar Refining

The present invention provides a method for refining sugars. Specifically, the present method efficiently refines sugars from the acidic hydrolysate stream 1720-A containing a mineral acid (e.g., HCl or $H_2SO_4$). An output cellulose sugar composition according to embodiments disclosed herein has a high content of monomeric sugars.

An exemplary method of cellulose sugar refining according to some embodiments of the present invention is provided in FIG. 19 (process 1900). The acidic hydrolysate stream 1720-A can be subject to S1 solvent extraction 1921, during which the acidic hydrolysate stream 1720-A is contacted with a S1 solvent extractant, and acids are extracted from the 1720-A stream into the S1 solvent extractant. The resulting mixture is separated into a first stream 1921-A (organic stream) containing the acid and the S1 solvent extractant and a second stream 1921-B (aqueous stream) containing cellulose sugars.

Optionally, S1 solvent extraction 1921 can be conducted in multiple steps, e.g., two or more steps. Preferably, S1 solvent extraction 1921 is conducted in two steps: 1921-I and 1921-II. In some methods, during extraction 1921-I, the acid concentration in the acidic hydrolysate stream 1720-A is reduced to less than 15%, less than 14% less than 13%, less than 12%, or less, resulting in a partially deacidified hydrolysate. In some methods, the partially deacidified hydrolysate is evaporated to remove water, resulting in increased sugar and acid concentrations (e.g., an acid concentration between 13% and 14% weight/weight). Preferably, the concentrated partially deacidified hydrolysate is extracted with S1 solvent again during extraction 1921-II, resulting in a sugar stream containing less than 5% less than 4% less than 3%, preferably between 2 and 3% acid or less.

In some methods, stream 1921-A is washed to recover sugars by extraction with a HCl stream at 20-25%. In some methods, extraction 1921-A, extraction 1921-B, contacting the first stream 1921-A and back extraction 1950 are conducted at 40 to 60° C., at 45 to 55° C., preferably at 50° C.

In some methods, the second stream 1921-B is diluted with oligomeric sugars 1931 from downstream fractionation process 1930 and optionally with additional aqueous streams. When oligomeric sugars 1931 is combined with the second stream 1921-B, the oligomeric sugars is hydrolyzed by the residual acids in the second stream 1921-B (the "secondary hydrolysis" process 1929 in FIG. 19).

The second stream 1921-B can be optionally contacted with a strong acid cation exchanger 1922 to convert salts to their respective acids. The sugar stream is then extracted with an amine extractant to remove mineral acid(s), organic acids, furfurals, acid soluble lignins (process 1923 in FIG. 19), during which the sugar stream is contacted with an amine extractant comprising and amine and a diluent. The resulting mixture is separated into a third stream 1923-A (organic stream) containing the acid and the amine extractant and a fourth stream 1923-B (aqueous stream) containing cellulose sugars. In some methods, contacting with the amine extractant is conducted at 50-80° C., at 55-70° C., preferably at 70° C.

The fourth stream 1923-B is then purified by evaporation to remove residual diluent which is dissolved in the aqueous phase followed by ion exchange means 1924, including a strong acid cation exchanger 1925 to remove amines and optionally followed by a weak base anion exchanger 1926. The amine-removed and neutralized hydrolysate 1924-A can be optionally evaporated (process 1927 in FIG. 19) to form a cellulose sugar stream 1928, which can be further fractionated to obtain high monomeric C6 sugars such as glucose (process 1930 in FIG. 19). Fractionation separates a monomeric sugars stream 1932 from an oligomeric sugar stream 1931.

The monomeric sugar stream 1932 can be optionally evaporated to higher concentration (process 1933) followed by neutralization using an ion exchanger (process 1934). The neutralized monomeric sugar stream is then optionally evaporated again (process 1935 in FIG. 19) to produce a cellulose sugar mixture 1936.

The acids in the sugar depleted stream 1921-A can be recovered (process 1940 in FIG. 19). At least a portion of the solvent can be purified and recycled back to S1 solvent extraction 1921. A portion of the S1 solvent can be further purified using a lime solution (e.g. calcium oxide, calcium hydroxide, calcium carbonate, or a combination thereof) and the purified solvent can be recycled back to the S1 solvent extraction 1921.

The third stream 1923-A can be back-extracted with an aqueous solution containing a base (process 1950 in FIG. 19). The back-extracted amine can be recycled back to amine extraction 1923. At least a portion of the solvent can be purified using a lime solution ((e.g. calcium oxide, calcium hydroxide, calcium carbonate, or a combination thereof)) (process 1960 in FIG. 19) and the purified solvent can be recycled back to amine extraction 1923.

A more detailed description of these exemplary cellulose sugar refining embodiments is provided below.

1. Pre-Evaporation

After the cellulose hydrolysis and prior to S1 solvent extraction 1921, the acidic hydrolysate stream 1720-A can be optionally evaporated (process 1910 in FIG. 19) to concentrate the sugars and remove the mineral acid (e.g., HCl). For example, the HCl concentration in the stream (e.g., ~33%) is higher than its azeotrope (~22%), the sugar stream can be first evaporated to remove the acid gas to azeotrope. The 1720-A stream is then evaporated to the sugar concentration target at the azeotrope which allows multiple effect concentration. An evaporated sugar solution having about 30% dry solid contents can be obtained by this process.

The evaporated sugar stream (e.g., having azeotropic HCl) can be extracted with an extractant (process 1921 in FIG. 19) as described below. Alternatively, the acidic hydrolysate stream 1720-A (e.g., having super-azeotropic HCl, e.g., 22-33% or more HCl) can be directly extracted with an extractant without the evaporation step.

2. Extraction

Preferred extractant is an extractant containing an S1 solvent (process 1921 in FIG. 19). The S1 solvent suitable for use in the extraction is a solvent that has a boiling point at 1 atm between 100° C. and 200° C. and forms a heterogeneous azeotrope with water. In some S1 solvents, the heterogeneous azeotrope has a boiling point at 1 atm of less than 100° C. For example, the S1 solvent can be a solvent containing an alcohol or kerosene. Examples of alcohols suitable for making a S1 solvent include butanol, isobutanol, hexanol, octanol, decanol, dodecanol, tetradecanol, pentadecanol, hexadecanol, octadecanol, eicosanol, docosanol, tetracosanol, and triacontanol. Preferably, the S1 solvent is a long chain alcohol (e.g. C6, C8, C10, C12, C14, C16 alcohol), or kerosene. More preferably, the S1 solvent comprises n-hexanol or 2-ethyl-hexanol or mixtures thereof. Most preferably, the S1 solvent comprises n-hexanol. In some embodiments, the S1 solvent consists essentially of, or consists of, n-hexanol.

Optionally, the S1 solvent comprises one or more additional components. In some methods, the S1 solvent comprises one or more ketones, one or more aldehydes having at least 5 carbon atoms, or another alcohol.

The extraction can be conducted in a countercurrent system. Optionally, the extraction can be conducted in multiple extraction columns, e.g., two extraction columns. In the first column, the acid is extracted into the extractant, leaving the acid concentration in the sugar stream less than azeotrope. The extractant leaving the column 1 can be optionally washed with azeotropic acid water solution to recover any sugars absorbed in the extractant back to the water solution, which can be recycled in the hydrolysis. The sugar stream, now having less than azeotropic acid concentration, is distilled. The sugar solution is re-concentrated, thereby achieving a higher acid concentration again. The re-concentrated sugar solution can be extracted with the extractant to remove residual acid. Overall the acid recovery can be more than 97.5%.

A portion (e.g., 5-20, 10-15%) of the extractant washed with azeotropic acid water solution can be purified by various methods to remove acids, esters, soluble impurities such as furfurals and phenols. For example, the extractant can be purified by liming as disclosed in WO2012018740 (incorporated herein by reference for all purposes). Preferably, the extractant is treated with lime at a 10% concentration. Preferably, the purification is conducted using 5-10:1 lime to solvent ratio. The mixture is heated for, e.g., 1 hour at 85° C. The residual salts in the mixture can be removed by separation means such as filtration or centrifugation. The purified extractant is then recycled back to the washed extractant.

3. Acid Recovery

The first stream 1921-A (acid-loaded S1 solvent extractant) can be back-extracted with water to recover the acids (process 1940 in FIG. 19). After the acid recovery, an acid-free extractant (e.g., having less than 0.3-0.5% acid contents) is returned to extraction. An aqueous solution containing about 15-20% acids is recovered, which can be used in downstream processes, e.g., for washing lignin.

Optionally, prior to the acid recovery 1940, the first stream 1921-A can be washed with an aqueous solution (preferably an acidic aqueous solution) to recover any sugars in the stream. In some methods, the first stream 1921-A is washed with an azeotropic acid solution. Typically, after the washing, the amine extractant stream 1923-A has less than 5%, 2%, 1%, 0.5%, 0.2%, 0.1%, 0.05% sugars.

The acid recovery can be carried out by any suitable methods. Preferably, the acid recovery is carried out by treating at least a fraction of the back-extract in an evaporation module having at least one low-pressure evaporator and at least one high-pressure evaporator.

In some methods, evaporation module can generate a super-azeotropic aqueous HCl solution and a sub-azeotropic aqueous HCl solution. For example, the low-pressure evaporator generates the super-azeotropic aqueous HCl solution and the high-pressure evaporator generates the sub-azeotropic aqueous HCl solution. In some embodiments, "high pressure" indicates super-atmospheric pressure, and "low pressure" indicates sub-atmospheric pressure. "Super-azeotropic" and "sub-azeotropic" indicates an HCl concentration relative to the azeotropic HCl concentration of a water/HCl mixture at ambient temperature and ambient pressure. "Sub-azeotropic"

In some other methods, evaporation module generates a sub-azeotropic acid condensate, and super-azeotropic gaseous HCl. Optionally, low-pressure evaporator generates a sub-azeotropic acid condensate containing, e.g., up to 2%, 1%, 0.1% or 0.01% HCl on as is basis. Optionally, high-pressure evaporator generates super-azeotropic gaseous HCl. Preferably, low-pressure evaporator generates a sub-azeotropic acid condensate and high-pressure evaporator generates super-azeotropic gaseous HCl.

The recycled HCl stream includes the gaseous HCl from the high-pressure evaporator (e.g. after absorption into an aqueous solution at an absorber). The gaseous HCl can be mixed with azeotropic stream to produce 42% acid for hydrolysis in a two-stage falling film absorber system.

The first stream 1921-A can be further treated with a lime suspension (e.g., a 5%, 10%, 15%, 20%, 25% weight/weight lime solution). The solvent to lime suspension ratio can be in the range 4-10, 4-5, 5-6, 6-7, 7-8, 8-9, or 9-10. Treatment may be conducted in any suitable device, e.g., a thermostatic mixed tank. The solution can be heated for at least 1 hour at 80-90° C. Lime reacts with residual organic acids and esters of organic acids and adsorbs effectively organic impurities present in the organic phase such as acid soluble lignin and furfurals, as visualized by change of color from dark to light. The contaminated lime and impurities can be filtered or centrifuged to recover the purified organic phase, which is washed with water and recycled back to the S1 solvent extraction 1921. The aqueous stream may be diverted to other aqueous waste streams. Any solid cake that may be formed by the lime reaction may be used in the waste water treatment plant as a neutralization salt for residual acids from ion exchange regenerations for example.

4. Secondary Hydrolysis

The second stream 1921-B (acid-removed sugar stream) still contains a residual amount of acids and oligomeric sugars, typically 2-3%. The present method optionally provides a secondary hydrolysis step 1929 in which the residual acid in the sugar stream catalyzes the conversion of oligomeric sugars to monomeric sugars.

Optionally, the second stream 1921-B is combined with a recovered oligomeric sugar stream 1931 from downstream fractionation step and optionally with additional aqueous streams.

The secondary hydrolysis can be conducted at a temperature greater than 60° C., e.g., at 70° C.-130° C., 80° C.-120° C. or 90° C.-110° C. Preferably, the reaction is conducted at 120° C. The secondary hydrolysis can be carried out for at least 10 minutes, between 20 minutes and 6 hours, between 30 minutes and 4 hours or between 45 minutes and 3 hours. Preferably, the reaction is conducted for about one hour.

Typically, secondary hydrolysis under these conditions increases the yield of monomeric sugars with minimal or no sugars degradation. Prior to secondary hydrolysis, the sugar stream typically contains 30-50% oligomeric sugars.

After secondary hydrolysis, the monomeric sugar content of the sugar stream as a fraction of total sugars can be is greater than 70%, 75, 80%, 85%, or 90%. Preferably, the sugar stream after secondary hydrolysis contains 86-89% or even more than 90% monomeric sugars as a fraction of total sugars. Typically, degradation of monomeric sugars during the hydrolysis can be less than 1%, less than 0.2%, less than 0.1% or less than 0.05%.

The second hydrolysis method can be applied more generally for hydrolyzing any oligomeric sugar stream. Preferably, the oligomeric sugar stream (e.g., the second stream 1921-B, the recovered oligomeric sugar stream 1931, or a mixture of the second stream 1921-B and the recovered oligomeric sugar stream 1931) is diluted before the second hydrolysis (e.g., to a sugar concentration less than 5%, 6%, 7%, 8%, 9%, 10%, 11%, 12%, 13%, 14%, 15%, 16%, 17%, 18%, 19%, 20% weight/weight). In some second hydrolysis methods, the acid concentration in the sugar stream can be increased by adding an acid into the sugar stream. In some methods, the acid concentration for carrying out the secondary hydrolysis is 0.1%, 0.2%, 0.3%, 0.4%, 0.5%, 0.6%, 0.7%, 0.8%, 0.9%, 1.0%, 2.0%, or 5.0%. Preferably, the sugar stream contains 0.6-0.7% acid and 11% sugar.

5. Amine Extraction

Preferably, the sugar stream from the extraction and/or secondary hydrolysis 1929 is deacidified to deplete acids in the stream. Optionally, the stream can first be contacted with a strong acid cation exchanger 1922 to convert salts into their respective acids. The sugar stream can then be subjected to extraction (e.g., counter-currently) with an extractant containing an amine base and a diluent to remove mineral acid(s), organic acids, furfurals, acid soluble lignins (process 1921 in FIG. 19). The amine extraction can be conducted under conditions identical or similar to those described above in connection with hemicellulose sugar purification.

The amine extractant can contain 10-90% or preferably 20-60% weight/weight of one or a plurality of amines having at least 20 carbon atoms. Such amine(s) can be primary, secondary, and tertiary amines. Examples of tertiary amines include tri-laurylamine (TLA; e.g. COGNIS ALAMINE 304 from Cognis Corporation; Tucson Ariz.; USA), tri-octylamine, tri-isooctylamine, tri-caprylylamine and tri-decylamine.

Diluents suitable for use in the amine extraction include an alcohol such as butanol, isobutanol, hexanol, octanol, decanol, dodecanol, tetradecanol, pentadecanol, hexadecanol, octadecanol, eicosanol, docosanol, tetracosanol, and triacontanol. Preferably, the diluent is a long chain alcohol (e.g. C6, C8, C10, C12, C14, C16 alcohol), or kerosene. The diluent can have additional components. More preferably, the diluent comprises n-hexanol or 2-ethyl-hexanol. Most preferably, the diluent comprises n-hexanol. In some embodiments, the diluent consists essentially of, or consists of, n-hexanol.

Optionally, the diluent contains one or more additional components. In some methods, the diluent contains one or more ketones, one or more aldehydes having at least 5 carbon atoms, or another alcohol.

Preferably, the amine is tri-laurylamine and the diluent is hexanol. Preferably, the amine extraction solution contains tri-laurylamine and hexanol in a ratio of 3:7.

The amine extraction can be conducted at any temperature at which the amine is soluble, preferably at 50-70° C. Optionally, more than one extraction steps (e.g., 2, 3, or 4 steps) can be used. The ratio of the amine extractant stream (organic phase) to the hemicellulose sugar stream 1800-A (aqueous phase) can be 0.5-5:1, 1-2.5:1, or preferably, 1.5-3.0:1.

The amine extraction method can be applied more generally for refining or purifying any sugar stream (e.g., hemicellulose sugar stream, cellulose sugar stream, a mixed sugar stream), particularly a mildly acidic sugar stream (e.g., containing 1-5%, 0.1-1%, 1-2%, 2-3%, 3-4%, 5-6%, weight/weight acid). The amine extraction method according to some embodiments of the invention is particularly useful for refining or purifying a sugar stream containing impurities. Typical impurities in a sugar stream include ash, acid soluble lignin, fatty acids, organic acids such as acetic acid and formic acid, methanol, proteins and/or amino acids, glycerol, sterols, rosin acid and waxy materials. Typically, using the amine extraction method, a sugar stream can be purified to have less than 1%, 0.8%, 0.6%, 0.5%, 0.4%, 0.2% weight/weight or less impurities. In some methods, a sugar stream can be purified to have less than 1%, 0.8%, 0.6%, 0.5%, 0.4%, 0.2% weight/weight or less acids.

8. Back Extraction

The third stream 1923-A (acid-loaded amine extractant) contains mineral and organic acid, as well as impurities extracted from biomass and sugar degradation products. The acids can be extracted from the third stream 1923-A in a back extraction step 1950. The back extraction can be conducted under conditions identical or similar to those described above in connection with hemicellulose sugar purification.

Optionally, prior to the back extraction 1950, the amine extractant stream 1923-A can be washed with an aqueous solution to recover any sugars in the stream. Typically, after the washing, the amine extractant stream 1923-A has less than 5%, 2%, 1%, 0.5%, 0.2%, 0.1%, 0.05% sugars.

9. Solvent Purification

The amine extractant stream, now neutralized after acid removal, can be washed with water to remove salts remaining from the back extraction (process 1960 in FIG. 19). It is particularly preferred for certain blended extractants that can partially saturate with water (as is the case of certain alcohols for example). The wash stream may be combined with the back extraction aqueous stream. The solvent purification 1960 can be conducted under conditions identical or similar to those described above in connection with hemicellulose sugar purification.

The fraction diverted to purification step (process 1960 in FIG. 19) can be treated with a lime suspension (e.g., a 5%, 10%, 15%, 20%, 25% weight/weight lime solution). The solvent to lime suspension ratio can be in the range 4-10, 4-5, 5-6, 6-7, 7-8, 8-9, or 9-10. Treatment may be conducted in any suitable device, e.g., a thermostatic mixed tank. The solution can be heated for at least 1 hour at 80-90° C. Lime reacts with residual organic acids and esters of organic acids and adsorbs effectively organic impurities present in the organic phase such as acid soluble lignin and furfurals, as visualized by change of color from dark to light. The contaminated lime and impurities can be filtered or centrifuged to recover the purified organic phase, which is washed with water and recycled back to the amine extraction step (process 1923 in FIG. 19). The aqueous stream may be diverted to other aqueous waste streams. Any solid cake that may be formed by the lime reaction may be used in the waste water treatment plant as a neutralization salt for residual acids from ion exchange regenerations for example.

10. Sugar Purification

The sugars in the fourth stream 1923-B (de-acidified aqueous stream) can be further purified. The sugar purification can be conducted under conditions identical or similar to those described above in connection with hemicellulose sugar purification.

For example, the fourth stream 1923-B can be contacted with a strong acid cation (SAC) exchanger 1925 to remove any residual metallic cations and any residual amines, preferably followed by a weak base anion (WBA) exchanger 1926 to remove excess protons. The amine-removed and neutralized hydrolysate 1924-A can be pH adjusted and evaporated to 25-65% and preferably 30-40% weight/weight dissolved sugars in any conventional evaporator, e.g., a multiple effect evaporator or a Mechanical Vapor Recompression (MVR) evaporator (process 1927 in FIG. 19). Any residual solvent present in the aqueous phase can also be removed by evaporation. For example, the solvent forms a heterogeneous azeotrope with water and can be separated and returned to the solvent cycle. The concentrated sugar solution can be contacted with mixed bed resin system to remove any residual ions or color bodies. If desired, the now refined sugar solution may be concentrated further by and conventional evaporator or MVR.

The resulting cellulose sugar stream 1928 is a highly purified sugar solution having a high monomeric ratio, e.g., about 85-95% monosaccharides out of the total dissolved sugars. The composition of the sugars depends on the composition of the starting biomass. The purity of the stream in all cases may be sufficient for fermentation processes and/or catalytic processes utilizing these sugars.

11. Sugar Fractionation

The cellulose sugar stream 1928 can be fractionated into a monomeric sugar stream 1932 and an oligomeric sugar stream 1931 (process 1930 in FIG. 19). The cellulose sugar stream 1928 is a highly concentrated sugar stream. In some embodiments, the cellulose sugar stream 1928 can include at least 40%, 45%, 50%, 51%, 52%, 53%, 54%, 55%, 56% or 58% or intermediate or greater concentrations of total sugars. Optionally, the 1928 stream includes 40-75%, 45-60%, or 48-68% total sugars weight/weight.

Figure 16:
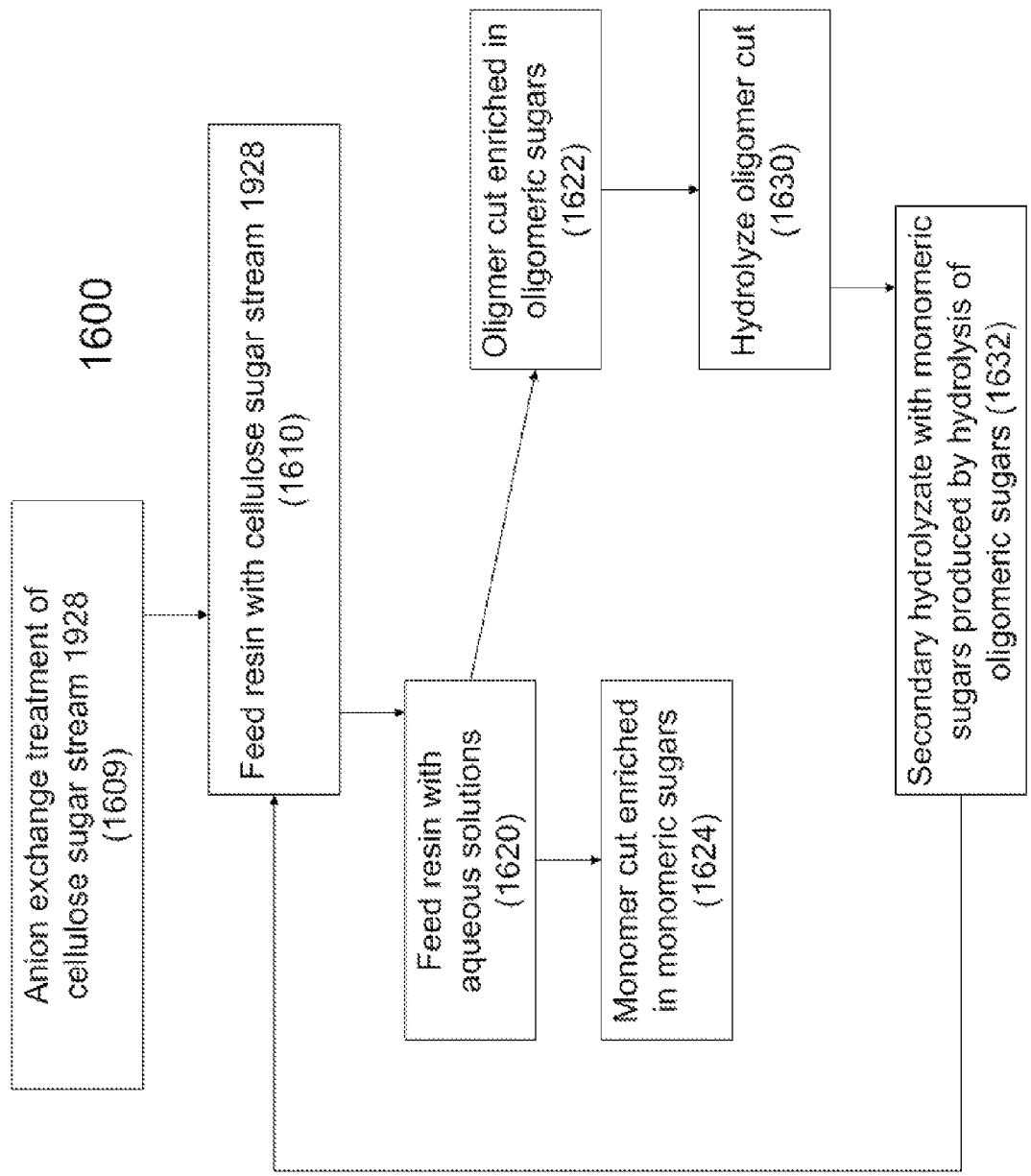
FIG. 16 is a simplified flow diagram of an exemplary of cellulosic sugar fractionation according to some embodiments of the present invention.

FIG. 16 is a simplified flow diagram of a method of cellulose sugar fractionation according to an exemplary embodiment of the invention. As shown in process 1610 of FIG. 16, in some embodiments, the cellulose sugar stream 1928 is contacted with an anion exchanger prior to feeding 1928 stream to a chromatographic resin in 1610. The anion exchanger can be a weak base resin anion exchanger (WBA) or an anion an amine having at least 20 carbon atoms.

The cellulose sugar stream 1928 (a mixture of cellulosic monomeric and oligomeric sugars) is then fed to a chromatographic resin. Optionally, sugars from secondary hydrolysis can be incorporated into the low acid (e.g., less than 0.5, 0.4, 0.3, 0.2 or 0.1% HCl) cellulose sugar stream 1928.

Next, the chromatographic resin is then fed with an aqueous solution (optionally water) to produce an oligomer cut 1622 enriched in oligomeric sugars (compared to total sugars) relative to the mixture fed at 1610 and a monomer cut 1624 enriched in monomeric sugars (relative to total sugars) relative to the mixture fed at 1610 (process 1620 in FIG. 16). In some embodiments, monomer cut 1624 can have at least 80, 82, 84, 86, 88, 90, 92, 94, 96 or 98% monomeric sugars out of total sugars (by weight). The aqueous solution fed to the chromatographic resin at process 1620 can be water from a previous evaporation step, or a stream of hemicellulose sugars from a pressure wash as described in co-pending application PCT/US2012/064541 (incorporated herein by reference for all purposes). In some embodiments, oligomer cut 1622 includes at least 5, 10, 20, 30, 40, 50% or intermediate or greater percentages of the total sugars recovered from the resin fed at 1610.

In some embodiments, oligomer cut 1622 can be further processed. For example, oligomer cut 1622 can be concentrated or evaporated. In some embodiments, oligomeric sugars in oligomer cut 1622 are hydrolyzed (process 1630), thereby increasing the ratio of monomers to oligomers in the oligomer cut 1622. In some embodiments, hydrolyzing 1630 is catalyzed by HCl at a concentration of not more than 1.5, 1.0, 0.8, 0.7, 0.6, or 0.5%. In some embodiments, hydrolyzing 1630 is catalyzed by HCl at a concentration of not more than 1.5, 1.2, 1, 0.9, 0.8, 0.7, 0.6, 0.5% on a weight basis. In some embodiments, hydrolyzing 1630 is catalyzed by HCl at a concentration of 0.3-1.5%; 0.4-1.2% or 0.45-0.9% weight/weight. In some embodiments, hydrolyzing 430 is performed at a temperature between 60 and 150° C.; between 70 and 140° C. or between 80 and 130° C. A secondary hydrolysate 1632 enriched with monomeric sugars (relative to total sugars) can be produced by hydrolysis 1630 of at least a portion of the oligomeric sugars in oligomer cut 1622. In some embodiments, sugars from secondary hydrolysate 1632 are used as a portion of the sugar mixture fed at 1610.

In some embodiments, secondary hydrolysate 1632 contains at least 70, 72, 74, 76, 78, 80, 82, 84, 86, 88, 90, or 95% monomeric sugars relative to the total sugar content. In some embodiments the total sugar content of secondary hydrolysate 1632 is at least 86, 88, 90, 92, 94, 96, 98, 99, 99.5, or 99.9% by weight of the sugar content.

The monomer cut 1624 forms a monomeric sugar stream 1932. The monomeric sugar stream 1932 can be optionally evaporated to higher concentration (process 1933 in FIG. 19) before it is neutralized using an ion exchanger 1934. The neutralized monomeric sugar stream is then optionally evaporated again (processes 1935 in FIG. 19). The end product is a high concentration cellulose sugar mixture 1936.

The resulting high concentration cellulose sugar mixture 1936 is characterized by one or more, two or more, three or more, four or more, five or more, six or more characteristics including (i) monosaccharides in a ratio to total dissolved sugars >0.85; (ii) glucose in a ratio to total dissolved sugars in the range of 0.40-0.70; (iii) 1-200 ppm chloride; (iv) furfurals in an amount up to 0.01% weight/weight; (v) phenols in an amount up to 500 ppm; and (vi) a trace amount of hexanol. For example, the sugar mixture can be a mixture characterized by a high monosaccharides (particularly glucose) to total dissolved sugars ratio. In some embodiments, the sugar mixture is characterized by a high monosaccharides to total dissolved sugars ratio, a high glucose to total dissolved sugars ratio, and 1-200 ppm chloride. In some embodiments, the sugar mixture is characterized by a high monosaccharides to total dissolved sugars ratio, a high glucose to total dissolved sugars ratio, and a low impurity contents (e.g., low furfurals and phenols). In some embodiments, the sugar mixture is characterized by a high monosaccharides to total dissolved sugars ratio, a high glucose to total dissolved sugars ratio, a low impurity contents (e.g., low furfurals and phenols), and a trace amount of hexanol. In some embodiments, the sugar mixture is characterized by a high monosaccharides to total dissolved sugars ratio, a high glucose to total dissolved sugars ratio, a low impurity contents (e.g., low furfurals and phenols), a trace amount of hexanol, and 1-200 ppm chloride.

The high concentration C6 sugar mixture has a high monosaccharide content. In some embodiments, the monomeric sugar stream contains a sugar mixture having monosaccharides to total dissolved sugars ratio larger than 0.60, 0.65, 0.70, 0.75, 0.80, 0.85, 0.90, 0.95, or 0.99. In some embodiments, the monomeric sugar stream contains a sugar mixture having glucose to total dissolved sugars ratio in the range of 0.40-0.70, 0.40-0.50, 0.50-0.60, 0.60-0.70, or 0.40-0.60. In some embodiments, the monomeric sugar stream contains a sugar mixture with a high monosaccharide content and a glucose to total dissolved sugars ratio in the range of 0.40-0.70.

In some embodiments, the monomeric sugar stream contains a sugar mixture having a xylose to total dissolved sugars ratio in the range of 0.03-0.12, 0.05-0.10, 0.03-0.05, 0.05-0.075, 0.075-0.10, 0.12-0.12, 0.12-0.15, or 0.15-0.20. In some embodiments, the monomeric sugar stream contains a sugar mixture having an arabinose to total dissolved sugars ratio in the range of 0.005-0.015, 0.025-0.035, 0.005-0.010, 0.010-0.015, 0.015-0.020, 0.020-0.025, 0.025-0.030, 0.030-0.035, 0.035-0.040, 0.040-0.045, or 0.045-0.050. In some embodiments, the monomeric sugar stream contains a sugar mixture having a mannose to total dissolved sugars ratio in the range of 0.14-0.18, 0.05-0.10, 0.10-0.15, 0.15-0.20, 0.20-0.25, 0.25-0.30, or 0.30-0.40.

The sugar mixture has very low concentration of impurities such as furfurals and phenols. In some resulting stream, the sugar mixture has furfurals in an amount up to 0.1%, 0.05%, 0.04%, 0.03%, 0.04%, 0.01%, 0.075%, 0.005%, 0.004%, 0.002%, or 0.001% weight/weight. In some resulting stream, the sugar mixture has phenols in an amount up to 500 ppm, 400 ppm, 300 ppm, 200 ppm, 100 ppm, 60 ppm, 50 ppm, 40 ppm, 30 ppm, 20 ppm, 10 ppm, 5 ppm, 1 ppm, 0.1 ppm, 0.05 ppm, 0.02 ppm, or 0.01 ppm. The sugar mixture is further characterized by a trace amount of hexanol, e.g., 0.01-0.02%, 0.02-0.05%, 0.05-0.1%, 0.1%-0.2%, 0.2-0.5%, 0.5-1%, or less than 1, 0.5, 0.2, 0.1, 0.05, 0.02, 0.01, 0.005, 0.002, 0.001%, weight/weight hexanol. In addition, the sugar mixture is characterized by a trace amount of chloride, e.g., 1-10, 10-20, 20-30, 30-40, 40-50, 50-100, 100-150, 150-200, 10-100, or 10-50 ppm chloride.

VI. Lignin Processing

After the cellulose hydrolysis, the remaining residues in the lignocellulosic biomass are mostly lignins. The present invention provides methods of making novel lignin compositions using a unique processing and refining system. An exemplary method of lignin processing according to some embodiments of the present invention is provided in FIG. 20 (process 2000).

1. Lignin Washing

The lignin washing process 2020 is designed to remove free sugars and hydrochloric acid, which remain with acidic lignin stream 1720-B coming from the last reactor of the stirred tank reactors. Optionally, wet grinding 2010 of lignin prior to washing is conducted. The wet grinding 2010 contributes to an increase in washing efficiency.

The lignin washing process 2020 can use various numbers of washing stages (e.g., two washing stages). In some method, 2-9 or 3-10 washing stages are used. Each washing stage can consist of a separator (e.g., a hydroclone, screen, filter, membranes) where the mixture of acid, sugar, and lignin solids is separated with the liquid stream moving to the previous stage and the concentrated lignin solids stream moving to the next stage of washing. The temperature of each washing stage can be the same or different. For example, the last stage can be conducted at a slightly elevated temperature as compared to early reactors, e.g. 25° C.-40° C. versus 10° C.-20° C. Preferably, the method uses a 7-stage counter-current system.

In some methods, each washing stage is carried out in a hydro-cyclone. The pressure in the hydro-cyclones can be 40 to 90 psig. In some methods, two wash streams serve more than two hydro-cyclones. For example, the first wash stream has an HCl concentration of 40 to 43% and the second wash stream has an HCl concentration of 32 to 36%. The first wash stream can enter the first hydro-cyclone and the second wash stream enters the last hydro-cyclone. Optionally, washing temperature increases as HCl concentration decreases in the wash.

Preferably, the wash system is counter current with an azeotropic acid solution added to the last washing stage. The lignin containing free sugars and concentrated acid enters the first washing stage. Use of azeotropic concentration is advantageous as it does not dilute the solution with water, that later necessitates re-concentration of the acid solution at increased cost.

Optionally, the wash system is counter current with a weak acid wash (5-20% HCl concentration) added to the last washing stage. The lignin containing free sugars and concentrated acid enters the first washing stage.

The multi stage washing process can remove up to 99% of the free sugars and 90% of the excess acid entering the washing process with the lignin. The washed lignin leaves the last stage for further processing.

As discussed above in connection with acid recovery during sugar refining process, the acid-loaded extractant can be back-extracted with water to recover the acids. The recovered acid stream contains about 15-23% acids at a temperature around 50° C. Preferably, this recovered acid stream is used for lignin washing.

The exiting acid stream from lignin washing can contain up to 38-42% acid, which can be recycled in hydrolysis.

The lignin exiting lignin washing can contain 0.5-1.5% sugars. The lignin can be pressed to remove excess liquid. The pressed lignin can contain up to 35-50% solids, and preferably less than 1% residual sugars and 13-20% HCl.

2. Deacidification

The washed (and optionally pressed) lignin 2020-A is then deacidified by contacting with a hydrocarbon solvent 2040-A (process 2040 in FIG. 20). Optionally, wet grinding 2030 prior to contacting is conducted. The wet grinding contributes to an increase in efficiency of de-acidification. This increased efficiency is in terms of a reduced time for contacting and/or a reduction in the ratio of wash stream to feed stream.

Various hydrocarbon solvents can be used. Preferably, the hydrocarbon has a boiling point at atmospheric pressure between 100-250° C., 120-230° C., or 140-210° C. Examples of hydrocarbons suitable for the present invention include dodecane and various isoparaffinic fluids (e.g. ISOPAR G, H, J, K, L or M from ExxonMobil Chemical, USA). In some methods, the selected isoparaffinic fluid is substantially insoluble in water.

In some deacidification processes, the hydrocarbon solvent is mixed with lignin to make a slurry. For example, the hydrocarbon solvent is mixed with lignin in a ratio of hydrocarbon (e.g., Isopar K) to dry lignin is about 7/1; 9/1; 11/1; 15/1; 30/1; 40/1 or 45/1 w/w (or intermediate or greater ratios). Preferably, 9 parts of hydrocarbon (e.g., Isopar K) are contacted with 1 part of washed lignin stream (e.g. about 20% solid lignin on as is basis).

The mixture is then evaporated to remove acid from the slurry. The acid evaporates together with the hydrocarbon solvent. The evaporated acid can be recovered and recycled in the hydrolysis process.

De-acidified lignin stream can include less than 2%, 1.5%, 1.0%, 0.5%, 0.3%, 0.2% or 0.1% HCl. De-acidified lignin stream can contain at least 60%, 70%, 80%, 90%, 95%, 96%, 97%, 98% or 99% solid lignin.

Optionally, the de-acidified lignin is dried to remove the hydrocarbon solvent. Preferably, the dried, de-acidified lignin has less than 5% solvent and less than 0.5% acid.

VII. Lignin Refining

The dried, de-acidified lignin can be pelletized to make fuel pellets, or it can be further processed to produce novel lignin compositions as described below. An exemplary method of lignin refining according to some embodiments of the present invention is provided in FIG. 21 (process 2100).

1. Alkali Solubilization

According to some exemplary embodiments of the present invention, the lignin (e.g., the de-acidified lignin) is solubilized to generate an aqueous lignin solution. For example, the lignin can be solubilized by a pulping, a milling, a biorefining process selected from kraft pulping, sulfite pulping, caustic pulping, hydro-mechanical pulping, mild acid hydrolysis of lignocellulose feedstock, concentrated acid hydrolysis of lignocellulose feedstock, supercritical water or sub-supercritical water hydrolysis of lignocellulose feedstock, ammonia extraction of lignocellulose feedstock. Preferably, the lignin is solubilized using an alkaline solution. In one exemplary embodiment as shown in FIG. 19, the deacidified lignin 2040-B or the dried, de-acidified lignin 2050-A is dissolved in an alkali solution to form an alkaline lignin solution 2110-A. The alkali solubilization 2110 can be conducted at a temperature greater than 100° C., 110° C., 120° C. or 130° C., or lower than 200° C., 190° C., 180° C., 170° C., 160° C. or 150° C. Preferably, the alkali solubilization 2110 is conducted at 160-220° C., 170-210° C., 180-200° C., or 182-190° C. The reaction can be conducted for a duration of at least 10, 20, 30, 40, 50, 60, 70, 80, 90 or 120 minutes, or less than 10, 9, 8, 7, 6, 5.5, 5, 4.5, 4 or 3.5 hours. Preferably, the alkali solubilization 2110 is conducted for about 6 hours (e.g. at 182° C.). An increase in cooking time and/or in cooking temperature contributes to an increase in lignin fragmentation and/or degradation.

An alkaline concentration of at least 5%, 6%; 7%, 8%, 9%, 10%, 11%, 12%, 13%, 14%, 15% or intermediate or greater percentages (when expressed as 100× base/(base+ water) on a weight basis) can be used for alkali solubilization. Optionally, alkali solution includes ammonia and/or sodium hydroxide and/or sodium carbonate.

Upon alkali solubilization, residual hydrocarbon (e.g. IsoPar K or dodecane) from de-acidification separates easily into a separate organic phase which is decanted and recycled.

2. Limited-Solubility Solvent Purification

The aqueous lignin solution (e.g., the alkaline lignin solution) can be processed to prepare novel high-purity lignin material using a limited-solubility solvent (process 2120 in FIG. 21). It was surprisingly discovered lignin can be dissolved in a limited-solubility solvent 2120-B (e.g., methylethylketone), and that the lignin purified using a limited-solubility solvent has unexpected, superior properties. In some embodiments, the limited-solubility solvent is an organic solvent having a solubility in water at 20° C. of less than about 30% wt solvent in water.

For example, the alkaline solution can be contacted with an acidulant 2120-A (e.g., HCl) and simultaneously or subsequently mixed with a limited-solubility solvent 2120-B to form a two phase system containing acidic lignin. Various acidulants known in the art can be used to adjust the pH of the alkaline solution to less than 7.0, 6.0, 5.0, 4.0, 3.0, 2.0, or 1.0. Preferably, the pH is about 4.0, e.g., ~3.5-4.0. The acidulant 2120-A converts basic lignin into acidic lignin. The lignin dissolves into the solvent phase whereas water soluble impurities and salts stay in the aqueous phase. The lignin in the solvent phase can be washed with water and optionally purified using a strong acid cation exchanger to remove residual cations.

The limited-solubility solvent should have low solubility in water, solubility at room temperature should be less than 35% wt, less than 28% wt, less than 10% wt. The solvent should form two phases with water, and the solubility of water in it should be up to 20%, up to 15%, up to 10% up to 5% at room temperature. Preferably the solvent should be stable at acidic conditions at temperature up to 100° C. Preferably, the solvent should form a heterogeneous azeotrope with water, having a boiling point of less than 100° C. where the azeotrope composition contains at least 50% of the solvent, at least 60% of the solvent out of total azeotrope. The solvent should have a least one hydrophilic functional group selected from ketone, alcohol and ether or other polar functional group. Preferably said solvent should be commercially available at low cost.

Examples of solvents suitable for the present invention include methylethylketone, methylisobutylketone, diethylketone, methyl isopropyl ketone, methylpropylketone, mesityl oxide, diacetyl, 2,3-pentanedione, 2,4-pentanedione, 2,5-dimethylfuran, 2-methylfuran, 2-ethylfuran, 1-chloro-2-butanone, methyl tert-butyl ether, diisopropyl ether, anisol, ethyl acetate, methyl acetate, ethyl formate, isopropyl acetate, propyl acetate, propyl formate, isopropyl formate, 2-phenylethanol, toluene, 1-phenylethanol, phenol, m-cresol, 2-phenylethyl chloride, 2-methyl-2H-furan-3-one, γ-butyrolactone, acetal, methyl ethyl acetal, dimethyl acetal. Optionally, the limited-solubility solvent includes one or more of esters, ethers and ketones with 4 to 8 carbon atoms.

To obtain high purity solid lignin, the limited-solubility solvent is separated from lignin (process 2140 in FIG. 21). For example, the limited-solubility solvent can be evaporated. Preferably, the limited-solubility solvent can be separated from lignin by mixing the solvent solution containing acidic lignin with water at an elevated temperature (e.g., 75° C., 85° C., 90° C.). The precipitated lignin can be recovered by, e.g., filtration or centrifugation. The solid lignin can be dissolved in any suitable solvents (e.g., phenylethyl alcohol) for making lignin solutions.

Alternatively, the limited-solubility solvent solution containing acidic lignin can be mixed with another solvent (e.g., toluene). The limited-solubility solvent can be evaporated whereas the replacement solvent (e.g., toluene) stays in the solution. A lignin solution in a desired solvent can be prepared.

3. High Purity Lignin

The high purity lignin obtained using the limited-solubility solvent purification method has unexpected and superior properties over natural lignins. It was discovered that the high purity lignin has low aliphatic hydroxyl group and high phenolic hydroxyl group, indicating cleavage or condensation along the side chain and condensation between phenolic moieties. The high purity lignin of the invention is more condensed as compared to natural lignins or other industrial lignins. It has less methoxyl content and aliphatic chains and a very high degree of demethylation.

In some embodiments, the high purity lignin is characterized by one or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, characteristics including (a) lignin aliphatic hydroxyl group in an amount up to 2 mmole/g; (b) at least 2.5 mmole/g lignin phenolic hydroxyl group; (c) at least 0.35 mmole/g lignin carboxylic hydroxyl group; (d) sulfur in an amount up to 1% weight/weight; (e) nitrogen in an amount up to 0.05% weight/weight; (f) chloride in an amount up to 0.1% weight/weight; (g) 5% degradation temperature higher than 250° C.; (h) 10% degradation temperature higher than 300° C.; (i) low ash content; (j) a formula of $C_aH_bO_c$; wherein a is 9, b is less than 10 and c is less than 3; (k) a degree of condensation of at least 0.9; (l) a methoxyl content of less than 1.0; (m) an O/C weight ratio of less than 0.4, (n) at least 97% lignin on a dry matter basis; (o) an ash content in an amount up to 0.1% weight/weight; (p) a total carbohydrate content in an amount up to 0.05% weight/weight; (q) a volatiles content in an amount up to 5% weight/weight at 200° C.; and (r) a non-melting particulate content in an amount up to 0.05% weight/weight.

In some embodiments, the high purity lignin is characterized by one or more, two or more, three or more, four or more, five or more, characteristics including (a) at least 97% lignin on a dry matter basis; (b) an ash content in an amount up to 0.1% weight/weight; (c) a total carbohydrate content in an amount up to 0.05% weight/weight; (d) a volatiles content in an amount up to 5% weight/weight at 200° C.; and (e) a non-melting particulate content in an amount up to 0.05% weight/weight. For example, the high purity lignin can be a lignin characterized by (a) at least 97% lignin on a dry matter basis; (b) an ash content in an amount up to 0.1% weight/weight; (c) a total carbohydrate content in an amount up to 0.05% weight/weight; and (d) a volatiles content in an amount up to 5% weight/weight at 200° C.

In some embodiments, the high purity lignin of the invention has a high purity. In some cases, the high purity lignin is more than 80, 85, 90, 91, 92, 93, 94, 95, 96, 97, 98, 99, 99.5, 99.7, or 99.9% pure. In some embodiments, the high purity lignin of the invention has a low ash content. In some cases, the high purity lignin has an ash content in an amount up to 5, 2, 1, 0.9, 0.8, 0.7, 0.6, 0.5, 0.4, 0.3, 0.2, 0.1, 0.05, 0.02, 0.01% weight/weight. In some embodiments, the high purity lignin of the invention has a low carbohydrate content. In some case, the high purity lignin has a total carbohydrate content in an amount up to 0.005, 0.0075, 0.01, 0.015, 0.020, 0.025, 0.030, 0.035, 0.04, 0.045, 0.05, 0.06, 0.07, 0.08, 0.09, 0.1, 0.2, 0.5, 1.0, 2.0, 5.0% weight/weight. In some cases, the high purity lignin has a volatile content at 200° C. in an amount up to 0.1, 0.2, 0.5, 1, 2, 3, 4, 5, 6, 7, 8, 9, 10% weight/weight.

In some embodiments, the high purity lignin of the invention has a low non-melting particulate content. In some cases, the high purity lignin has a non-melting particulate content in an amount up to 0.005, 0.0075, 0.01, 0.015, 0.020, 0.025, 0.030, 0.035, 0.04, 0.045, 0.05, 0.06, 0.07, 0.08, 0.09, 0.1, 0.2, 0.5, 1.0, 2.0, 5.0% weight/weight.

In some embodiments, the high purity lignin is characterized by one or more, two or more, three or more, four or more, five or more, six or more, seven or more, eight or more, nine or more, ten or more, eleven or more, twelve or more, thirteen or more, characteristics including (a) lignin aliphatic hydroxyl group in an amount up to 2 mmole/g; (b) at least 2.5 mmole/g lignin phenolic hydroxyl group; (c) at least 0.35 mmole/g lignin carboxylic hydroxyl group; (d) sulfur in an amount up to 1% weight/weight; (e) nitrogen in an amount up to 0.05% weight/weight; (f) chloride in an amount up to 0.1% weight/weight; (g) 5% degradation temperature higher than 250° C.; (h) 10% degradation temperature higher than 300° C.; (i) low ash content; (j) a formula of CaHbOc; wherein a is 9, b is less than 10 and c is less than 3; (k) a degree of condensation of at least 0.9; (l) a methoxyl content of less than 1.0; and (m) an O/C weight ratio of less than 0.4. For example, the high purity lignin can be a lignin characterized by (a) lignin aliphatic hydroxyl group in an amount up to 2 mmole/g; (b) at least 2.5 mmole/g lignin phenolic hydroxyl group; and (c) at least 0.35 mmole/g lignin carboxylic hydroxyl group. In some embodiments, the high purity lignin is characterized by (a) lignin aliphatic hydroxyl group in an amount up to 2 mmole/g; (b) at least 2.5 mmole/g lignin phenolic hydroxyl group; (c) at least 0.35 mmole/g lignin carboxylic hydroxyl group, (d) sulfur in an amount up to 1% weight/weight, (e) and nitrogen in an amount up to 0.05% weight/weight. In some embodiments, the high purity lignin is characterized by (a) less than 2 mmole/g lignin aliphatic hydroxyl group; (b) at least 2.5 mmole/g lignin phenolic hydroxyl group; (c) at least 0.35 mmole/g lignin carboxylic hydroxyl group, (d) sulfur in an amount up to 1% weight/weight, (e) nitrogen in an amount up to 0.05% weight/weight and (f) chloride in an amount up to 0.1% weight/weight. In some embodiments, the high purity lignin is characterized by its thermal degradation properties, e.g., a higher than 250° C. 5% degradation temperature; a higher than 300° C. 10% degradation temperature. In some embodiments, the high purity lignin is characterized by a formula of CaHbOc; wherein a is 9, b is less than 10 and c is less than 3, a degree of condensation of at least 0.9, a methoxyl content of less than 1.0, and an O/C weight ratio of less than 0.4. In other embodiments, the high purity lignin is characterized by an O/C weight ratio of less than 0.40, 0.39, 0.38, 0.37, 0.36, 0.35, 0.34, 0.33, 0.32, 0.31, 0.30, 0.29, 0.28, 0.27, 0.26, 0.25, 0.24, 0.23, 0.22, 0.21, 0.20, or 0.20-0.22, 0.22-0.24, 0.24-0.26, 0.26-0.28, 0.28-0.30, 0.32-0.34, 0.34-0.36, 0.36-0.38, or 0.38-0.40.

In some embodiments, the high purity lignin of the invention has a low content of aliphatic hydroxyl group. In some cases, the high purity lignin has lignin aliphatic hydroxyl group in an amount up to 0.1, 0.2, 0.3, 0.4, 0.5, 0.6, 0.7, 0.8, 0.9, 1.0, 1.2, 1.4, 1.6, 1.8, 1.9, or 2.0 mmole/g. In some embodiments, the high purity lignin of the invention has a high content of lignin phenolic hydroxyl group. In some cases, the high purity lignin has more than 2.0, 2.2, 2.4, 2.5, 2.6, 2.7, 2.8, 2.9, 3.0, 3.1, 3.2, 3.3, 3.4, 3.5, 3.6, 3.7, 3.8, 3.9, or 4.0 mmole/g lignin phenolic hydroxyl group. In some embodiments, the high purity lignin of the invention has a high content of lignin carboxylic hydroxyl group. In some cases, the high purity lignin has more than 0.20, 0.25, 0.30, 0.35, 0.40, 0.45, 0.50, 0.60, 0.70, 0.80, 0.90, 1.0 mmole/g lignin carboxylic hydroxyl group. In some embodiments, the high purity lignin of the invention has a low content of aliphatic hydroxyl group, a high content of lignin phenolic hydroxyl group, and a high content of lignin carboxylic hydroxyl group. In some cases, the high purity lignin of the invention has lignin aliphatic hydroxyl group in an amount up to 2 mmole/g, at least 2.5 mmole/g lignin phenolic hydroxyl group, and at least 0.35 mmole/g lignin carboxylic hydroxyl group. In some cases, the high purity lignin of the invention has lignin aliphatic hydroxyl group in an amount up to 1 mmole/g, at least 2.7 mmole/g lignin phenolic hydroxyl group, and at least 0.4 mmole/g lignin carboxylic hydroxyl group. In some cases, the high purity lignin of the invention has lignin aliphatic hydroxyl group in an amount up to 0.5 mmole/g, at least 3.0 mmole/g lignin phenolic hydroxyl group, and at least 0.9 mmole/g lignin carboxylic hydroxyl group.

In some embodiments, the high purity lignin of the invention has a low content of sulfur. In some cases, the high purity lignin has sulfur in an amount up to 0.1, 0.2, 0.3, 0.4, 0.5, 0.6, 0.7, 0.8, 0.9, 1.0, 1.5, 2, 2.5, 3, 3.5, 4, 4.5, 5.0, 10.0% weight/weight. In some embodiments, the high purity lignin of the invention has a low content of nitrogen. In some cases, the high purity lignin has nitrogen in an amount up to 0.005, 0.0075, 0.01, 0.015, 0.020, 0.025, 0.030, 0.035, 0.04, 0.045, 0.05, 0.06, 0.07, 0.08, 0.09, 0.1, 0.2, 0.5, 1.0, 2.0, 5.0% weight/weight. In some embodiments, the high purity lignin of the invention has a low content of chloride. In some cases, the high purity lignin has chloride in an amount up to 0.01, 0.02, 0.05, 0.10, 0.15, 0.20, 0.25, 0.5, 0.75, 1.0, 2.0% weight/chloride. In some embodiments, the high purity lignin of the invention has a low ash content.

The high purity lignin of the invention also has superior thermal properties such as thermal stability. In some embodiments, the high purity lignin of the invention has a 5% degradation temperature higher than 100, 150, 200, 210, 220, 230, 240, 250, 260, 270, 280, 290, or 300° C. In some embodiments, the high purity lignin of the invention has a 10% degradation temperature higher than 200, 250, 275, 280, 290, 300, 310, 320, 330, 340, 350, 360, 370, 380, 390, or 400° C.

In some embodiments, the high purity lignin of the invention can be characterized by a formula of CaHbOc; wherein a is 9, b is less than 10 and c is less than 3. In some cases, b less than 9.5, 9.0, 8.5, 8.0, 7.5, or 7.0. In some cases, c is less than 2.9, 2.7, 2.6, or 2.5. In other embodiments, the high purity lignin is characterized by an O/C weight ratio of less than 0.40, 0.39, 0.38, 0.37, 0.36, 0.35, 0.34, 0.33, 0.32, 0.31, 0.30, 0.29, 0.28, 0.27, 0.26, 0.25, 0.24, 0.23, 0.22, 0.21, 0.20, or 0.20-0.22, 0.22-0.24, 0.24-0.26, 0.26-0.28, 0.28-0.30, 0.32-0.34, 0.34-0.36, 0.36-0.38, or 0.38-0.40.

In some embodiments, the high purity lignin of the invention has a high degree of condensation. In some cases, the high purity lignin of the invention has a degree of condensation of at least 0.7, 0.8, 0.9, 0.95, 1.0, 1.1, 1.2, 1.3, 1.4, or 1.5. In some embodiments, the high purity lignin of the invention is characterized with a low a methoxyl content. In some cases, the high purity lignin of the invention has a methoxyl content of less than 1.0, 0.9, 0.8, 0.7, 0.6, or 0.5.

4. Downstream Processing

Exemplary Anti-Solvent Processing:

In some embodiments, an anti-solvent is used for desolventization. For example, methyl-ethyl ketone (MEK) has a solubility of 27.5 gram in 100 gram aqueous solution (the acidic lignin dissolved in a limited-solubility solvent which is MEK in this embodiment). In some embodiments, spraying lignin dissolved in MEK into water (e.g. at ambient temperature) dissolves the MEK in the water. The solubility of lignin in the MEK water mixture (at appropriate water:

MEK ratio) is low so that lignin precipitates. In some embodiments, MEK is separated from the mixture by distilling its azeotrope (73.5° C., 89% MEK).

Each solvent/anti-solvent combination represents an additional embodiment of the invention. Exemplary solvent/anti-solvent combinations include MEK-water; MEK-decanol and MEK-decane.

Exemplary Processing by Distillation:

In some embodiments limited-solubility solvent (e.g. MEK; boiling point=79.6° C.) is distilled away from the lignin dissolved in it. In some embodiments, the distillation includes contacting the limited-solubility solvent with lignin dissolved in it with a hot gas (e.g. spray drying). Optionally contacting with a hot gas is conducted after a pre-evaporation which increases the lignin concentration in the limited-solubility solvent. In some embodiments, the distillation includes contacting the limited-solubility solvent with lignin dissolved in it with a hot liquid. In some embodiments, the contacting includes spraying the limited-solubility solvent with lignin dissolved in it into a hot liquid (optionally after some pre-concentration). In some embodiments, the hot liquid includes water and/or oil and/or Isopar K. In some embodiments, the hot liquid includes an anti-solvent. In some embodiments, the distillation includes contacting the limited-solubility solvent with lignin dissolved in it with a hot solid surface.

In some embodiments, a hot liquid is contacted with the limited-solubility solvent with lignin dissolved in it. Hydrophilic/hydrophobic properties of the hot liquid affect the surface properties of the separated solid lignin. In some embodiments, in those distillation embodiments which employ contacting the limited-solubility solvent with lignin dissolved in it with a hot liquid, the chemical nature of the lignin solvent affects the surface properties of the separated solid lignin. In some embodiments, the hot liquid influences the nature and availability of reactive functions on the separated solid lignin. In some embodiments, the nature and availability of reactive functions on the separated solid lignin contribute to efficiency of compounding, e.g. with other polymers. In some embodiments, a temperature of the hot liquid influences the molecular weight of the separated solid lignin.

Exemplary Spinning Processes:

In some embodiments, spraying lignin dissolved in limited-solubility solvent into a hot liquid and/or contacting with an anti-solvent produce lignin in a form suitable for wet spinning. These processes can be adapted to produce lignin in a form suitable for wet spinning by adjusting various parameters such as, for example, absolute and/or relative temperatures of the two liquids and/or the concentration of lignin dissolved in the limited-solubility solvent. In some embodiments, the concentration of lignin dissolved in the limited-solubility solvent contributes to viscosity of the lignin/solvent solution.

Exemplary Modifying Reagents:

In some embodiments, the hot liquid with which the lignin dissolved in limited-solubility solvent is contacted includes a modifying reagent. Optionally, the hot liquid is the modifying reagent. In some embodiments, upon contact with the hot liquid, lignin reacts with and/or is coated by the modifying reagent.

Exemplary Coating Processes:

Some exemplary embodiments in which distillation is accomplished by contacting the lignin dissolved in limited-solubility solvent with a hot solid surface result in coating of the solid surface with a lignin layer. According to some embodiments such coating serves to encapsulate the solid surface. Encapsulation of this type is useful, for example, in slow-release fertilizer formulation and/or in provision of a moisture barrier. In some embodiments, the solid to be coated is provided as fibers. The resultant coated fibers are useful, for example, in the manufacture of composite materials. In some embodiments, the lignin is dissolved in a volatile solvent (e.g. MEK). Use of a volatile limited-solubility solvent contributes to a capacity for coating of thermally sensitive solids. In some embodiments, a plasticizer is added to the lignin dissolved in limited-solubility solvent. Optionally, the plasticizer contributes to an improvement in the resultant coating.

Polymer Organization:

In some embodiments, the lignin dissolved in limited-solubility solvent is co-sprayed with a second polymer that has a linear arrangement to cause formation of rod like assemblies of lignin molecules. Resultant co-polymer arrangements with a high aspect ratio are useful in structural applications (e.g. carbon fibers).

VIII. Direct Lignin Extraction from Lignocellulosic Biomass

As discussed above in connection with hemicellulose sugars extraction, the present invention in one aspect provides a novel method of extracting lignin directly from lignocellulosic biomass after hemicellulose sugars are extracted. The method utilizes a limited-solubility solvent, and works well with biomass particles of various sizes. Therefore, it is not necessary to grind the particles prior to lignin extraction.

The extraction of hemicellulose sugars from the biomass results in a lignin-containing remainder. In some methods, the extraction of hemicellulose sugars does not remove a substantial amount of the cellulosic sugars. For example, the extraction of hemicellulose sugars does not remove more than 1, 2, 5, 10, 15, 20, 30, 40, 50, 60% weight/weight cellulose. In some methods, the lignin-containing remainder contains lignin and cellulose. In some methods, the lignin-containing remainder contains less than 50, 45, 40, 35, 30, 25, 20, 15, 10, 5, 2, 1% hemicellulose. In some embodiments, the lignin can be directly extracted from lignocellulosic biomass without removing hemicellulose sugars.

The lignin extraction solution contains a limited-solubility solvent, an acid, and water. Examples of limited-solubility solvents suitable for the present invention include methylethylketone, diethylketone, methyl isopropyl ketone, methyl propyl ketone, mesityl oxide, diacetyl, 2,3-pentanedione, 2,4-pentanedione, 2,5-dimethylfuran, 2-methylfuran, 2-ethylfuran, 1-chloro-2-butanone, methyl tert-butyl ether, diisopropyl ether, anisol, ethyl acetate, methyl acetate, ethyl formate, isopropyl acetate, propyl acetate, propyl formate, isopropyl formate, 2-phenylethanol, toluene, 1-phenylethanol, phenol, m-cresol, 2-phenylethyl chloride, 2-methyl-2H-furan-3-one, γ-butyrolactone, acetal, methyl ethyl acetal, dimethyl acetal, morpholine, pyrrol, 2-picoline, 2,5-dimethylpyridine. Optionally, the limited-solubility solvent includes one or more of esters, ethers and ketones with 4 to 8 carbon atoms. For example, the limited-solubility solvent can include ethyl acetate. Optionally, the limited-solubility solvent consists essentially of, or consists of, ethyl acetate.

The ratio of the limited-solubility solvent to water suitable for carrying out the lignin extraction can vary depending on the biomass material and the particular limited-solubility solvent used. In general, the solvent to water ratio is in the range of 100:1 to 1:100, e.g., 50:1-1:50, 20:1 to 1:20, and preferably 1:1.

Various inorganic and organic acids can be used for lignin extraction. For example, the solution can contain an inorganic or organic acid such as $H_2SO_4$, HCl, acetic acid and formic acid. The acidic aqueous solution can contain 0 to 10% acid or more, e.g., 0-0.4%, 0.4-0.6%, 0.6-1.0%, 1.0-2.0%, 2.0-3.0%, 3.0-4.0%, 4.0-5.0% or more. Preferably, the aqueous solution for the extraction and hydrolysis includes 0.6-5%, preferably 1.2-1.5% acetic acid. The pH of the acidic aqueous solution can be, for example, in the range of 0-6.5.

Elevated temperatures and/or pressures are preferred in lignin extraction. For example, the temperature of lignin extraction can be in the range of 50-300° C., preferably 160 to 200° C., e.g., 175-185° C. The pressure can be in the range of 1-10 mPa, preferably, 1-5 mPa. The solution can be heated for 0.5-24 hours, preferably 1-3 hours.

Figure 22:
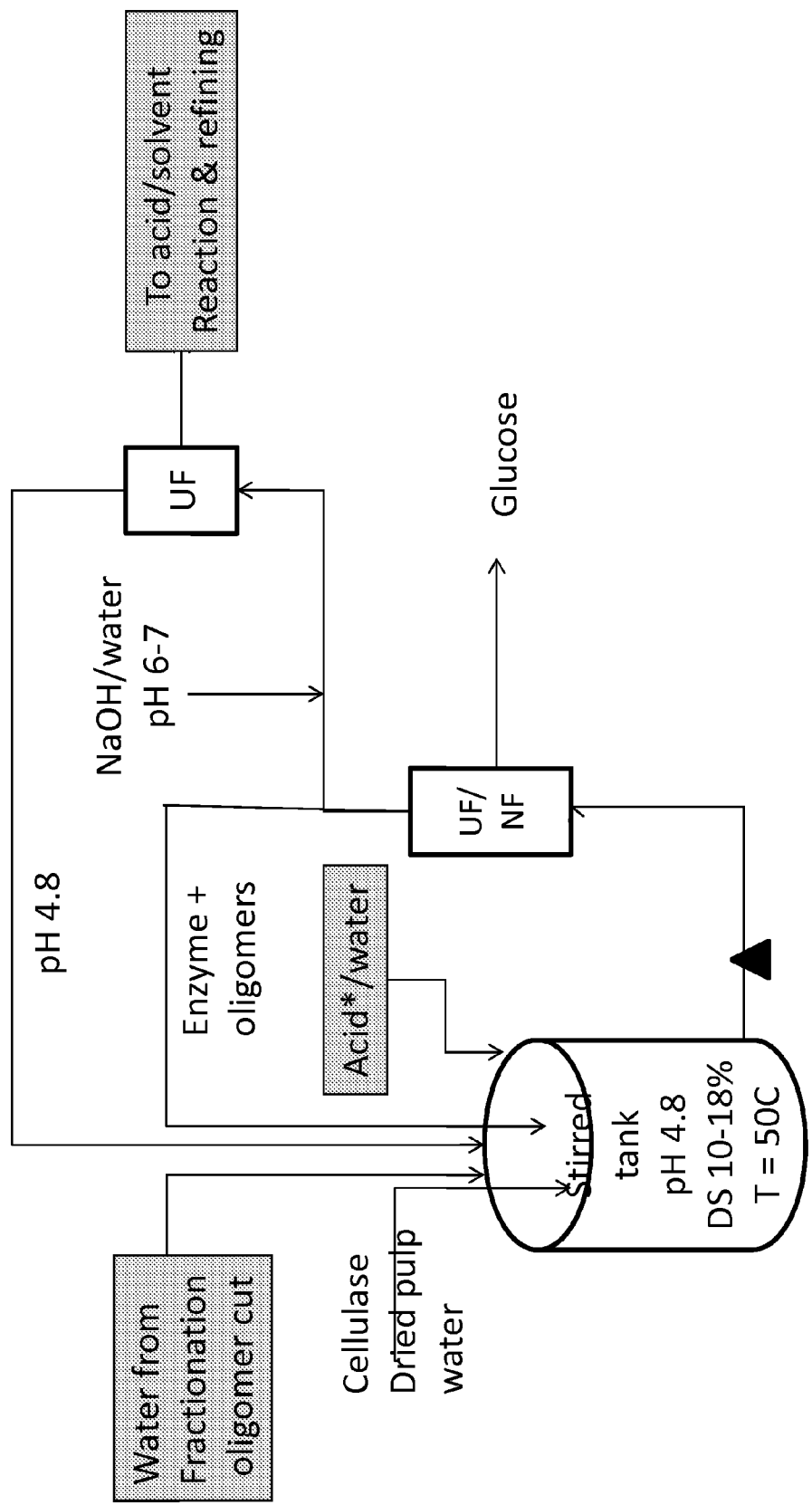
FIG. 22 depicts an exemplary method of hydrolysis of cellulose by cellulase according to some embodiments of the present invention.

Lignin is extracted in the limited-solubility solvent (organic phase), the remaining solid contains mostly cellulose. After the solid phase is washed to remove residual lignin, the cellulose can be used to produce pulp, or as starting material for hydrolysis (acidic or enzymatic). An exemplary method of hydrolysis of cellulose by cellulase according to some embodiments of the present invention is shown in FIG. 22. In some exemplary embodiments, cellulose hydrolysis and cellulose sugar refining can be carried out under conditions identical or similar to those described above in sections IV and V. The residual lignin can be processed and refined using procedures described above in sections VI and VII.

Optionally, the pH of the solvent is adjusted to 3.0 to 4.5 (e.g., 3.5-3.8). At this pH range, the lignin is protonated and is easily extracted into the organic phase. The organic phase comprising solvent and lignin is contacted with strong acid cation exchanger to remove residual metal cations. To obtain high purity solid lignin, the limited-solubility solvent is separated from lignin, e.g., evaporated. Preferably, the limited-solubility solvent can be separated from lignin by mixing the solvent solution containing acidic lignin with water at an elevated temperature (e.g., 80° C.). The precipitated lignin can be recovered by, e.g., filtration or centrifugation. The solid lignin can be dissolved in any suitable solvents (e.g., phenylethyl alcohol) for making lignin solutions.

Alternatively, the limited-solubility solvent solution containing acidic lignin can be mixed with another solvent (e.g., toluene). The limited-solubility solvent can be evaporated whereas the replacement solvent (e.g., toluene) stays in the solution. A lignin solution in a desired solvent can be prepared.

Figure 43:
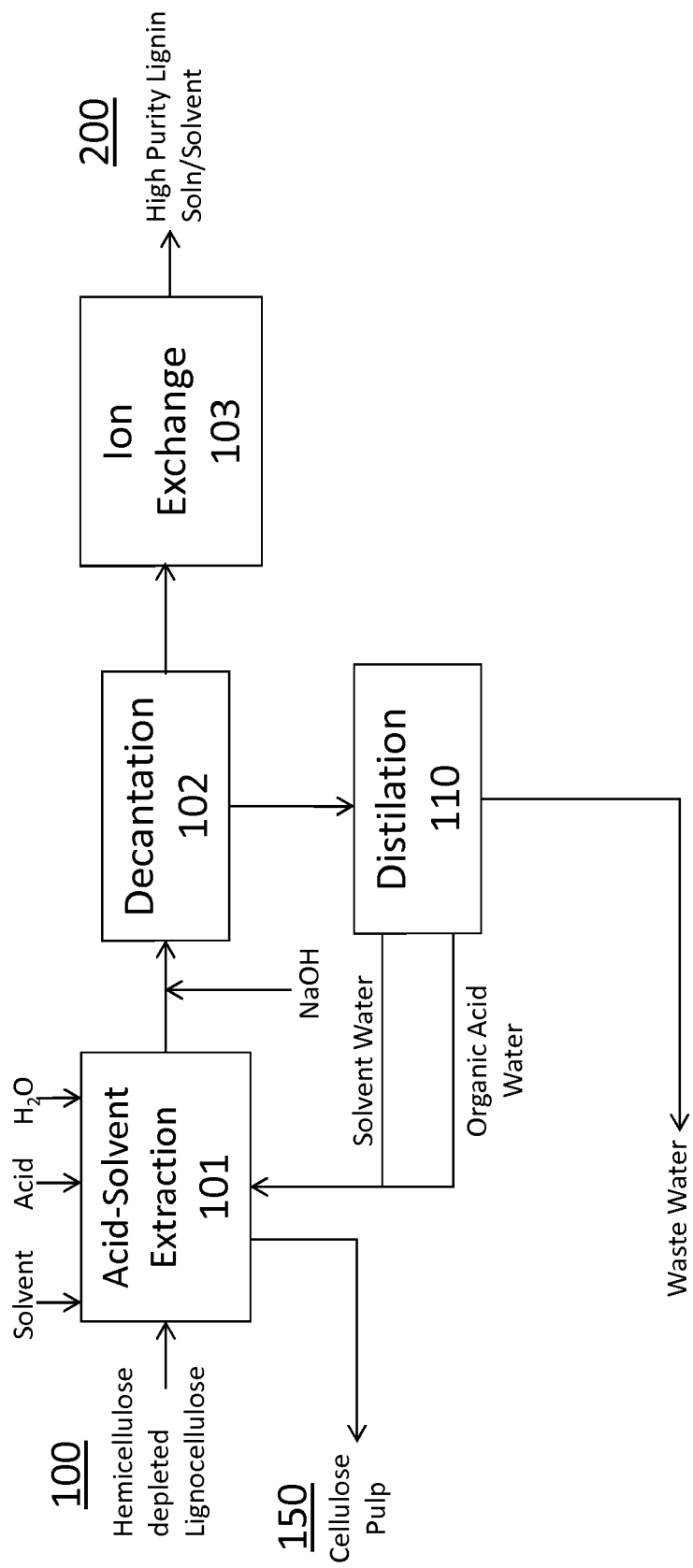
FIG. 43 is a simplified flow scheme of a method according to alternative lignin solubilization embodiments of the invention.

FIG. 43 is a schematic description of a process for acid-solvent extraction of lignin from hemicellulose depleted lignocellulose matter and for the refining of the solvent-soluble lignin according to certain embodiments of the invention. This process results in stream 200, comprising the solvent and dissolved lignin, where residual ash is less than 1000 ppm, preferably less than 500 ppm, wherein polyvalent cations are less than 500 ppm, preferably less than 200 ppm relative to lignin (on dry base) and residual carbohydrate is less than 500 ppm relative to lignin (on dry base). The solution is free of particulate matter.

IX. Waste Water Treatment

To utilize the energy stored in organic solutes and to comply with environmental requirements, aqueous waste streams that contain organic matter can be treated in anaerobic digesters to produce methane, which can be burned. However, anaerobic digesters are known to be poisoned by too high levels of sulfate ions per a given chemical oxygen demand (COD) level, and are also limited to the incoming stream having less than 400 ppm calcium ions to prevent calcium carbonate build up in the digester. The aqueous waste streams produced in various stages of the current invention as described above comply with these requirements. Furthermore, as disclosed above, back extraction may be conducted in several steps allowing better control of the inorganic ion level versus the organic matter.

X. Lignin Applications

The high purity lignin composition according to embodiments disclosed herein has a low ash content, a low sulfur and/or phosphorous concentration. Such a high purity lignin composition is particularly suitable for use in catalytic reactions by contributing to a reduction in catalyst fouling and/or poisoning. A lignin composition having a low sulfur content is especially desired for use as fuel additives, for example in gasoline or diesel fuel.

Some other potential applications for high purity lignin include carbon-fiber production, asphalt production, and as a component in biopolymers. These uses include, for example, oil well drilling additives, concrete additives, dyestuffs dispersants, agriculture chemicals, animal feeds, industrial binders, specialty polymers for paper industry, precious metal recovery aids, wood preservation, sulfur-free lignin products, automotive brakes, wood panel products, bio-dispersants, polyurethane foams, epoxy resins, printed circuit boards, emulsifiers, sequestrants, water treatment formulations, strength additive for wallboard, adhesives, raw materials for vanillin, xylitol, and as a source for paracoumaryl, coniferyl, sinapyl alcohol.

Disclosed in Sections XI-XIV are additional embodiments of the invention.

IX. Alternative Lignocellulosic Biomass Processing and Acid Recovery Embodiments Embodiments disclosed in this section in general relate to processing of a lignocellulosic substrate to produce sugars and/or lignin, and acid recovery (e.g., HCl recovery).

For example, some embodiments disclosed herein can be used to produce an HCl solution with a concentration greater than 37% by back-extracting HCl from an S1 solvent based extractant to generate a sub-azeotropic HCl solution, followed by distillation at greater than atmospheric pressure to generate HCl gas. The HCl gas is then absorbed by the sub-azeotropic HCl solution to produce an HCl solution with a concentration greater than 37%.

First Exemplary Method

Figure 23:
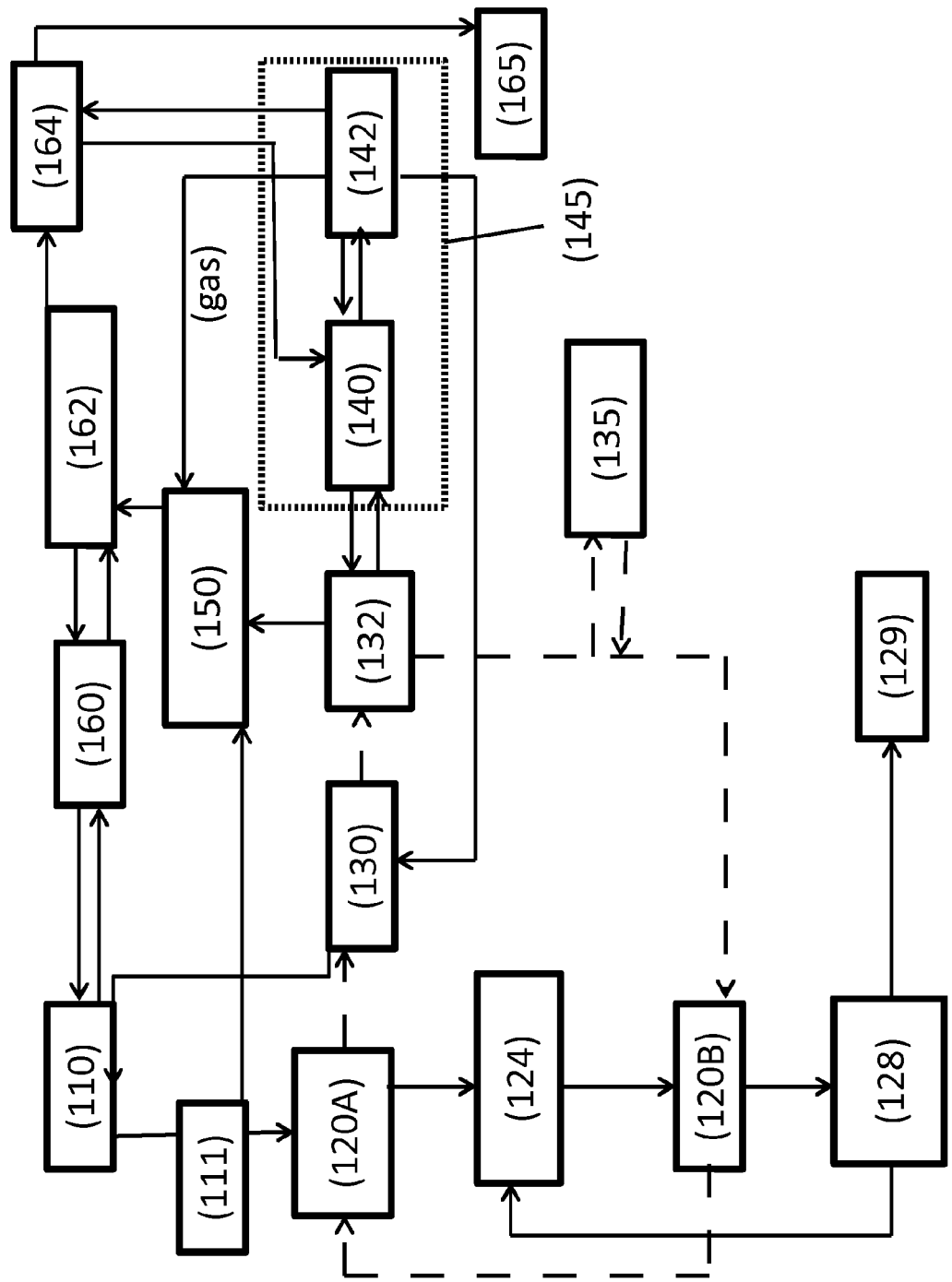
FIG. 23 is a simplified flow scheme according to some alternative lignocellulosic biomass processing and acid recovery embodiments of the invention.

FIG. 23 is a simplified flow scheme of a method according to some embodiments. In FIG. 23, dashed lines indicate a flow of solvent and solid lines indicate a flow of HCl (gas or aqueous solution) and/or sugars and/or lignin.

The depicted exemplary method includes, hydrolyzing 110 a lignocellulosic material (not depicted) with a recycled HCl stream (e.g. from 130 and/or 160) to form an aqueous hydrolysate (which progresses downwards from 110 in the drawing) and a solid lignin stream (i.e. a stream including solid lignin which progresses rightwards from 110 in the drawing). Optionally, the solid lignin stream is subjected to grinding (e.g. after 110 and before 160). In some embodiments, the hydrolysate includes a sugar mixture and HCl at more than 20%, 25%, 26%, 27%, 28%, 29%, 30%, 31%, 32%, 33%, 34% or 35% weight/weight HCl/[HCl and water] and/or the lignin stream includes HCl at more than 25%, 26%, 27%, 28%, 29%, 30%, 31%, 32%, 33%, 34% or 35% weight/weight HCl/[HCl and water].

The depicted exemplary method also includes extracting (120A and/or 120B) the hydrolysate with a recycled extractant including an S1 solvent. The extraction involves at least two extraction steps (120A and 120B). In some embodiments, the extract from 120A includes more than 20%, more than 25%, more than 30%, more than 35% or 40% weight/weight or more HCl/[HCl and water]. Due to the nature of S1 solvents, acid and water are preferentially extracted over sugars.

Optionally, the method includes increasing a monomeric sugar to oligomeric sugar ratio in the sugar mixture (e.g. by secondary hydrolysis 124) and polishing (e.g. by chromatography 128) the mixture to produce a polished mixture (129) containing at least 70%, at least 75%, at least 80%, at least 85%, at least 90% or at least 95% weight/weight monomeric sugars out of total sugars and less than 1%, less than 0.7%, less than 0.5%, less than 0.3, less than 0.1% or less than 0.01% weight/weight HCl on as is basis. In some embodiments, increasing a monomeric sugar to oligomeric sugar ratio in the sugar mixture includes chromatographic separation 128 to separate a monomer cut from an oligomer cut. In some embodiments, the monomer cut is harvested as polished sugars 129 and the oligomer cut is recycled to secondary hydrolysis 124 as indicated by the upward arrow from 128 to 124.

Treatment of the sugar mixture from hydrolysis 110 by extractions 120A and 120B in conjunction with secondary hydrolysis 124 and chromatography 128 is described in PCT/US2012/024033 (incorporated herein by reference for all purposes).

The depicted exemplary method also includes back-extracting (e.g. 130 and/or 132) the extract with an aqueous solution to form a de-acidified extractant and an aqueous back-extract. The aqueous solution can be water. The aqueous solution can also include one or more solutes.

The depicted exemplary method also includes incorporating the de-acidified extractant into the recycled extractant (dashed line from 132 to 120B). In some embodiments, at least a portion of the extractant is diverted to purification 135. Exemplary methods for purification 135 are described in PCT/US2011/046153 (incorporated herein by reference for all purposes).

The depicted exemplary embodiment includes evaporating 111 a mixture of water and HCl from the hydrolysate prior to extracting (120A and/or 120B). In some embodiments, the evaporated mixture goes to absorber 150. In some embodiments at least a portion of the evaporated mixture is condensed and routed to high-pressure evaporator 142 (See FIG. 24). Optionally, routing of the evaporated mixture to absorber 150 contributes to a reduction in energy consumption at evaporation module 145. In some embodiments, a reduction in volume of liquid or a reduction in HCl concentration of the stream from 120A to 130 contributes to the reduction in energy consumption at 145. In some embodiments, at least a portion of the mixture of water and HCl from evaporating 111 (after passing through absorber 150) washes the solid lignin stream (e.g. at 162 and/or 160).

In some embodiments, the aqueous back-extract produced at 130 is incorporated into the recycled HCl stream arriving at hydrolysis 110. In some embodiments, the back extract from 130 returns to extraction 120A (see FIG. 24).

In some embodiments, the increasing includes at least one of chromatographic separation 128 and acid-catalyzed (secondary) hydrolysis 124 of oligomeric sugars. Optionally, the increasing includes both chromatographic separation 128 and acid-catalyzed hydrolysis 124 of oligomeric sugars.

In some embodiments, oligomeric sugars are hydrolyzed to monomeric sugars (124) between a pair of the at least two extraction steps (e.g. 120A and 120B). In other embodiments, the method includes hydrolyzing oligomeric sugars to monomeric sugars (124) after the extraction step/s or prior to the extraction step/s (not depicted). In some embodiments, hydrolysis 124 is catalyzed by acid remaining in the aqueous stream exiting extraction 120A. Optionally, the acid is further diluted by an aqueous stream from chromatography 128 which is delivered to hydrolysis 124.

In some embodiments, the increasing includes chromatographic separation 128 conducted on the mixture after extracting 120A and 120B. In some embodiments, the polishing includes chromatographic separation 128 conducted on the mixture after extracting 120A and 120B. In some embodiments, the increasing and polishing include chromatographic separation 128 conducted on the mixture after extracting 120A and 120B. Optionally, chromatographic separation 128 generates a sugar cut and an oligomer cut. In some embodiments, the sugar cut serves as polished mixture 129 and the oligomer cut is enriched in oligomeric sugars. In some embodiments, the oligomer cut is enriched in HCl. In some embodiments, chromatographic separation 128 contributes to both increasing and to polishing. In some embodiments, the increasing includes acid-catalyzed hydrolysis 124 of oligomeric sugars and the oligomer cut is recycled to acid-catalyzed hydrolysis 124 (see arrow from 128).

In some embodiments the lignin stream contains sugars. The solid lignin stream is washed with at least a fraction of the back-extract or at least a fraction of the dilute back extract. A washed lignin stream and a wash liquor are generated. The wash liquor is included as at least a portion of the recycled HCl stream. In FIG. 23, this occurs as the back-extract flows from 132 via absorber 150 to second lignin wash 162. The solid lignin flows forward from second lignin wash 162 to de-acidification 164 and the wash liquor proceeds backwards to hydrolysis 110 via first lignin wash 160. In some embodiments, the wash liquor includes 70%, 75%, 80%, 85%, 90% or 95% weight/weight, or intermediate or greater percentages of the sugars originally present in the lignin stream (prior to washing). In some embodiments, the solid lignin stream is washed with at least a portion of the mixture of water and HCl from evaporating 111 (e.g. at 162 and/or 160). In some embodiments, the at least a portion of the mixture of water and HCl passes through absorber 150 prior to washing the lignin. Exemplary methods for washing of a lignin stream with a re-cycled HCl stream are described in greater detail in PCT/IL2011/000424 (incorporated herein by reference for all purposes). De-acidified lignin 165 contains less than 0.5%, less than 0.3% or less than 0.2% weight/weight HCl.

In some embodiments, at least a fraction of the back-extract from 132 is treated in an evaporation module 145. Depicted exemplary evaporation module 145 includes at least one low-pressure evaporator 140 and at least one high-pressure evaporator 142. In some embodiments, evaporation module 145 generates a sub-azeotropic acid condensate, and super-azeotropic gaseous HCl and the recycled HCl stream includes the gaseous HCl. Optionally, low-pressure evaporator 140 generates a sub-azeotropic acid condensate. Optionally, high-pressure evaporator 142 generates super-azeotropic gaseous HCl. In some embodiments, the sub-azeotropic acid condensate contains HCl in an amount up to 2%, 1%, 0.1% or 0.01% weight/weight on as is basis. In some embodiments, the recycled HCl stream includes the gaseous HCl from 142 (e.g. after absorption into an aqueous solution at absorber 150).

In some embodiments, the solid lignin stream is washed with another fraction of the back-extract to generate a washed lignin stream and a wash liquor. In some embodiments, this other fraction includes gaseous HCl from 142 which joins the back-extract from 132 at absorber 150 and proceeds to second lignin wash 162. In some embodiments, this other fraction includes at least a portion of the mixture of water and HCl from evaporating 111 which joins the back-extract from 132 at absorber 150 and proceeds to second lignin wash 162.

In some embodiments, evaporation module 145 generates a super-azeotropic aqueous HCl solution and a sub-azeotropic aqueous HCl solution. In some embodiments, the at least one low-pressure evaporator 140 generates the super-azeotropic aqueous HCl solution and the at least one high-pressure evaporator 142 generates the sub-azeotropic aqueous HCl solution.

In some embodiments, the lignin stream is deacidified 164 to form de-acidified lignin and a de-acidification HCl stream, and incorporating the de-acidification HCl stream into the recycled HCl stream. In FIG. 23 the de-acidification HCl stream proceeds via low-pressure distillation 140 to high-pressure distillation 142. In some embodiments, gaseous HCl from 142 is recycled to hydrolysis 110 via absorbers 150 and/or an aqueous flow of dilute liquid HCl is recycled to hydrolysis 110 via back extraction 130. In some embodiments, de-acidifying 164 is conducted in the presence of an azeotropic HCl solution and/or a super-azeotropic HCl solution formed as bottoms of low-pressure distillation 140 and/or a sub-azeotropic HCl solution formed as bottoms of high-pressure distillation 142. In some embodiments, the de-acidification HCl stream from 164 is treated in evaporation module 145 containing a high-pressure distillation to form a sub-azeotropic HCl solution and gaseous HCl and incorporating the gaseous HCl stream into the recycled HCl stream. In some embodiments, high-pressure distillation unit 142 forms the sub-azeotropic HCl solution and the gaseous HCl stream.

In some embodiments, back-extracting 130 and/or 132 is conducted with water and/or a dilute (sub-azeotropic) acid solution (e.g. formed as a condensate of low-pressure distillation 140) and/or a sub-azeotropic HCl solution (e.g. formed as bottoms of high-pressure distillation 142). In some embodiments, the back-extracting is conducted in two stages (130 and 132), a dilute stage and a concentrated stage. Optionally, the dilute stage is conducted with at least one of water and a dilute acid solution (e.g. formed as a condensate of low-pressure evaporation 140). In some embodiments, the concentrated stage is conducted with at least one of an azeotropic HCl solution, a super-azeotropic HCl solution (e.g. formed as bottoms of low-pressure evaporation 140) and a sub-azeotropic HCl solution (e.g. formed as bottoms of high-pressure evaporation 142).

In some embodiments, the extract from 120A goes first through a concentrated-stage back-extraction 130 forming a concentrated back-extract and then through a dilute-stage back-extraction 132 forming a dilute back-extract. In some embodiments, the extract includes sugars and the concentrated back-extract includes at least 70% of those sugars. Optionally, the method includes incorporating the concentrated back-extract into the recycled HCl stream (arrow from 130 to 110 in FIG. 23). In other exemplary embodiments of the invention the concentrated back-extract is incorporated into extraction 120A where it optionally contributes to sugar recovery (see FIG. 24). Optionally, incorporating the concentrated back-extract into the recycled HCl stream contributes to sugar recovery.

When back extraction is conducted in two stages (130 and 132), reducing a concentration of HCl in the back extractant in the second stage (132) contributes to an increase of efficiency of HCl extraction in that second stage.

In some embodiments, a fraction of the dilute back-extract is treated in evaporation module 145 containing at least one low-pressure evaporator 140 and at least one high-pressure evaporator 142 to generate a sub-azeotropic acid condensate and (super-azeotropic) gaseous HCl and the method includes incorporating the gaseous HCl into the recycled HCl stream. Optionally, low-pressure evaporator 140 generates the sub-azeotropic dilute acid condensate. Optionally, high-pressure evaporator 142 generates the gaseous HCl.

In some embodiments, the lignin stream is washed with a fraction of the dilute back-extract from 132 (after passage through absorber 150; FIG. 23) and/or with a fraction of the mixture from 111 (FIG. 24) to generate a washed lignin stream and a wash liquor containing sugars. In some embodiments, the washed lignin stream proceeds forward to de-acidification 164 and the wash liquor flows backwards so that it is incorporated into the recycled HCl stream arriving at hydrolysis 110.

In some embodiments, the solid lignin stream includes sugars, and the solid lignin stream is washed with a fraction of dilute back-extract from 132. Optionally, the method includes absorbing HCl in the fraction of dilute back-extract from 132 prior to the washing. In some embodiments the method includes absorbing HCl (150) in at least a portion of the mixture from 111 prior to washing (see FIG. 24).

In some embodiments, the method includes contacting super-azeotropic HCl with a concentrated HCl stream to generate an HCl solution of intermediate concentration and/or the method includes contacting sub-azeotropic HCl with a concentrated HCl stream to generate an HCl solution of intermediate concentration. In some embodiments, the concentrated HCl stream is a gaseous stream (e.g. from 142 and/or from 111) and the contacting includes absorption in a gas-liquid absorber (e.g. at 150). In some embodiments, the method includes contacting the evaporated mixture of water and HCl from said hydrolysate produced at 111 with at least one other HCl stream. In some embodiments, the method includes washing 162 the solid lignin stream with the HCl solution of intermediate concentration (e.g. from 150).

Additional Exemplary Method

Referring again to FIG. 23, some embodiments relate to a method including hydrolyzing 110 a lignocellulosic material with a recycled HCl stream containing wash liquor (optionally a lignin wash liquor). In some embodiments, hydrolysis 110 forms an aqueous hydrolysate and a solid lignin stream. Optionally, the hydrolysate includes a sugar mixture and HCl at more than 20%, 25%, 26%, 27%, 28%, 29%, 30%, 31%, 32%, 33%, 34% or 35% weight/weight HCl/[HCl and water] and/or the lignin stream contains HCl more than 25%, 26%, 27%, 28%, 29%, 30%, 31%, 32%, 33%, 34% or 35% weight/weight HCl/[HCl and water] and sugars.

In some embodiments, the method includes extracting (120A and/or 120B) the hydrolysate with a recycled extractant (optionally de-acidified) including an S1 solvent. In some embodiments, extraction involves at least two extraction steps (120A and 120B are depicted) to form an extract containing more than 20% or more than 25% weight/weight HCl/[HCl and water]. In some embodiments, the extraction is conducted in a single extraction step.

Optionally, the method includes increasing a monomeric sugar to oligomeric sugar ratio in the sugar mixture and polishing the sugar mixture to produce a polished mixture containing at least 70% monomeric sugars out of total sugars and less than 1% weight/weight HCl (e.g. by secondary hydrolysis 124 and/or by chromatography 128).

In some embodiments, the method includes back-extracting (130 and/or 132) the extract with an aqueous solution to form a de-acidified extractant. In some embodiments, back-extraction involves at least two back-extraction stages (130 and 132). Optionally, one of these back extractions is a concentrated stage (130) forming a concentrated back-extract and an HCl-depleted extract and the other is a dilute stage (132) forming a dilute back-extract and a de-acidified extractant.

In some embodiments, the method includes washing the solid lignin stream with a lignin washing stream containing at least a fraction of the back-extract from 132 to produce a washed lignin stream and a wash liquor. In some embodiments, the washing stream passes through absorber 150 where the HCl concentration is increased by contact with gaseous HCl.

In some embodiments, the method includes de-acidifying 164 the washed lignin stream to form de-acidified washed lignin 165 and a de-acidification HCl stream (arrow from 164 to 140).

In some embodiments, the method includes evaporating an aqueous LP-HCl solution (i.e. feed to 140 from 132) in at least one low-pressure evaporator 140 to generate a sub-azeotropic dilute acid condensate and a super-azeotropic aqueous HCl solution and evaporating an aqueous HP-HCl solution (i.e. feed to 142 from 140) in at least one high-pressure evaporator 142 to generate gaseous HCl and sub-azeotropic aqueous HCl solution. In some embodiments, the aqueous LP-HCl solution includes the sub-azeotropic HCl solution and/or dilute back-extract and/or the de-acidification HCl stream. In some embodiments, the aqueous HP-HCl solution includes the super-azeotropic HCl solution and/or the de-acidification HCl stream or the dilute back-extract. In some embodiments, concentrated back-extraction stage 130 employs the super-azeotropic solution from low-pressure evaporation 140 or the sub-azeotropic solution from high-pressure evaporation 142 as a back extractant. In some embodiments, the sub-azeotropic acid condensate from low-pressure evaporation 140 serves as a back extractant in the dilute stage 132 of the back-extracting.

In some embodiments, the method includes pre-evaporating 111 a mixture of water and HCl from the hydrolysate prior to the extracting (120A and/or 120B). Various possible uses of this mixture and/or their effects on energy consumption at evaporation module 145 are as described hereinabove. In some embodiments, at least a portion of the mixture of water and HCl from evaporating 111 washes solid lignin (e.g. at 162 and/or 160). In some embodiments, this washing occurs after the at least a portion of the mixture passes through absorber 150.

In some embodiments, the lignin washing stream includes a fraction of the dilute back-extract from 132 and a fraction of said gaseous HCl generated in high-pressure evaporation 142 (arrow from 150 to 162).

Figure 24:
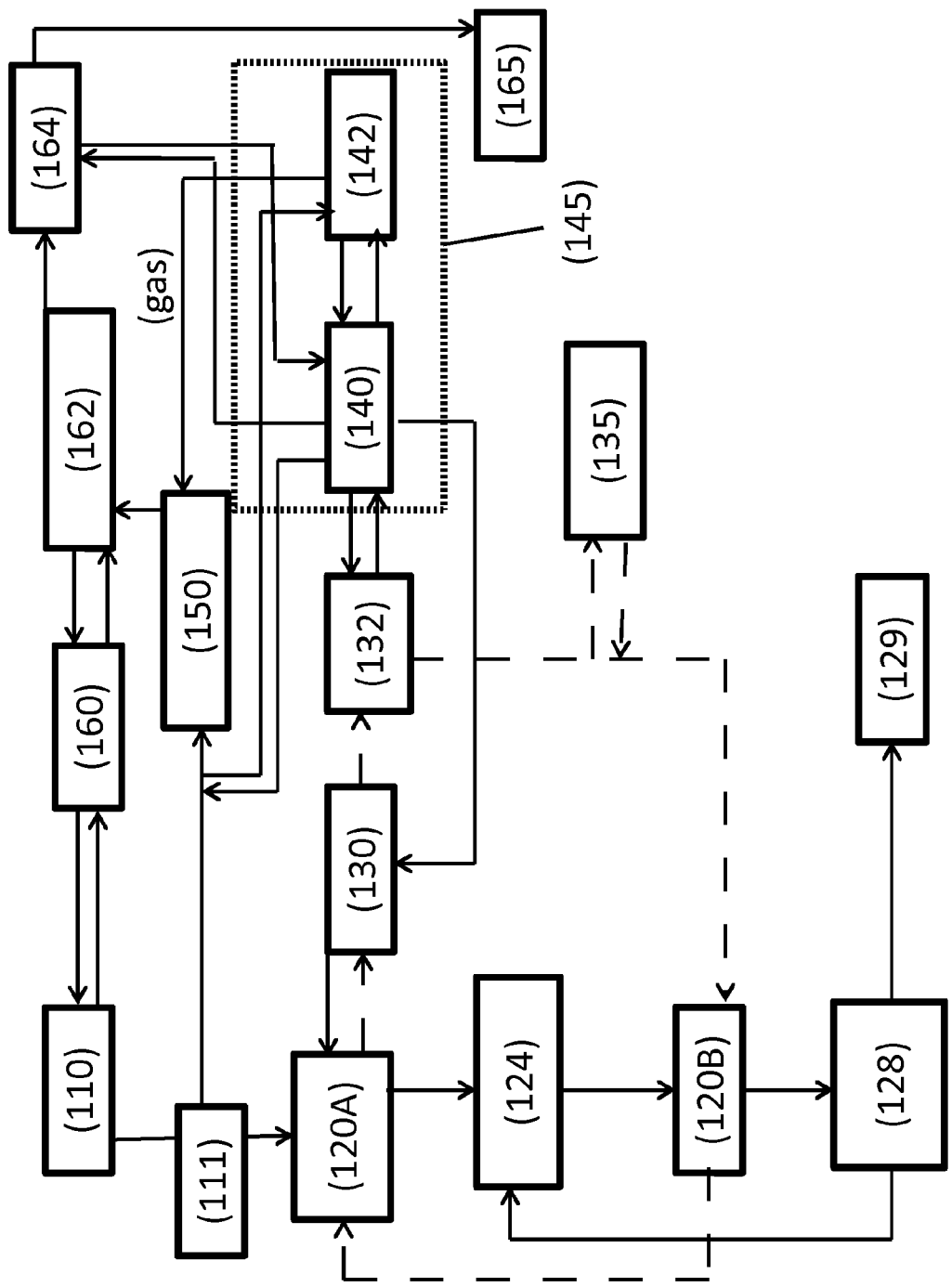
FIG. 24 is a simplified flow scheme according to some alternative lignocellulosic biomass processing and acid recovery embodiments of the invention.

In some embodiments, the method includes contacting super-azeotropic HCl with a concentrated HCl stream to generate an HCl solution of intermediate concentration. In some embodiments, the method includes contacting sub-azeotropic HCl with a concentrated HCl stream to generate an HCl solution of intermediate concentration. In some embodiments, the concentrated HCl stream is a gaseous stream (e.g. from 142) and the contacting includes absorption in a gas-liquid absorber (e.g. at 150). In some embodiments, the method includes contacting the evaporated mixture of water and HCl from the hydrolysate (arrow from 111 to 150; FIG. 23 and/or to 142; FIG. 24) with at least one other HCl stream. In some embodiments, washing the solid lignin stream (e.g. at 162) employs the HCl solution of intermediate concentration (e.g. from 150).

Additional Exemplary Flow Paths

Referring now to FIG. 24, in some embodiments, streams of HCl/water are delivered from low pressure evaporation unit 140 to back extraction 130 and/or lignin-deacidification 164. In some embodiments, a stream of HCl/water is delivered from low pressure evaporation unit 140 to absorber 150 (e.g. by mixing with the stream from 111 as depicted).

Exemplary System

Referring again to FIG. 23, some embodiments of the present invention provides a system including an absorber 150 adapted to receive a flow of gaseous HCl from an evaporation module 145, optionally from high-pressure evaporation unit 142 and absorb the gaseous HCl into an aqueous solution to produce a concentrated HCl solution. In some embodiments, absorber 150 absorbs a mixture of HCl and water from pre-evaporation module 111.

In some embodiments, the system includes a lignin de-acidification module (160+162+164) adapted to contact the concentrated HCl solution (from 150) with an acidic lignin stream in a countercurrent flow. In some embodiments, the system includes a back extraction module (132 and/or 130) adapted to provide the aqueous solution by back-extracting an S1 solvent extract of an acid hydrolysate of lignocellulosic material. In some embodiments, the system includes an extraction module (120A and/or 120B) adapted to provide the S1 solvent extract to back extraction module (132 and/or 130). In some embodiments, the system includes a hydrolysis vessel 110 adapted to receive a lignocellulosic material and output an acidic lignin stream and a hydrolysate containing sugars and HCl. In some embodiments, the system includes a solvent recycling loop (see dashed arrow from 132 to 120B, with or without purification 135. In some embodiments, the system includes an evaporation module 145 including at least one low-pressure evaporation unit 140 and at least one high-pressure evaporation unit 142. In some embodiments, the system includes a pre-evaporation module 111 configured to evaporate a mixture of water and HCl from the hydrolysate and deliver at least a portion of the mixture to absorber 150. In some embodiments, low-pressure evaporation unit 140 is adapted to produce a sub-azeotropic acid condensate and a super-azeotropic HCl solution from a back-extract provided by back extraction module 132. In some embodiments, high-pressure evaporation unit 142 is adapted to produce the gaseous HCl and a sub-azeotropic HCl solution.

Exemplary Evaporation Considerations

In some embodiments, low-pressure evaporation 140 is conducted at about 50° C. and about 100 millibar (bottoms). In some embodiments, high-pressure evaporation 142 is conducted at about 135° C. and about 4 bar (bottoms).

XII. Alternative Cellulose Sugar Refining Embodiments

Figure 26A:
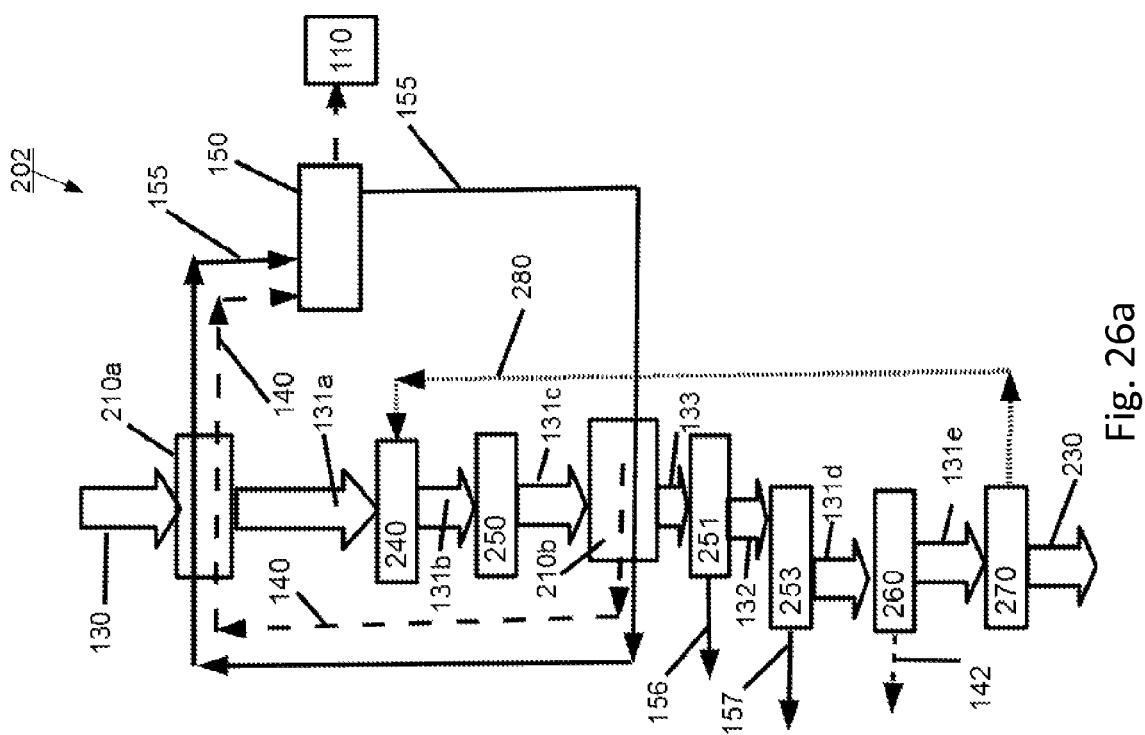
FIG. 26a is a schematic overview of a de-acidification system in accord with some exemplary cellulose sugar refining embodiments of the invention.

FIG. 26a is a schematic representation of an exemplary embodiment of a sugar refining module indicated generally as 202. This specification refers to HCl as an exemplary acid, although other acids could be employed. Reference is made specifically to HCl as an example in this section. Other acids (e.g. sulfuric acid) can be used.

Module 202 is a system including a secondary hydrolysis unit 240 adapted to receive an input stream 131a including a sugar mixture in a super azeotropic HCl aqueous solution, and increase a ratio of monomeric sugars to oligomeric sugars in an output stream 131b and a chromatography component 270 adapted to separate said output stream to produce a monomer cut 230 enriched in monomeric sugars and an oligomer cut 280 enriched in oligomeric sugars. In some embodiments, stream 131a includes at least 20% weight/weight sugar in an aqueous solution of HCl. In some embodiments, oligomer cut 280 is recycled to secondary hydrolysis unit 240. Optionally, this recycling contributes to a reduction in acid and/or sugar concentration during hydrolysis.

In some embodiments, the separation of monomers from oligomers is not absolute. In some embodiments, monomer cut 230 includes at least 65%, 70%, 75%, 80%, 85%, 90%, 95%, 97.5% or 99% weight/weight (or intermediate or greater percentages) monomeric sugars as a percentage of total sugars. In other embodiments, oligomer cut 280 includes at least 65%, 70%, 75%, 80%, 85%, 90%, 95%, 97.5% or 99% weight/weight (or intermediate or greater percentages) oligomeric sugars as a percentage of total sugars. In some embodiments, oligomer cut 280 includes residual acid.

Figure 25:
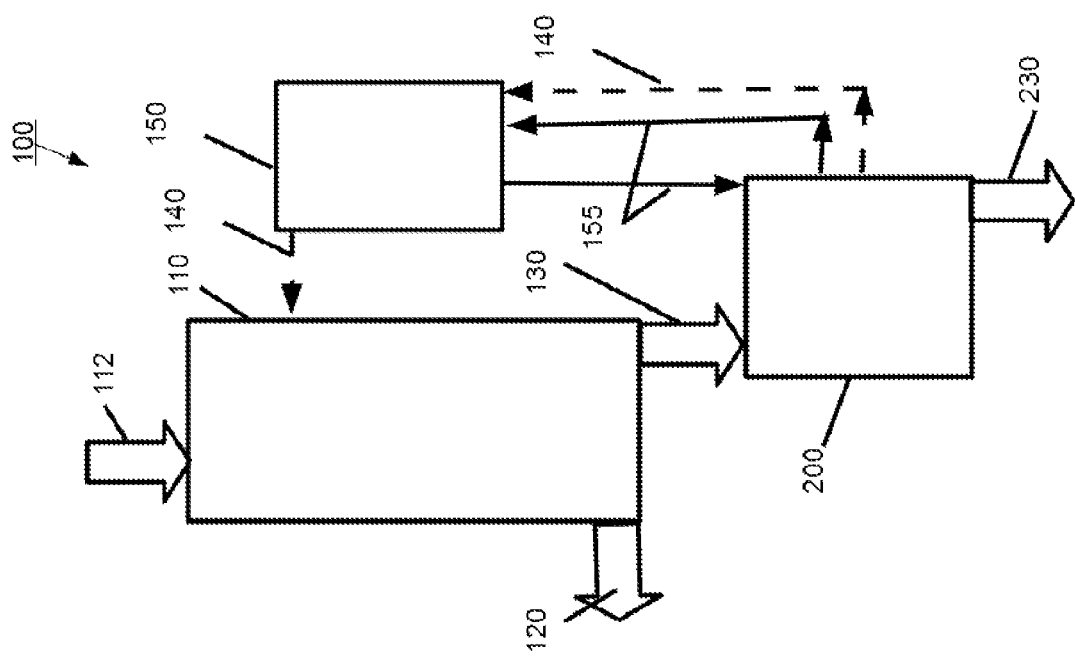
FIG. 25 is a schematic overview of an exemplary hydrolysis system which produces a lignin stream that serves as an input stream in various exemplary embodiments of the invention.

In some embodiments, the system includes an acid extractor (two extractors 210a and 210b are depicted) adapted to contact at least one of input stream 130 and output stream 131b or 131c with an extractant containing an S1 solvent 155. In some embodiments, removal of acid by extraction contributes to a reduction in re-oligomerization of monomers and/or to a reduction in damage to resins and/or to an ability to recycle acid to main hydrolysis reactor 110 (FIG. 25). In some embodiments, the acid extractor includes at least two acid extractors 210a and 210b arranged in series. In some exemplary embodiments, the arrangement is as depicted in the figure so that secondary hydrolysis reactor 240 is disposed between any pair of the at least two acid extractors (210a and 210b).

In some embodiments, the system includes a filtration unit 250 positioned to filter output stream 131b from secondary hydrolysis unit 240. In some embodiments, the system includes an ion exchange component 251 adapted to remove residual acid 156 from output stream 131c or 133. In some embodiments, provision of acid extractor 210b contributes to a reduction in the amount of residual acid at 156. In some embodiments, the system includes an evaporation unit 260 disposed between secondary hydrolysis unit 240 and chromatography component 270. Evaporation unit 260 increases a total sugar concentration in stream 131e entering chromatography unit 270. Optionally, the higher concentration of sugars contributes to an efficiency of separation of monomers from oligomers at 270. In some embodiments, the system includes an evaporation unit (290; FIG. 26c) disposed upstream of said secondary hydrolysis reactor. Unit 290 is described in greater detail in the context of FIG. 26c.

Module 202 can also be described as a system including an acid extractor 210 (two extractors 210a and 210 b are depicted in the drawing) and a chromatography component 270. In some embodiments, chromatography component 270 employs simulated moving bed (SMB) and/or sequential simulated moving bed (SSMB) technology. In some embodiments, 12 columns operating in an SSMB mode are used. In other exemplary embodiments of the invention, larger or smaller numbers of columns are employed. In some embodiments, chromatography component functions to separate an oligomer cut 280 enriched in oligomeric sugars from a monomer cut 230 enriched in monomeric sugars (enrichment here being relative to total sugars).

Depicted exemplary acid extractors 210a and 210b are adapted to extract acid from an input stream 130 an input stream containing a sugar mixture in a super azeotropic HCl aqueous solution. In some embodiments, the sugar mixture includes at least 20%; at least 22%; at least 24%; at least 26% or at least 28% weight/weight sugar in a super azeotropic HCl aqueous solution. In some embodiments, the super azeotropic HCl aqueous solution includes 22, 23, 24, 25, 26, 27, 28, 29, 30% weight/weight or intermediate or greater percentages of % HCl/[HCl and water]. According to other exemplary embodiments of the invention the super azeotropic HCl aqueous solution includes less than 40%, 38%, 36%, 34% or less than 32% weight/weight HCl/[HCl and water]. In some embodiments, adaptation includes regulation of relative flow rates and/or extractant composition and/or temperature conditions. In some embodiments, extraction is with an extractant including an S1 solvent (as defined hereinabove) to produce an output sugar stream 131a. In some embodiments, the S1 solvent includes at least one of n-hexanol and 2-ethyl-hexanol. In some embodiments, the S1 solvent is hexanol and the extraction is conducted at a temperature of 45 to 55° C., optionally about 50° C. In FIG. 26a the extractant is depicted as solvent 155 for clarity. In actual practice, materials in addition to S1 solvent may be present in the extractant. In some embodiments, these additional materials result from extractant recycling.

Chromatography component 270 is adapted to separate sugars from output stream 131a to produce an oligomer cut 280 enriched in oligomeric sugars and a monomer cut 230 enriched in monomeric sugars. (relative to input stream to chromatography component 270). In some embodiments, chromatography component 270 includes an ion exchange resin. Exemplary adaptations include resin choice, flow rate and elution conditions.

In some embodiments, acid extractor (210+210b) produces a counter current flow between input stream 130 and extractant including solvent 155. At some point during the extraction, HCl 140 (dashed arrows) is separated from stream 130 and begins to flow together with solvent 155 (solid arrows) in the extractant. In some embodiments, the resultant S1/HCl liquid phase containing more than 20%, 22%, 24%, 26%, 28%, 30%, 32%, 34%, 36%, 38% or 40% weight/weight [HCl/(HCl and water)]. Optionally, the resultant S1/HCl liquid phase containing less than 50%, less than 48%, less than 46%, less than 44% or less than 42% weight/weight [HCl/(HCl and water)].

In some embodiments, the counter current flow is created by delivering extractant containing solvent 155 from recovery module 150 to a bottom end of acid extractor 210b while input stream 130 is delivered to a top end of acid extractor 210a. In some embodiments, one or more pumps (not depicted) deliver extractant containing solvent 155 and/or input stream 130 to extractor(s) 210. In some embodiments, acid extractor 210 includes at least one pulsed column. Optionally, the pulsed column is a Bateman pulsed column (Bateman Litwin, Netherlands).

The Bateman pulsed column includes a large diameter vertical pipe filled with alternating disc & doughnut shaped baffles which insure contact between descending stream 130 and ascending extractant 155 as they pass through the column. The solvent in extractant 155 removes at least 35%, 40%, 45%, 50%, 55%, 60%, 65%, 70%, 75%, 80%, 85%, 90% or at least 92% weight/weight or intermediate or greater percentages of acid 140 from stream 130.

In some embodiments, sugars exit extractor(s) 210 in an acid depleted stream 131a and enter secondary hydrolysis module 240.

The various exemplary embodiments of the invention deal with both sugar refining, and considerations relating to recycling of HCl and/or solvent. In order to prevent confusion, the following description will follow sugar stream 130 as it proceeds through module 202 to emerge as monomer cut 230. In some embodiments, monomer cut 230 is substantially free of acid (e.g. less than 0.1 or less than 0.05% on as is basis.). In other embodiments, monomer cut 230 includes less than 0.9%, 0.8%, 0.7%, 0.6%, 0.5%, 0.4%, 0.3%, 0.2% or even less than 0.1% weight/weight HCl on as is basis.

Returning now to a sequential description of input sugar stream 130 as it moves through module 202: stream 130 flows through extractor 210 (depicted here as 210a and 210b) and is extracted with an extractant including both an S1 solvent 155 and HCl 140. In some embodiments, stream 130 includes at least 20% total sugars and a super azeotropic concentration of HCl in an aqueous solution prior to extraction at 210a. These total sugars may include as much as 30, 40, 50, 60 or even 70% (weight basis) oligosaccharides or intermediate or greater percentages.

In some embodiments, the sugars emerge from extractors 210a and 210b as an acid reduced stream 131a. Optionally, extraction at 210 removes water and/or HCl so that sugar concentration at 131a is higher than at 130. The ratio of monomeric sugars to oligomeric sugars remains substantially unchanged at this stage. The HCl concentration has been reduced by extraction at 210. HCl 140 and S1 solvent 155 exit extractor 210a to recovery module 150. In some embodiments, HCl 140 and S1 solvent 155 are subjected to distillation. Recovery module 150 recycles separated HCl (dashed arrow) to hydrolysis reactor 110 and sends separated solvent 155 to extractor 210b. In some embodiments, recovery module 150 employs back extraction as described in section XI.

In some embodiments, acid reduced stream 131a flows to secondary hydrolysis reactor 240 where it is optionally mixed with an oligomer cut 280 (finely dashed arrow) from chromatography unit 270. In some embodiments, hydrolysis reactor 240 is disposed between acid extractor(s) 210 and chromatography component 270.

Since oligomer cut 280 is more dilute with respect to both total sugars and HCl than stream 131a, this mixing serves to reduce the sugar concentration (and HCl concentration) in secondary hydrolysis 240. Optionally, additional aqueous streams are added at this stage to further reduce the total sugar concentration and/or to reduce the acid concentration and/or to increase the proportion of oligomeric sugars. Optionally, reduction of sugar concentration contributes to a lower equilibrium concentration of oligomers.

For example, oligomer cut 280 caries additional sugars, primarily oligomeric sugars. The effect of this mixing is that the HCl concentration is reduced to 1.0%, 0.9%, 0.8%, 0.7%, 0.65, 0.5% weight/weight or less on as is basis. Optionally, the HCl concentration is reduced to between 0.3% to 1.5%, between 0.4%-1.2% or between 0.45%-0.9% weight/weight. In some embodiments, the total sugar concentration at 240 is reduced to below 25%, below 22%, below 19%, below 16%, below 13% or even below 10% weight/weight. In some embodiments, oligomer cut 280 functions as an oligomeric sugar return loop.

Following this mixing, the resultant sugar solution in dilute HCl is subject to a secondary hydrolysis reaction in module 240. In some embodiments, this secondary hydrolysis continues for at least 1, at least 2 or at least 3 hours or intermediate or longer times. Optionally, this secondary hydrolysis lasts 1 to 3 hours, optionally about 2 hours. In some embodiments, the temperature is maintained below 150, 140, 130, 120, 110, 100 or below 90° C. or intermediate or lower temperatures. In some embodiments, the temperature is maintained between 60° C. to 150° C., between 70° C. to 140° C. or between 80° C. to 130° C. In some embodiments, the secondary hydrolysis conducted in module 240 results in monomeric sugars proportion of 80 to 90%, optionally 85 to 88%, optionally about 86% of the total sugars. In some embodiments, the secondary hydrolysis conducted in module 240 results in monomeric sugars proportion of at least 72%, 74%, 76%, 78%, 80%, 82%, 84%, 86%, 88% or even at least 90% weight/weight of the total sugars. In some embodiments, the resultant secondary hydrolysate 131b contains at least 20%, 22, 24%, 26%, 28%, 30%, 32%, 34%, 36%, 38%, 40%, 42%, 44%, 46%, 48% or 50% weight/weight total sugars.

Although a single secondary hydrolysis reactor 240 is depicted between the acid extractor (210a and 210b) and chromatography component 270 for simplicity, one or more hydrolysis reactors 240 can be provided.

In some embodiments, hydrolysis reactor(s) 240 operate at 95, 100, 105, 110, 115, 120 or 125° C. or intermediate or lower temperatures. In some embodiments, hydrolysis reactor(s) 240 operate at a pressure of 1.8, 1.9, 2.0, 2.1 or 2.2 bar. In some embodiments, the hydrolysis reaction continues for 1 to 3 hours, 1.5 to 2.5 hours or 1.7 to 2 hours. In some embodiments, the hydrolysis reaction at 240 is conducted at 95° C. for about 2 hours at atmospheric pressure. In other exemplary embodiments of the invention, the hydrolysis reaction at 240 is conducted at 125° C. for about 1.7 hours at about 2 bar.

In some embodiments, the resultant secondary hydrolysate 131b leaves module 240 and proceeds to filtration unit 250. In some embodiments, filtration unit 250 is positioned to filter an exit stream from secondary hydrolysis reactor 240. In some embodiments, filtration unit 250 removes fine particles from secondary hydrolysate 131b. In some embodiments, these particles are periodically washed off the filter and sent back to extractor(s) 210, optionally using a mixture of acid (e.g. HCl), S1 solvent and water. In some embodiments, filtration unit 250 includes microfiltration components. In some embodiments, filtered secondary hydrolysate 131c proceeds to anion exchanger 251 disposed between secondary hydrolysis reactor 240 and chromatography component 270.

In some embodiments, anion exchanger 251 includes weak base anion exchange resin (WBA) and/or an amine including at least 20 carbon atoms. In some embodiments, anion exchanger 251 separates residual acid (e.g. HCl) 156 from stream 131c. Stream 156 contains, according to alternative embodiments, the acid, its salt or a combination thereof. In some embodiments, the anion exchanger at 251 is an amine and the salt in 156 includes amine chloride. In some embodiments, use of an amine as an anion exchanger at 251 contributes to removal of color of from sugars and/or contributes to a reduction in downstream sugar polishing.

In some embodiments, regenerating the anion exchanger is by treating the HCl-loaded anion exchanger with a base. In some embodiments, the base selected from hydroxides, bicarbonates and carbonates of alkali metals and ammonia. In some embodiments, the regeneration forms a chloride salt of the alkali metals or ammonia and the salt is treated to reform HCl and the base. In some embodiments, the base is an ammonium base and ammonium chloride is formed and is used at least partially as a fertilizer.

Optionally, residual HCl or salt 156 is discarded as waste. In some embodiments, greater than 80, 82, 84, 86, 88, 90, 92, 94, 96 or greater than, 98% weight/weight of HCl entering anion exchanger 251 exits in stream 156. In some embodiments, in some embodiments the HCl concentration in stream 132 is less than 2.5%, 2%, 1.5%, 1.0%, 0.5%, 0.3%, 0.2%, 0.1%, less than 0.05% or less than 0.01% weight/weight on as is basis.

In some embodiments, anion exchanger 251 includes an amine and operates at temperature(s) of 40 to 60° C., optionally about 50° C. In some embodiments, stream 132 which exits anion exchanger 251 proceeds to a cation exchanger module 253. In some embodiments, cation exchanger module 253 separates divalent cations (e.g. Mg++ and/or Ca++) from the sugar stream. In some embodiments, sugars 131d are eluted separately from a divalent cation stream 157. In some embodiments, anion exchanger 251 and/or cation exchanger module 253 dilute the concentration of total sugars in stream 131d which exits cation exchanger module 253. In some embodiments, sugar stream 131d is concentrated by evaporation unit 260. In some embodiments, evaporation unit 260 is positioned between anion exchanger 251 and chromatography component 270. In some embodiments, evaporation unit 260 operates at a temperature of 60, 70, 80 or 90° C. or intermediate or higher temperatures. In some embodiments, evaporation unit 260 operates at a pressure of 150, 250, 350, 450, 550, 650, 750, 850 or 950 mbar or intermediate or greater pressures. In some embodiments, temperature and/or pressure conditions vary in a controlled manner in evaporation unit 260 during evaporation. Optionally, contents of unit 260 are divided into portions and each portion is evaporated under different conditions. In some embodiments, heat from a previous portion evaporates a next portion.

Evaporation unit 260 removes water 142 from stream 131d. Optionally, at least a portion of water 142 from evaporation unit 260 serves as an eluent for chromatography component 270 and/or as a diluent at secondary hydrolysis module 240. Evaporation of water causes sugar concentration to increase. This increase in sugar concentration can contribute to oligomerization (re-oligomerization) of sugars, especially if HCl is present. In some embodiments, removal of HCl 140 and/or 156 contributes to a reduction in the re-oligomerization. Exemplary ways to reduce such re-oligomerization are discussed in "Exemplary equilibrium considerations" of this section.

Concentrated filtered secondary hydrolysate 131e leaves evaporation unit 260 with at least 32%, optionally at least 35% weight/weight sugars. In some embodiment, 131d leaves evaporation unit 260 with between 40% to 75%, between 45% to 60% or between 48% to 68% weight/weight sugars. In some embodiments, an increase in sugar concentration contributes to an increase in efficiency of chromatographic separation.

In some embodiments, concentrated filtered secondary hydrolysate 131e leaves evaporation unit 260 with at least 30, 40, 50 or 60% weight/weight or greater percentages of total sugars. Concentrated filtered secondary hydrolysate 131e proceeds to chromatography component 270, which optionally includes an ion exchange resin. Concentrated filtered secondary hydrolysate 131e includes a lower concentration of acid than hydrolysate 131c due to removal of HCl 156 at 251. In some embodiments, concentrated filtered hydrolysate 131e includes less than 1%, less than 0.9%, less than 0.8%, 0.7%, 0.6%, 0.5%, 0.4%, 0.3%, 0.2%, 0.1% or 0.05% weight/weight HCl on as is basis. "Exemplary equilibrium considerations" is described in this section.

Stream 131e is fed onto the chromatography resin and eluted using an aqueous solution. In some embodiments, aqueous solution 142 delivered from evaporator 260 can serve as an eluting stream. This elution produces an oligomer cut 280 (fine dashed arrows to secondary hydrolysis module 240) and a monomer cut 230.

Chromatographic separation 270 includes contacting with the sugar mixture and with eluting stream. The eluting stream is water or an aqueous solution. In some embodiments, the aqueous solution is formed in another stage of the process. In some embodiments, an aqueous stream of hemicellulose sugars is used. Optionally, the aqueous stream of hemicellulose sugars is a product of pretreating lignocellulosic material with hot water. Exemplary methods for pretreating lignocellulosic material with hot water are described in PCT/US2012/064541 (incorporated herein by reference for all purposes).

In some embodiments, a cation exchange resin is employed for chromatographic separation 270. According to some embodiments, the resin is loaded at least partially with cations of alkaline metals or ammonium.

In some embodiments, monomer cut 230 contains 80%, 85%, 90%, 95% or 97.5% weight/weight or intermediate or greater percentages of the sugars which were originally present in mixture 130. In some embodiments, these sugars are about 80 to 98%, optionally about 89 to 90% monomeric sugars and about 2 to 20%, optionally about 10 to 11% weight/weight oligomeric sugars. In some embodiments, these sugars are at least 80%, at least 82, at least 84%, at least 86%, at least 88%, at least 90%, at least 92%, at least 94%, at least 96, at least 98% weight/weight or intermediate or greater percentages monomeric sugars out of total sugars. In some embodiments, monomer cut 230 contains at least 20%, at least 22, at least 24%, at least 26%, at least 28%, at least 30%, at least 32%, at least 34%, at least 36%, at least 38%, at least 40%, at least 42%, at least 44%, at least 46%, at least 48% or at least 50% weight/weight total sugars. Any sugars that remain in the oligomer cut can be recovered to a great extent in subsequent rounds of recycling. In some embodiments, sugars that remain in the oligomer cut can be converted from an oligomer rich mixture to a mixture that is primarily monomeric sugars.

Although the refining process has been described as a linear progression for the sake of clarity, in practice it can be both continuous and/or cyclical in part.

Optional Additional Refining Components

FIG. 26b depicts additional optional components of module 200 depicted generally as module 204. Optional module 204 further refines output 230 of module 202. Depicted exemplary module 204 includes a desolventizer 272 adapted to remove any remaining residual solvent 155 from monomer cut 230. This solvent can be recovered by sending it to recovery module 150, or to extraction unit 210 (210a is indicated in the drawing). The sugars continue to purification media 274 adapted to remove impurities likely to adversely affect downstream fermentation. In some embodiments, purification media 274 includes granular carbon, optionally provided in a column. Optionally, the granular carbon removes impurities including color bodies, color precursors, hydroxymethylfurfural, nitrogen compounds, furfural, and proteinaceous materials. Each of these materials has the potential to inhibit fermentation.

In some embodiments, purification media 274 includes an ion exchange resin. In some embodiments, ion exchange resin removes any anions and/or cations. In some embodiments, these anions and/or cations include amino acids, organic acids and mineral acids. Optionally, the ion exchange resin includes a combination of strong acid cation resin and weak base anion resins.

In some embodiments, purification media 274 polishes the sugars with a mixed bed system using a combination of strong cation resin and strong base anion resin. In some embodiments, the sugars concentration at this stage is about 34 to 36%. In some embodiments, a concentrator 276 adapted to increase a solids content of monomer cut 230 is employed. Concentrator 276 optionally evaporates water. In some embodiments, resultant refined sugar output 230' is a solution of 77 to 80% sugar with 70% or more, 80% or more, 90% or 95% weight/weight or more of the sugars present as monomers.

In some embodiments, a resultant product (e.g. resulting from 230) includes at least 50%, 60%, 65%, 70% or 75% weight/weight sugar. In some embodiments, the resultant product includes at least 92%, 94%, 96%, 97% or 98% weight/weight monomeric sugars relative to total sugars. In some embodiments, the resultant product includes less than 0.3%, 0.2%, 0.1% or 0.05% weight/weight HCl on as is basis.

Exemplary Optional Pre-Evaporation Module

FIG. 26c depicts additional optional components of module 200 depicted generally as module 205. In those embodiments which include it, optional module 205 is positioned upstream of extractor 210a (FIG. 26a). In some embodiments, input stream 130 (as described above) enters pre-evaporation module 290. Pre-evaporation optionally includes distillation and/or application of vacuum pressure. Pre-evaporation in module 290 produces a gaseous mixture 292 of HCl and water and a modified input stream 131g. In some embodiments, modified input stream 131g has a higher sugar concentration and a lower HCl concentration than input stream 130. For example, in some embodiments, module 290 increases the sugar concentration in the stream from 25% to 30% weight/weight. In some embodiments, module 290 decreases the HCl concentration from 33% to 27% weight/weight [HCl/(HCl and water)].

In some embodiments, module 290 operates at a temperature of 50 to 70° C., optionally about 55 to 60° C. In some embodiments, module 290 operates at a pressure of 100 to 200 mbar, optionally 120 to 180 mbar, optionally about 150 mbar. In some embodiments, evaporation at 290 produces a vapor phase with a higher HCl concentration than in feed stream 130. According to those embodiments, pre-evaporation at 290 decreases HCl concentration by at least 2%, 4%, 6%, 8%, 10%, 12%, 14% or 16% weight/weight relative to its concentration in 130. In some embodiments, pre-evaporation at 290 increases total sugar concentration by at least 2%, 4%, 6%, 8%, 10%, 12%, 14% or 16% weight/weight relative to its concentration in 130.

In some embodiments, the HCl concentration in the vapor phase from 290 is greater than 30, 35, 40, 42, 44, 46, 48, 50, 52, 54, 56, 58 or 60% weight/weight or intermediate or greater percentages [HCl/(HCl and water)].

According to those embodiments of the invention that include pre-evaporation module 290, stream 131g replaces 130 as an input stream for extractor 210a in FIG. 26a.

Exemplary Considerations in Use of an Amine Extractant as an Anion Exchanger

Figure 26D:
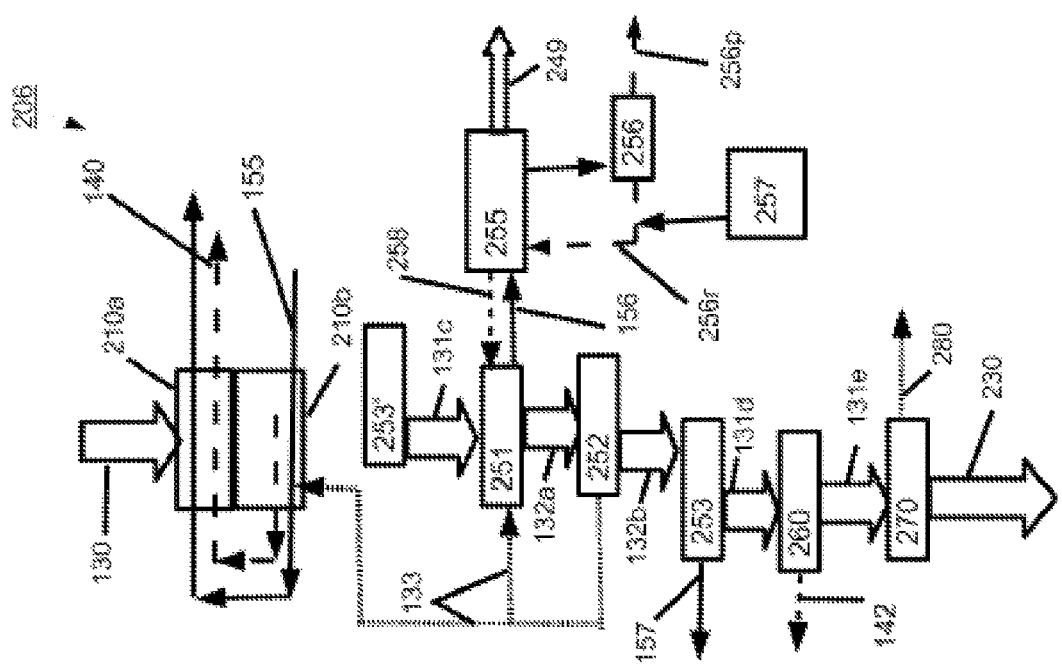
FIG. 26d is a schematic overview of a de-acidification system similar to that of FIG. 26a depicting optional additional or alternative components.

FIG. 26d depicts a de-acidification system similar to that of FIG. 26a with optional additional or alternative components indicated generally as 206. Numbers in FIG. 26d which are used also in FIG. 26a indicate like components or streams. Some items depicted in FIG. 26a and explained hereinabove are not depicted in FIG. 26d for clarity. The depicted exemplary configuration 206 is suitable for embodiments of the invention which employ an amine extractant at anion exchange 251.

In some embodiments, filtered secondary hydrolysate 131c contains 6 to 16%, 7 to 15%, 8 to 14%, 9 to 13% or 10 to 12% weight/weight sugars. In some embodiments, filtered secondary hydrolysate 131c contains less than 1.2%, 1.1%, 1.0%, 0.9%, 0.8% or 0.7% weight/weight HCl on an as is basis. In some embodiments, filtered secondary hydrolysate 131c contains more than 0.2%, 0.3%, 0.4% or 0.5% weight/weight HCl on an as is basis.

In some embodiments, the amine at 251 is provided as part of an extractant. For example, in some embodiments the extractant includes 40 to 70%, 45 to 65%, 48 to 60% or 50 to 55% amine by weight and also includes a diluent. Amines suitable for use in the extractant at 251 include tri-laurylamine (TLA; e.g. COGNIS ALAMINE 304 from Cognis Corporation; Tucson Ariz.; USA), tri-octylamine, tri-caprylylamine and tri-decylamine. All these are tertiary amines. In other exemplary embodiments of the invention, secondary and primary amines with at least 20 carbon atoms are employed. Diluents suitable for use in the extractant at 251 include long chain alcohols (e.g. hexanol and/or dodecanol). In some embodiments, the diluent contains additional components.

In some embodiments, an organic:aqueous phase ratio of the amine extractant (relative to the 131c aqueous phase) at 251 is between 1:1 to 1:4; between 1:1.2 to 1:3.5; between 1:1.4 to 1:3.0, optionally about 1:2. In some embodiments, the extraction with an amine at 251 occurs in 4 or less, 3 or less, 2 or less, or 1 stage(s). In some embodiments, each stage occurs in a mixer settler. In some embodiments, mixing in a given stage continues for less than 10 minutes, 8 minutes, 6 minutes, 4 minutes or 2 minutes or intermediate or shorter times. In some embodiments, in some embodiments settling in a given stage continues for less than 10 minutes, 8 minutes, 6 minutes, 4 minutes, 2 minutes or 1 minute or intermediate or shorter times. In some embodiments, the extraction with an amine at 251 occurs at 40° C. to 80° C.; 45° C. to 75° C.; 50° C. to 70° C. or about 60° C.

In some embodiments, sugar stream 132 (e.g. 132a in FIG. 26d) exiting 251 contains less than 1000 ppm, less than 800 ppm, less than 700 ppm, less than 600 ppm, less than 500 ppm, less than 400 ppm, less than 300 ppm, less than 200 ppm or less than 100 ppm HCl or intermediate or lower amounts of HCl. In some embodiments, sugar stream 132 (e.g. 132a in FIG. 26d) exiting 251 contains more than 20 ppm, more than 40 ppm, more than 60 ppm or more than 80 ppm or intermediate or greater amounts of HCl.

In some embodiments, extract 156 contains amine chloride. In some embodiments, extract 156 includes residual sugars. Optionally, these sugars are recovered by washing with water.

In some embodiments, sugar stream (raffinate) 132a exiting amine extraction 251 contains only small amounts of amine due to the low solubility of amine (e.g. TLA) in aqueous solution. Optionally, raffinate 132a is concentrated to about 40% to 80% (or saturation); about 45% to 75% (or saturation) or about 50% to 70%, optionally about 60% weight/weight sugars (evaporator 260) and/or treated on a cation exchanger 253 prior to chromatographic separation 270. In some embodiments, cation exchanger 253 removes amine (e.g. TLA) from raffinate 132b in stream 157.

In some embodiments, an optional stripping unit 252 evaporates residual hexanol 133 (used as a diluent at 251) from raffinate 132a. In some embodiments, recovered hexanol 133 is used in extraction 210b as depicted. In other exemplary embodiments of the invention, recovered hexanol 133 is used as part of the diluent in the extractant at 251 (not depicted). Hexanol depleted raffinate 132b proceeds to cation exchanger 253 and/or evaporation 260. Evaporation 260 increases the concentration of sugars to about 60 sugars % and/or removes any remaining hexanol.

Exemplary Amine Recovery by Back Extraction

Referring still to FIG. 26d, extraction with amine at 251 produces an extract 156 including a chloride salt of the amine. In some embodiments, back extraction 255 produces regenerated amine 258, and salts 256. Back extraction 255 employs a base 257 (e.g. Na2CO3; NH3 or NaOH). In some embodiments, Na2CO3 serves as base 257 and CO2 249 is produced. In other exemplary embodiments of the invention, NaOH serves as base 257 and NaOH is regenerated by water splitting electro-dialysis of salts 256 (NaCl). Contacting of an aqueous basic solution (base 257 diluted with a recycled portion salts 256 (indicated as 256r) with extract 156 transforms amine chloride to regenerated amine 258 and a chloride salt (e.g. NaCl; 256). If Na2CO3 serves as the base, CO2 249 is also produced. Since the amine (e.g. TLA) is immiscible with water, regenerated amine 258 separates from the aqueous phase in back extraction 255 and can be easily returned to anion exchange 251 for another round of amine extraction. Excess salts 256 are removed as a product stream 256p.

In some embodiments, salts 256 are recovered from back extraction 255 as an NaCl solution of 10%, 12%, 14%, 16%, 18% or 20% weight/weight or intermediate or greater percentages. In some embodiments, back extraction 255 contacts extract 156 with a recycled 20% NaCl solution (from 256 as indicated by dashed arrow) into which base 257 (e.g. Na2CO3) is added. Back extraction 255 produces regenerated amine 258 and salts 256. In some embodiments, a portion of salts 256 is re-cycled to back extraction 255. Remaining salts 256 are optionally removed as a product stream. In some embodiments, the ratio of organic phase: aqueous phase at 255 is between 7:1 to 1:1; between 6:1 to 2:1; between 5:1 to 3:1 or between 4.5:1 to 3.5:1. In some embodiments, back extraction 255 is conducted in a single step.

In some embodiments, the organic phase including regenerated amine 258 includes <0.3%; <0.25%; <0.2%; <0.15%; <0.1% or <0.05% weight/weight HCl on as is basis.

In some embodiments, the amount of base 257 (e.g. Na2CO3) is stoichiometric or 10%, 15%, 20%, 25% or 30% weight/weight above stoichiometric or intermediate or lower percentages above stoichiometric relative to HCl in 156. For example, if stream 156 also includes extracted carboxylic acids, the base used should be in an amount sufficient to transfer both chloride ions and the carboxylic acids to their salt form. In some embodiments, this results in regeneration of the amine. In some embodiments, back-extraction 255 is conducted at 60 to 100° C.; 65 to 95° C.; 70 to 90° C. or 75 to 85° C.

In some embodiments, the organic phase including regenerated amine 258 is washed with an aqueous solution to remove residual salts (e.g. NaCl, and/or organic acid salts) prior to return to 251 (not depicted).

Exemplary Diluent Considerations

In some embodiments, stream 131c entering amine extraction 251 (to be extracted by the amine) contains residual hexanol 155 from the extraction 210a and/or 210b. For example, the amount of residual hexanol is 0.05%; 0.1%; 0.2%; 0.3%; 0.4% or 0.5% or intermediate amounts in various exemplary embodiments of the invention. As described above, amine extraction at 251 employs an extractant including amine and diluent. In some embodiments, diluent component of the extractant includes hexanol. In some embodiments, the hexanol concentration (as part of the diluent of the extractant at 251) is 35%, 40%, 45%, 50% 55% or 60% or intermediate or lesser percentages relative to total extractant at 251. According to these embodiments, both raffinate 132a from amine extraction 251 and extract 156 (and the salt product 256) contain small amounts of hexanol. For example, raffinate 132a contains 0.3%, 0.4%, 0.5% or 0.6% hexanol in various exemplary embodiments of the invention.

In some embodiments, salts 256 contain 0.10%, 0.14%, 0.18%, 0.22%, 0.26%, 0.38% in various exemplary embodiments of the invention. In exemplary embodiments, both raffinate 132a and salts 256 are concentrated and hexanol 133 in raffinate 132a is distilled out at stripper 252.

In some embodiments, hexanol concentration in the extractant is maintained at a desired level (e.g. 44%) by providing "make-up" hexanol prior to a next amine extraction cycle at 251. The amount of make-up hexanol is, for example, about 1.5% relative to the desired level of hexanol in the extractant. In some embodiments, make-up hexanol is provided by distillation of hexanol 133 from raffinate 132a and delivery of hexanol 133 to amine extraction 251. In some embodiments, the organic phase including regenerated amine 258 is washed with an aqueous solution including condensed hexanol 133 to combine the wash of residual salts and hexanol re-introduction.

In other exemplary embodiments of the invention, the diluent of the amine extractant (e.g. TLA) includes kerosene and/or an alcohol of a chain length greater than 10, e.g. C12, C14 or C16 as a primary component. According to these embodiments, hexanol from stream 131c accumulates in the amine extractant. In some embodiments, accumulated hexanol in the amine extractant is removed by distillation.

Exemplary Carboxylic Acid Considerations

In some embodiments, sugar stream 131c contains anions of carboxylic acids resulting from hydrolysis 110 (FIG. 25). For example, these carboxylic acids include acetic acid and/or formic acid in various embodiments of the invention.

In some embodiments, a number of equivalents of protons in sugar solution 131c is smaller than the number of equivalents of anions (including chloride). In some embodiments, solution 131c is treated on a cation exchanger 253' in acid form prior to amine extraction 251. In some embodiments, cation exchanger 253' converts anions in solution 131c to their acid form. In some embodiments, cation exchanger 253' removes organic impurities and/or contributes to an improvement in phase contact and/or phase separation in amine extraction 251.

In some embodiments, amine extraction 251 removes HCl and/or organic acids from sugars in stream 131c. In some embodiments, such removal contributes to a decrease in load on polishing components located downstream. In some embodiments, 60%, 65%, 70%, 75%, 80%, 85%, 90% or 95% weight/weight or intermediate or greater percentages of organic acids are removed by amine extraction 251.

In some embodiments, back-extraction 255 with base (e.g. Na2CO3) is divided into two stages. In the first stage, the amount of Na2CO3 is equivalent to that of carboxylic acid and only the carboxylic acids are back-extracted to produce a solution of their (e.g. sodium) salt(s). In the second stage, HCl is back-extracted. In that case, the first stage is done with a base, but not with a recycled NaCl solution. The second stage uses recycled NaCl as described hereinabove.

These carboxylic acid considerations also apply to HCl removal when a weak-base anion-exchange resin is employed at 251. Such a weak-base anion-exchange resin also adsorbs carboxylic acids after the cation-exchanger treatment 253'.

First Exemplary Method

Figure 27:
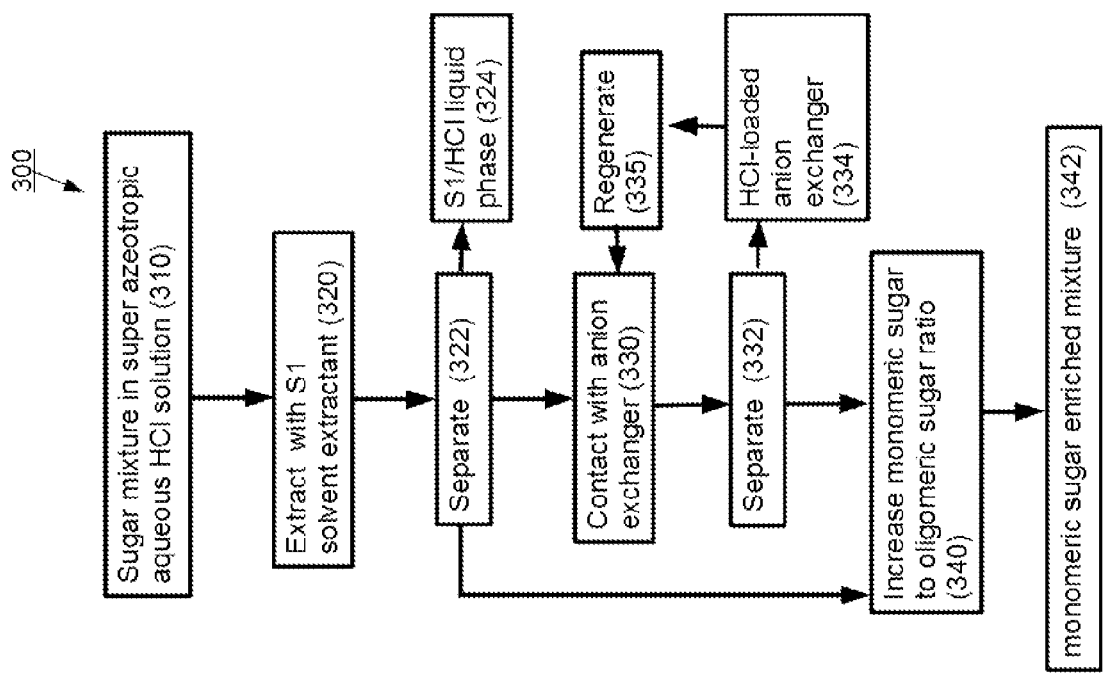
FIG. 27 is a simplified flow diagram of a method according to alternative cellulose sugar refining embodiments of the invention.

FIG. 27 is a simplified flow diagram of a method according to an exemplary embodiment of the invention depicted generally as 300. Method 300 includes extracting 320a sugar mixture 310 in a super azeotropic HCl aqueous solution with an extractant including an S1 solvent. In some embodiments, the super azeotropic HCl solution includes aqueous solution of 22, 23, 24, 25, 26, 27, 28, 29, 30% weight/weight or intermediate or greater percentages of % HCl/[HCl and water]. In some embodiments, the super azeotropic HCl solution includes 40, 38, 36, 34 or 32% weight/weight or intermediate or lower percentages of % HCl/[HCl and water].

In some embodiments, method 300 includes separating 322 an S1/HCl liquid phase 324 containing more than 20, 22, 24, 26, 28, 30, 32, 34, 36, 38 or, 40% weight/weight HCl/[HCl and water] and/or less than 50, 48, 46, 44 or 42% weight/weight HCl/[HCl and water] from the sugar mixture. Optionally, method 300 includes separating the S1 from the HCl, for example by distillation and/or back extraction. In some embodiments, this separation is conducted concurrently with washing of lignin stream 120 (FIG. 25) as described in section XI above and in co-pending application WO/2011/151823 (incorporated herein by reference for all purposes).

In some embodiments, sugar mixture 310 includes hydrolysate 130 (FIG. 25 or 26a) and/or an acidic stream received from washing of the S1 extractant from the extract. Optionally, washing of the S1 extractant from the extract includes back extraction.

In some embodiments, the method includes contacting 330 a resultant aqueous phase with an anion exchanger and separating 332 an HCl-loaded anion exchanger 334 from the sugar mixture.

Depicted exemplary method 300 includes increasing 340 a monomeric sugar to oligomeric sugar ratio (of sugars from the mixture) to produce a monomeric sugar enriched mixture 342 containing at least 70, 75, 80, 85, 90, 95, 96, 97.5 or even 99% weight/weight or intermediate or greater percentages of monomeric sugars (relative to total sugars) by weight. In some embodiments, this increase may be achieved by secondary hydrolysis (see 240 in FIG. 26a) and/or chromatographic separation (see 270 in FIG. 26a). In some embodiments, a combination of these techniques is employed. Thus, increasing 340 can occur after separation 322 and/or after separation 332 as depicted.

In some embodiments, increasing 340 includes performing chromatographic separation (see 270 in FIG. 26a). In some embodiments, a feed to chromatographic separation 270 includes less than 1.0, 0.9, 0.7, 0.5, 0.3 or 0.1% weight/weight or intermediate or lower percentages HCl on HCl/(HCl and water) basis. In some embodiments, chromatographic separation 270 includes employing a cation exchange resin for the separation. In some embodiments, the cation exchange resin is at least partially loaded with cations of alkaline metals (e.g. sodium or potassium) and/or ammonium. In some embodiments, chromatographic separation 270 includes contacting the resin with the sugar mixture and with an eluting stream. In some embodiments, the eluting stream is water or an aqueous solution. In some embodiments, the aqueous solution is formed in another stage of the process. In some embodiments, the aqueous stream includes hemicellulose sugars. Optionally, a stream containing hemicellulose sugars results from pre-treating substrate 112 (FIG. 25) with hot water. Exemplary hot water treatments of substrate 112 are disclosed in co-pending application PCT/US2012/064541 (incorporated herein by reference for all purposes). In those embodiments which employ a cation exchange resin, elution includes contacting with an aqueous solution including hemicellulose sugars in some cases.

In those embodiments of the invention in which increasing 340 includes chromatographic separation (see 270 in FIG. 26a) the monomeric sugar to oligomeric sugar ratio is increased to 80, 82, 84, 84, 86, 88, 90, 92, 94, 96 or 98% weight/weight or intermediate or grater percentages.

In some embodiments, hydrolyzing occurs between extracting 320 and contacting 330 (see 240 in FIG. 26a). In some embodiments, increasing 340 by hydrolyzing 240 increases the monomeric sugar to oligomeric sugar ratio to 72, 74, 76, 78, 80, 82, 88 or 90% weight/weight or intermediate or greater percentages.

In some embodiments, the chromatographic separation (see 270 in FIG. 26a) produces an oligomer cut (280; FIG. 26a) enriched in oligomeric sugars relative to sugar mixture 310 and a monomer cut (230; FIG. 26a) enriched in monomeric sugars relative to sugar mixture 310 on a weight basis. In those embodiments of the invention which do not include contact 330 with an anion exchanger monomeric sugar enriched mixture may include residual HCl.

In those exemplary embodiments of the invention in which increasing 340 includes both secondary hydrolysis 240 and chromatographic separation 270, the ratio of monomeric sugars to oligomeric sugars in monomeric sugar enriched mixture 342 (e.g. monomer cut 230 in FIG. 26a) is 72, 74, 76, 78, 80, 82, 84, 86, 88, 90, 92, 94, 96 or 98% weight/weight or intermediate or greater percentages.

In some embodiments, extracting 320 of sugar mixture 310 concludes prior to beginning increasing 340 a monomeric sugar to oligomeric sugar ratio in the mixture as depicted in FIG. 27. In many embodiments of the invention extracting 320 is less than 100% efficient so that the mixture still contains HCl after extracting 320 is concluded. In other exemplary embodiments of the invention, increasing 340 includes hydrolyzing (e.g. 240 in FIG. 26a) oligomeric sugars to monomeric sugars prior to beginning extracting 320 sugar mixture 310 (not depicted in FIG. 27). This option is depicted in FIG. 26a if stream 130 proceeds directly to 240.

In some embodiments, hydrolyzing occurs between separating 322 and contacting 330 (see 240 in FIG. 26a). In some embodiments, the chromatographic separation (see 270 in FIG. 26a) produces an oligomer cut (280; FIG. 26a) enriched in oligomeric sugars relative to sugar mixture 310 and a monomer cut (230; FIG. 26a) enriched in monomeric sugars relative to sugar mixture 310 on a weight basis.

Depicted exemplary method 300 includes separating 322 an S1/HCl liquid phase 324 from mixture 310 (e.g. by extraction 320). In some embodiments, S1/HCl liquid phase 324 includes more than 20, 25, 30, 35 or even more than 40% HCl/[HCl and water]. In some embodiments, S1/HCl liquid phase 324 includes less than 50, 48, 46, 44 or 42% weight/weight HCl/[HCl and water].

In some embodiments, the S1 solvent includes n-hexanol or 2-ethyl-hexanol. Optionally, one of these two solvents is combined with another S1 solvent. In some embodiments, the S1 solvent consists essentially of n-hexanol. In some embodiments, the S1 solvent consists essentially of 2-ethyl-hexanol. Optionally, the S1 solvent includes another alcohol and/or one or more ketones and/or one or more aldehydes having at least 5 carbon atoms. In some embodiments, the S1 solvent has a boiling point at 1 atm between 100° C. and 200° C. and forms a heterogeneous azeotrope with water, which azeotrope has a boiling point at 1 atm of less than 100° C.

In some embodiments, extracting 320 includes counter current extraction. In some embodiments, extraction 320 serves to reduce the HCl concentration to less than 10%, 5%, 2.5% or 1% weight/weight or intermediate or lower percentages. In some embodiments, the monomeric sugar enriched mixture 342 contains at least 20, 22, 24, 26, 28, 30, 32, 34, 36, 38, 40, 42, 44, 46, 48 or 50% weight/weight or intermediate or greater percentages of total sugars. In some embodiments, this concentration is higher than in mixture 310.

In some embodiments, monomeric sugar enriched mixture 342 includes less than 25, 20, 15 or 10% or 5%, 3% weight/weight or less oligomeric sugars (i.e. dimers or higher oligomers) out of the total sugars. In some embodiments, the anion exchanger at contacting 330 is a weak base resin (WBA). Optionally, regeneration 335 of WBA is by contact with a base. In some embodiments, the base includes a hydroxide and/or a bicarbonate and/or a carbonate of one or more alkali metals and/or ammonia. In some embodiments, regeneration 335 forms a chloride salt of the alkali metal(s) and/or ammonia and the salt is treated to reform HCl and the base. In some embodiments, the base is an ammonium base and ammonium chloride is formed as the salt. Optionally, formation of ammonium chloride adds value to the process because ammonium chloride is useful as a fertilizer.

In some embodiments, contacting 330 occurs after said extracting 320 as depicted. In some embodiments, contacting 330 occurs after secondary hydrolysis 240 (FIG. 26*a*) conducted on sugar mixture 130 (131*a*). In some embodiments, contacting 330 occurs before chromatographic separation 270 (FIG. 26*a*). In some embodiments, contacting 330 is with a stream with acid concentration similar to that of secondary hydrolysis 240. In some embodiments, contacting 330 lowers HCl concentration to less than 1, 0.9, 0.7, 0.5, 0.3 or 0.1% weight/weight or intermediate or lower concentrations of HCl on HCl/(HCl and water) basis. In some embodiments, the mixture after contacting 330 is concentrated prior to chromatographic separation (see 260 and 270 in FIG. 26*a*). Optionally, the absence of acid at this stage contributes to a reduction in re-oligomerization and/or degradation of sugars to an insignificant level.

In some embodiments, the anion exchanger at contacting 330 is an amine comprising at least 20 carbon atoms. In some embodiments, the amine is a tertiaryamine, e.g. tri-octylamine, tri-caprylylamine, tri-decylamine or tri-laurylamine.

In some embodiments, method 300 includes decreasing an HCl concentration in the super azeotropic HCl aqueous solution to prepare sugar mixture 310 prior to extracting 320. In some embodiments, this decrease is a relative decrease of 2, 4, 6, 8, 10, 12, 14 or 16% weight/weight or intermediate or greater relative percentages. Optionally, evaporation at 290 (FIG. 27*c*) contributes to this reduction.

In some embodiments, method 300 includes increasing a sugar concentration in sugar mixture 310 prior to extracting 320. In some embodiments, this increase is a relative increase of 2, 4, 6, 8, 10, 12, 14 or 16% weight/weight or intermediate or greater relative percentages. Optionally, evaporation at 290 (FIG. 26*c*) contributes to this increase.

Exemplary Product by Process

Some embodiments relate to a composition produced by a method 300. In some embodiments, the composition includes at least 50% sugars by weight on an as is basis, at least 90% monomeric sugars relative to total sugars and less than 0.3% HCl on as is basis. In some embodiments, the relative monomer concentration in the composition is 92, 94, 96, 97 or 98% weight/weight or intermediate or greater percentages relative to total sugars. In some embodiments, the composition includes at least 55, 60, 65, 70 or 75% weight/weight total sugars by weight. In some embodiments, the composition includes less than 0.2, 0.1 or 0.05 HCl on as is basis.

Second Exemplary Method

Figure 28:
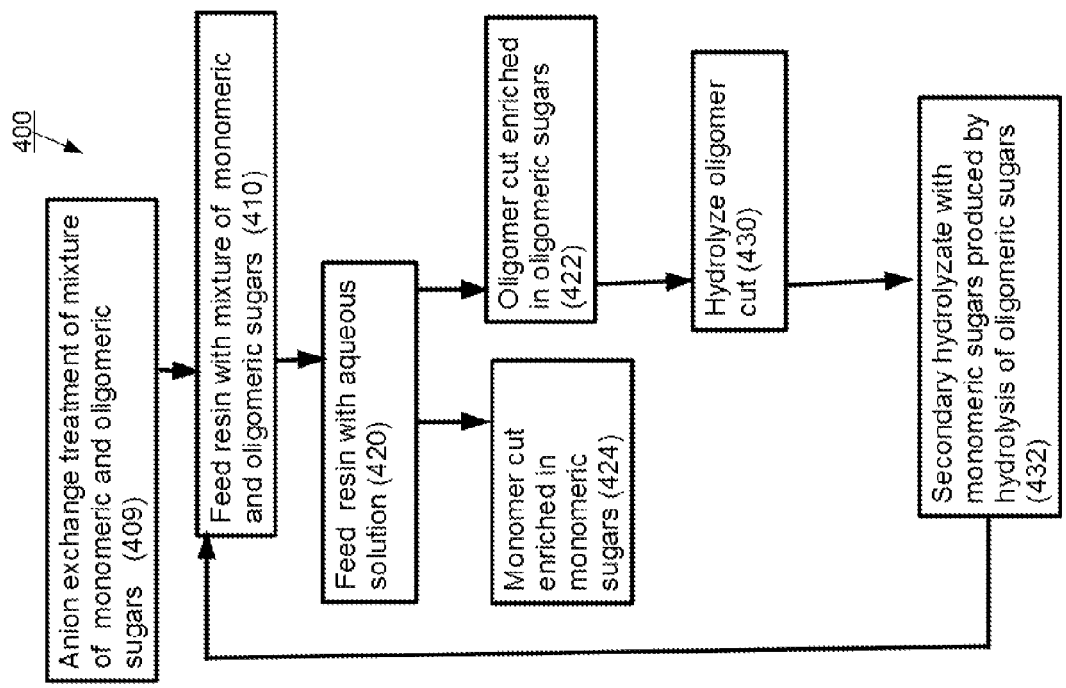
FIG. 28 is a simplified flow diagram of a method according to alternative cellulose sugar refining embodiments of the invention.

FIG. 28 is a simplified flow diagram of a method of sugar refining according to another exemplary embodiment of the invention depicted generally as 400. Method 400 includes feeding 410 a resin in a chromatographic mode with an aqueous, low acid sugar mixture including cellulosic monomeric and oligomeric sugars. In some embodiments, the method includes incorporating sugars from secondary hydrolysis (e.g., 240 in FIG. 26*a*) into the aqueous, low acid sugar mixture. The term "low acid" as used here and in the corresponding claims indicates less than 0.5, 0.4, 0.3, 0.2 or 0.1% weight/weight HCl on an as is basis. In some embodiments, the sugar mixture is provided as an aqueous solution. Optionally, the mixture includes residual S1 solvent. Suitable resins are described in "Exemplary Chromatography Resins" of this section. Optionally, a strong acid cation resin is employed.

In some embodiments, the sugar mixture includes at least 40%, 45%, 50%, 51%, 52%, 53%, 54%, 55%, 56% or 58% weight/weight or intermediate or greater concentrations of total sugars. Optionally, the sugar mixture includes 40 to 75% weight/weight total sugars by weight, in some embodiments about 45 to 60%, in some embodiments about 48 to 68% weight/weight.

Depicted exemplary method 400 includes feeding 420 the resin with an aqueous solution (optionally water) to produce an oligomer cut 422 enriched in oligomeric sugars (compared to total sugars) relative to the mixture fed at 410 and a monomer cut 424 enriched in monomeric sugars (relative to total sugars) relative to the mixture fed at 410. In some embodiments, monomer cut 424 is at least 80, 82, 84, 86, 88, 90, 92, 94, 96 or 98% or intermediate or greater percentages monomeric sugars out of total sugars (by weight).

In some embodiments, the aqueous solution fed at 420 includes water from a previous evaporation step (e.g. 142 in FIG. 26*a*). In some embodiments, the aqueous solution fed at 420 includes a stream of hemicellulose sugars from a pressure wash as described in co-pending application PCT/US2012/064541 (incorporated herein by reference for all purposes).

Optionally, oligomer cut 422 includes at least 5, at least 10, optionally 20, optionally 30, optionally 40, optionally 50% weight/weight or intermediate or greater percentages of the total sugars recovered from the resin fed at 410.

In some embodiments, oligomer cut 422 is subject to adjustment. In some embodiments, adjustment includes hydrolyzing 430 oligomeric sugars in oligomer cut 422. Other adjustment strategies (not depicted) include concentration and/or water evaporation. In some embodiments, adjustment increases the ratio of monomers to oligomers. In some embodiments, hydrolyzing 430 is catalyzed by HCl at a concentration of not more than 1.5%; 1.0%; 0.8,%0.7%, 0.6%, or 0.5% weight/weight or intermediate or lower percentages on as is basis.

In those exemplary embodiments of the invention in which adjustment include hydrolysis 430, a secondary hydrolysate 432 enriched with monomeric sugars (relative to total sugars) is produced by hydrolysis of at least a portion of the oligomeric sugars in oligomer cut 422 is produced. Optionally, hydrolysis 430 is conducted together with hydrolysis 240 (FIG. 26*a*) on a mixture of 131*a* (FIG. 26*a*)

and oligomer cut 422. Optionally, oligomer cut 422 dilutes sugars in 131*a* and this dilution improves hydrolysis kinetics.

In some embodiments, sugars from secondary hydrolysate 432 are used as a portion of the sugar mixture fed at 410 as indicated by the upward arrow.

In some embodiments, hydrolyzing 430 is catalyzed by HCl at a concentration of not more than 1.5%, 1.2%, 1%, 0.9%, 0.8%; 0.7%; 0.6% or 0.5% weight/weight or intermediate or lower values on a weight basis. In some embodiments, hydrolyzing 430 is catalyzed by HCl at a concentration of 0.3 to 1.5%; 0.4 to 1.2% or 0.45 to 0.9% weight/weight. In some embodiments, hydrolyzing 430 is performed at a temperature between 60 and 150° C.; between 70 and 140° C. or between 80 and 130° C.

In some embodiments, secondary hydrolysate 432 contains at least 70%; at least 72%; 74%; 76%; 78%; 80%; 82%; 84%; 86%; 88% or 90% weight/weight; (or intermediate or greater percentages) monomeric sugars relative to the total sugar content. In some embodiments, the total sugar content of secondary hydrolysate 432 is at least 86, 88, 90, 92, 94, 96, 98, 99 or even 99.5% weight/weight or intermediate or greater percentages by weight of the sugar content of the mixture fed at 410.

Figure 29:
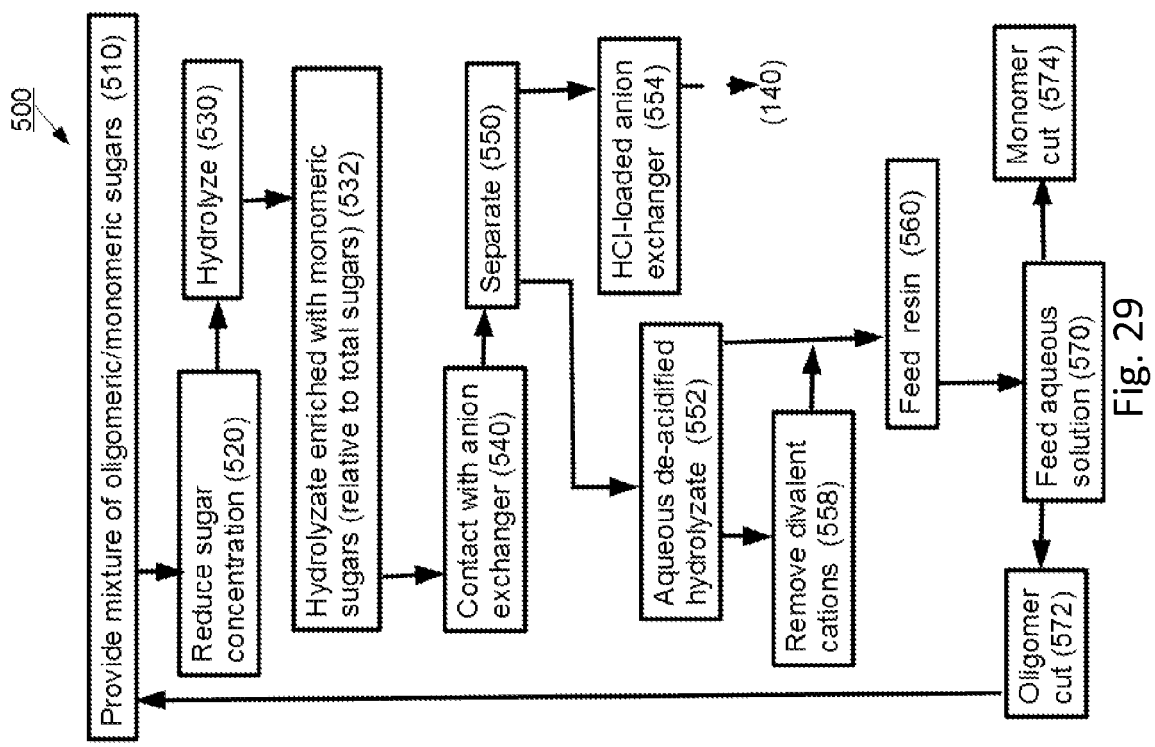
FIG. 29 is a simplified flow diagram of a method according to alternative cellulose sugar refining embodiments of the invention.

In some embodiments, method 400 includes treating 409 the sugar mixture including cellulosic monomeric and oligomeric sugars with an anion exchanger. According to these embodiments, the treated mixture from 409 proceeds to 410 as depicted. In some embodiments, the anion exchanger includes a weak base resin anion exchanger (WBA) and/or an anion an amine having at least 20 carbon atoms Third Exemplary Method FIG. 29 is a simplified flow diagram of a sugar refining method according to another exemplary embodiment of the invention depicted generally as 500. Method 500 includes hydrolyzing 530 a mixture 510 of oligomeric and monomeric sugars. Specifically, method 500 includes providing 510 a mixture of oligomeric and monomeric sugars at a total concentration of at least 20, 22, 24, 26, 28, 30, 32, 34, 36, 38 or 40% weight/weight or intermediate or greater percentages in an aqueous solution of at least 1.5% HCl and/or less than 38% weight/weight HCl.

In some embodiments, the mixture provided at 510 has 20 to 38%, 22 to 36%, 24 to 30% or 26 to 32% weight/weight HCl. In other exemplary embodiments of the invention, the mixture provided at 510 has 1.7 to 6%, 1.9 to 5.5%, 2.1 to 5%, 2.3 to 4.5% weight/weight HCl on as is basis. In some embodiments, the mixture provided at 510 has 30% total sugars and/or 27% HCl (e.g. if pre-evaporation 290 is present but extraction 210*a* is absent). In other exemplary embodiments of the invention, the mixture provided at 510 has 25% total sugars and/or 33% HCl (e.g. if pre-evaporation 290 and extraction 210*a* are both absent). In some embodiments, the mixture provided at 510 includes at least 4% HCl; at least 6% HCl or at least 8% HCl (by weight). In some embodiments, the mixture provided at 510 includes less than 10% HCl; less than 8% HCl; less than 6% HCl or less than 4% HCl (by weight). In some embodiments, method 500 includes reducing 520 the sugar concentration in the mixture below 25%; below 22%; below 20%; below 18% or below 16% (by weight). In some embodiments, the HCl concentration remains above 4, 6, 8 or 10 after reducing 520.

Depicted exemplary method 500 includes hydrolyzing 530. Hydrolysis 530 produces a secondary hydrolysate 532 enriched with monomeric sugars (relative to total sugars).

In some embodiments, method 500 includes contacting 540 secondary-hydrolysate 532 with an anion exchanger. In some embodiments, contacting 540 facilitates separation 550 of sugars in hydrolysate 532 from the catalyst of the reaction (e.g. HCl).

In some embodiments, separation 550 includes recovery of an aqueous de-acidified hydrolysate 552 from the HCl loaded anion exchanger 554. In some embodiments, HCl 140 is washed from loaded anion exchanger 554 to regenerate the anion exchanger. In some embodiments, this regeneration is via washing with a base that forms a salt, so that 140 includes a chloride salt and not HCl per se.

In some embodiments, the anion exchanger at 540 includes a weak base resin anion exchanger (WBA) and/or an amine having at least 20 carbon atoms.

In some embodiments, hydrolysis 530 employs a mineral acid, such as HCl, as a catalyst. Optionally, enrichment results from hydrolysis of at least a portion of the oligomeric sugars in the mixture. Optionally, hydrolysate 532 contains at least 72%, at least 78%, at least 82%, at least 88%, at least 90% or at least 93% weight/weight monomeric sugars or intermediate or higher percentages relative to the total amount of sugars therein.

In some embodiments, HCl concentration in the mixture at 510 can be in the range of 2 to 3%, e.g. 2.5 or 2.6% by weight. In some embodiments, hydrolysis 530 is catalyzed by 0.5; 0.6; 0.7; 0.8; 0.9; 1.0; 1.1; 1.2; 1.3; 1.4 or 1.5% HCl, 0.3 to 1.5%; 0.4 to 1.2% or 0.45 to 0.9% by weight on as is basis. In some embodiments, hydrolyzing 530 is catalyzed by HCl at a concentration of not more than 1.2%.

In some embodiments, the HCl percentage is reduced by diluting the mixture prior to hydrolysis 530. In some embodiments, dilution is with oligomer cut 280 (see FIG. 26*a*). In some embodiments, hydrolyzing 530 is performed at a temperature in the range between 60° C. and 150° C.; 70° C. and 140° C. or 80° C. and 130° C. Optionally, less than 1% non-hydrolytic degradation of sugars occurs during hydrolysis 530. In some embodiments, the total sugar content of (secondary) hydrolysate 532 is at least 90; 95; 97.5 or 99 (or intermediate or greater percentages) by weight of the sugar content of the mixture provided at 510. In some embodiments, hydrolysate 532 enriched with monomeric sugars contains at least 70, at least 75, at least 80, at least 85 or at least 90% (or intermediate or greater percentages) by weight monomeric sugars out of total sugars.

In some embodiments, method 500 includes evaporating water 260 (see FIG. 26*a*) from hydrolysate 532. Optionally, at least part of this evaporation occurs at a temperature of less than 70° C. or less 80° C. than Optionally, at least 63%, optionally at least 70% of the total sugars are monomers after evaporation 260. In some embodiments, less than 10, 5, 2.5 or even less than 1% or intermediate or lower percentages of monomeric sugars in hydrolysate 532 oligomerize during evaporation 260 (see FIG. 26*a*).

In some embodiments, contacting 540 is prior to the evaporating (see 251 and 260 in FIG. 26*a*) and an aqueous, de-acidified hydrolysate 132 (FIG. 26*a*) is formed.

In some embodiments, method 500 includes removing 558 divalent cations from aqueous, de-acidified hydrolysate 552 (optionally before the evaporation) with a cation exchanger. Optionally, removal 558 lowers the sugar concentration, since some water is added to wash sugars from the cation exchanger.

Depicted exemplary method 500 includes feeding 560 a resin in a chromatographic mode (see 270 in FIG. 26*a*) with hydrolysate 552 (optionally after removal 558) and feeding 570 the resin with an aqueous solution to produce an oligomer cut 572 enriched in oligomeric sugars (in proportion to total sugars) relative to hydrolysate 552 and a monomer cut 574 enriched in monomeric sugars (in proportion to total sugars) relative to hydrolysate 552. Optionally, feeding 570 an aqueous solution serves to release sugars from the resin. In some embodiments, the resin is an ion exchange resin.

Referring again to FIG. 26a, feed 131e to chromatographic separation 270 is enriched in monomeric sugars relative to feed 131a to secondary hydrolysis 240, while monomer cut 230 from chromatographic treatment 270 is enriched in monomeric sugars compared to feed stream 131e.

Optionally, oligomer cut 572 is recycled (upwards arrow) so that the mixture provided at 510 includes sugars from a previous oligomer cut 572.

In some embodiments, method 500 includes separating 550 an HCl-loaded anion exchanger 554 from hydrolysate 532 to form aqueous, de-acidified (i.e. low acid) hydrolysate 552. Optionally, contacting 540 is prior to an evaporation procedure (see 260 in FIG. 26a) and aqueous, de-acidified hydrolysate 552 is formed.

Fourth Exemplary Method

Figure 32:
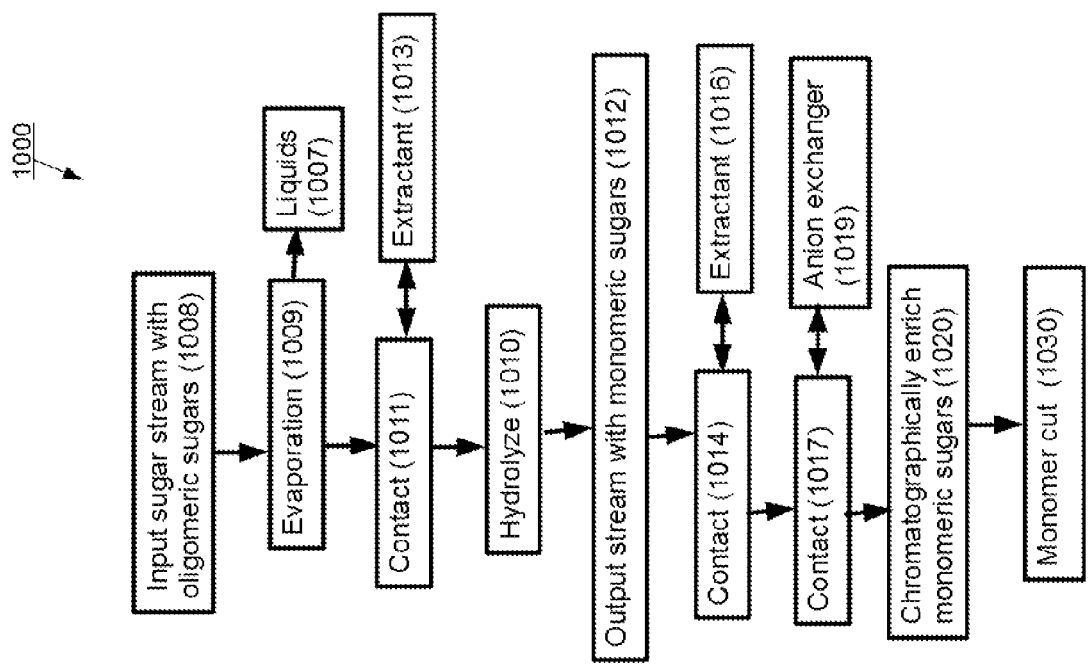
FIG. 32 is a simplified flow diagram of a method according to alternative cellulose sugar refining embodiments of the invention.

FIG. 32 is a simplified flow diagram of a method for increasing the ratio of monomeric sugars to total sugars in an input sugar stream indicated generally as method 1000. In some embodiments, method 1000 includes hydrolyzing 1010 oligomeric sugars in an input sugar stream 1008 to produce an output stream 1012 including monomeric sugars. In some embodiments, input stream 1008 is a mixture of monomeric and oligomeric sugars. In some embodiments, stream 1008 includes 30, 40, 50, 60, 70 or 80% by weight oligomeric sugars (or intermediate or greater percentages) relative to total sugars. In some embodiments, stream 1008 has a total sugar concentration of 20%, 25%, 30%, 35% or 40% or intermediate or greater concentrations. In some embodiments, stream 1008 has an HCl/[HCl and water] concentration of 20%, 25%, 30% or 35% by weight or intermediate or greater concentrations.

In some embodiments, method 1000 includes chromatographically enriching 1020 monomeric sugars from output stream 1012 to produce a monomer cut 1030. In some embodiments, monomer cut 1030 includes 80%, 85%, 90%, 95%, 97.5% or 99% by weight or more monomers as a percentage of total sugars.

In some embodiments, method 1000 includes at least two of the following optional actions:
(i) evaporating 1009 HCl (and/or water) 1007 from input sugar stream 1008;
(ii) contacting (1011 and/or 1014) input sugar stream 1008 and/or output stream 1012 with an extractant (1013 and/or 1016) including an S1 solvent; and
(iii) contacting 1017 output stream 1012 with an anion exchanger 1019 adapted to remove acid from the stream.

Some embodiments include only actions (i) and (ii). Other exemplary embodiments of the invention include only actions (i) and (iii). Still other exemplary embodiments of the invention include only actions (ii) and (iii). Still other exemplary embodiments of the invention include all three of actions (i), (ii) and (iii). Among those embodiments of the invention which include action (i), liquids 1007 optionally include HCl and/or water. Optionally, evaporation 1009 serves to reduce HCl concentration and/or to increase total sugar concentration in stream 1008. Among those embodiments which include action (ii), some embodiments include only contacting 1011 input sugar stream 1008 with extractant 1013 including an S1 solvent; other embodiments include only contacting 1014 output stream 1012 with extractant 1016 including an S1 solvent; still other embodiments include both contacting 1011 input sugar stream 1008 and contacting 1014 output stream 1012 with extractant 1016 containing an S1 solvent. As depicted in FIG. 26a, in some embodiments, extractant 1016 is re-used as extractant 1013 (See 210a and 210 b of FIG. 26a and accompanying explanation).

In some embodiments, method 1000 includes contacting 1011, extractant 1013 and at least one of evaporation 1009 and contacting 1014 with anion exchanger 1019.

Fifth Exemplary Method

Figure 33:
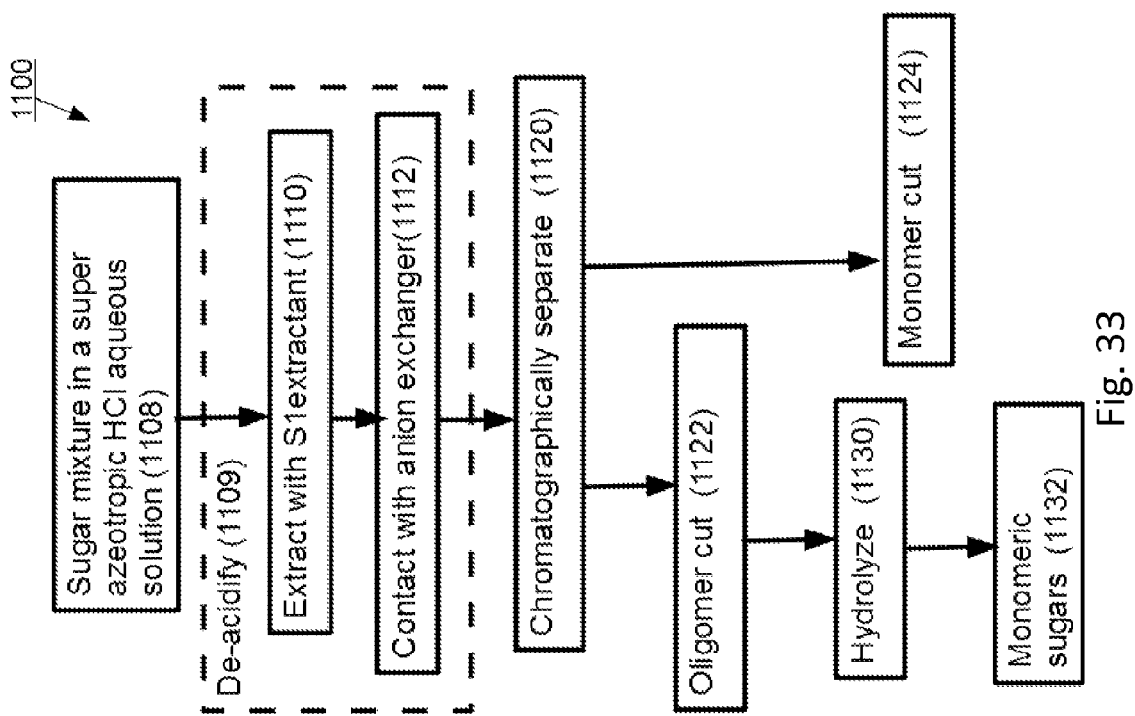
FIG. 33 is a simplified flow diagram of a method according to alternative cellulose sugar refining embodiments of the invention.

FIG. 33 is a simplified flow diagram of a sugar refining method according to another exemplary embodiment of the invention depicted generally as 1100. Method 1100 includes de-acidifying 1109 a sugar mixture 1108 in a super azeotropic HCl aqueous solution. In some embodiments, the super azeotropic HCl aqueous solution is has an HCl concentration as described hereinabove. De-acidifying 1109 includes extracting 1110 with an extractant including an S1 solvent and then contacting 1112 with an anion exchanger and chromatographically separating 1120 an oligomer cut 1122 enriched in oligomeric sugars relative to sugar mixture 1108 and a monomer cut 1124 enriched in monomeric sugars relative to sugar mixture 1108 on a weight basis. In some embodiments, the anion exchanger at 1112 includes a weak base resin (WBA) and/or an amine comprising at least 20 carbon atoms.

In some embodiments, method 1100 includes hydrolyzing 1130 sugars from oligomer cut 1122 to form monomeric sugars 1132.

Referring again to FIG. 26a, method 1100 routes stream 131a to anion exchanger 251 and routes stream 132 to chromatography component 270 (optionally via cation exchanger 253 and/or evaporator 260 as depicted).

Exemplary Hybrid Method

Referring again to FIG. 26a, in some embodiments a portion of stream 131a is routed to anion exchanger 251 without secondary hydrolysis at 240 while a second portion of stream 131a proceeds via secondary hydrolysis 240 to anion exchanger 251. Both portions eventually reach a chromatography component 270 (either the same one or different ones) and the resultant oligomer cut(s) 280 is returned to secondary hydrolysis at 240.

Exemplary Solvent Selection Considerations

In some embodiments, extraction 320 (FIG. 27) of the sugar mixture with the S1 containing extractant results in a selective transfer or selective extraction of HCl from the sugar mixture to the extractant to form an S1/HCl-liquid phase (324) and an HCl-depleted sugar mixture (e.g. 131a in FIG. 26a).

The selectivity of extraction of HCl over water ($S_{A/W}$) can be determined by equilibrating hydrolysate with the extractant and analyzing the concentrations of the acid and of the water in the equilibrated phases. In that case, the selectivity is:

$$S_{A/W} = (C_A/C_W)\text{org}/(C_A/C_W)\text{aq}$$

wherein $(C_A/C_W)$ aq is the ratio between acid concentration and water concentration in the aqueous phase and $(C_A/C_W)$ org is the ratio between acid concentration and water concentration in the organic phase.

$S_{A/W}$ may depend on various parameters, such as temperature and the presence of other solutes in the aqueous phase, e.g. carbohydrates. Selective extraction of acid over water means $S_{A/W} > 1$.

In some embodiments, extraction 320 of HCl from sugar mixture 310 provides, under at least some conditions, an $S_{A/W}$ of at least about 1.1, optionally at least about 1.3 and optionally at least about 1.5.

Similarly, selectivity to acid over a carbohydrate ($S_{A/C}$) can be determined by equilibrating the hydrolysate with said extractant and analyzing the molar concentrations of the acid and the carbohydrate in the equilibrated phases. In that case, the selectivity is:

$$S_{A/C}=(C_A/C_C)\text{org}/(C_A/C_C)\text{aq}.$$

wherein ($C_A/C_C$) aq is the ratio between acid concentration and the concentration of the carbohydrate (or carbohydrates) in the aqueous phase and ($C_A/C_C$) org is the ratio of acid concentration and the concentration of the carbohydrate (or carbohydrates) in the organic phase.

$S_{A/C}$ may depend on various parameters, such as temperature and the presence of other solutes in the aqueous phase, e.g. HCl. Selective extraction of acid over carbohydrate means $S_{A/C}>1$.

In some embodiments, extraction 320 of HCl from sugar mixture 310 by the extractant has, under at least some conditions, an $S_{A/C}$ of at least about 2, optionally at least about 5 and optionally at least about 10.

N-hexanol has a relatively high SA/W and a relatively low SA/C. 2-ethyl-1-hexanol has a relatively low SA/W and a relatively high SA/C.

These characteristics of the two hexanols caused previous efforts to use them in the context of separating sugars from HCl to focus on combining the two of them, or using one of them in combination with a complementary solvent (see for example U.S. Pat. No. 4,237,110 to Forster et al.).

In some embodiments, n-hexanol or 2-ethyl-1-hexanol is employed as the sole S1 solvent in extraction 320.

Exemplary Primary Hydrolysis Efficiency

In some embodiments, at least 70% wt (optionally, more than 80, 90, 95% by weight) of polysaccharides in lignocellulosic substrate 112 hydrolyze into soluble carbohydrates in hydrolysis reactor 110. In some embodiments, the concentration of soluble carbohydrates in the hydrolysis medium increases with the progress of the hydrolysis reaction.

Exemplary Extractant Considerations

Optionally, the extractant includes a mixture of an alcohol and the corresponding alkyl chloride. Optionally, the extractant includes hexanol and hexyl chloride. In some embodiments, the extractant includes 2-ethyl-1-hexanol and 2-ethyl-1-hexyl chloride. Optionally, the extractant includes hexanol, 2-ethyl-1-hexanol, hexyl chloride and 2-ethyl-1-hexyl chloride. Optionally, the alcohol/alkyl chloride w/w ratio is greater than about 10 optionally greater than about 15, optionally greater than about 20, and optionally greater than about 30. In some embodiments, the extractant also includes water. In some embodiments, a non-carbohydrate impurity is selectively extracted into the extractant, causing purification of the carbohydrate in extract 131a (FIG. 26a). Optionally, the degree of selective extraction varies so that 30%, optionally 40%, optionally 50%, optionally 60%, optionally 70%; optionally 80%; optionally 90% or intermediate or greater percentages are achieved.

Exemplary Selective Transfer Parameters

Optionally, extraction 320 selectively transfers HCl from sugar mixture 310 to the extractant to form extract 131a and S1/HCl liquid phase 324. In some embodiments, at least 85% of the HCl from the sugar mixture transfers to the extractant, at least 88%, at least 92% or at least 95% (by weight). In some embodiments, extract 131a contains residual HCl. Optionally, the residual HCl is equivalent to about 0.1 to about 10% of the HCl in sugar mixture 310, optionally about 0.5 to about 8% and optionally about 2 to about 7% by weight.

Exemplary Weight Ratios

In some embodiments, a total soluble carbohydrate concentration in oligomer cut 280 or 422 is in the range between 1% and 30%, optionally between 2% and 20% and optionally between 3% and 10% by weight. In some embodiments, HCl concentration in oligomer cut 422 is less than 0.2%, less than 0.1% or less than 0.05% by weight.

Exemplary Secondary Hydrolysis Conditions

In some embodiments, hydrolysis 430 (FIG. 28) and/or 340 (FIG. 27) of oligomers in oligomer cut 422 (FIG. 28) is conducted at a temperature greater than 60° C., optionally between 70° C. and 130° C., optionally between 80° C. and 120° C. and optionally between 90° C. and 110° C. In some embodiments, hydrolysis 430 and/or 340 proceeds at least 10 minutes, optionally between 20 minutes and 6 hours, optionally between 30 minutes and 4 hours and optionally between 45 minutes and 3 hours.

In some embodiments, secondary hydrolysis under these conditions increases the yield of monomeric sugars with little or no degradation of sugars. In some embodiments, monomers as a fraction of total sugars is greater than 70%, optionally greater than 80%, optionally greater than 85% and optionally greater than 90% by weight after hydrolysis 340 and/or 430. In some embodiments, degradation of monomeric sugars during the hydrolysis is less than 1%, optionally less than 0.2%, optionally less than 0.1% and optionally less than 0.05% by weight.

Exemplary Chromatography Resins

Some embodiments employ an ion exchange (IE) resin (e.g. at 410 and/or 270).

There are four main types of ion exchange resins differing in their functional groups: strongly acidic (for example using sulfonic acid groups such as sodium polystyrene sulfonate or polyAMPS), strongly basic (for example using quaternary amino groups, for example, trimethylammonium groups, e.g., polyAPTAC), weakly acidic (for example using carboxylic acid groups) and weakly basic (for example using primary, secondary and/or ternary amino groups, such as polyethylene amine).

Resins belonging to each of these four main types are commercially available. In some embodiments, resins of one or more of these four types are employed.

In some embodiments, the resin employed at 410 (FIG. 28) and/or 270 (FIG. 26b) is a strong acid cation exchange resin in which sodium, potassium, or ammonium replace, at least partially hydrogen ions on the resin.

Strong acid cation resins include Purolite® resins such as PUROLITE Resin PCR 642H+ and/or 642K (The Purolite Company, Bala Cynwood, Pa., USA).

In some embodiments, purification media 274 (FIG. 26b) includes a resin. Optionally, this resin is a mixed bed system using a combination of strong cation resin and strong base anion resin. Mixed bed resins suitable for use in this context are also available from The Purolite Company (Bala Cynwood, Pa., USA).

Exemplary Anion Exchangers

A wide variety of weak base resins (WBA) are commercially available. Many of these are suitable for use in the context of various embodiments of the invention (e.g. at 251 in FIG. 26a). Suitable resins include DOWEX 66 (Dow Chemical Co.; USA) and A100 and/or A103S and/or A105 and/or A109 and/or A111 and/or A120S and/or 133S and/or A830 and/or A847 (The Purolite Co.; USA).

In some embodiments, a wide variety of amine extractants with less than 20 carbon atoms are available. Exemplary amine extractants suitable for use in embodiments of the invention include tertiary amines, e.g. tri-octylamine, tri-caprylylamine, tri-decylamine or tri-laurylamine.

Exemplary IX

A wide variety of ion exchangers (IX) are commercially available. Many of these are suitable for use in the context of various embodiments of the invention (e.g. at 253 in FIG. 26*a*). Suitable resins include strong acid cation exchange resins such as DOWEX 88 (Dow Chemical Co.; USA) or C100 and/or C100E and/or C120E and/or C100X10 and/or SGC650 and/or C150 and/or C160 (The Purolite Co.; USA).

Exemplary Equilibrium Considerations

HCl catalyzes both hydrolysis of oligomeric sugars and oligomerization of monomeric sugars. Over a suitable period of time, an equilibrium would be established. Reaction direction is influenced by sugar concentration and ratio of monomers:oligomers. Reaction kinetics can be influenced by temperature and/or HCl concentration.

Referring again to FIG. 26*a* and secondary hydrolysis unit 240: in some embodiments, the input sugar concentration has an excess of oligomers relative to equilibrium conditions. Dilution with the oligomer cut returning from chromatography unit 270 shifts the monomer:oligomer balance even further away from equilibrium conditions. Under these conditions, HCl drives the reaction in the direction of hydrolysis.

The sugar composition leaving hydrolysis unit 240 is much closer to equilibrium conditions, since oligomers have been hydrolyzed. However, evaporation 260 might shift the balance to monomeric excess. If this occurs, HCl would tend to catalyze re-oligomerization of monomers. The chromatographic separation 270 is operated according to an embodiment at a sugars concentration significantly higher than that of secondary hydrolysis 240. In order to avoid re-oligomerization during the concentration of the sugars, acid 156 is removed by contacting with an anion exchanger 251 in some embodiments of the invention.

In equilibrium of the secondary hydrolysis reaction, the ratio between monomeric sugars and oligomeric sugars is a function of the total sugar concentration. The kinetics of the reaction is set by the temperature and by the HCl concentration. The choice of temperature and HCl concentration is a matter of optimization, taking into account capital and operating costs. In any case, equilibrium may be reached. Alternatively, the reaction may be stopped prior to reaching equilibrium. It is a matter of optimization of several factors such as degradation of monomeric sugars and operational and capital costs. In some embodiments, the secondary hydrolysis is stopped when it reaches at least 70, 75, 80, 85, or 90% by weight of the equilibrium ratio or intermediate or greater percentages.

Exemplary Flow Control Considerations

In some embodiments, liquids with varying degrees of viscosity must be transported from one module or component to another. In some embodiments, sugar concentration and/or solvent concentration and/or HCl concentration contribute to the viscosity of a solution. In some embodiments, this transport relies, at least partially, upon gravity. In some embodiments, pumps may be employed to transport liquids. In some embodiments, liquids move in different directions and/or at different rates. Optionally, some liquids are held in reservoirs for later use. In some embodiments, a controller serves to regulate one or more liquid flows.

Figure 30:
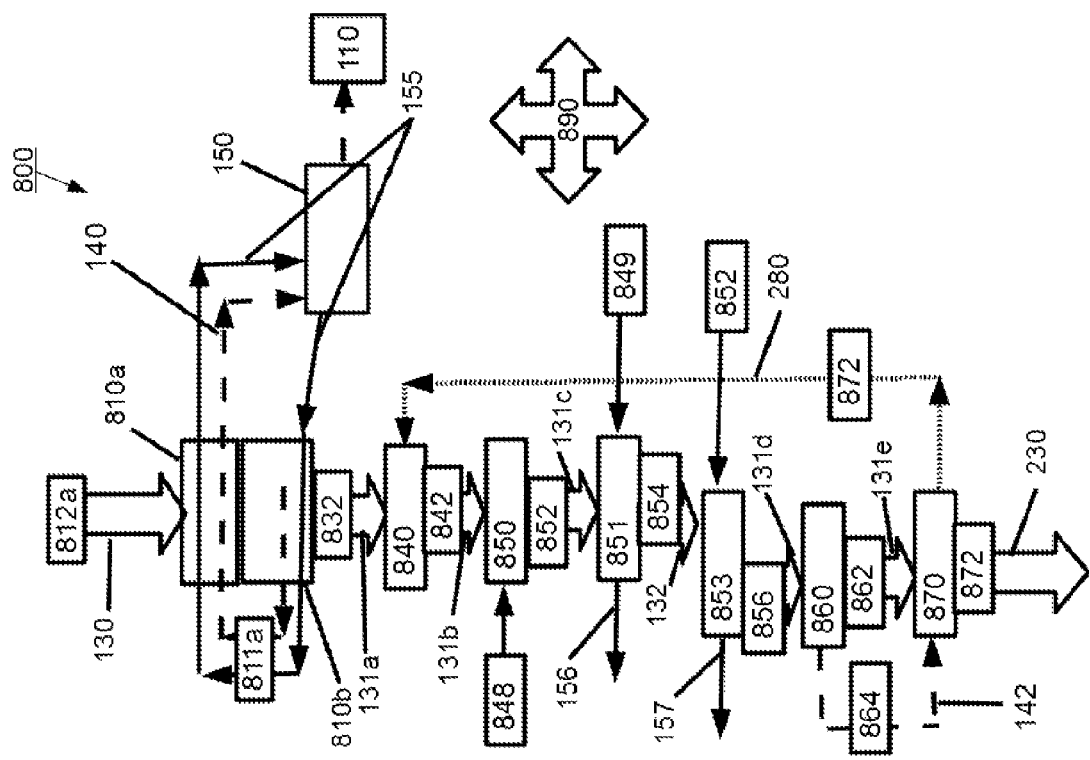
FIG. 30 is a schematic representation of a system similar to that in FIG. 26b indicating flow control components.

FIG. 30 is a schematic representation indicating flow control components of a sugar refining module similar to that of FIG. 26*a* indicated generally as 800. In the context of system 100, module 800 is analogous to module 200. Numbers beginning with the numeral "1" refer to solutions or streams described hereinabove. Many of the numbers beginning with the numeral "8" refer to similar numbers beginning with the numeral "2" in FIG. 26*a* and are described only in terms of their relation to flow control components here.

In some embodiments, pump 811*a* provides a flow of S1 based extractant 155 through acid extractors 810*a* and 810*b*. The flow carries HCl 140 along with it. The extractors are arranged in series and the flow is pumped through 810*b* to 810*a*. In some embodiments, a single extractor 810 is used.

Pump 812*a* provides a flow of sugar mixture 130 to acid extractor(s) 810*a*. In some embodiments, controller 890 regulates flow rates of pumps 812*a* and 811*a* to insure efficient extraction of acid by the extractant. Optionally, a correct relative flow rate contributes to this efficiency. In some embodiments, pumps 812*a* and 811*a* are provided as part of a Bateman pulsed column as described hereinabove. In some embodiments, flow rates in pumps 812*a* and/or 811*a* are varied to adapt acid extractor 810*a* to provide a desired degree of extraction efficiency.

In some embodiments, acid-reduced stream 131*a* emerges from extractor 810*a* and is drawn through secondary hydrolysis module 840 by pump 842. Again, controller 890 regulates a flow rate through module 840 to insure that a desired degree of hydrolysis is achieved. Optionally, an additional pump 832 moves stream 131*a* to secondary hydrolysis module 840 as depicted. The resultant secondary hydrolysate 131*b* is pumped to filtration unit 850. Optionally, filtration pump 852 draws hydrolysate 131*b* through filters in the unit and/or pumps filtered secondary hydrolysate 131*c* to anion exchanger 851. In some embodiments, a separate pump 848 periodically provides a rinse flow (rightward pointing arrow) to filtration unit 850 to wash accumulated debris from the filters. In some embodiments, controller 890 coordinates operation of pumps 848 with 842 and/or 852 to assure proper operation of filter unit 850.

In some embodiments, filtered stream 131*c* is pumped through anion exchanger 851 by pump 854 to produce a de-acidified hydrolysate 132. In some embodiments, a separate pump 849 delivers a wash stream to anion exchanger 851 to produce a dilute stream of HCl 156. In some embodiments, controller 890 coordinates operation of pumps 854 with 849 and/or 856 to assure proper operation of anion exchanger 851.

In some embodiments, pump 856 draws de-acidified hydrolysate 132 through cation exchanger module 853. Output stream 131*d* is reduced in cation content. In some embodiments, a separate pump 852 delivers a wash stream to module 853 to produce a stream of eluted cations 157. In some embodiments, controller 890 coordinates operation of pumps 852 with 856 and/or 862 to assure proper operation of module 853.

In some embodiments, exit stream 131*d* is drawn into evaporation unit 860 by pump 862 which increases the sugar concentration by evaporating water. The resultant concentrated filtered secondary hydrolysate 131*e* is pumped to chromatography component 870 by pump 872.

In some embodiments, water 142 produced by evaporator 860 is pumped by collection mechanism 864 to chromatography unit 870 for use as an elution fluid. Since chromatography unit 870 cyclically alternates between sample feeding and elution in some embodiments, collection mechanism 864 optionally includes a water reservoir as well as a pump.

In some embodiments, controller 890 coordinates action of collection mechanism 864 and pump 872 to cyclically feed the resin in chromatography unit 870 with a sample stream and an elution stream. This cyclic feeding and elution produces an oligomer cut 280 which is recycled to hydrolysis unit 840 by pump 872 and a monomer cut 230 which is optionally pumped by pump 872 to module 204 (FIG. 26*b*).

Optionally, controller 890 responds to feedback from sensors (not depicted) positioned at entrances and/or exits of various modules and/or units. In some embodiments, these sensors include flow sensors and controller 890 regulates relative flow rates. In some embodiments, a division between the oligomer cut and the monomer cut is made based upon historical performance data of the resin in chromatography unit 870 in terms of bed volumes of effluent after sample feeding.

In some embodiments, the sensors include parametric detectors. Optionally, the parametric detectors monitor sugar concentration and/or acid concentration. In some embodiments, sugar concentration is measured by assaying refractive index and/or viscosity. Optionally, acid concentration is monitored by pH measurement. In some embodiments, a division between the oligomer cut and the monomer cut is made based upon actual performance data of the resin in chromatography unit 870 in terms of concentration of specific sugars as assayed by refractive index and/or acid concentration as estimated from pH.

Exemplary Monomer Concentrations

Referring again to FIG. 26*a*, in various exemplary embodiments of the invention, monomeric sugar enriched mixture 131*b* produced by secondary hydrolysis 240 includes 72, 74, 76, 78, 80, 82, 84, 86, 88 or 90% by weight by weight or intermediate or greater percentages of monomeric sugars by weight relative to total sugars. In some embodiments, in various exemplary embodiments of the invention, monomer cut 230 from chromatography 270 includes 80, 82, 84, 86, 88, 90, 92, 94, 96, 98, 99 or 99.5% by weight or intermediate or greater percentages of monomeric sugars by weight relative to total sugars.

Exemplary Orders of Operations

Referring again to FIG. 26*a*, many exemplary embodiments of the invention include secondary hydrolysis unit 240 and chromatography component 270 and various combinations of other components and/or units.

In some embodiments, sugars from stream 130 proceed directly to secondary hydrolysis unit 240 and secondary hydrolysate 131*b* proceeds (optionally via filtration unit 250) to acid extractor 210*b*, to anion exchanger 251 and then (optionally via cation exchanger module 253) and then to evaporation unit 260 and then to chromatography unit 270.

In some embodiments, sugars from stream 130 proceed directly to secondary hydrolysis unit 240 and secondary hydrolysate 131*b* proceeds (optionally via filtration unit 250) to acid extractor 210*b* and then to evaporation unit 260 and then to chromatography unit 270.

In some embodiments, stream 130 is pre-evaporated at 290 (FIG. 26*c*) and then sugars from stream 130 proceed to secondary hydrolysis unit 240 and secondary hydrolysate 131*b* proceeds (optionally via filtration unit 250) to acid extractor 210*b*, to anion exchanger 251 and then (optionally via cation exchanger module 253) and then to evaporation unit 260 and then to chromatography unit 270.

In some embodiments, stream 130 is pre-evaporated at 290 (FIG. 26*c*) and then sugars from stream 130 proceed to secondary hydrolysis unit 240 and secondary hydrolysate 131*b* proceeds (optionally via filtration unit 250) to acid extractor 210*b* and then to evaporation unit 260 and then to chromatography unit 270.

In some embodiments, stream 130 is extracted at acid extractor 210*a* and then sugars from stream 130 proceed to secondary hydrolysis unit 240 and secondary hydrolysate 131*b* proceeds (optionally via filtration unit 250) to acid extractor 210*b*, to anion exchanger 251 and then (optionally via cation exchanger module 253) and then to evaporation unit 260 and then to chromatography unit 270.

In some embodiments, stream 130 is pre-evaporated at 290 (FIG. 26*c*), extracted at acid extractor 210*a* and then sugars from stream 130 proceed to secondary hydrolysis unit 240 and secondary hydrolysate 131*b* proceeds (optionally via filtration unit 250) to acid extractor 210*b*, to anion exchanger 251 and then (optionally via cation exchanger module 253) and then to evaporation unit 260 and then to chromatography unit 270.

In some embodiments, stream 130 is pre-evaporated at 290 (FIG. 26*c*), extracted at acid extractor 210*a* and then sugars from stream 130 proceed to secondary hydrolysis unit 240 and secondary hydrolysate 131*b* proceeds (optionally via filtration unit 250) to acid extractor 210*b*, to evaporation unit 260 and then to chromatography unit 270.

In some embodiments, stream 130 is pre-evaporated at 290 (FIG. 26*c*), extracted at acid extractor 210*a* and then sugars from stream 130 proceed to secondary hydrolysis unit 240 and secondary hydrolysate 131*b* proceeds (optionally via filtration unit 250) to evaporation unit 260 and then to chromatography unit 270.

In some embodiments, stream 130 is extracted at acid extractor 210*a* and then sugars from stream 130 proceed to secondary hydrolysis unit 240 and secondary hydrolysate 131*b* proceeds (optionally via filtration unit 250) to evaporation unit 260 and then to chromatography unit 270.

Additional Exemplary Methods and Related Products

Figure 31A:
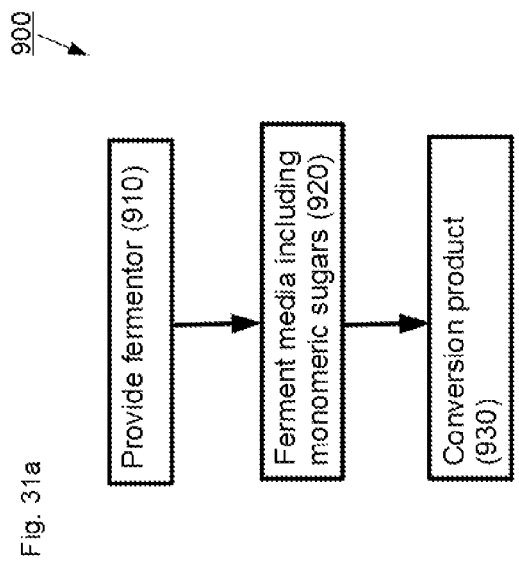
FIG. 31a is a simplified flow diagram of a method according to alternative embodiments of monosaccharides fermentation and chemical conversions.

FIG. 31*a* is a simplified flow diagram of a method according to another exemplary embodiment of the invention depicted generally as 900. Method 900 includes providing 910 a fermentor and fermenting 920 a medium including monomeric sugars to produce a conversion product 930. In some instances processes depicted in FIGS. 25 and 26*a* and/or 26*b* and/or 26*c* are conducted in a single plant or system together with fermenting 920.

Figure 31B:
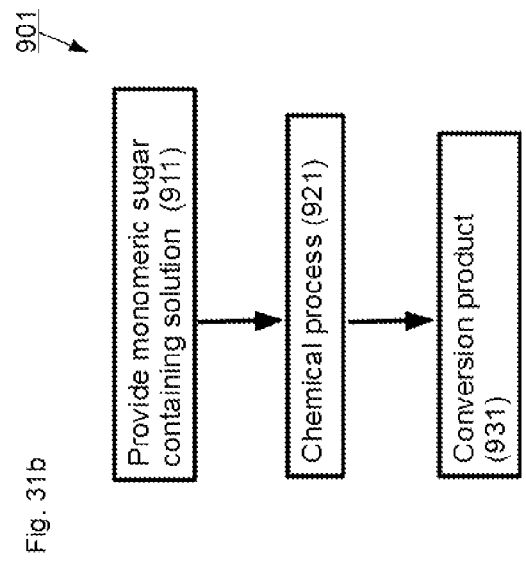
FIG. 31b is a simplified flow diagram of a method according to alternative embodiments of monosaccharides fermentation and chemical conversions.

FIG. 31*b* is a simplified flow diagram of a method according to another exemplary embodiment of the invention depicted generally as 901. Method 901 includes providing 911 a monomeric sugar containing solution and converting sugars in the solution to a conversion product 931 using a chemical process 921.

In some embodiments, the monomeric sugars, or monomeric sugar containing solution, may be provided as monomeric sugar enriched mixture (e.g. 342 or 1032) and/or as a monomer cut (e.g. 230 or 574) and/or as a hydrolysate containing monomeric sugars (e.g. 510, 532 or 552).

In some embodiments, fermentation 920 and/or chemical process 921 are as described in U.S. Pat. No. 7,629,010; U.S. Pat. No. 6,833,149; U.S. Pat. No. 6,610,867; U.S. Pat. No. 6,452,051; U.S. Pat. No. 6,229,046; U.S. Pat. No. 6,207,209; U.S. Pat. No. 5,959,128; U.S. Pat. No. 5,859,270; U.S. Pat. No. 5,847,238; U.S. Pat. No. 5,602,286; and U.S. Pat. No. 5,357,035, the contents of which are incorporated by reference. In various embodiments, the processes described in the above US patents are combined with one or more methods as described herein, for example, with secondary hydrolysis and/or chromatography as described herein.

In some embodiments, fermentation 920 may employ a genetically modified organism (GMO). A wide range of GMOs are potentially compatible with sugars produced by the methods described herein. GMOs may include members of the genera *Clostridium, Escherichia, Salmonella, Zymomonas, Rhodococcus, Pseudomonas, Bacillus, Enterococcus, Alcaligenes, Lactobacillus, Klebsiella, Paenibacillus, Corynebacterium, Brevibacterium, Pichia, Candida, Hansenula* and *Saccharomyces*. Hosts that may be particularly of interest include *Oligotropha carboxidovorans, Escherichia coli, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Bacillus subtilis* and *Saccharomyces cerevisiae*. Also, any of the known strains of these species may be utilized as a starting microorganism. In various exemplary embodiments, the microorganism is an actinomycete selected from *Streptomyces coelicolor, Streptomyces lividans, Streptomyces hygroscopicus*, or *Saccharopolyspora erytraea*. In various exemplary embodiments, the microorganism is a *eubacterium* selected from *Escherichia coli, Pseudomonas fluorescens, Pseudomonas putida, Pseudomonas aeruginosa, Bacillus subtilis* or *Bacillus cereus*.

In some exemplary embodiments, the GMO is a gram-negative bacterium. In some exemplary embodiments, the recombinant microorganism is selected from the genera *Zymomonas, Escherichia, Alcaligenes* and *Klebsiella*. In some exemplary embodiments, the recombinant microorganism is selected from the species *Escherichia coli, Cupriavidus* necator and *Oligotropha* carboxidovorans. In some exemplary embodiments, the recombinant microorganism is an *E. coli* strain.

In some embodiments, fermentation 920 produces lactic acid as conversion product 930. The potential of lactic acid as a commodity chemical, for example for use in the production of various industrial polymers, is known. This has been described, for example, in U.S. Pat. Nos. 5,142,023; 5,247,058; 5,258,488; 5,357,035; 5,338,822; 5,446,123; 5,539,081; 5,525,706; 5,475,080; 5,359,026; 5,484,881; 5,585,191; 5,536,807; 5,247,059; 5,274,073; 5,510,526; and 5,594,095. (The complete disclosures of these seventeen patents, which are owned by Cargill, Inc. of Minneapolis, Minn., are incorporated herein by reference.) There has been general interest in developing improved techniques for generation and isolation of lactic acid. Also, because of their potential commercial value, there is great interest in isolation of the other valuable related lactate products such as lactide, lactate esters and amides, and oligomers; see e.g. the same 17 patents.

In general, large amounts of lactic acid can be readily generated by the conduct of large-scale, industrial, microbial fermentation processes, particularly using sugars produced by exemplary methods as described herein, such as dextrose, in the media, along with suitable mineral and amino acid based nutrients. Typically, such productions occur at broth temperatures of at least 45° C., usually around 48° C.

Issues of concern with respect to lactic acid generation include, inter alia, appropriate control of pH within the fermentation system to ensure proper environment for microbial action, separation and isolation of either or both of lactic acid and lactate salts from the fermentation process and downstream isolation and production involving the isolated lactic acid or lactic acid derived product.

In some embodiments, the sugars produced by the exemplary methods described herein are incorporated into a fermentation product as described in the following US patents, the contents of each of which are hereby incorporated by reference: U.S. Pat. No. 7,678,768; U.S. Pat. No. 7,534,597; U.S. Pat. No. 7,186,856; U.S. Pat. No. 7,144,977; U.S. Pat. No. 7,019,170; U.S. Pat. No. 6,693,188; U.S. Pat. No. 6,534,679; U.S. Pat. No. 6,452,051; U.S. Pat. No. 6,361,990; U.S. Pat. No. 6,320,077; U.S. Pat. No. 6,229,046; U.S. Pat. No. 6,187,951; U.S. Pat. No. 6,160,173; U.S. Pat. No. 6,087,532; U.S. Pat. No. 5,892,109; U.S. Pat. No. 5,780,678; and U.S. Pat. No. 5,510,526.

In some embodiments, the conversion product (930 or 931) can be, for example, an alcohol, carboxylic acid, amino acid, monomer for the polymer industry or protein. In some embodiments, the conversion product (930 or 931) is processed to produce a consumer product selected from the group consisting of a detergent, a polyethylene-based product, a polypropylene-based product, a polyolefin-based product, a polylactic acid (polylactide)-based product, a polyhydroxyalkanoate-based product and a polyacrylic-based product. Optionally, the detergent includes a sugar-based surfactant, a fatty acid-based surfactant, a fatty alcohol-based surfactant or a cell-culture derived enzyme. Optionally, the polyacrylic-based product is a plastic, a floor polish, a carpet, a paint, a coating, an adhesive, a dispersion, a flocculant, an elastomer, an acrylic glass, an absorbent article, an incontinence pad, a sanitary napkin, a feminine hygiene product and a diaper. Optionally, the polyolefin-based products is a milk jug, a detergent bottle, a margarine tub, a garbage container, a plumbing pipe, an absorbent article, a diaper, a non-woven, an HDPE toy or an HDPE detergent packaging. Optionally, the polypropylene based product is an absorbent article, a diaper or a non-woven. Optionally, the polylactic acid based product is a packaging of an agriculture product or of a dairy product, a plastic bottle, a biodegradable product or a disposable. Optionally, the polyhydroxyalkanoate based products is packaging of an agriculture product, a plastic bottle, a coated paper, a molded or extruded article, a feminine hygiene product, a tampon applicator, an absorbent article, a disposable non-woven or wipe, a medical surgical garment, an adhesive, an elastomer, a film, a coating, an aqueous dispersant, a fiber, an intermediate of a pharmaceutical or a binder. Optionally, conversion product 930 or 931 is ethanol, butanol, isobutanol, a fatty acid, a fatty acid ester, a fatty alcohol or biodiesel.

In some embodiments, method 900 or 901 includes processing of conversion product 930 or 931 to produce at least one product such as, for example, an isobutene condensation product, jet fuel, gasoline, gasohol, diesel fuel, drop-in fuel, diesel fuel additive or a precursor thereof.

Optionally, the gasohol is ethanol-enriched gasoline and/or butanol-enriched gasoline.

In some embodiments, the product produced from conversion product 930 or 931 is diesel fuel, gasoline, jet fuel or a drop-in fuel.

Various exemplary embodiments of the invention include consumer products, precursors of consumer product, and ingredients of consumer products produced from conversion product 930 or 931.

Optionally, the consumer product, precursor of a consumer product, or ingredient of a consumer product includes at least one conversion product 930 or 931 such as, for example, a carboxylic or fatty acid, a dicarboxylic acid, a hydroxylcarboxylic acid, a hydroxyldicarboxylic acid, a hydroxyl-fatty acid, methylglyoxal, mono-, di-, or poly-alcohol, an alkane, an alkene, an aromatic, an aldehyde, a ketone, an ester, a biopolymer, a protein, a peptide, an amino acid, a vitamin, an antibiotics and a pharmaceutical.

For example, the product may be ethanol-enriched gasoline, jet fuel, or biodiesel.

Optionally, the consumer product has a ratio of carbon-14 to carbon-12 of about $2.0 \times 10^{-13}$ or greater. Optionally, the consumer product includes an ingredient of a consumer product as described above and an additional ingredient produced from a raw material other than lignocellulosic material. In some embodiments, ingredient and the additional ingredient produced from a raw material other than lignocellulosic material are essentially of the same chemical composition. Optionally, the consumer product includes a marker molecule at a concentration of at least 100 ppb.

In some embodiments, the marker molecule can be, for example, furfural, hydroxymethylfurfural, products of furfural or hydroxymethylfurfural condensation, color compounds derived from sugar caramelization, levulinic acid, acetic acid, methanol, galacturonic acid or glycerol.

XIII. Alternative Lignin Processing Embodiments

FIG. 25 is a schematic representation of an exemplary hydrolysis system which produces a lignin stream that serves as an input stream indicated generally as 100. System 100 includes a hydrolysis vessel 110 which takes in lignocellulosic substrate 112 and produces two exit streams. The first exit stream is an acidic hydrolysate 130 containing an aqueous solution of HCl with dissolved sugars. The second exit stream 120 is a lignin stream. Processing of lignin stream 120 to remove HCl and water is one focus of this application. Recycling of the removed HCl is an additional focus of this application. Ways to accomplish this recycling without diluting the HCl are an important feature of some exemplary embodiments described herein. In some embodiments, lignin stream 120 contains less than 5%, less than 3.5%, less than 2% or less than 1% weight/weight cellulose relative to lignin on a dry matter basis.

In some embodiments, hydrolysis vessel 110 is of the type described in co-pending international application PCT/US2011/057552 (incorporated herein by reference for all purposes). In some embodiments, the hydrolysis vessel may include hydrolysis reactors of one or more other types. In some embodiments, substrate 112 contains pine wood. Processing of hydrolysate stream 130 occurs in sugar refining module 201 and produces refined sugars 230 which are substantially free of residual HCl. For purposes of the overview of system 100, it is sufficient to note that module 201 produces a re-cycled stream 140 of concentrated HCl which is routed to hydrolysis vessel 110. In some embodiments, HCl 140 is recovered from hydrolysate 130 by extracting with a solvent based extractant 155. Optionally, this extraction occurs in refining module 201. In some embodiments, extractant 155 is separated from HCl 140 in solvent recovery module 150. In some embodiments, lignin stream 120 includes significant amounts of HCl and dissolved sugars.

Exemplary Method

Figure 34:
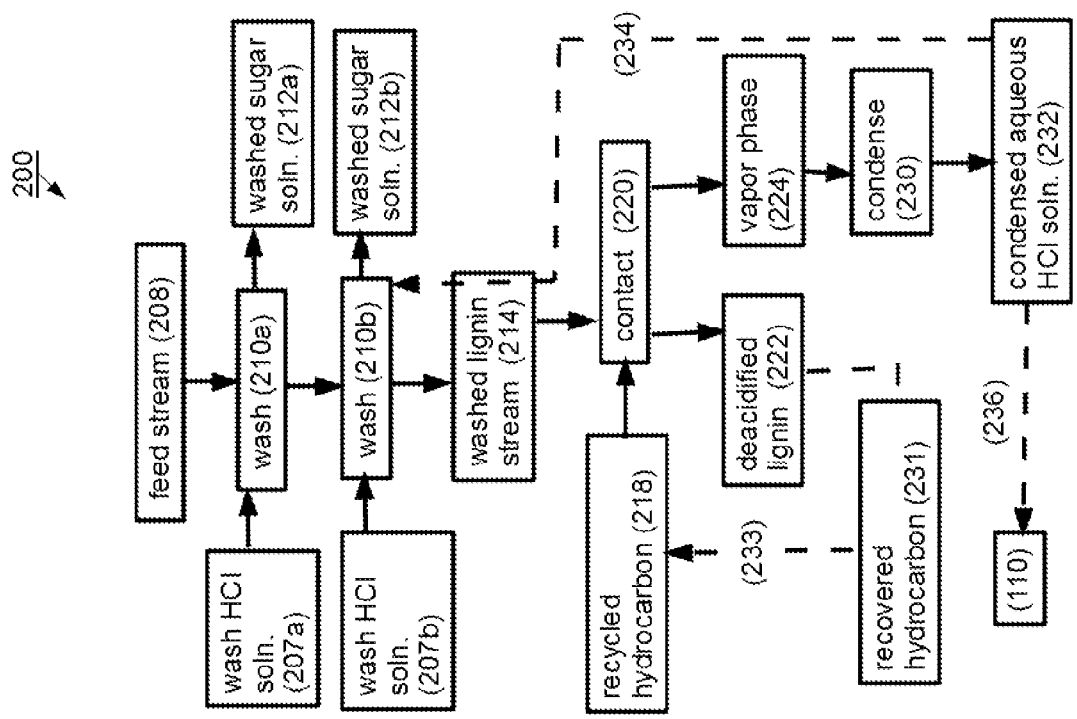
FIG. 34 is a simplified flow diagram of a method according to alternative lignin processing embodiments of the invention.

FIG. 34 is a simplified flow diagram of a method for processing a lignin stream indicated generally as 200. Feed stream 208 corresponds to lignin stream 120 of FIG. 25.

Method 200 includes washing (210a and/or 210b) a feed stream 208. Feed stream 208 includes one or more sugars dissolved in an aqueous super-azeotropic HCl solution and solid lignin. In many cases the solid lignin in stream 208 is wetted by, or impregnated with, the solution. In some embodiments, washing (210a and/or 210b) serves to remove sugars from the lignin. In some embodiments, washing (210a and/or 210b) are performed with a washing-HCl solution (207a and/or 207b) including at least 5% wt HCl to form a washed sugars solution (212a and/or 212b) and a washed lignin stream 214. In some embodiments, washed lignin stream 214 includes solid lignin, water and HCl.

Method 200 also includes contacting 220 washed lignin stream 214 with recycled hydrocarbon 218 to form a de-acidified lignin 222 stream and a vapor phase 224 containing HCl and water. In some embodiments, contacting 220 of recycled hydrocarbon 218 with washed lignin stream 222 occurs at 65, 70, 75, 80, 85 or 90° C. or intermediate or higher temperatures. Optionally, contacting 220 is conducted at a temperature at which hydrocarbon 218 boils. In some embodiments, vapor phase 224 also contains hydrocarbon 218 (not depicted). In some embodiments, de-acidified lignin stream 222 includes solid lignin and less than 2% HCl by weight.

In some embodiments, method 200 includes condensing 230 vapor phase 224 to form a condensed aqueous HCl solution 232. In some embodiments, method 200 includes using 234 condensed aqueous HCl solution 232 in washing 210a and/or 210b. In some embodiments, method 200 include using 236 condensed aqueous HCl solution 232 in hydrolysis 110 of a lignocellulosic material 112 (see FIG. 25). In some embodiments, condensing 230 produces additional recovered hydrocarbon 231 (not depicted). In some embodiments, recovered hydrocarbon 231 is recycled 233 from de-acidified lignin 222 to 218. In some embodiments, recycling 233 includes one or more of centrifugation, vapor condensation, evaporation and distillation.

Exemplary Washing Considerations

In some embodiments, a concentration of lignin in feed stream at 208 is between 5% and 50%, 15% and 45%, 20% and 40% or 25% and 35% weight/weight on as is basis. In some embodiments, in some embodiments a concentration of HCl in feed stream is between 35 and 45%, 37% and 44%, 38% and 43% or 39% and 42.5% weight/weight HCl/[HCl and water]. In some embodiments, a concentration of sugar in stream 208 is between 5% and 35%, 10% and 30%, 12% and 27%, 15% and 25% weight/weight on as is basis.

In some embodiments, glucose contains at least 50%, at least 60%, at least 70%, at least 80% or at least 90% weight/weight of the total sugars in feed stream 208. In some embodiments, glucose contains 50% to 80%, 50% to 85%, 50% to 90%, 50% to 95%, 50% to 99%, 60% to 80%, 60% to 85%, 60% to 90%, 60% to 95% or 60% to 99% weight/weight of the total sugar in feed stream 208. In some embodiments, stream 208 contains one or more C5 sugars and the C5 sugars are less than 50, less than 40, less than 30, less than 20, less than 10 or less than 5% of the total sugars in stream 208.

In some embodiments, washing 210a and/or 210b of feed stream 208 includes at least one counter current contacting. In some embodiments, an HCl concentration in solution 207a and/or 207b is at least 20, at least 25, at least 30, at least 35 or at least 40 wt %.

In some embodiments, washing feed stream 208 includes a first counter current contacting 210a with a first solution 207a containing at least 5% wt HCl to form a first washed sugars solution 212a and a second counter current contacting 210b with a second solution 207b containing at least 5% wt HCl to form a second washed sugars solution 212b. In some embodiments, an HCl concentration in first solution 207a is at least 35, at least 37, at least 39, at least 41 or at least 42% wt. In some embodiments, an HCl concentration in second solution 207b is at least 20, at least 25, at least 28, at least 30 or at least 32% wt. In some embodiments, a sugar concentration in washed lignin stream 214 is less than 5%, 4%, 3%, 2% or 1% on as is basis.

In some embodiments, the number of wash stages varies. In FIG. 34 two wash stages are depicted (210a and 210b). In other exemplary embodiments of the invention, a larger number of wash stages is implemented. For example, three to ten wash stages are implemented in some embodiments of the invention. In some embodiments, a temperature of the wash changes between stages. For example, in some embodiments the last stage or stages are conducted at a slightly elevated temperature compared with early stages, e.g. 25° C. to 40° C., compared with 10° C. to 20° C. In some embodiments, each wash stage is carried out in a hydro-cyclone. Optionally, pressure in the hydro-cyclones is 40 to 90 psig. In some embodiments, two wash streams (207a and 207b) serve more than two hydro-cyclones. In some embodiments, wash stream 207a has an HCl concentration of 40 to 43% and wash stream 207b has an HCl concentration of 32 to 36%. In some embodiments, stream 207a enters the first hydro-cyclone (from the standpoint of feed stream 208) and stream 207b enters the last hydro-cyclone (from the standpoint of feed stream 208). Optionally, washing temperature increases as HCl concentration decreases in the wash.

Exemplary Optional Grinding

In some embodiments, wet grinding of feed stream 208 prior to washing 210 (210a and/or 210b) is conducted. Optionally, the wet grinding contributes to an increase in efficiency of washing. In some embodiments, wet grinding of stream 214 prior to contacting 220 is conducted. Optionally, the wet grinding contributes to an increase in efficiency of de-acidification. This increased efficiency is in terms of a reduced time for contacting 220 and/or a reduction in the ratio of wash stream 210a and/or 210b to feed stream 208.

Exemplary Contacting Considerations

In some embodiments, the hydrocarbon employed at contacting 220 has a boiling point at atmospheric pressure between 100° C. and 250° C., 120° C. and 230° C. or 140° C. and 210° C. Suitable hydrocarbons include isoparaffinic fluids (e.g. ISOPAR G, H, J, K, L or M from ExxonMobil Chemical, USA). In some embodiments, the selected isoparaffinic fluid is substantially insoluble in water. In some embodiments, dodecane is employed as a hydrocarbon 218 at contacting 220.

In some embodiments, 9 parts of Isopar K as hydrocarbon 218 are contacted 220 with 1 part of washed lignin stream 214 (e.g. about 20% solid lignin on as is basis). According to these embodiments, a ratio of Isopar K to dry lignin is about 7/1; 9/1; 11/1; 15/1; 30/1; 40/1 or 45/1 w/w (or intermediate or greater ratios) is contacted in 220.

In some embodiments, washing 210a and/or 210b is at a pressure between 40 and 90 psig. In some embodiments, contacting 220 is conducted at atmospheric pressure. In some embodiments, de-acidified lignin stream 222 includes less than 2%, less than 1.5%, less than 1.0%, less than 0.5%, less than 0.3%, less than, 0.2% or less than 0.1% HCl weight/weight on as is basis. In some embodiments, de-acidified lignin stream 222 contains at least at least 60%, at least 70%, at least 80%, at least 90%, at least 95%, at least 96%, at least 97%, at least 98% or at least 99% weight/weight solid lignin on as is basis.

Exemplary Condensing Considerations

In some embodiments, an HCl concentration in condensed aqueous HCl solution 232 is greater than 20%, greater than 22%, greater than 24%, greater than 26% or greater than 28% weight/weight as HCl/(HCl and water).

Additional Exemplary Recycling Loops

In some embodiments, method 200 includes using washed sugars solution 212a or 212b in hydrolyzing a lignocellulosic material (e.g. at 110 in FIG. 25). In some embodiments, method 200 includes using first washed sugars solution 212a in hydrolysis of a lignocellulosic material. In some embodiments, method 200 includes using second washed sugars solution 212b in hydrolysis of a lignocellulosic material.

Exemplary Hydrolysis Considerations

In some embodiments, lignocellulosic material 112 (FIG. 25) includes softwood (e.g. pine). In some embodiments, lignocellulosic material 112 includes hardwood (e.g. eucalyptus or oak). In some embodiments, a temperature of hydrolyzing at 110 (FIG. 25) is less than 25, less than 23, less than 21, less than 19, less than 17 or, less than 15° C.

Second Exemplary Method

Figure 35:
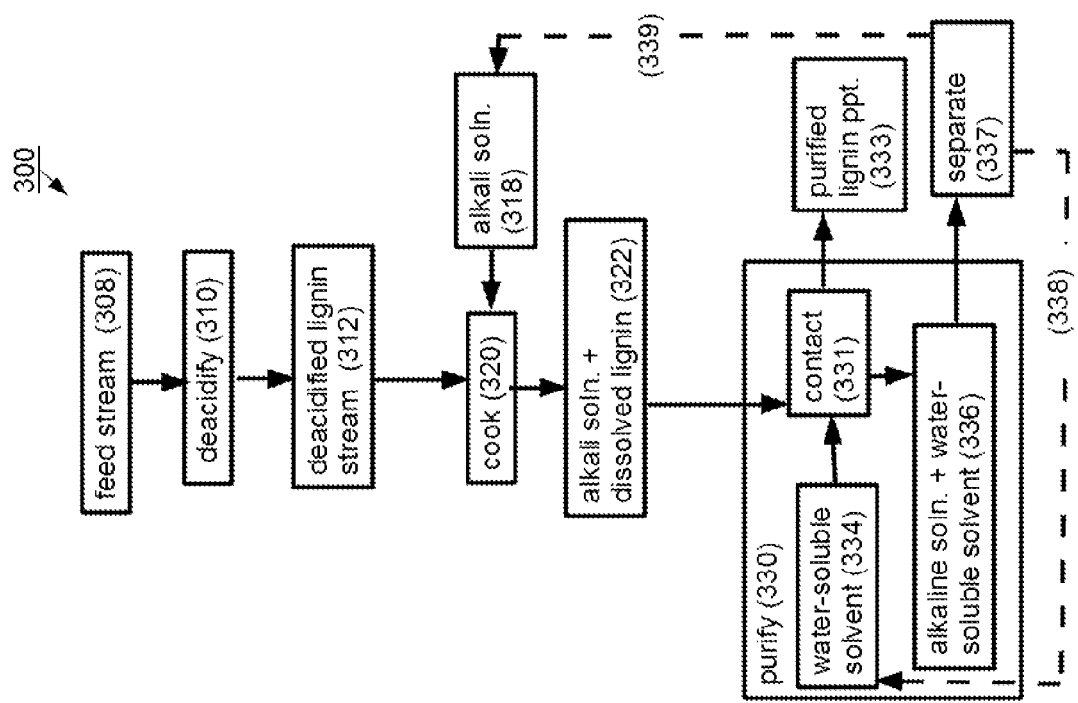
FIG. 35 is a simplified flow diagram of a method according to alternative lignin processing embodiments of the invention.

FIG. 35 is a simplified flow diagram of a method for processing a lignin stream indicated generally as 300 according to some embodiments. In some embodiments, feed stream 308 corresponds to lignin stream 120 of FIG. 25.

Method 300 includes de-acidifying 310 a feed stream 308 containing solid lignin, an aqueous super-azeotropic HCl solution and at least one sugar to form a de-acidified lignin stream 312. In some embodiments, stream 312 includes solid lignin and less than 2%, less than 1.5%, less than 1.0%, less than 0.5%, less than 0.3%, less than 0.2 or less than 0.1% HCl weight/weight on as is basis. In some embodiments, stream 312 includes lignin which is at least 70%, at least 75%, least 80%, at least 85%, least 90% or at least 95% weight/weight solid (or intermediate or greater percentages).

The depicted method also includes cooking 320 the solid lignin of 312 in an alkali solution 318 to form an alkaline solution 322 including dissolved lignin. In some embodiments, the yield of lignin dissolved in alkaline solution 322 is at least 85%, 90%, 92.5%, 95%, 97.5%, 99%, 99.5% or substantially 100% weight/weight of the amount of lignin in stream 312. In some embodiments, the concentration of dissolved lignin at 322 is at least 5%, 7%, 8%, 10%, 15%, 20% or 25% weight/weight or intermediate or greater percentages (expressed as dissolved solids). In some embodiments, cooking 320 is conducted at a temperature greater than 100° C., greater than 110° C., greater than 120° C. or greater than 130° C. In some embodiments, cooking 320 is conducted at a temperature lower than 200° C., lower than 190° C., lower than 180° C., lower than 170° C., lower than 160° C. or lower than 150° C. In some embodiments, cooking 320 is conducted at a temperature between 160° C. and 220° C., 170° C. and 210° C., 180° C. and 200° C., or 182° C. and 190° C. In some embodiments, cooking 320 has a duration of at least 10, at least 20, at least 30, at least 40, at least 50, at least 60, at least 70, at least 80, at least 90 or at least 120 minutes. In some embodiments, cooking 320 has a duration of less than 10, less than 9, less than 8, less than 7, less than 6, less than 5.5, less than 5, less than 4.5, less than 4 or less than 3.5 hours. In some embodiments, the cooking time is about 6 hours (e.g. at 182° C.). In some embodiments, an increase in cooking time and/or in cooking temperature contributes to an increase in lignin fragmentation and/or degradation. In some embodiments, cooking 320 is cooking in an alkali solution containing less than 20%, less than 15%, less than 10%, less than 5% or less than 2% solvent. Optionally, cooking 320 is cooking in an alkali solution that is substantially free of solvent. Cooking 320 is conducted on a composition that is practically free of cellulose so that it is very different from wood pulping.

In some embodiments, an alkaline concentration of alkaline solution 318 is adjusted so that the alkaline concentration at 320 is at least 5%, 6%; 7%, 8%, 9%, 10%, 11%, 12%, 13%, 14%, 15% weight/weight or intermediate or greater percentages when expressed as 100× base/(base and water)

on a weight basis. The table below illustrates exemplary amounts and relationships of components at cooking 320 from laboratory scale experiments.

Exemplary conditions from laboratory scale experiments

| Line | Lignin(g) | NaOH (g) | Lignin/ NaOH | Water (g) | NaOH/ (NaOH + water) × 100 |
|---|---|---|---|---|---|
| 1 | 50 | 20 | 2.5 | 200 | 9% |
| 2 | 60 | 20 | 3.0 | 200 | 9% |
| 3 | 20 | 14 | 1.4 | 200 | 6.5% |
| 4 | 75 | 30 | 2.5 | 200 | 13% |

The lab scale conditions from line 3 of Table 1 were scaled up to a semi-industrial procedure as follows:
30 lbs Lignin at 50% moisture/volatiles (15 lbs dry Lignin solids)
10.5 lbs NaOH dry solids provided as 50% caustic solution
150 lbs water (includes 10.5 lbs water in the 50% caustic solution)
15 lbs IsoPar K (in the wet lignin; residual solvent at 222 in FIG. 34)

In the scaled semi-industrial procedure the ratio of lignin/NaOH was 1.42 and the alkaline concentration was 6.5% (compare to line 3 in the table above).

In some embodiments, lignin stream 312 contains residual hydrocarbon (e.g. dodecane) from de-acidification 310. Upon cooking 320, the lignin in stream 312 dissolves into the alkaline aqueous phase, so that the residual hydrocarbon separates easily into a separate organic phase which is decanted and recycled. In some embodiments, alkali solution 318 includes ammonia and/or sodium hydroxide and/or sodium carbonate.

Method 300 includes purifying 330 the dissolved lignin to form purified lignin precipitate 333. In some embodiments, purifying 330 includes contacting 331 alkaline solution 332 containing dissolved lignin with a water-soluble solvent 334 to form a solid lignin precipitate 333 and an alkaline solution 336 including the water-soluble solvent. In some embodiments, water soluble solvent 334 includes methanol and/or ethanol and/or acetone.

In some embodiments, precipitate 333 contains basic lignin. In some embodiments, separation 337 facilitates recycling 338 of water soluble solvent 334 and/or recycling 339 of alkali solution 318. Separation 337 optionally includes evaporation (e.g. distillation) and/or cooling and/or pH adjustment.

Exemplary Lignin States

In some embodiments, lignin carries acidic phenol function(s) in protonated form —ROH— and/or in dissociated form —RO(-), In some embodiments, lignin carries carboxylic function(s), in protonated form —RCOOH— and/or dissociated form —RCOO(-). The "acid functions" referred to here are a combination of phenol and carboxylic function which are either in protonated or dissociated form. In some embodiments, acidic lignin is a lignin in which more than one half of the acid functions are in protonated form and basic lignin is a lignin in which more than one half of the acid functions are in dissociated form.

Third Exemplary Method

Figure 36:
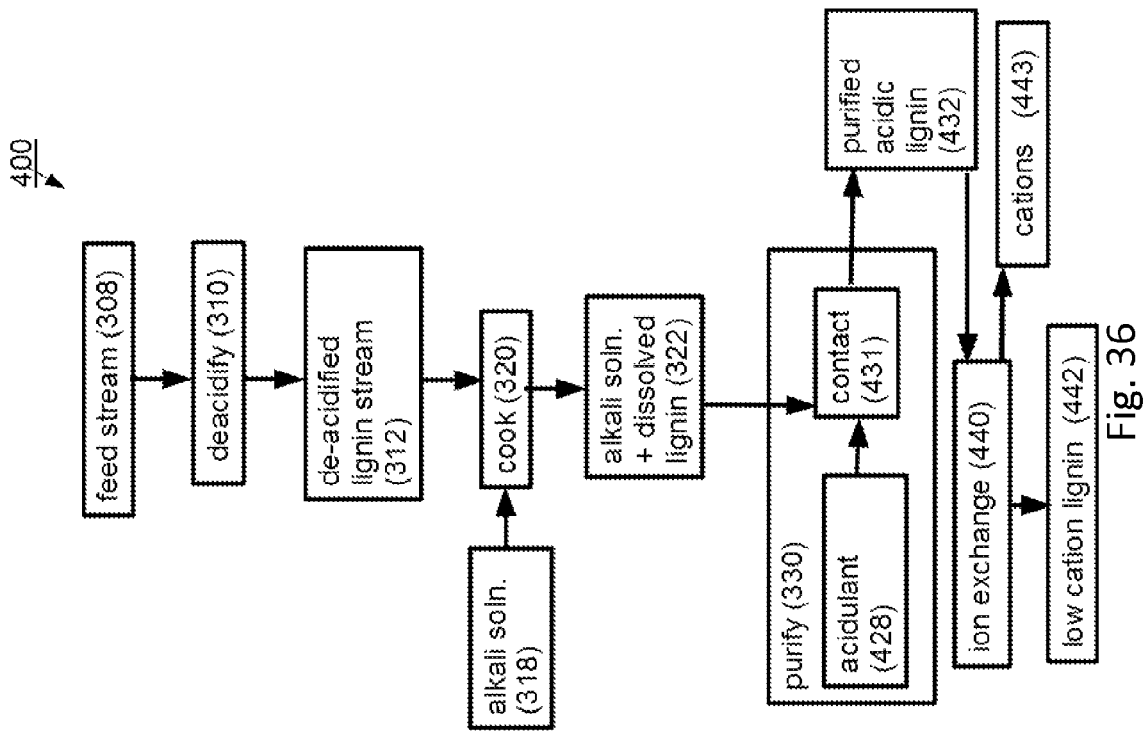
FIG. 36 is a simplified flow diagram of a method according to alternative lignin processing embodiments of the invention.

FIG. 36 is a simplified flow diagram of a method for processing a lignin stream indicated generally as 400. In some embodiments, feed stream 308 corresponds to lignin stream 120 of FIG. 25. Method 400 is similar to method 300 in FIG. 35 in most respects. The main difference between method 400 and method 300 is in the way that purifying 330 is performed. This difference in purifying 330 results in different forms of lignin (i.e. 333 relative to 432).

In some embodiments of method 400 the solid lignin at 312 is acidic. In some embodiments, cooking 320 in alkaline solution 318 produces an alkaline solution 322 containing dissolved basic lignin. In some embodiments of depicted method 400, purifying 330 of basic lignin from solution 322 includes contacting 431 alkaline solution 322 with an acidulant 428 to produce purified acidic lignin 432. In some embodiments, a solution of HCl serves as acidulant 428. In some embodiments, acidulant 428 is added until the pH decreases to 3.7, to 3.6, to 3.5 or to 3.4

In some embodiments, in purified acidic lignin 432 at least 50%, at least 60%, at least 70%, at least 80%, at least 90% or, at least 95% of the acid functions are in protonated form. In some embodiments, in the basic lignin at least 50%, at least 60%, at least 70%, at least 80%, at least 90% or, at least 95% of the acid functions are in dissociated form. In some embodiments, purified acidic lignin 432 is dissolved in solvent 334. In some embodiments, de-acidified lignin stream 312 contains less than 2%, less than 1.5%, less than 1.0%, less than 0.5%, less than 0.3%, less than 0.2 or less than 0.1% HCl weight/weight on as is basis.

Additional Exemplary Purification Options

Referring now to both FIG. 35 and FIG. 36:

In some embodiments, purifying 330 includes contacting 331 alkaline solution 322 with a water-soluble solvent 334 to form a basic solid lignin precipitate 333 and an alkaline solution 336 containing said water-soluble solvent, separating precipitate 333 and contacting 431 (FIG. 36) separated basic solid lignin precipitate 333 (FIG. 35) with acidulant 428. In some embodiments, purifying 330 includes contacting 431 alkaline solution 322 with acidulant 428 to form an acidic solid lignin precipitate 432. In some cases addition of alkaline solution 322 is in an amount that is just sufficient to solubilize the lignin (i.e. stoichiometry). In some embodiments, purifying 330 includes contacting 431 alkaline solution 322 with acidulant 428 and with a limited-solubility solvent (e.g. MEK; not depicted) to form a solvent solution containing acidic lignin 432 dissolved therein. Optionally, the solvent is separated (e.g. by evaporation) to form a solid purified acidic lignin and a solvent stream to be recycled (not depicted). In some embodiments, residual hydrocarbon (e.g. ISOPAR K) from de-acidification 310 forms a separate phase on top of alkaline solution 322 and is removed prior to contact with the limited-solubility solvent. For example, in some embodiments, lignin is decanted from the bottom of the cooking (320) vessel before the limited-solubility solvent is added. In some embodiments, purifying 330 includes contacting said separated basic (solid) lignin precipitate 333 with an acidulant 428 and with a limited-solubility solvent (not depicted) to form a solvent solution containing dissolved acidic lignin 432. Optionally, the limited-solubility solvent is separated (e.g. by evaporation) to form a solid purified acidic lignin and a solvent stream to be recycled (not depicted).

Exemplary De-Acidification Options

In some embodiments of method 300 (FIG. 35) and method 400 (FIG. 36), de-acidifying 310 includes contacting the lignin in feed stream 308 with hydrocarbon (optionally recycled hydrocarbon) to form a de-acidified lignin stream 312 containing solid, optionally acidic, lignin. In some embodiments, stream 312 includes solid lignin and less than 2%, less than 1.5%, less than 1%, less than 0.5%, less than 0.3%, less than 0.2% or less than 0.1% weight/weight HCl on as is basis and a vapor phase 224 containing HCl and water and optionally hydrocarbon. This option is described hereinabove in the context of FIG. 34.

Exemplary Washing Options

In some embodiments of method 300 and method 400, the lignin in stream 308 is washed with a washing HCl solution including at least 5% wt HCl on as is basis to form a washed sugars solution and a washed lignin stream containing solid lignin (optionally acidic), water and HCl. This option is described in the context of FIG. 34. Optionally, the washing is conducted prior to the de-acidifying.

Exemplary Purification Variations

In some embodiments, contacting 431 of the separated basic solid lignin precipitate with acidulant 428 includes washing with a solution of acidulant 428. Optionally, this washing is conducted in two or more stages of contacting/ 431 and/or in countercurrent mode. In some embodiments, contacting 431 basic lignin precipitate with acidulant 428 converts the basic lignin precipitate to acidic solid lignin 432. In some embodiments, contacting 431 alkaline solution 322 with acidulant 428 includes contacting with $CO_2$ under a super-atmospheric pressure. In some embodiments, the super-atmospheric pressure is 2, 4, 6, 8 or 10 bar or intermediate or greater pressure.

In some of the embodiments, contacting 431 alkaline solution 322 includes contacting with acidulant 428 and with a limited-solubility solvent concurrently. In other embodiments, the contacting of alkaline solution 322 with acidulant 428 is conducted prior to the contacting with a limited-solubility solvent. In other exemplary embodiments of the invention, the contacting of alkaline solution 322 with acidulant 428 is conducted after the contacting with the limited-solubility solvent. In some embodiments, the limited-solubility solvent has a boiling point of less than 150, less than 140, less than 130, less than 120 or less than 110° C. at atmospheric pressure.

Exemplary Cation Removal

Figure 39:
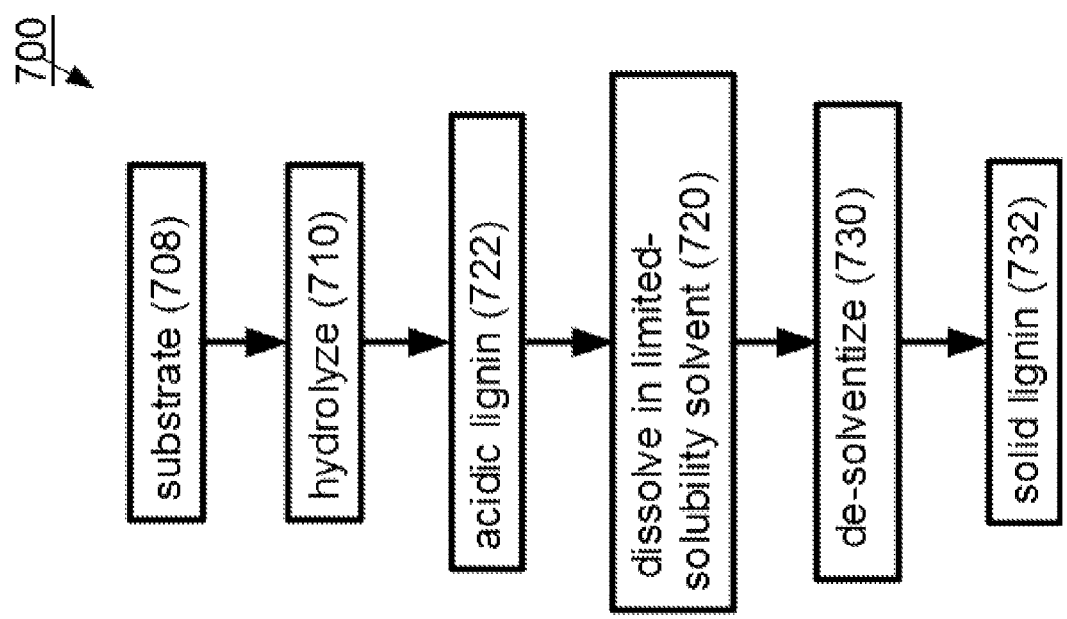
FIG. 39 is a simplified flow diagram of a method according to some exemplary lignin processing embodiments of the invention.

Referring again to FIG. 36, method 400 include removal of cations from purified acidic lignin 432 (dissolved in limited-solubility solvent). In some embodiments, ion exchange 440 removes cations 443 from purified acidic lignin 432 in the limited solubility solvent (e.g. MEK) to produce low cation lignin 442. In some embodiments, ion exchange 440 employs a strong acid cation exchange (SAC) resin (e.g. PUROLITE C150 in the H+ form; Purolite, Bala Cynwyd, Pa., USA). Anion exchange can be viewed as part of preparing 710 (FIG. 39).

The table below summarizes cation concentrations remaining on low cation lignin 442 from two batches of lignin 432 subjected to ion exchange 440 with PUROLITE C150. Batch II, which has a lower total cation concentration, employed more resin per amount of lignin and a slower rate of feed.

| Cations associated with lignin after SAC treatment | | |
|---|---|---|
| Element | Batch | |
| (ppm) | I | II |
| Ca | 400 | 2 |
| K | 77 | <1 |
| Mg | 35 | <1 |
| Na | 170 | 101 |
| Si | 180 | 93 |

| Cations associated with lignin after SAC treatment | | |
|---|---|---|
| Element | Batch | |
| (ppm) | I | II |
| Cu | 5 | 2 |
| Fe | 14 | 104 |
| Total | 881 | 304 |

Exemplary Sugar Concentrations

In some embodiments, a sugar concentration in de-acidified lignin stream 312 is less than 5%, less than 4%, less than 3%, less than 2% or less than 1% weight/weight on as is basis. In some embodiments, a sugar concentration in alkaline solution 322 is less than 3%, less than 2%, less than 1%, less than 0.5% or less than 0.3% weight/weight on as is basis.

Exemplary Solvents

Some embodiments employ limited-solubility solvent. Optionally, the limited-solubility solvent includes one or more of esters, ethers and ketones with 4 to 8 carbon atoms. In some embodiments, the limited-solubility solvent includes ethyl acetate. Optionally, the limited-solubility solvent consists essentially of, or consists of, ethyl acetate. Some embodiments employ water soluble solvent. Optionally, the water soluble solvent includes one or more of methanol, ethanol and acetone.

Exemplary Acidulants

In some embodiments, acidulant 428 includes one or more mineral acids and/or one or more organic acids. In some embodiments, acidulant 428 includes acetic acid and/ or formic acid and/or $SO_2$ and/or $CO_2$.

Additional Exemplary Method

FIG. 39 is a simplified flow diagram of a method for preparing solid lignin indicated generally as 700 according to some embodiments. Method 700 includes dissolving 720 acidic lignin 722 in a limited-solubility solvent (e.g. MEK) and de-solventizing 730 to produce solid lignin 732. In some embodiments, acidic lignin 722 is formed by hydrolyzing 710 cellulose in a lignocellulosic substrate 708 (corresponds to 112 in FIG. 25) with an acid. In some embodiments, acidic lignin 722 is derived from lignin stream 120 (FIG. 25) and includes lignin which remains after substantially all of the cellulose in substrate 112 has been hydrolyzed at 110.

In some embodiments, preparing 710 includes precipitating the acidic lignin (e.g. 432 of FIG. 36) from an alkaline solution and dissolving the acidic lignin in the limited-solubility solvent (e.g. methyl ethyl ketone; MEK). In some embodiments, preparing 710 includes precipitating basic lignin from an alkaline solution (e.g. by contacting 331 with water soluble solvent 334 to form ppt. 333; FIG. 27); and acidifying basic lignin 333 to form acidic lignin 432 and dissolving acidic lignin 432 in the limited-solubility solvent. In some embodiments, preparing 710 includes contacting an alkaline solution including dissolved basic lignin (e.g. 322 of FIG. 35) with an acidulant (e.g. 428 of FIG. 36) and with a limited-solubility solvent to form a solvent solution containing dissolved acidic lignin. In some embodiments, the ratio of limited-solubility solvent to alkaline solution 322 is between 1:3 and 10:1. In some embodiments, the ratio of limited-solubility solvent to alkaline solution 322 is about 3:1. Under these conditions, contacting produces two phases.

In some embodiments, acidulant 428 (e.g. HCl) is added to obtain a pH of 3.7, to 3.6, to 3.5, to 3.4, to 3.3 or to 3.2 or intermediate pH. In some embodiments, upon contacting 431 with a sufficient amount of acidulant 428, the organic phase separates from the aqueous phase and lignin precipitates and partially dissolves in the limited-solubility solvent (e.g. MEK). In some embodiments, inorganic contaminants (e.g. ash and/or salts) dissolve in the aqueous phase.

In some embodiments, de-solventizing 720 includes contacting the acidic lignin dissolved in a limited-solubility solvent prepared at 710 with an anti-solvent (e.g. water and/or hydrocarbon(s)). In some embodiments, method 700 includes evaporation of the limited-solubility solvent. (e.g. anti-solvent is water and evaporation includes azeotropic distillation of MEK).

In some embodiments, de-solventizing 720 includes evaporating the limited-solubility solvent. In some embodiments, evaporating of the limited-solubility solvent includes spray drying and/or contacting with a hot liquid and/or contacting with a hot solid surface. In some embodiments, contacting with a hot solid surface produces a coating of solid lignin on the hot solid surface.

In some embodiments, the hot liquid has a boiling point greater than that of the limited-solubility solvent by at least 10° C. Examples of such liquids include water, hydrocarbons and aromatic compounds.

In some embodiments, method 700 includes wet-spinning the lignin during de-solventization 720. In some embodiments, method 700 includes contacting the lignin with a modifying reagent. In some embodiments, the modifying reagent is added to the limited-solubility solvent. In some embodiments, the modifying reagent is added to an anti-solvent used for de-solventizing. In either case, the lignin contacts the modifying reagent when the limited-solubility solvent contacts the anti-solvent. In some embodiments, adding the modifying reagent occurs prior to or during the de-solventization.

For example, a plasticizer (i.e. modifying reagent) is added to the limited-solubility solvent in some embodiments of the invention. In some embodiments, the modifying reagent includes a surfactant. In some embodiments, the modifying reagent has a physical and/or a chemical interaction with the lignin.

In some embodiments, method 700 includes coating a solid surface with solid lignin 722 (e.g. during de-solventizing 720). In some embodiments of method 700 which employ spray drying for de-solventization 720, the method includes co-spraying the lignin with a second polymer that has a linear arrangement. In some embodiments, this co-spraying contributes to formation of a rod-like assembly of resultant solid lignin 722.

Exemplary Compositions

Some embodiments relate to a lignin composition prepared by a method as described hereinabove. Such a composition has at least 97% weight/weight lignin on a dry matter basis (i.e. less than 3% weight/weight non-lignin material). In some embodiments, such a composition has an ash content of less than 0.1% weight/weight and/or a total carbohydrate content of less than 0.05% weight/weight and/or a volatiles content of less than 5% weight/weight at 200° C. In some embodiments, the composition has a non-melting particulate content (>1 micron diameter; at 150° C.) of less than 0.05% weight/weight. In some embodiments, the composition includes lignin at a concentration of 97% to 99%, 97% to 99.5%, 97% to 99.9%, or 98% to 99% weight/weight on a dry matter basis. In some embodiments, the lignin concentration is about 97.5%, about 98%, about 98.5%, about 99%, or about 99.5% weight/weight. In some embodiments, the ash content is 0.001% to 0.1%, 0.01% to 0.1%, 0.05% to 0.1% or 0.001% to 0.05% weight/weight. In some embodiments, the ash content is about 0.1%, about 0.05%, about 0.02%, about 0.01%, or about 0.005% weight/weight. In some embodiments, the volatiles content is 0.01% to 5%, 0.05% to 5%, 0.3% to 5%, 0.4% to 5%, 0.5% to 5%, 1 to 5%, 0.1% to 1%, 0.1% to 2%, or 0.1% to 1% weight/weight. In some embodiments, the volatiles content is about 0.01%, about 0.02%, about 0.03%, about 0.04%, about 0.05%, about 0.06%, about 0.07%, about 0.08%, about 0.09%, about 0.1%, about 0.12%, about 0.15%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 4.0%, or about 5.0% weight/weight. In some embodiments, the lignin composition has a chloride content of less than 500 ppm, less than 200 ppm, less than 100 ppm, less than 50 ppm, less than 20 ppm, less than 10 ppm, or less than 5 ppm. In some embodiments, the chloride content is about 200 ppm, about 100 ppm, about 50 ppm, about 20 ppm, about 10 ppm, about 5 ppm, or about 1 ppm. In some embodiments, the chloride content is 0.1 to 10 ppm, 1 to 20 ppm, 1 to 50 ppm, or 1 to 100 ppm.

The present invention provides a lignin composition comprising: (i.e. less than 3% non-lignin material); an ash content of less than 0.1% weight/weight; a total carbohydrate content of less than 0.05% weight/weight; a volatiles content of less than 5% at 200° C.; and at least 1 ppm of hydrocarbon of boiling point greater than 140° C., 150° C., 160° C., 170° C. or 180° C. In some embodiments, the hydrocarbon concentration is 1 to 10 ppm, 1 to 20 ppm, 1 to 30 ppm, 1 to 40 ppm, 1 to 50 ppm, 1 to 100 ppm, 1 to 1,000 ppm, 10 to 100 ppm, 20 to 100 ppm, 50 to 200 ppm, 50 to 500 ppm. In some embodiments, the hydrocarbon concentration is about 1 ppm, 5 ppm, 10 ppm, 15 ppm, 20 ppm, 25 ppm, 30 ppm, 35 ppm, 40 ppm, or 50 ppm. Optionally, the composition has a non-melting particulate content (>1 micron diameter; at 150° C.) of less than 0.05%. In some embodiments, the non-melting particulate content is 0.0001 to 0.05%, 0.001 to 0.05% or 0.01 to 0.05% weight/weight. In some embodiments, the concentration the non-melting particulate content is about 0.001%, about 0.005%, about 0.01%, about 0.02%, about 0.03%, about 0.04%, about 0.05% weight/weight.

Exemplary Thermogravimetric Profiles

Figure 37:
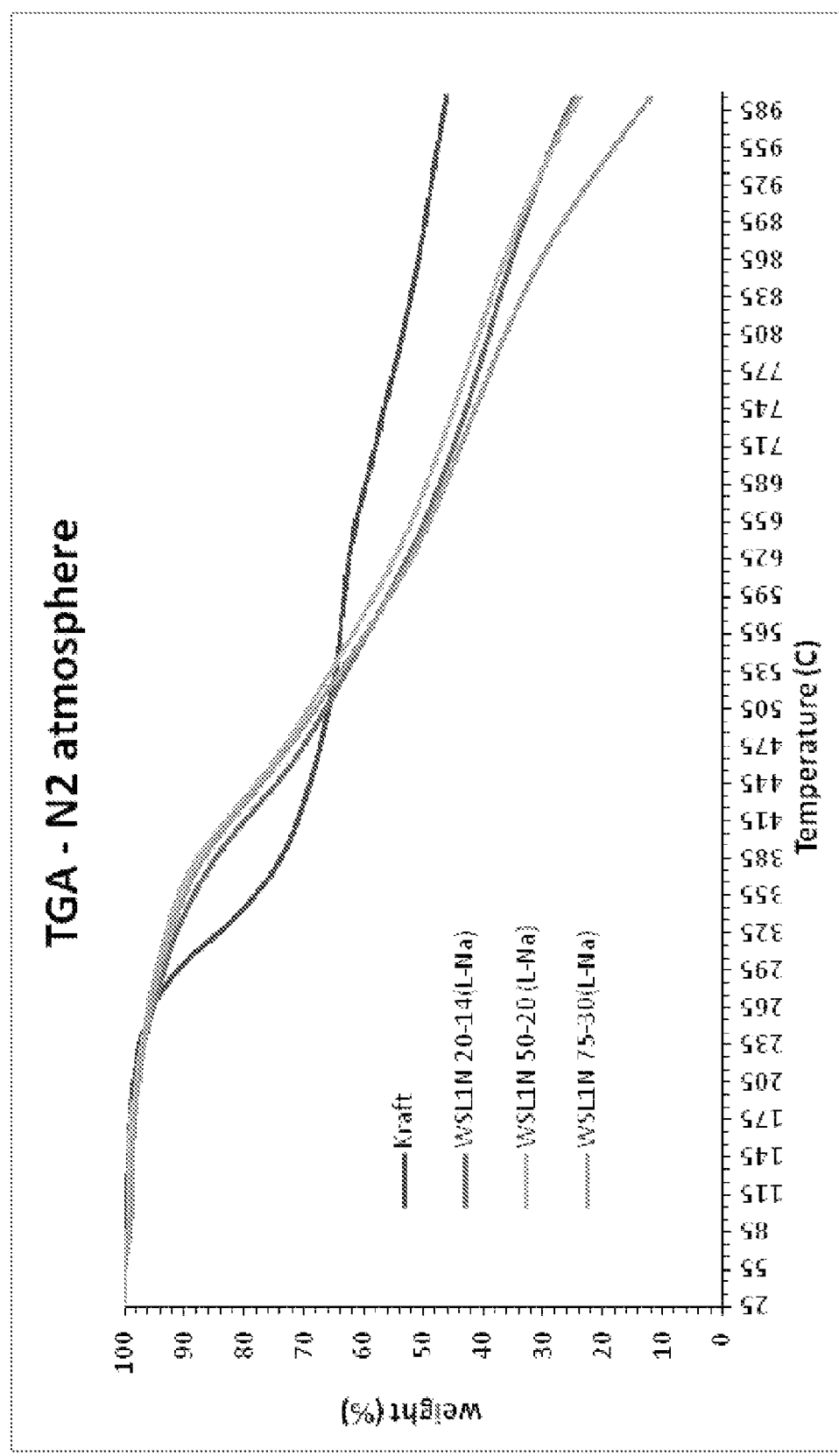
FIG. 37 is a plot of thermo-gravimetric analysis data (TGA) indicating weight percent as a function of temperature for samples of high purity lignin according to exemplary embodiments of the invention incubated in $N_2$.
Figure 38:
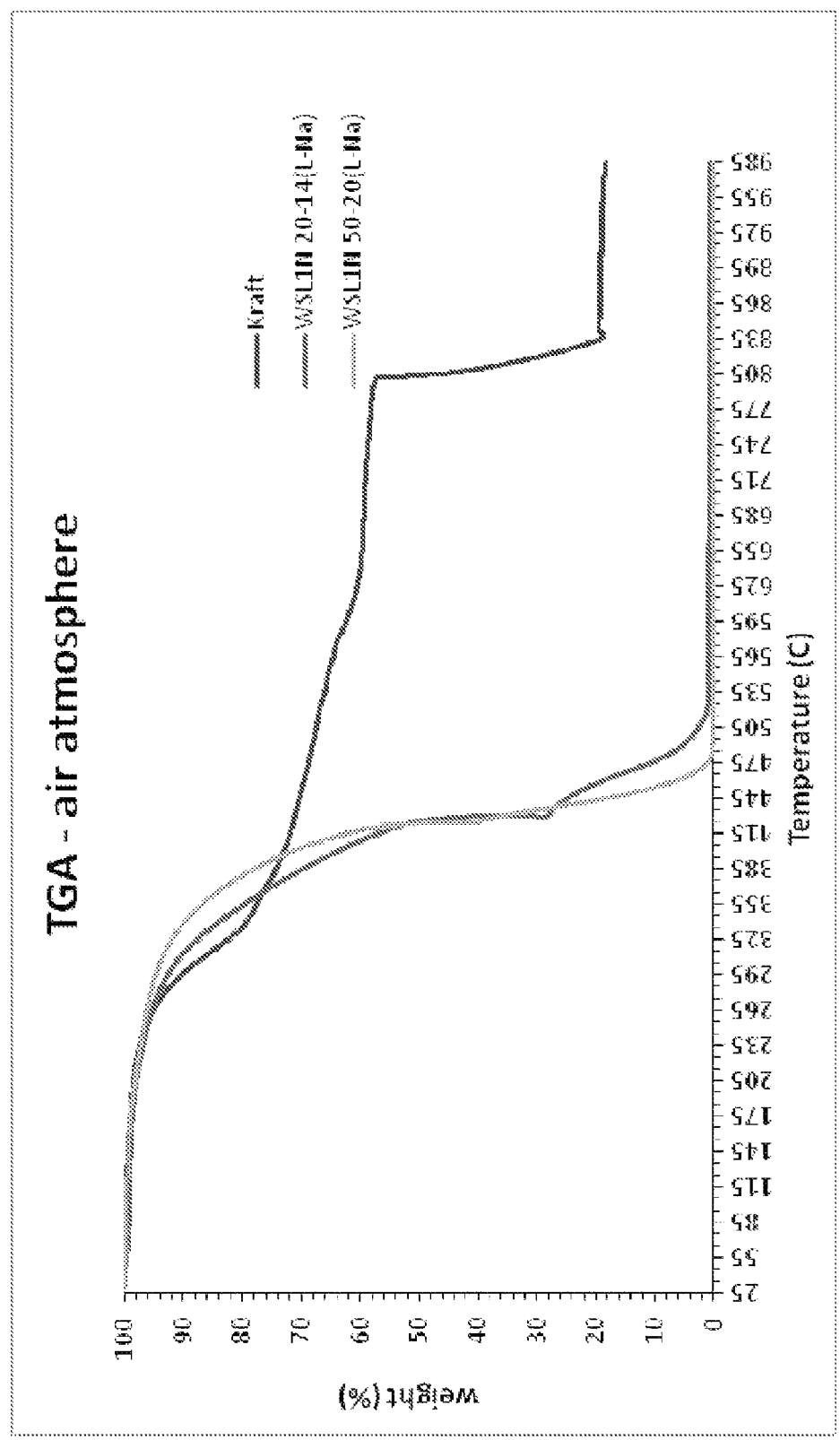
FIG. 38 is a plot of thermo-gravimetric analysis data (TGA) indicating weight percent as a function of temperature for samples of lignin as in FIG. 37 incubated in air.

FIGS. 37 and 38 present thermogravimetric profiles for lignin according to exemplary embodiments of the invention relative to similar profiles for commercially available Kraft Lignin (Sigma-Aldrich; St. Louis; Mo; USA). FIG. 37 is a plot of thermo-gravimetric analysis data (TGA) indicating weight percent as a function of temperature for samples of lignin according to exemplary embodiments of the invention and conventional Kraft lignin incubated in $N_2$. Analysis of the derivative of the TGA data indicated that lignin according to tested exemplary embodiments of the invention is stable to about 420° C. while Kraft lignin is significantly degraded at 310° C.

FIG. 38 is a plot of thermo-gravimetric analysis data (TGA) indicating weight percent as a function of temperature for samples of lignin as in FIG. 37 incubated in air. Analysis of the derivative of the TGA data indicated that lignin according to tested exemplary embodiments of the invention is fully oxidized at about 420° C. while Kraft lignin chars at this temperature.

XIV. Alternative Lignin Solubilization Embodiments

Figure 40:
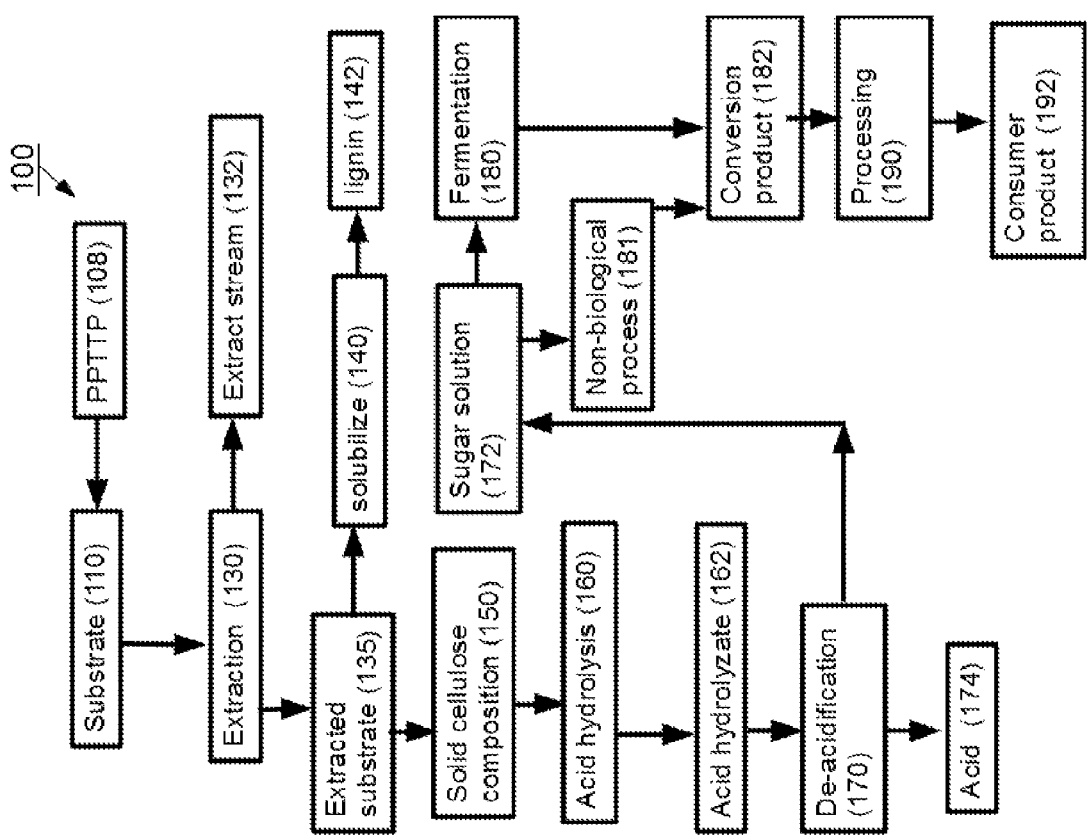
FIG. 40 is a simplified flow scheme of a method according to alternative lignin solubilization embodiments of the invention. PPTTP stands for "predetermined pressure-temperature-time profile."

FIG. 40 is a simplified flow scheme depicting a lignocellulose processing method indicated generally as method 100. Depicted method 100 includes extracting 130 ash, one or more lipophilic materials, and one or more hemicellulose sugars from a lignocellulose substrate 110 to form at least one extract stream 132 and an extracted substrate 135 containing cellulose and lignin. Extracting 130 ash, one or more lipophilic materials, lignin and one or more hemicellulose sugars can occur in any order. For example, the extraction can occur sequentially or concurrently. In some embodiments, one or more extracted solutes is separated from the substrate separately from one or more other extracted solutes. Optionally, this includes two or more extractions. According to the depicted exemplary method, extract stream 132 is separated from extracted substrate 135.

Method 100 also includes solubilizing 140 lignin in extracted substrate 135 to produce a solid cellulose composition 150 containing at least 60% cellulose on dry basis and a lignin stream 142. In some embodiments solid cellulose composition 150 includes 70%, 80%, 90%, or even 95% or more cellulose. In some embodiments, solubilizing 140 includes contacting with an alkaline solution (e.g. pH≥9.0) and/or an organic solvent and/or a base and/or a super-critical solvent and/or a sulfonation agent and/or an oxidizing agent.

Method 100 also includes hydrolyzing 160 solid cellulose composition 150 with an acid to form a hydrolysate 162 including soluble sugars and the acid and de-acidifying 170 hydrolysate 162 to form a de-acidified sugar solution 172. In some embodiments, hydrolyzing 160 is performed in a vessel and at least 90% of available sugars in solid cellulose composition 150 have a residence time in the vessel ≤16 hours.

In some embodiments, a chemical reaction which increases extractability of one or more solutes in the substrate is conducted prior to, or concurrent with, the extraction. For example, lignin may be reacted with a sulfonating agent or an oxidizing agent to solubilize it and make it more extractable. In some embodiments, extraction conditions may be adjusted to increase solubility of one or more potential solutes in the substrate. Extraction conditions that can be altered to increase solubility of a potential solute include temperature, degree of oxidation and pH. In some embodiments, the substrate is treated mechanically (e.g. by grinding or comminution) to increase transfer rate of one or more potential solutes into an applied solvent (extraction liquid). In some embodiments, the substrate is chemically modified to render one or more substrate components more soluble under the extraction conditions.

In some embodiments, extraction includes removal of monomeric or oligomeric subunits released from polymers as solutes. For example, hemicellulose consists primarily of water insoluble polymeric sugars which have a solubility of 1% or less in water at 100° C. However, under appropriate conditions, depolymerization releases sugars with a solubility of more than 1% in water at 100° C. (e.g. monomers such as xylose, mannose, or arabinoses; oligomers containing one or more of these monomers). Lipohilic material includes fatty, water insoluble compounds, for example tall oils, pitch and resins, terpenes, and other volatile organic compounds.

In some embodiments, extraction 130 extracts one or more proteinaceous materials. In some embodiments, extraction 130 removes pectin or oligomers of galactauronic acid from the substrate. In some embodiments, the extracting includes a single extraction 130 which produces a single extract stream 132. In other embodiments, the extracting includes two or more extractions 130 which produce two or more extract streams 132. In some embodiments, a single extraction is conducted in multiple stages. In some embodiments, hydrolysis 160 employs HCl as a catalyst. Optionally, hydrolyzing 160 includes contacting solid cellulose composition 150 with an HCl solution wherein HCl/(HCl+H2O) is at least 25, 30%, 35%, 37%, 39% or at least 41% weight/weight. In some embodiments, the lignin content of hydrolysate 162 is in an amount up to 5%, 4%, 3%, 2% or 1% weight/weight. Optionally, hydrolysate 162 is essentially free of lignin. In some embodiments, the solids content of hydrolysate 162 is in an amount up to 5%, 4%, 3%, 2% or 1%. Optionally, hydrolysate 162 is essentially free of solids. In some embodiments, de-acidifying 170 includes contacting with an S1 solvent. Optionally, the S1 solvent includes hexanol and/or 2-ethyl hexanol.

In some embodiments, method 100 includes applying a predetermined pressure-temperature-time profile (PPTTP) 108 to lignocellulose substrate 110. In some embodiments, PPTTP 108 is characterized by a severity factor of at least 3, 3.2, 3.4, 3.6, 3.8, or 4.0. In some embodiments, PPTTP 108 is characterized by a severity factor of less than 5, 4.8, 4.6, 4.4 or 4.2. Optionally, PPTTP 108 is characterized by a severity factor of 3.4 to 4.2, optionally 3.6 to 4.0, optionally 3.8 to 24.

Exemplary Extraction Conditions

In some embodiments, extracting 130 includes hydrolyzing polysaccharides (not to be confused with hydrolysis 160) in substrate 110 and removing formed water-soluble polysaccharides. Optionally, the removing includes washing and/or pressing. In some embodiments, a moisture content of substrate 110 is at least 40%, at least 50% or at least 60% during both this hydrolyzing and the removing.

In some embodiments, during both this hydrolyzing and the removing a temperature of the substrate is at least 50° C., at least 60° C., at least 70° C., at least 80° C. or at least 90° C.

In some embodiments, this hydrolyzing is conducted at a temperature greater than 100° C. and the removing is conducted at a temperature lower than 100° C. In some embodiments, this hydrolyzing is conducted at a super-atmospheric pressure and the removing is conducted at atmospheric pressure. Optionally, the removing includes washing with a solution of an acid. In some embodiments, the acid includes sulfuric and/or sulfurous acid. In those embodiments employing sulfuric acid, the concentration is optionally 5% or less.

In some embodiments, extracting 130 includes contacting with an extractant containing a water-soluble organic solvent. Examples of suitable water soluble organic solvents include to alcohols and ketones. In some embodiments, the solvent includes acetone. Optionally, the solvent includes a weak acid such as sulfurous acid, acetic acid or phosphorous acid. In some embodiments, extracting 130 includes contacting with an alkaline solution (pH≥9.0) and/or an organic solvent and/or a base and/or a super-critical solvent and/or a sulfonation agent and/or an oxidizing agent. In some embodiments, extracting 130 involves contacting substrate 110 with a solvent at an elevated temperature. In some embodiments, extracting 130 involves contacting with an alkali or alkaline solution at an elevated temperature. In some embodiments, extracting 130 involves oxidation and/or sulfonation and/or contacting with a reactive fluid. Various methods for extracting 130 are described in Carvalheiro et al. (2008; Journal of Scientific & Industrial Research 67:849-864); E. Muurinen (Dissertation entitled: "Organosolv pulping: A review and distillation study related to peroxyacid pulping" (2000) Department of Process Engineering, Oulu University, Finland) and Bizzari et al. (CEH Marketing research report: Lignosulfonates (2009) pp. 14-16).

Exemplary Extracted Substrate Characteristics

In some embodiments, a ratio of cellulose to lignin in extracted substrate 135 is greater than 0.6, greater than 0.7 or even greater than 0.8. In some embodiments, extracted substrate 135 includes ≤0.5% ash. In some embodiments, extracted substrate 135 includes ≤70 PPM sulfur. In some embodiments, extracted substrate 135 includes ≤5% soluble carbohydrate. In some embodiments, extracted substrate 135 includes ≤0.5% tall oils.

Exemplary Solid Cellulose Composition Characteristics

In some embodiments, solid cellulose composition 150 includes at least 80%, 85%, 90%, 95%, or 98% cellulose on a dry matter basis. In some embodiments, the cellulose in solid cellulose composition 150 is at least 40%, 50%, 60%, 70% or 80% crystalline. In some embodiments, less than 50%, 40%, 30% or 20% of the cellulose in solid cellulose composition 150 is crystalline cellulose.

In some embodiments, solid cellulose composition 150 includes at least 85%, 90%, 95% or 98% of the cellulose in lignocellulose substrate 110. In some embodiments, solid cellulose composition 150 includes less than 50%, less than 60%, less 70% or less than 80% of the ash in lignocellulose substrate 110. In some embodiments, solid cellulose composition 150 includes less than 50%, less than 60%, less than 70% or less than 80% of the calcium ions in lignocellulose substrate 110. In some embodiments, solid cellulose composition 150 includes less than 30% 20%, 10% or even less than 5% weight/weight of the lipophilic materials in lignocellulose substrate 110. In some embodiments, solid cellulose composition 150 includes in an amount up to 30% 20%, 10% or 5% weight/weight of the lignin in lignocellulose substrate 110. In some embodiments, solid cellulose composition 150 includes water-soluble carbohydrates at a concentration of less than 10% wt, 8% wt, 6% wt, 4% wt, 2% wt, or 1% wt. In some embodiments, solid cellulose composition 150 includes acetic acid in an amount ≤50%, ≤40%, ≤30 or even ≤20% weight/weight of the acetate function in 110.

In some embodiments, lignocellulose substrate 110 includes pectin. Optionally, solid cellulose composition 150 includes less than 50%, 40%, 30%, or 20% weight/weight of the pectin in substrate 110. In some embodiments, lignocellulose substrate 110 includes divalent cations. Optionally, solid cellulose composition 150 includes less than 50%, 40%, 30%, or 20% weight/weight of divalent cations present in substrate 110.

Exemplary Acid Hydrolysis Parameters

In some embodiments, acid hydrolysis 160 is performed in a vessel and ≤99% of solid cellulose composition 150 is removed from the vessel as hydrolysate 162 while ≥1% of solid cellulose composition 150 is removed as residual solids. Exemplary vessel configurations suitable for use in these embodiments are described in co-pending PCT application US2011/57552 (incorporated by reference herein for all purposes). In some embodiments, the vessel employs a trickling bed. Optionally, there is essentially no solids removal from the bottom of the vessel. In some embodiments, the vessel has no drain.

In some embodiments, at least 90% of available sugars in solid cellulose composition 150 have a residence time in vessel ≤16 hours; ≤14; ≤12; ≤10≤15 or even ≤2 hours.

Exemplary Hemicellulose Stream Characteristics

In some embodiments, extracting 130 produces a hemicellulose sugar stream (depicted as extract stream 132) characterized by a purity of at least 90%, at least 92%, at least 94%, at least 96% or at least 97% weight/weight on a dry matter basis.

In some embodiments, the hemicellulose sugar stream has a w/w ratio of sugars to hydroxymethylfurfural greater than 10:1, greater than 15:1 or greater than 20:1. In some embodiments, the hemicellulose sugar stream has hydroxymethylfurfural content of less than 100 PPM. 75 PPM, 50 PPMH or even less than 25 PPM.

Optionally, the hemicellulose sugar stream includes soluble fibers.

In some embodiments, the hemicellulose sugar stream includes acetic acid in an amount equivalent to at least 50%, at least 60%, at least 70% or even at least 80% weight/weight of the acetate function in substrate 110.

In some embodiments, substrate 110 includes pectin and the hemicellulose sugar stream includes methanol in an amount equivalent to at least 50%, at least 60%, at least 70% or at least 80% weight/weight of the methanol in the pectin.

In some embodiments, the hemicellulose sugar stream includes divalent cations in an amount equivalent to at least 50%, at least 60%, at least 70%, at least or even %, at least 80% weight/weight of their content in 110.

Exemplary Sugar Conversion

In some embodiments, method 100 (FIG. 40) includes fermenting 180 de-acidified sugar solution 172 to produce a conversion product 182. In other embodiments, method 100 (FIG. 40) includes subjecting de-acidified sugar solution 172 to a non-biological process 181 to produce a conversion product 182. Exemplary non-biological processes include pyrolysis, gasification and "bioforming" or "aqueous phase reforming (APR)" as described by Blommel and Cartwright in a white paper entitled "Production of Conventional Liquid Fuels from Sugars" (2008) as well as in U.S. Pat. No. 6,699,457; U.S. Pat. No. 6,953,873; U.S. Pat. No. 6,964,757; U.S. Pat. No. 6,964,758; U.S. Pat. No. 7,618,612 and PCT/US2006/048030; (incorporated by reference herein for all purposes).

In some embodiments, method 100 includes processing 190 conversion product 182 to produce a consumer product 192 selected from the group consisting of detergent, polyethylene-based products, polypropylene-based products, polyolefin-based products, polylactic acid (polylactide)-based products, polyhydroxyalkanoate-based products and polyacrylic-based products.

In some embodiments, detergent contains a sugar-based surfactant, a fatty acid-based surfactant, a fatty alcohol-based surfactant, or a cell-culture derived enzyme. In some embodiments, a polyacrylic-based product is selected from plastics, floor polishes, carpets, paints, coatings, adhesives, dispersions, flocculants, elastomers, acrylic glass, absorbent articles, incontinence pads, sanitary napkins, feminine hygiene products, and diapers. In some embodiments, polyolefin-based products are selected from milk jugs, detergent bottles, margarine tubs, garbage containers, water pipes, absorbent articles, diapers, nonwovens, HDPE toys and HDPE detergent packaging. In some embodiments, polypropylene based products are selected from absorbent articles, diapers and nonwovens. In some embodiments, polylactic acid based products are selected from packaging of agriculture products and of dairy products, plastic bottles, biodegradable products and disposables. In some embodiments, polyhydroxyalkanoate based products are selected from packaging of agriculture products, plastic bottles, coated papers, molded or extruded articles, feminine hygiene products, tampon applicators, absorbent articles, disposable nonwovens and wipes, medical surgical garments, adhesives, elastomers, films, coatings, aqueous dispersants, fibers, intermediates of pharmaceuticals and binders. In other exemplary embodiments of the invention, conversion product 182 includes at least one member of the group consisting of ethanol, butanol, isobutanol, a fatty acid, a fatty acid ester, a fatty alcohol and biodiesel.

According to these embodiments, method 100 can include processing 190 of conversion product 182 to produce at least one consumer product 192 selected from the group consisting of an isobutene condensation product, jet fuel, gasoline, gasohol, diesel fuel, drop-in fuel, diesel fuel additive, and a precursor thereof. In some embodiments, gasahol is ethanol-enriched gasoline or butanol-enriched gasoline. In some embodiments, consumer product 192 is selected from the group consisting of diesel fuel, gasoline, jet fuel and drop-in fuels.

Exemplary Consumer Products from Sugars

The present invention also provides a consumer product 192, a precursor of a consumer product 192, or an ingredient of a consumer product 192 produced from conversion product 182. Examples of such consumer products 192, precursor of a consumer products 192, and ingredients of a consumer product 192 include at least one conversion product 182 selected from carboxylic and fatty acids, dicarboxylic acids, hydroxylcarboxylic acids, hydroxyldicarboxylic acids, hydroxyl-fatty acids, methylglyoxal, mono-, di-, or poly-alcohols, alkanes, alkenes, aromatics, aldehydes, ketones, esters, biopolymers, proteins, peptides, amino acids, vitamins, antibiotics, and pharmaceuticals.

In some embodiments, consumer product 192 is ethanol-enriched gasoline, jet fuel, or biodiesel. Optionally, consumer product 192, or its precursor precursor of a consumer product, or an ingredient of thereof has a ratio of carbon-14 to carbon-12 of about $2.0 \times 10^{-13}$ or greater. In some embodiments, consumer product 192 includes an ingredient as described above and an additional ingredient produced from a raw material other than lignocellulosic material. In some embodiments, the ingredient and the additional ingredient produced from a raw material other than lignocellulosic material are essentially of the same chemical composition. In some embodiments, consumer product includes 192 a marker molecule at a concentration of at least 100 ppb. In some embodiments, the marker molecule is selected from the group consisting of furfural, hydroxymethylfurfural, products of furfural or hydroxymethylfurfural condensation, color compounds derived from sugar caramelization, levulinic acid, acetic acid, methanol, galcturonic acid, and glycerol.

In some embodiments, solubilizing 140 produces a lignin stream 142.

Exemplary Lignin Stream Characteristics

Figure 41:
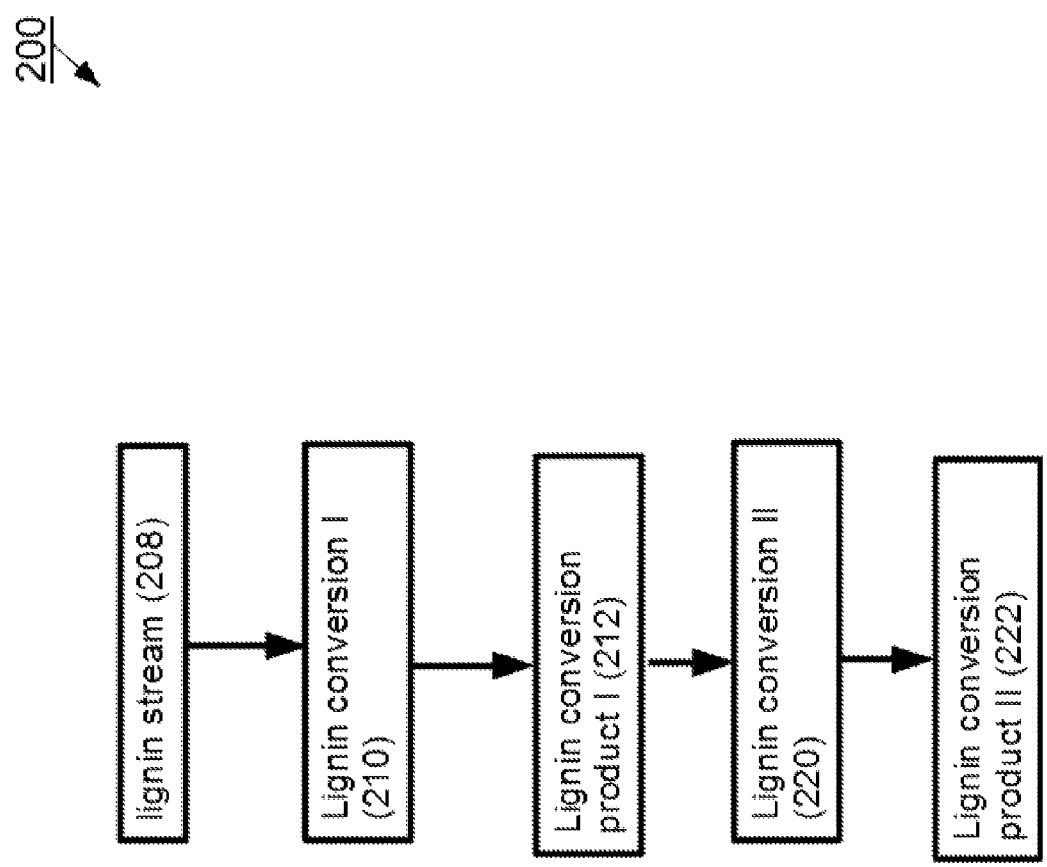
FIG. 41 is a simplified flow scheme of a method according to some exemplary lignin conversion processes.

FIG. 41 is a simplified flow scheme of a method for processing a lignin stream indicated generally as method 200. In depicted embodiment 200, lignin stream 208 corresponds to lignin stream 142 of FIG. 40.

In some embodiments, lignin stream 208 is characterized by a purity of least 90%, 92%, 94%, 96% or 97% weight/weight or more. Purity of lignin stream 208 is measured on a solvent free basis. In some embodiments, the solvent includes water and/or an organic solvent. Concentrations of impurities in lignin stream 208 are on as is basis. In some embodiments, lignin stream 208 includes chloride (Cl) content in an amount up to 0.5%, 0.4%, 0.3%, 0.2%, 0.1 or 0.05% weight/weight. In some embodiments, lignin stream 208 includes ash content in an amount up to 0.5%, 0.4%, 0.3%, 0.2%, or 0.1% weight/weight. In some embodiments, lignin stream 208 includes phosphorus at a concentration of less than 100 PPM, less than 50 PPM, less than 25 PPM, less than 10 PPM, less than 1 PPM, less than 0.1 PPM, or less than 0.01 PPM. In some embodiments, lignin stream 208 includes a soluble carbohydrate content in an amount up to 5%, 3%, 2%, or 1% weight/weight. In some embodiments, lignin stream 208 includes one or more furfurals at a total concentration of at least 10 PPM, at least 25 PPM, at least 50 PPM, or even at least 100 PPM. In some embodiments, lignin stream 208 includes ≤0.3%, ≤0.2% or ≤0.1% weight/weight divalent cations. In some embodiments, lignin stream 208 includes ≤0.07%, ≤0.05% or ≤0.03% weight/weight sulfur. In some embodiments, lignin stream 208 includes lignin in solution and/or a suspension of solid lignin in a liquid. In some embodiments, the liquid includes water and/or an organic solvent. Alternatively, lignin stream 208 can be provided as a wet solid or a dry solid. In those embodiments including lignin in solution, the lignin concentration can be greater than 10%, 20%, 30% or greater than 40% weight/weight.

Exemplary Lignin Conversion Method

Referring again to FIG. 41, in some embodiments, method 200 includes converting 210 at least a portion of lignin in lignin stream 208 to a conversion product 212. In some embodiments, converting 210 employs depolymerization, oxidation, reduction, precipitation (by neutralization of the solution and/or by solvent removal), pyrolysis, hydrogenolysis, gasification, or sulfonation. In some embodiments, conversion 210 is optionally conducted on lignin while in solution, or after precipitation. In some embodiments, converting 210 includes treating lignin with hydrogen. In some embodiments, converting 210 includes producing hydrogen from lignin.

In some embodiments, conversion product 212 includes at least one item selected from the group consisting of bio-oil, carboxylic and fatty acids, dicarboxylic acids, hydroxylcarboxylic, hydroxyldicarboxylic acids and hydroxyl-fatty acids, methylglyoxal, mono-, di- or poly-alcohols, alkanes, alkenes, aromatics, aldehydes, ketones, esters, phenols, toluenes, and xylenes. In some embodiments, the conversion product includes a fuel or a fuel ingredient. Optionally, the conversion product includes para-xylene.

In some embodiments, converting 210 includes aqueous phase reforming. In some embodiments, converting 210 includes at least one bioforming reaction. Exemplary bioforming reaction types include catalytic hydrotreating and catalytic condensation, zeolite (e.g. ZSM-5) acid condensation, base catalyzed condensation, hydrogenation, dehydration, alkene oligomerization and alkylation (alkene saturation). In some embodiments, the converting occurs in at least two stages (e.g. 210 and 220) which produce conversion products 212 and 222 respectively. Optionally, a first stage (210) includes aqueous phase reforming. In some embodiments, second stage 220 includes at least one of catalytic hydrotreating and catalytic condensation.

Optionally, method 200 is characterized by a hydrogen consumption of less than 0.07 ton per ton of product 212 and/or 222.

Exemplary Lignin Products

The present invention also provides a consumer product, a precursor of a consumer product or an ingredient of a consumer product produced from a lignin stream 208. In some embodiments, the consumer product is characterized by an ash content of less than 0.5% wt and/or by a carbohydrates content of less than 0.5% wt and/or by a sulfur content of less than 0.1% wt and/or by an extractives content of less than 0.5% wt. In some embodiments, the consumer product produced from lignin stream 208 includes one or more of bio-oil, carboxylic and fatty acids, dicarboxylic acids, hydroxylcarboxylic, hydroxyldicarboxylic acids and hydroxyl-fatty acids, methylglyoxal, mono-, di- or poly-alcohols, alkanes, alkenes, aromatics, aldehydes, ketones, esters, biopolymers, proteins, peptides, amino acids, vitamins, antibiotics, and pharmaceuticals. In some embodiments, the consumer product includes one or more of dispersants, emulsifiers, complexants, flocculants, agglomerants, pelletizing additives, resins, carbon fibers, active carbon, antioxidants, liquid fuel, aromatic chemicals, vanillin, adhesives, binders, absorbents, toxin binders, foams, coatings, films, rubbers and elastomers, sequestrants, fuels, and expanders. In some embodiments, the product is used in an area selected from the group consisting of food, feed, materials, agriculture, transportation and construction. Optionally, the consumer product has a ratio of carbon-14 to carbon-12 of about $2.0 \times 10^{-13}$ or greater.

Some embodiments relate to a consumer product containing an ingredient as described above and an ingredient produced from a raw material other than lignocellulosic material. In some embodiments, the ingredient and the ingredient produced from a raw material other than lignocellulosic material are essentially of the same chemical composition.

In some embodiments, the consumer product includes a marker molecule at a concentration of at least 100 ppb. In some embodiments, the marker molecule is selected from the group consisting of furfural and hydroxymethylfurfural, products of their condensation, color compounds, acetic acid, methanol, galactauronic acid, glycerol, fatty acids and resin acids.

In some embodiments, the product is selected from the group consisting of dispersants, emulsifiers, complexants, flocculants, agglomerants, pelletizing additives, resins, carbon fibers, active carbon, antioxidants, liquid fuel, aromatic chemicals, vanillin, adhesives, binders, absorbents, toxin binders, foams, coatings, films, rubbers and elastomers, sequestrants, fuels, and expanders.

EXAMPLES

It is understood that the examples and embodiments described herein are for illustrative purposes only and are not intended to limit the scope of the claimed invention. It is also understood that various modifications or changes in light the examples and embodiments described herein will be suggested to persons skilled in the art and are to be included within the spirit and purview of this application and scope of the appended claims. All publications, patents, and patent applications cited herein are hereby incorporated by reference in their entirety for all purposes.

Example 1

Small Scale Hemicellulose Sugar Extraction

Table 1 provides a summary of chemical analysis of the liquor resulting from hemicellulose sugar extraction of various biomass types. The % monomeric sugar is expressed as % weight out of total sugars weight. All other results are expressed as % weight relative to dry biomass.

All treatments were carried out in a 0.5 L pressure reactor equipped with a stirrer and heating-cooling system. The reactor was charged with the biomass and the liquid at amounts given in the table. The reactor was heated to the temperature indicated in the table, time count was started once the reactor reached 5° C. below the designated temperature. Once the time elapsed, the reactor was cooled down. Solid and liquid were separated, and the content of the obtained liquor was analyzed, all data was back calculated relative to dry biomass weight. HPLC methods were applied to evaluate % Total Sugars in the liquor, % monomeric sugars and % Acetic Acid. The % Degradation product is the sum of % Furfurals (GC or HPLC analysis), % Formic acid (HPLC) and % Levullinic acid (HPLC). Acid Soluble Lignin was analyzed according to NREL TP-510-42627 method.

TABLE 1

Treatment conditions and chemical analysis of the resulting liquor

| Ref# | Biomass Type | Biomass Dry wt, g | Soln. wt. | Acid(s) con. % wt | T ° C. | Time, min | % TS[1]/ DB[2] | % DP1[3]/ % TS | % AcOH[4]/ DB | % Degradation Products[5]/ DB | % ASL/ DB |
|---|---|---|---|---|---|---|---|---|---|---|---|
| 9114 | Eucalyptus | 45.2 | 198.2 | 0.7[6] | 140 | 40 | 22.4 | NA | 1.7 | NA | NA |
| 5a | Eucalyptus | 33.2 | 199.5 | 0.7[6] | 135 | 90 | | | | | |
| 90 | 60 | | | | | 60 | 21.8 | 91 | 3.6 | 1.3 | 3.5 |
| 9004 | Acacia | 33.7 | 201.8 | 0.7[6] | 145 | 40 | 21.2 | 79 | 3.3 | 0.9 | 2.6 |
| 9012 | Leucaena | 34.1 | 201.8 | 0.7[6] | 145 | 60 | 22.0 | 96 | 3.4 | 1.3 | 2.0 |
| 9018 | EFB | 34.6 | 203.8 | 0.7[6] | 145 | 40 | 25.2 | 79 | 1.3 | 0.7 | 1.2 |
| 9019 | Bagasse | 13.3 | 194.8 | 0.7[6] | 145 | 40 | 29.8 | 96 | 2.5 | 0.7 | 2.5 |
| YH Tp8 3/15 | Pine | 18.1 | 190.5 | 0.7[7] | 160 | 15 | 22.9 | 95 | 0.07 | 1.5 | 0.9 |

[1] % Total Sugars (% TS) measured by HPLC in the liquor
[2] DB—Dry Biomass
[3] % Monomers out of total dissolved sugars measured by HPLC in the liquor
[4] % Acetic Acid measured by HPLC in the liquor
[5] % Degradation Products = % Furfurals + % Formic Acid + % Levullinic Acid. % Furfurals measured by GC or HPLC, % Formic acid and % Levullinic acid measured by HPLC
[6] 0.5% $H_2SO_4$ + 0.2% $SO_2$
[7] 0.7% $H_2SO_4$ + 0.03% Acetic acid

Example 2

Large Scale Chemical Analysis of Lignocellulose Matter after Hemicellulose Sugar Extraction Table 2 provides a summary of chemical analysis of various types of biomass after hemicellulose sugar extraction.

Pine (ref A1202102-5): Fresh Loblloly pine chips (145.9 Lb dry wood) were fed into a Rapid Cycle Digester (RDC, Andritz, Springfield, Ohio. An acid aqueous solution (500 Lb) was prepared by adding 0.3% H2SO4 and 0.2% SO2 to water in a separate tank. The solution was heated to 135 C and then added to the digester to cover the wood. The solution was circulated through the wood for 40 minutes while maintaining the temperature. After 60 minutes, the resulting liquor was drained to a liquor tank and using steam the wood was blown to a cyclone to collect the wood (128.3 Lb dry wood) and vent the vapor. The extracted wood was analyzed for sugar content, carbohydrate composition, ash, elements (by ICP), and DCM extractives. The analyses of the hemi depleted lignocellulose material show extraction of 42.4% Arabinan, 10.5% Galactan, 9.6% Xylan, 14.3% Manan, and 11.8% Glucan, indicating that mostly hemicellulose is extracted. Analyses also show 11.6% of "others", Eucalyptus (ref A120702K6-9): Fresh Eucalyptus Globulus chips (79.1 Kg dry wood) were fed into a Rapid Cycle Digester (RDC, Andritz, Springfield, Ohio). An acid aqueous solution was prepared by adding 0.5% H2SO4 and 0.2% SO2 to water in a separate tank. The solution was heated to 145 C and then added to digester to cover the wood. The solution was circulated through the wood for 60 minutes while maintaining the temperature, then heating was stopped while circulation continued for another 60 minute, allowing the solution to cool. After 120 minutes, the resulting liquor was drained to a liquor tank and using steam the wood was blown to a cyclone to collect the wood (58.8 Kg dry wood) and vent the vapor. The material was analyzed as described above. Analyses showed that 20.1% of the carbohydrates were extracted from the wood (dry wood base) xylose containing 70% of these sugars, 91% of the sugars in the liquor present as monomers. Under these conditions acetic acid concentration in the liquor was 3.6% (dry wood base) showing maximal removal of acetate groups from hemicellulose sugars; 4.2% (dry wood base) of acid soluble lignin. These results indicate effective extraction of hemicellulose and in particularly xylose, along with hydrolysis of the acetate groups from substituted xylosans. At the same time a significant amount of acid soluble lignin, extractives and ash are also extracted into the liquor.

TABLE 2

Chemical analysis of lignocellulose matter after hemicellulose sugar extraction

| Ref | Biomass Type | Ash % wt | Ca ppm | Na ppm | Mg ppm | K ppm | % Arabinan | % Galactan | % Glucan | % Xylan | % Mannan | % Total Carbohydrate | DCM Extractives |
|---|---|---|---|---|---|---|---|---|---|---|---|---|---|
| A1202102-5[1] | Pine | 0.59 | 248 | NA | 123 | 92 | 0.25 | 1.33 | 48.13 | 4.75 | 8.48 | 62.94 | NA |
| A1204131-14(K1)[2] | Pine | 0.31 | 113 | 388 | 44 | 23 | 0.21 | 0.38 | 51.68 | 3.14 | 4.89 | 60.30 | 1.07 |
| A120702K6-9[3] | Eucalyptus | 0.35 | 95 | 109 | 30 | 72 | <0.01 | 0.03 | 67.48 | 2.13 | 0.20 | 69.54 | 0.26 |

[1]Hemicellulose sugar extraction: 135° C. for 60 minutes, 0.3% H$_2$SO$_4$, 0.2% S0$_2$.
[2]Hemicellulose sugar extraction: 135° C. for 180 minutes, 0.3% H$_2$SO$_4$, 0.2% S0$_2$.
[3]Hemicellulose sugar extraction: 145° C. for 60 minutes + cool down 60 minutes, 0.3% H2SO4, 0.2% S0$_2$.

including ASL, extractives and ash. The overall fraction of carbohydrates in the remaining solid is not different within the error of the measurement to that of the starting biomass due to this removal of "others". It is however easily notices that the extracted woodchips are darker in color and are more brittle than the fresh biomass.

Pine (ref A1204131-14(K1)): Fresh Loblloly pine chips (145.9 Lb dry wood) were fed into a Rapid Cycle Digester (RDC, Andritz, Springfield, Ohio). An acid aqueous solution (500 Lb) was prepared by adding 0.3% H2SO4 and 0.2% SO2 to water in a separate tank. The solution was heated to 135 C and then added to the digester to cover the wood. The solution was circulated through the wood for 180 minutes while maintaining the temperature. After 180 minutes, the resulting liquor was drained to a liquor tank and using steam the wood was blown to a cyclone to collect the wood (121.6 Lb dry wood) and vent the vapor. The material was analyzed as described above. The analyses of the hemi depleted lignocellulose material show extraction of 83.9% Arabinan, 84.3% Galactan, 50.1% Xylan, 59.8% Manan and no extraction of glucan, indicating effective extraction of hemicellulose. Analyses also show extraction of 21.8% of "others" including lignin, extractives and ash.

Example 3

Aqueous and Organic Streams Resulting from Amine Extraction with Hardwood

The acidic hemicellulose sugar stream resulting from hemicellulose sugar extraction of Eucalyptus chips (as exemplified in Example 2) was used in this small scale experiment. The aqueous stream before the extraction was prepared by extracting eucalyptus in a solution containing 0.5% H$_2$SO$_4$ and 0.2% SO$_2$, separating the liquid from the solid, and contacting the liquid with a strong cation exchange resin. The results provided were obtained in a batch experiment, where the organic phase (amine extractant; tri-laurylamine:hexanol ratio 3:7) to aqueous phase (hemicellulose sugar stream) ratio was 4:1, contact time 15 minutes at 60° C. A highly efficient extraction of sulfuric acid and acetic acid is observed, along with good extraction of acid soluble lignin (75%) and minimal loss of sugars (2%) into the organic phase.

Table 3 provides chemical analysis of the aqueous stream before and after the amine extraction, expressed as % weight of the aqueous solution.

TABLE 3

Chemical composition of the aqueous stream before and after amine extraction

| Solute | Aqueous Stream Before Amine Extraction | Aqueous Stream After Amine Extraction | % Extracted |
|---|---|---|---|
| % Acetic acid | 0.856 | 0.017 | 98 |
| % Sulfuric acid | 0.5131 | 0.0001 | 100 |
| % Total sugar | 5.07 | 4.97 | 2 |
| % ASL | 0.25 | 0.063 | 75 |
| % 2-Furfural | 0.041 | 0.003 | 93 |
| % HMF | 0.0007 | 0.0000 | 98 |

Example 4

Back Extraction of the Acid from the Amine Extractant

The amine extractant of Example 3 was contacted with a 1% sodium carbonate solution at a 1:1 ratio for 15 minutes at 60° C. It was observed that 84% of the acetic acid and 89% of the sulfuric acid were back extracted from the amine extractant organic phase. Organic acids can be recovered from the back extraction. Alternatively, the back extraction can be diverted to waste treatment. Table 4 summarizes the acid concentrations in the amine extractant before and after the back extraction.

TABLE 4

Mineral acid and acetic acid concentration in the organic stream before and after back extraction

| parameters | Amine extractant before back extraction | Amine extractant after back extraction |
|---|---|---|
| % acetic acid | 0.213 | 0.035 |
| % sulfuric acid | 0.128 | 0.014 |

Example 5

Eucalyptus Sugar Composition

Eucalyptus sugar composition (DH2C001): *Eucalyptus Globulus* chips were extracted by treating about 1200 Lb wood (dry base) with an aqueous solution containing 0.5% $H_2SO_4$ and 0.2% $SO_2$, at a ratio of 2.66 liquid to solid in an agitated, temperature controlled tank at average temperature of 130-135° C. for 3 hours. The collected liquor was collected, the chips were washed with water, the wash water was then used to prepare the acid solution of the next batch by adding acids as needed. The hemicellulose-depleted chips were then milled to 1400 micron and dried to ~15% moisture.

The acidic hemicellulose sugar stream ran through a SAC column. The sugar stream was then extracted batchwise for two times with an extractant having tri-laurylamine:hexanol at a ratio of 30:70. The extractant to sugar stream ratio 2:1. The resulting aqueous phase was further purified by using a SAC column, a WBA resin and a mixed bed resin. The pH of the resulting stream was adjusted to 4.5 with 0.5% HCl and the sugar solution was evaporated to final concentration of ~70% DS.

The resulting hemicellulose sugar mixture was evaporated to a total sugar concentration of 70-80%, to render it osmotically stable. Table 5A provides a chemical analysis of the resulting hemicellulose sugar mixture.

TABLE 5A

Chemical analysis of a hemicellulose sugar mixture produced by hemicellulose sugar extraction and purification of *eucalyptus* chips

| PARAMETER | RESULT | UNITS |
|---|---|---|
| APPEARANCE | Colorless | |
| pH | 3.13 | |
| Saccharides | | |
| DS (HPLC) | 72.37 | % wt/wt |
| % Total monosaccharides | 91.71 | DS/DS (w/w) |
| Composition (HPAE-PAD) | | |
| XYLOSE | 67.23 (48.65) | DS/DS (w/w) |
| ARABINOSE | 3.09 (2.24) | DS/DS (w/w) |
| MANNOSE | 5.83 (4.22) | DS/DS (w/w) |
| GLUCOSE | 4.64 (3.36) | DS/DS (w/w) |
| GALACTOSE | 8.22 (5.95) | DS/DS (w/w) |
| FRUCTOSE | 3.40 (2.46) | DS/DS (w/w) |
| Impurities | | |
| Furfurals (UV) | 0.0005 | % wt/wt |
| Phenols (FC) | 0.047 | % wt/wt |
| Metals & inorganics (ICP) | | |
| Ca | <2 | ppm |
| Cu | <2 | ppm |
| Fe | <2 | ppm |
| K | <2 | ppm |
| Mg | <2 | ppm |
| Mn | <2 | ppm |
| Na | 22 | ppm |
| S | 6.7 | ppm |
| P | 4.2 | ppm |

Bagasse sugar composition (DB4D01): Baggase was shredded in a wood shredder. In a temperature controlled tank, 60 Lb bagasse (dry base) was then treated with an aqueous solution containing 0.5% $H_2SO_4$, at a liquid to solid ratio of 14.2. The average temperature of the temperature controlled tank was maintained at 130-135° C. for 3 hours. The solution was circulated by pumping. The resulting liquor was collected, and the solids were washed with water. The wash water was then used to prepare the acid solution for the next batch by adding acids as needed. The hemicellulose-depleted lignocellulosic matter was collected and dried.

The acidic hemicellulose sugar stream ran through a SAC column. The sugar stream was then extracted continuously in a series of mixer settlers (2 stages) with an extractant having tri-laurylamine:hexanol at a ratio of 30:70. The extractant to sugar stream ratio was kept in the range of 2:1 to 1.5:1. The resulting aqueous phase was further purified by using a SAC resin, a WBA resin, a granulated active carbon and a mixed bed resin. The pH of the resulting stream was adjusted to 4.5 with 0.5% HCl and the sugar solution was evaporated to a concentration of ~30% DS. The resulting sugar stream contains about 7% arabinose, 2.5% galactose, 6.5% glucose, 65% xylose, 1.5% mannose, 4% fructose and 14% oligosaccharides (all % weight/total sugars). This sugar solution was further processed by fractionation on an SSMB system, resulting in a xylose rich fraction and a xylose depleted fraction. Each fraction was concentrated by evaporation. Table 5B provides a chemical analysis of the resulting xylose rich sugar solution.

TABLE 5B

Chemical analysis of a hemicellulose sugar mixture produced by hemicellulose sugar extraction and purification of bagasse

| PARAMETER | RESULT | UNITS |
|---|---|---|
| APPEARANCE | Colorless | |
| pH | 3.58 | |
| Saccharides | | |
| % TS (HPLC) | 68.2 | % w/w |
| Composition (HPAE-PAD) | | |
| XYLOSE | 81.84 (55.81) | %/TS (% w/w) |
| ARABINOSE | 4.38 (2.99) | %/TS (% w/w) |
| MANNOSE | 1.99 (1.36) | %/TS (% w/w) |
| GLUCOSE | 5.07 (3.46) | %/TS (% w/w) |
| GALACTOSE | 0.91 (0.62) | %/TS (% w/w) |
| FRUCTOSE | 6.15 (4.20) | %/TS (% w/w) |
| Impurities | | |
| Furfurals (GC) | <0.005 | % w/w |
| Phenols (FC) | 0.04 | % w/w |
| Metals & inorganics (ICP) | | |
| Ca | <2 | ppm |
| Cu | <2 | ppm |
| Fe | <2 | ppm |
| K | <2 | ppm |
| Mg | <2 | ppm |
| Mn | <2 | ppm |
| Na | <2 | ppm |
| S | <10 | ppm |
| P | <10 | ppm |

Example 6

Fractionation of Xylose from Hemicellulose Sugar Mixture

Xylose was fractionated from hemicellulose sugar mixture containing 17% weight/weight glucose, 71% weight/weight xylose, 7% weight/weight arabinose, 0.3% weight/weight galactose, 0.2% weight/weight mannose, and 5% weight/weight mixed dimeric saccharides. The composition of this mixture is representative for hemicellulose sugar compositions from hardwood chips (e.g., *Eucalyptus* chips) and some grasses (e.g., bagasse).

A pulse test was conducted utilizing 250 ml of Finex AS 510 GC, Type I, SBA, gel form, styrene divinylbenzene copolymer, functional group trimethylamine, specific gravity 1.1-1.4 g/cm$^3$, mean bead size 280 millimicrons. The gel was in the sulfate form. It was pre-conditioned with 1.5 bed volume (BV) of 60 mM OH, adjusting the resin to 8-12% OH and leaving the remainder in the sulfate form. A 5 ml sample was injected, followed by water elution at 3 ml/min. Effective fractionation of xylose from the mixture was observed, with the mix sugars peaking at 0.61 and 0.65 BV, and xylose peaking at 0.7 BV. The pulse test results are described in FIG. 7.

In a pulse test, a column was loaded with a sample, and washed with an eluent. Elution fractions were collected and analyzed. For different sugars, the elution resulted in different interaction with the column materials, which lead to different elution profiles. Based on elution profile, it can be determined whether the elution conditions can be applied to a continuous method (e.g., SSMB) to fractionate sugars. An exemplary elution profile is provided in FIG. 7.

A pulse test chromatogram demonstrates that xylose eluting last, and all other monomeric sugars and oligomers elute first. The separation demonstrated is sufficient to support scaling up of this chromatographic fractionation to a simulated moving bed (SMB) mode or sequential simulated moving bed (SSMB) continuous system.

Example 7

Hydrolysis of Hemicellulose-Depleted Lignocellulosic Materials in a Counter-Current Continuous Hydrolysis System

*Eucalyptus* wood chips were subject to hemicellulose sugar extraction as described in Examples 1 and 2. The hemicellulose-depleted lignocellulose remainder material was used in this Example.

Figure 8B:
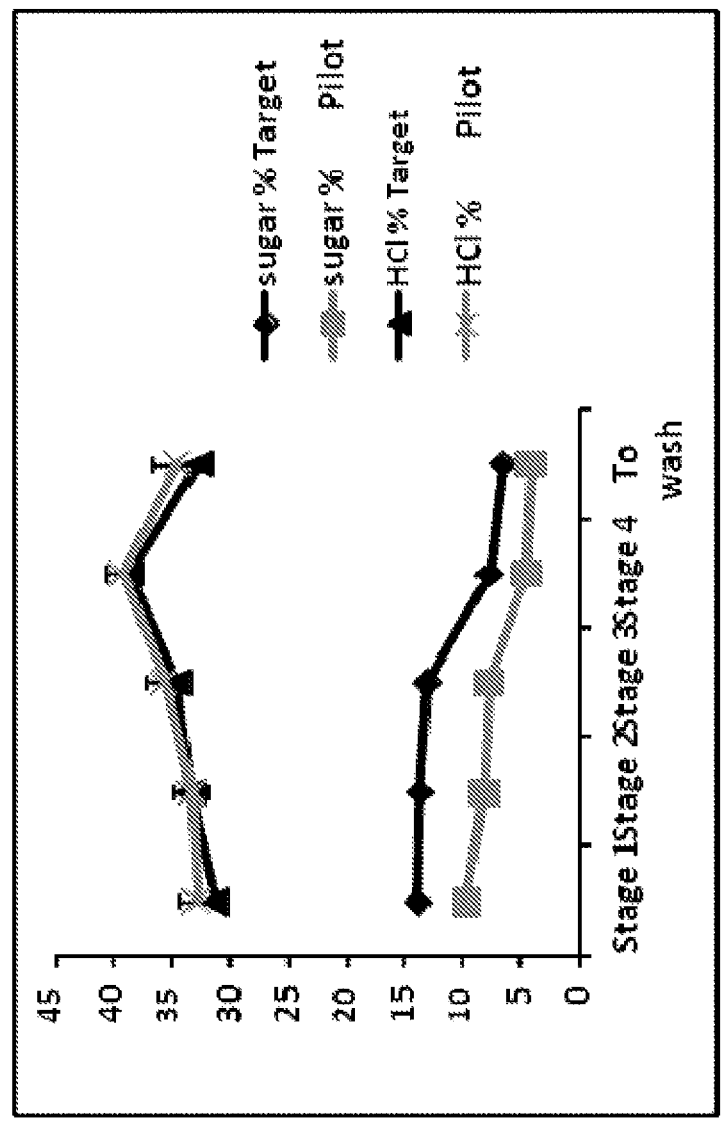
FIG. 8B summarizes results collected during a *eucalyptus* hydrolysis campaign utilizing the system described in FIG. 8A including 4 stirred tanks over 30 days of continuous operation. The black lines denote target values of acid and dissolved sugar; the gray lines denote acid and sugar levels of each stage (tank).

The stirred tank hydrolysis reactor system is described in FIG. 8A. An automatically controlled and monitored 4-tank system was used. Milled hemicellulose-depleted lignocellulose material (e.g., particles of an average size ~1400 microns) is suspended in an aqueous solution containing approximately 33% HCl and 8% sugar. The suspension has about 5% solids. The suspension is fed to tank 1 at a rate of 5 gph. Simultaneously, a 42% HCl solution is fed at approximately 2 gph to tank 4. The solution at each tank is circulated by a pump at a rate of 50 gpm to adequately keep the solution in the tank mixed and allow good cross sectional flow through the a separation membrane which is part of the flow loop. The permeate from the membrane of tank 1 is diverted to the hydrolysate collection tank for de-acidification and refining. The retentate of tank 1 is returned to the tank for further hydrolysis, and a portion of the flow is transferred to tank 2 in order to maintain a constant level in tank 1. All the tanks in series are set at the same parameters of permeate flow and level control. Typical acid and sugar concentrations are depicted in FIG. 8B. The temperature of each tank is typically held at 60 F, 55 F, 50 F, 50 F for tanks 1 through 4 respectively. The retentate for tank 4 is transferred to the lignin washing process based on the same level control.

The results of 30 days continuous hydrolysis of hemicellulose-depleted *eucalyptus* are depicted in FIG. 8B. The black lines show target value for % HCl at reactor 1 though 4 and the hydrolysate collection tank that transfers it to wash (de-acidify), and the % sugars (corresponding to total dissolved sugars in the solution) values for tanks 1 through 4 and the collection tank, while the gray lines show the average value collected over 30 days for the same points. The counter-current nature of the system is visualized: the acid entered the system at reactor 4 and progressed towards 3, 2, and 1. The sugars were continuously dissolved so that sugar level increased in the same direction. The solid mass entered at reactor 1, progressing and decreasing through 2, 3 and 4.

When an additional reactor ("reactor 0") is used before the hemicellulose-depleted lignocellulose material entered reactor 1, hydrolysis of highly oligomeric soluble sugars can be accelerated. In reactor 0, the hemicellulose-depleted lignocellulose material is contacted with acid for 15-20 minutes at elevated temperature (35-45° C.). Once these oligomers continue to hydrolyze to smaller units viscosity drops down sharply. It was observed that, when reactor 0 was used, the average % sugar at all stages increased. Typically this hydrolysis system yields greater than 97% of the cellulosic and remains of hemicellulosic polymers to dissolve in the hydrolysate as oligomeric and monomeric sugars. The solid leaving hydrolysis comprise essentially lignin and less than 5%, usually less than 3% bound cellulose.

Example 8

Hexanol Extraction, Back Extraction, and Acid Recovery

Figure 9A:
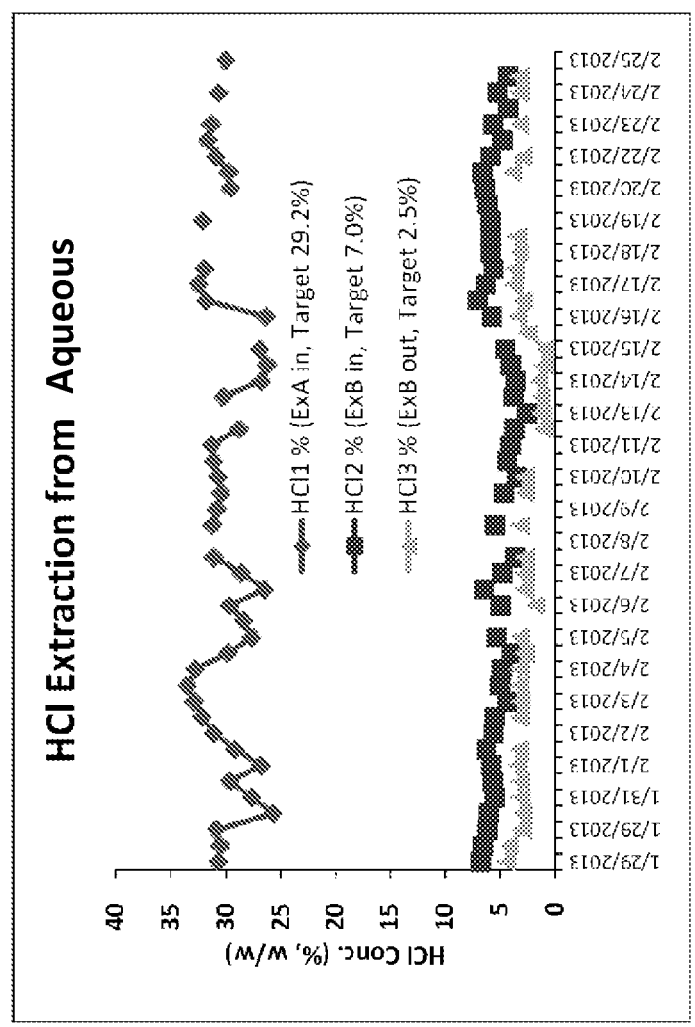
FIG. 9 A depicts the level of acid in the aqueous phase stream coming off the hydrolysis system (gray lines), the level after solvent extraction A (black lines) and the level after solvent extraction B (light gray lines).
FIG. 9B depicts the level of sugars in the solvent following acid extraction into the solvent (gray lines) and the level of sugars in the solvent after scrubbing the sugars into an acid solution (black lines).
FIG. 9C depicts the level of acid in the loaded solvent stream (light gray lines), the level of acid in the solvent after back extraction (black lines) and the resulting level in the aqueous phase (gray lines).

The hydrolysate produced in the hydrolysis system flows to the extraction system to remove the acid from the aqueous phase and recover it for further use. HCl is extracted in a counter-current extraction system including 2 extraction columns (extraction A and extraction B) utilizing hexanol as the extractant. All extraction and back extraction processes are performed at 50° C. FIG. 9A shows data collected over 30 days of the level of HCl in the hydrolysate moving into the extraction system (upper line), the level is ~30%; the level of acid after extraction A moving into extraction B (dark squares), the level is ~8%; the level of residual acid after extraction B (gray triangles) the level is less than 5%, typically 2-3%. Water is co-extracted with the acid, consequently the aqueous phase becomes more concentrated, typical sugar level is 16-20%.

Figure 9B:
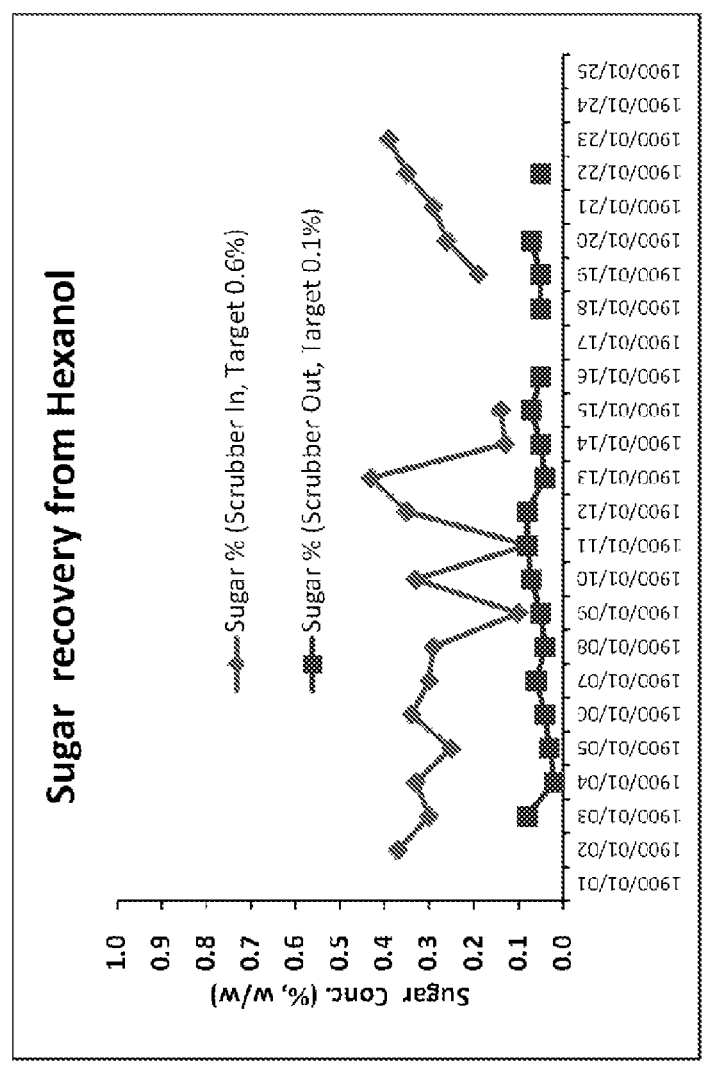
Figure 9C:
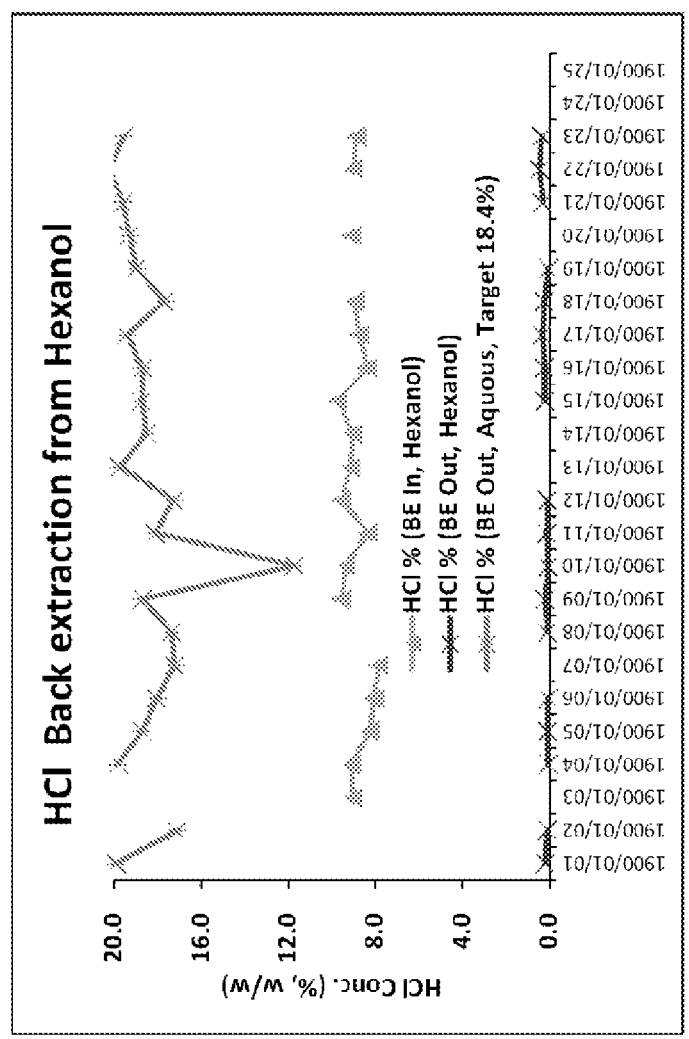

The aqueous phase is then directed to further treatment. The loaded organic phase is first washed to recover sugars from the solvent and the sugars, then to back extraction to recover the acid for recycling. The solvent wash is conducted in a column similar to that used for extraction with HCl solution at 20-25% weight/weight. FIG. 9B depicts the level of sugars in the solvent phase after extraction B entering the wash column (upper line) which is typically 0.2-0.4%, and the level of sugars in the washed solvent phase (lower line), typically less than 0.05%. Next, the solvent is back extracted in another counter current extraction column by running against an aqueous phase containing less than 1% HCl. FIG. 9C shows data accumulated over 30 days run, where the level of HCl in the solvent entering back extraction is ~8% (gray triangles), the level of HCl in the solvent after back extraction is less than 0.5% (bottom line), and the level of acid in the aqueous phase leaving back extraction is ~18.5%.

Example 9

Secondary Hydrolysis

Figure 10:
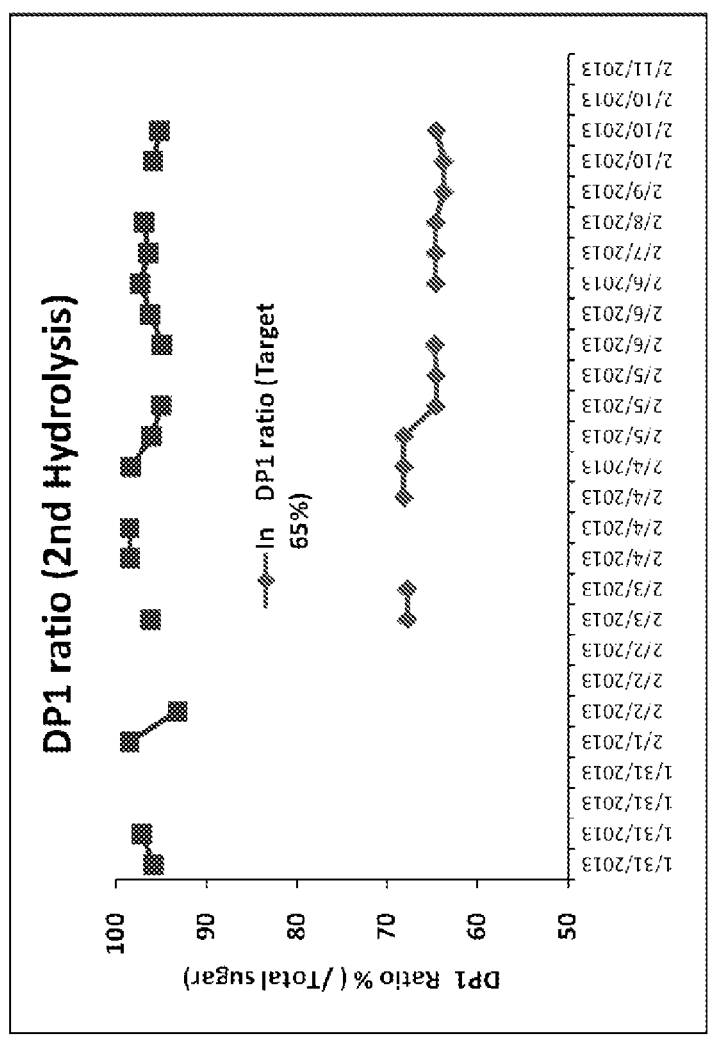
FIG. 10 Depicts the % mono sugars/total sugars in the aqueous solution after solvent extraction (gray lines) and after second hydrolysis (black lines). DP1 stands for monosaccharide.

The sugar solution coming out of extraction typically contains about 2.5% HCl and 16-20% sugars, however typically only 60-70% of these sugars are present as monomers. The sugar solution was diluted to have less than 13% sugars and about 0.6% residual acid. The solution was heated in a stirred tank to 120° C. for about 45 minutes, the resulting composition comprises more than 90% monomers. It was than cooled to lower than 60° C. to prevent re-condensation of the monomers. Data collected over 30 days is depicted in FIG. 10, showing the % monomeric sugars (out of total sugars) before secondary hydrolysis (lower line) and after secondary hydrolysis.

Example 10

Amine Purification

Figure 11A:
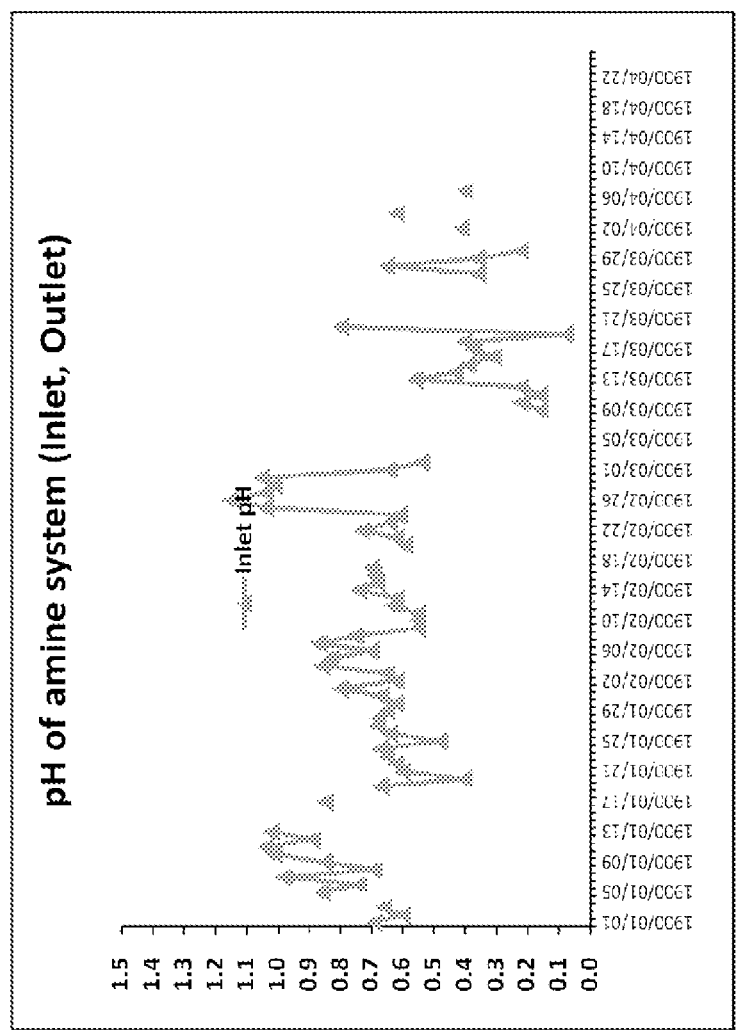
FIG. 11 A: the level of residual hydrochloric acid in the aqueous stream after second hydrolysis. B: percent removal of acidity from the aqueous phase into the amine solvent phase.
Figure 11B:
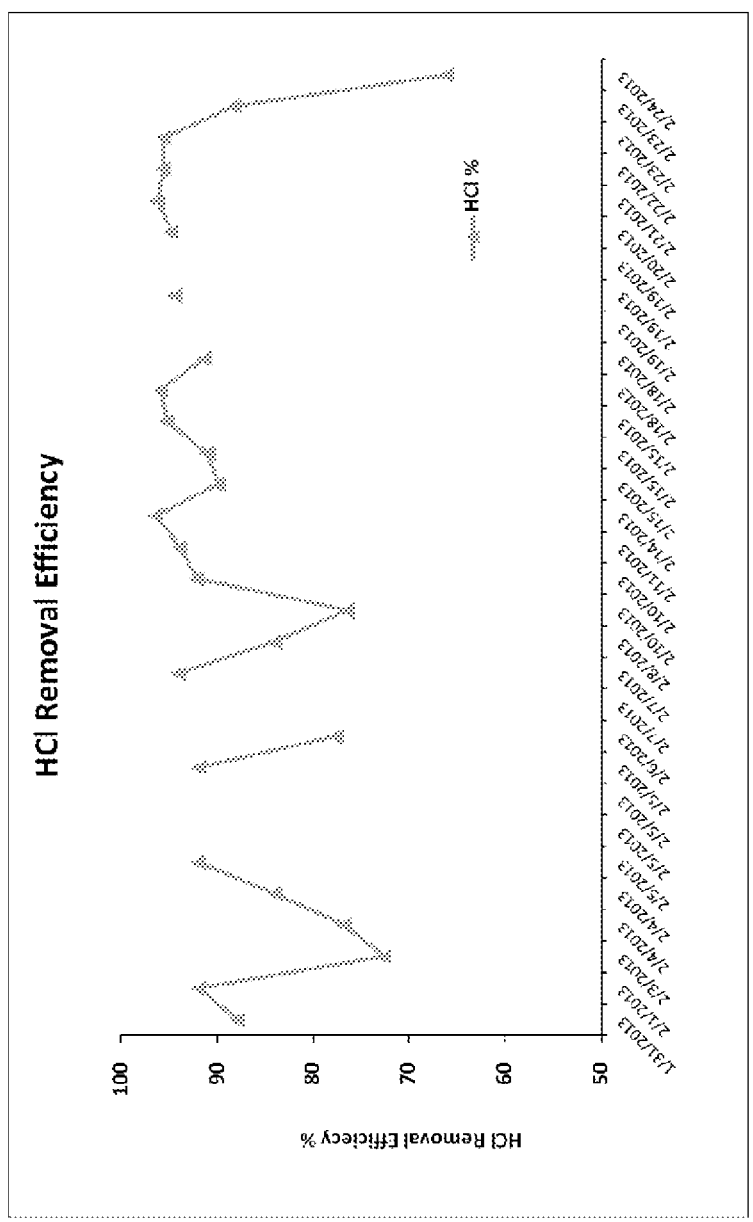

The sugar solution after secondary hydrolysis was sent to the amine extraction process where the solution was contacted with an extractant containing tri-laurylamine and hexanol in a 45:55 ratio. The extractant to sugar feed ratio (O/A) of 1.8:1 wt:wt was used and the extraction is controlled at a temperature of 50-60° C. Extraction is carried out in a mixer-settler. Residual acid was extracted into the organic phase, residual organic acids, furfurals and phenolic molecules (lignin related) were also extracted into this phase. FIG. 11A shows pH measured in the aqueous phase going into amine purification, FIG. 11B shows the calculated efficiency of acid extraction into the amine/hexanol phase as measured by titration of the organic phase. The loaded extractant is sent to another mixer-settler where the solvent was back-extracted with a base (typically $Mg(OH)_2$ or NaOH). Finally, the solvent was sent to a third mixer-settler where the solvent was washed with water. Once washed the solvent was recycled back to the first extraction stage.

Example 11

Hexanol Purification from the Main Solvent Extraction Step

The solvent from the main extraction process extracts along with acid and water much of the impurities present in the hydrolysate. In addition, organic acids react under the acidic conditions to form esters with the alcoholic solvent (e.g., hexyl acetate, hexyl formate). A fraction (e.g., ~10%) of the back extracted solvent from the previous extraction process was separated and treated with lime (e.g., with an aqueous phase containing 10% lime slurry). By doing so, these impurities were removed. The lime addition was set at approximately a 1.5 weight % of the hexanol charged to the reactor. The 2 phase system was agitated at 80° C. for 3 hours. The solution was then cooled to <50° C., the phases were separated in a mixer settler and the solvent phase was washed with water before returning to the extraction solvent feed.

Figure 12:
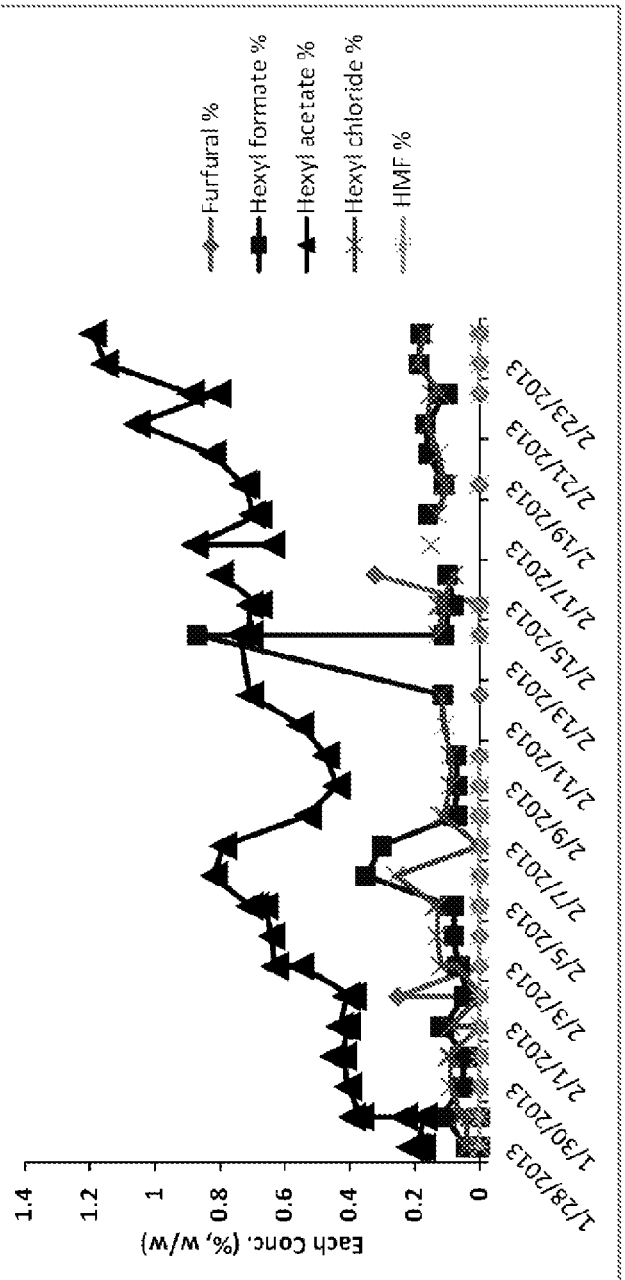
FIG. 12 Impurities analysis of the S1 solvent after purification by liming. Only accumulation of hexyl acetate is noticed while all other major impurities are maintained at a very low level, indicating that the purification process should be slightly stronger to remove acetate more effectively.

The level of impurities in the treated hexanol, including furfurals, hexyl formate, hexyl acetate, hexyl chloride and hydroxymethylfurfural, was detected by gas chromatography. Data collected over 30 days operation is depicted in FIG. 12. The only impurity that was building up was hexyl acetate. The kinetics of hydrolysis of hexyl acetate is the slowest of these impurities, which can be addressed by increasing treatment conditions or fraction.

Example 12

Acid Recovery

Production of 42% Acid in a HCl Absorber

Figure 13:
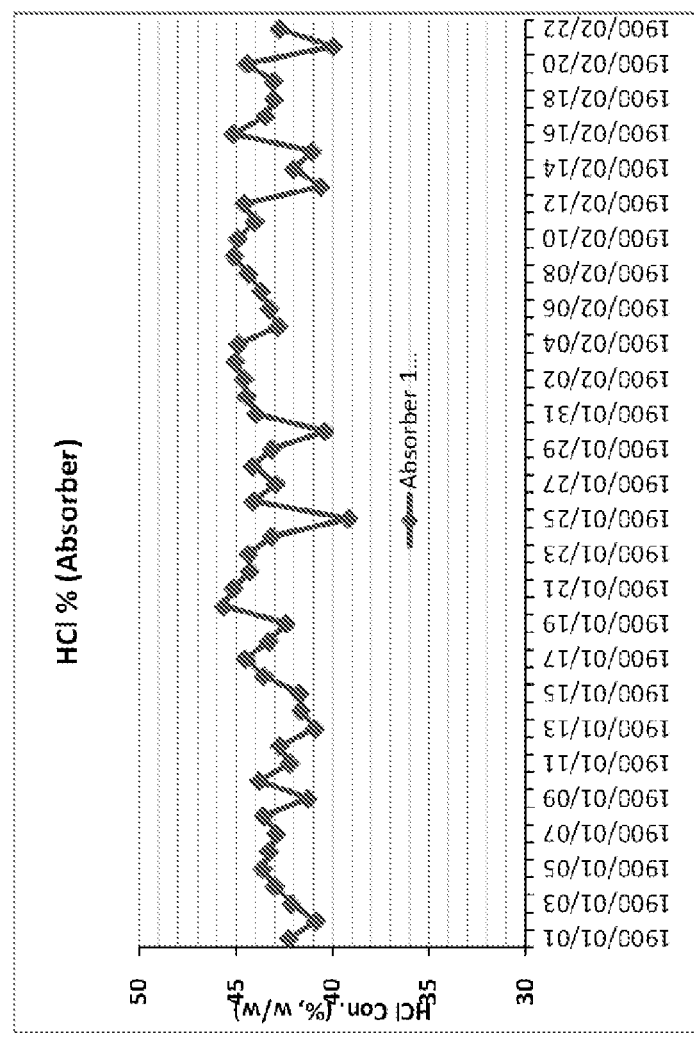
FIG. 13 depicts production of super azeotropic HCl solution of >41% obtained by directing a flow of HCl gas that is distilled from the aqueous solutions to a lower concentration HCl solution.

HCl gas recycled from the process by evaporation flew through a commercial falling film absorber (SGL). Two absorbers were used to ensure a complete absorption of HCL gas. The absorbers were kept at 5-10° C. (e.g., using a chiller). HCl gas was absorbed by a HCl solution in the absorber to increase HCl concentration to high concentration (e.g., greater than 41%). Data collected during a 30-day operation period is shown in FIG. 13, which shows that the target concentration is generally achieved.

Example 13

Lignin Washing

Figure 14A:
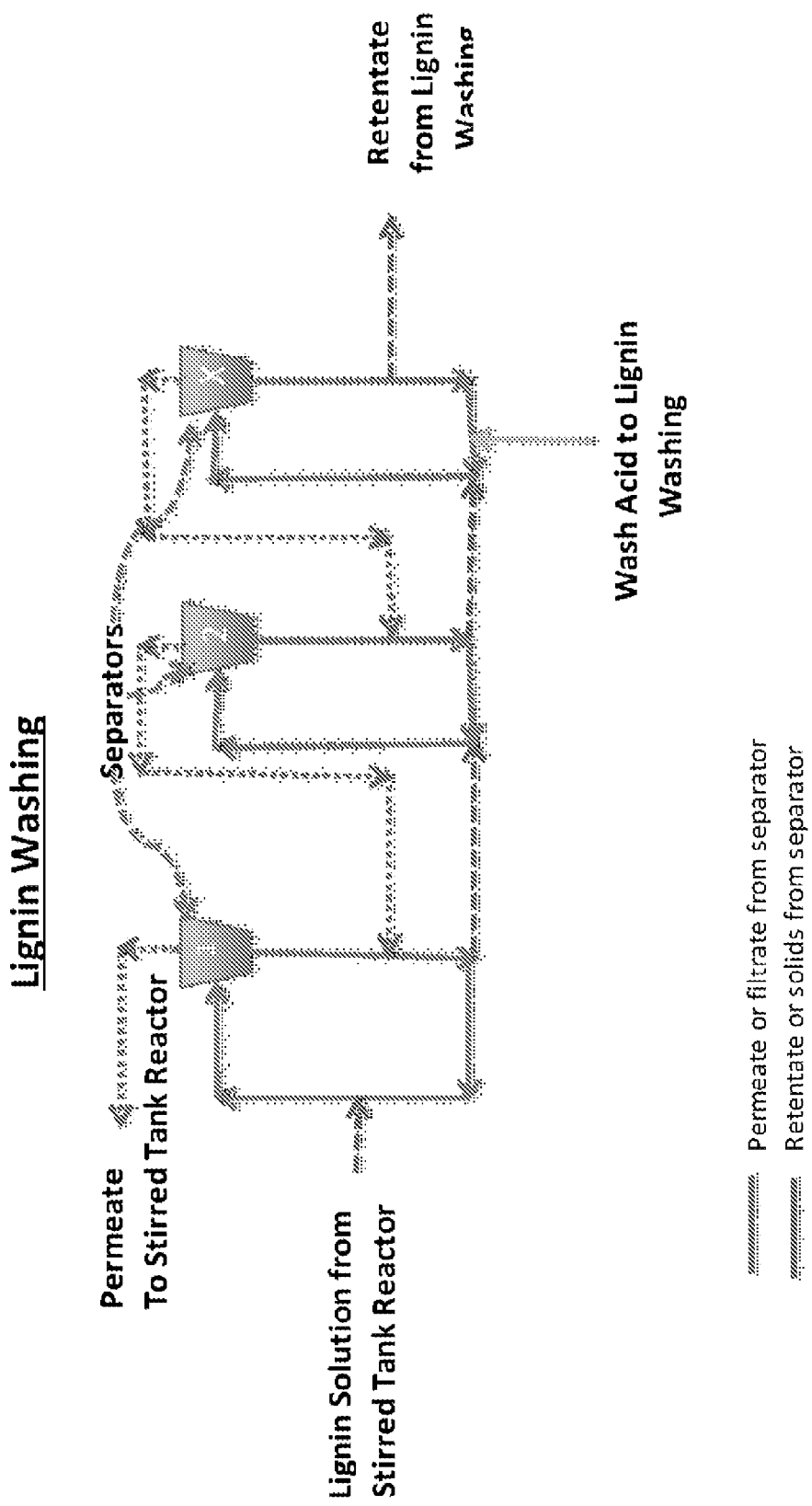
FIG. 14A is a simplified scheme of a system for lignin washing.
Figure 14B:
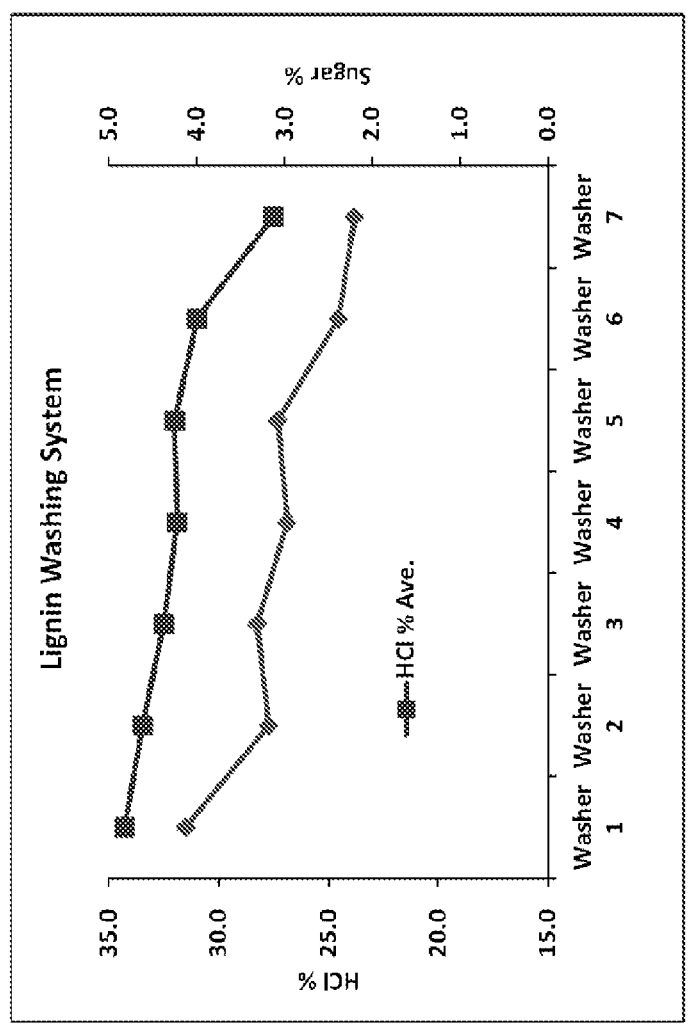
FIG. 14B depicts the average concentration of acid and sugar in the lignin wash system per stage: black lines—acid concentration; gray line—sugar concentration. Sugar concentration is reduced from more than 30% to less than 3%, while acid concentration is reduced from more than 33% to less than 5%.

A exemplary lignin washing system is shown in FIG. 14A. The lignin from the hydrolysis system entered the lignin wash system where it was washed in a counter-current system with a 5-20% HCl solution. A system of 7 wash stages was used. The concentration of acid and sugars at each stage (average result over 30 days of data collection) is shown in FIG. 14B. In stage 1 the lignin suspension had about 4% sugars and about 34% HCl. The concentration of sugars and acid decreased over the 7 stages. The suspension leaving stage 7 typically comprises less than 2.0% sugars and just over 27% HCl.

Example 14

Chemical Structure Characterization of High Purity Lignin Obtained from Limited-Solubility Solvent Purification Lignin solid were washed according to Example 13. The washed lignin was heated in Isopar K to 100° C. to de-acidify the lignin. The de-acidified lignin was then separated from the liquid phase. The solid de-acidified lignin (~20 Lb) was heated with a NaOH solution (28 lb NaOH and 197 lb of water) in an agitate reactor to 360° F. for 6 hours. The dissolved lignin solution was allowed to cool down. The Isopar K organic phase and aqueous phase were separated. The aqueous lignin solution was contacted with methylethylketone (MEK) at a ratio of ~1:2 volume/volume. The pH of the aqueous solution is adjusted to 3.3-3.5 with HCl. The MEK phase was collected and contacted with a strong acid cation exchanger. The refined lignin solution was flash evaporated by dropping it into a hot water bath (~85° C.). The precipitated lignin was filtered and washed with water on a filter press.

Element analysis of high purity lignin and a commercial lignin is provided in the table below:

| Element | Sigma Kraft lignin | High purity Pine lignin | High purity Eucalyptus lignin |
|---|---|---|---|
| % C | 47.96 | 56.17 | 65.9 |
| % H | 4.93 | 5.16 | 5.32 |
| % N | 0.1 | ≤0.05 | ≤0.05 |
| % S | 1.56 | ≤1 | ≤1 |
| % O | 25.57 | 23.06 | 28.1 |
| Total | 80.12 | 84.39 | 99.32 |
| Total %Cl | — | 0.02 | 0.04 |
| Formula | $C_9H_{11.02}O_{3.6}$ | $C_9H_{9.85}O_{2.77}$ | $C_9H_{8.65}O_{2.88}$ |

Inductively coupled plasma (ICP) analysis of high purity pine lignin is provided below:

| Element | Concentration (ppm) |
|---|---|
| Calcium | 2 |
| Magnesium | <1 |
| Potassium | <1 |
| Silicon | 93 |
| Sodium | 101 |
| Iron | 104 |
| Copper | 2 |
| Aluminum | 23 |

Thermal properties of pine lignin are provided in the table below.

| Moisture | 2.9 (Wt/%) |
|---|---|
| 5% degradation | 251 (° C.) |
| 10% degradation | 306 (° C.) |
| Char | 44.4 (Wt/%) |

Figure 15A:
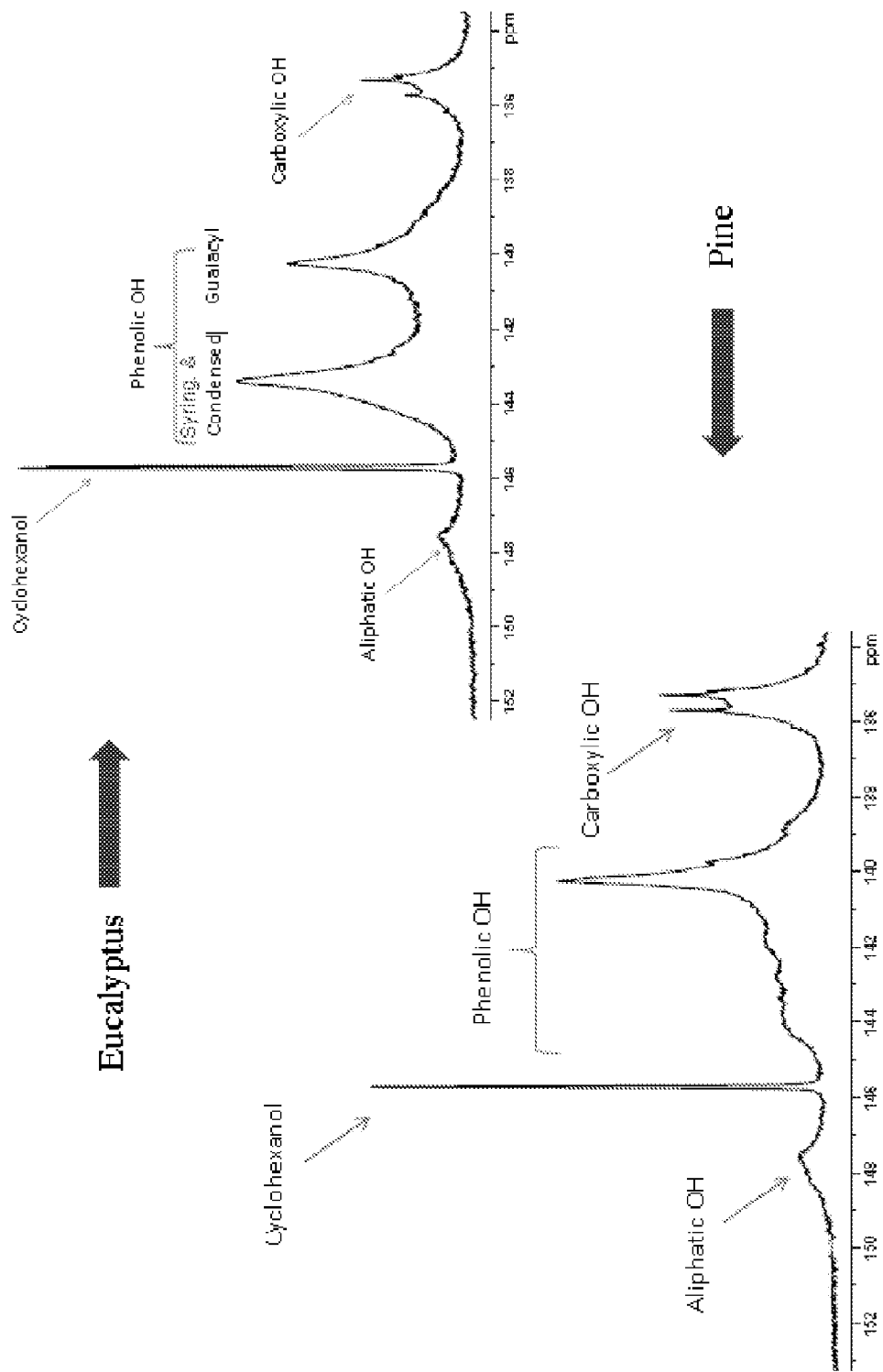
FIG. 15 (A) $^{31}$P NMR spectrum of high purity lignin; (B) $^{13}$C NMR spectrum of lignin.
Figure 15B:
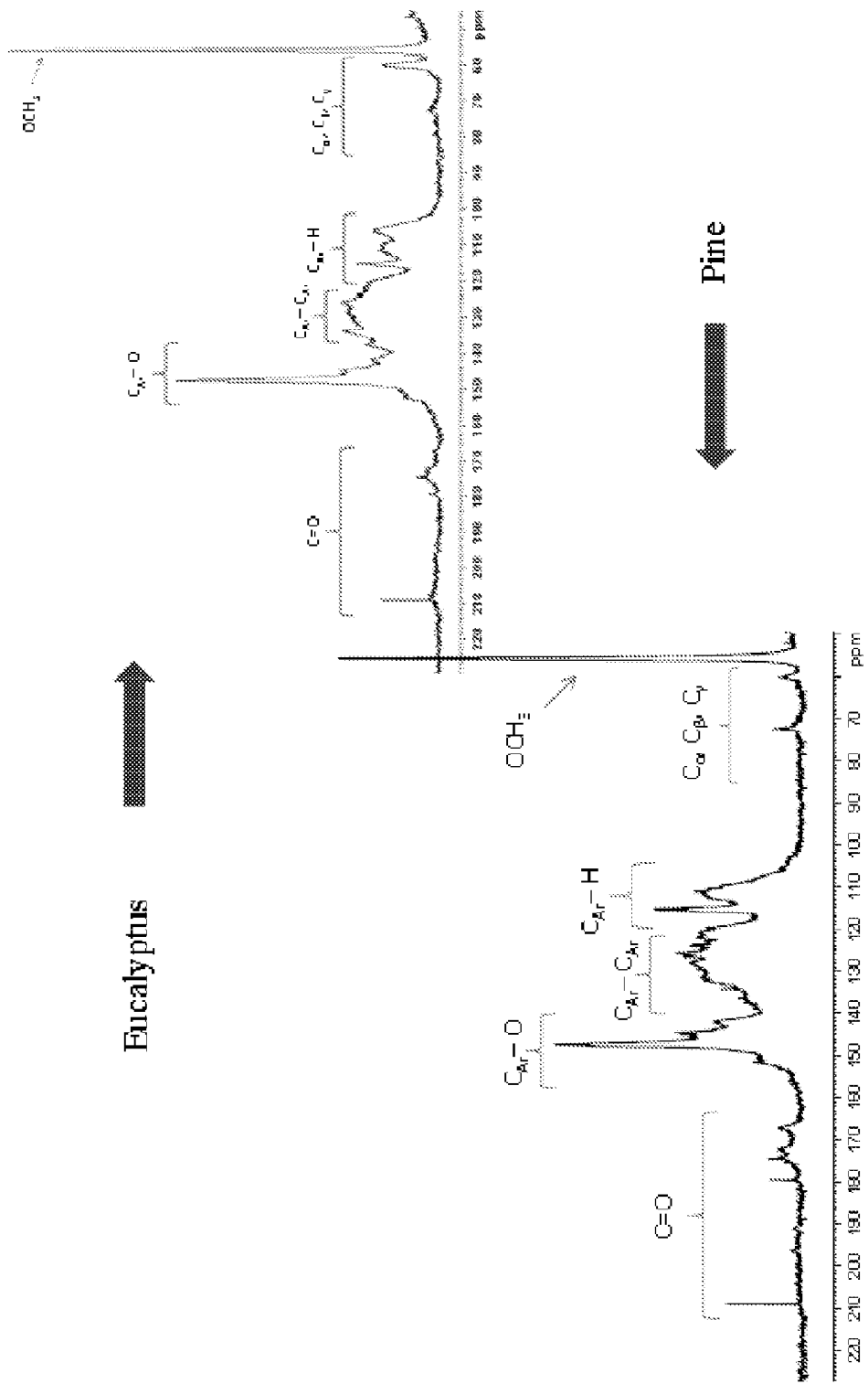

The NMR results indicated that the high purity lignin has low aliphatic hydroxyl group and high phenolic hydroxyl group, as shown in the tables below and FIG. 15. The values for natural lignin are values reported in literature.

Hydroxyl groups content in high purity lignin and natural lignins

| Species | Aliphatic OH (mmole/g lignin) | Phenolic OH (mmole/g lignin) | Carboxylic OH (mmole/g lignin) |
|---|---|---|---|
| High purity Pine Lignin (A) | 0.31 | 2.78 | 0.49 |
| Pine high purity Lignin (B) | 0.35 | 2.92 | 0.91 |
| *Eucalyptus* high purity Lignin | 0.31 | 3.24 | 0.46 |
| Loblolly pine | 4.16 | 0.77 | 0.02 |
| *Eucalyptus globulus* | 7.38 | 1.14 | 0.37 |
| Black spruce | 4.27 | 1.13 | 0.21 |
| Wheat straw | 3.49 | 1.46 | 0.12 |
| *Miscanthus* | 4.00 | 1.53 | 0.13 |
| Switchgrass | 3.88 | 1.00 | 0.29 |
| *P. tremuloides* | 5.72 | 0.74 | 0.06 |
| Pine Organosolv | 4.43 | 3.48 | — |
| Poplar Organosolv | 3.85 | 3.48 | — |
| Kraft lignin | 5.09 | — | — |
| EOL Loblolly pine | 7.30 | 2.40 | 0.30 |
| *Miscanthus* EOL | 1.26 | 3.93 | 0.28 |

$^{13}$C NMR characterization of lignin

| | *Native Pine Lignin | Virdia Pine HP Lignin | Virdia Eucalyptus HP Lignin | #Pine EOL | Residual Kraft Softwood | ^Native *Eucalyptus grandis* lignin |
|---|---|---|---|---|---|---|
| Degree of condensation | 0.4 | 0.9 | 0.9 | 1.1 | 1 | 0.2 |
| Methoxyl content (#/aryl group) | 1 | 0.7 | 0.8 | 0.9 | 0.8 | 1.6 |
| Aliphatic linkages (β-O-4') (#/aryl group) | 0.6 | 0.1 | 0.2 | 0.3 | 0.3 | 0.6 |
| Aromatic C—O (#/aryl group) | 2.0 | 1.8 | 1.9 | 2.1 | 2.1 | 2.0 |

-continued

$^{13}$C NMR characterization of lignin

| | *Native Pine Lignin | Virdia Pine HP Lignin | Virdia Eucalyptus HP Lignin | #Pine EOL | Residual Kraft Softwood | ^Native Eucalyptus grandis lignin |
|---|---|---|---|---|---|---|
| Aromatic C—C (#/aryl group) | 1.5 | 2.2 | 2.3 | 2.1 | 1.9 | 1.9 |
| Aromatic C—H (#/aryl group) | 2.6 | 2.1 | 1.7 | 2 | 2.0 | 2.1 |
| syringyl/ guaiacyl | — | — | 0.5 | — | — | 1.7 |

*"Effects of two-stage dilute acid pretreatment on the structure and composition of lignin and cellulose in loblolly pine". Ragauskas AJ, Bioenerg .Res 2008; 1 (3-4): 205-214.
"Lignin structural modifications resulting from ethanol organosolv treatment of loblolly pine".
Ragauskas AJ, Energ Fuel 2010; 24 (1): 683-689.
^"Quantitative characterization of a hardwood milled wood lignin by nuclear magnetic resonance spectroscopy". Kadla JF. J Agr Food. Chem. 2005; 53 (25): 9639-9649.

Example 15

Direct Lignin Extraction

After hemicellulose sugars were extracted from *eucalyptus* chips, the remainder was mainly cellulose and lignin. The remainder was delignified using an aqueous organic solution containing acetic acid according to the process described below.

*Eucalyptus* wood chips (20.0 g) were mixed with a solution of 50/50 v/v of methylethylketone (MEK) and water that contains 1.2% acetic acid w/w of solution at a ratio of 1:10 (100 mL water, 100 mL MEK, and 2.2 g acetic acid). The mixture was treated at 175° C. for 4 hours in an agitated reactor. Then the system was allowed to cool to 30° C. before the reactor is opened. The slurry was decanted and the solid is collected for further analysis.

After the reaction, there was 127 g free liquid, of which 47.2 g organic and 79.8 g aqueous. The organic phase contained 1.1 g acetic acid, 10.4 g water, and 5.5 g dissolved solids (0.1 g sugars and 5.4 g others, which is mainly lignin). The aqueous phase contained 1.4 g acetic acid, 2.1 g dissolved solids (1.5 g sugars and 0.6 g other).

After decanting of the liquid, black slurry and white precipitate were at the bottom of the bottle. This material was vacuum-filtered and washed thoroughly with 50/50 v/v MEK/water (119.3 g MEK 148.4 g water) at room temperature until the color of the liquid became very pale yellow. Three phases were collected; organic 19.7 g, aqueous 215 g, and white solid 7 g dry. The organic phase contained 0.08 g acetic acid and 0.37 g dissolved solids. The aqueous phase contained 0.56 g acetic acid and 0.6 g dissolved solids.

All organic phases were consolidated. The pH of the solution is adjusted to pH 3.8. The solution was then allowed to separate into an aqueous phase (containing salts) and an organic phase (containing lignin). The lignin-containing organic phase was recovered and purified using a strong acid cation column. The organic solution was then added dropwise into an 80° C. water bath to precipitate the lignin.

$^{13}$C Solids State NMR analysis of the white precipitate indicates that it comprises mostly cellulose (pulp). The amount of lignin is not detectable. The reaction is successful in delignifying the *eucalyptus* wood chips.

Example 16

Analysis of Hydrolyzed Cellulose Sugars from Pine Wood

Pine wood chips were subject to hemicellulose sugar extraction as described in Examples 1 and 2. The cellulose hydrolysis was carried out using a simulated moving bed hydrolysis system as described in PCT/US2011/057552 (incorporated herein by reference for all purposes). The cellulose sugar purification was conducted as described in Examples 8 and 9. A strong base anion exchanger was used instead of amine extraction for sugar purification similar to example 10 (all is the same except that the amine is in a solid phase, which is the SBA resin). The compositions of the cellulose sugars were described in the table below.

Analysis of hydrolyzed cellulose sugars from pine wood is provided below:

| PARAMETER | RESULT | UNITS |
|---|---|---|
| APPEARANCE | Clear colorless viscous liquid | |
| pH | 3.85 | |
| Saccharides | | |
| DS (HPLC) | 73.5 | % wt/wt |
| % Total monosaccharides | 96.7 | DS/DS |
| Composition (HPAE-PAD) | | |
| XYLOSE | 6.09 (4.59) | DS/DS (w/w) |
| ARABINOSE | 1.13 (0.86) | DS/DS (w/w) |
| MANNOSE | 16.89 (12.73) | DS/DS (w/w) |
| GLUCOSE | 56.61 (42.66) | DS/DS (w/w) |
| GALACTOSE | 3.16 (2.39) | DS/DS (w/w) |
| FRUCTOSE | 14.31 (10.79) | DS/DS (w/w) |
| Impurities | | |
| Furfurals (UV) | <0.001 | % wt/wt |
| Phenols (UV) | 0.02 | % wt/wt |
| Metals & inorganics (ICP) | | |
| Ca | <2 | ppm/DS |
| Cu | <2 | ppm/DS |
| Fe | <2 | ppm/DS |
| K | <2 | ppm/DS |
| Mg | <2 | ppm/DS |
| Mn | <2 | ppm/DS |
| Na | 30 | ppm/DS |
| S | 2.7 | ppm/DS |
| P | 9.5 | ppm/DS |

Example 17

Analysis of Hemicellulose Sugars from Pine Wood

Pine wood chips were subject to hemicellulose sugar extraction as described in Examples 1 and 2. The hemicellulose sugar was purified as described in Examples 3 and 5 except that a strong base anion exchanger containing solid phase amine was used. The resulting sugar solution was concentrated. The compositions of the hemicellulose sugars were described in the table below.

Analysis of hemicellulose sugars from pine wood is provided below:

| PARAMETER | RESULT | UNITS |
|---|---|---|
| APPEARANCE | Clear, slightly yellow viscous liquid | |
| Odor | Pass | |
| pH | 3.10 | |
| Saccharides | | |
| DS (HPLC) | 70.0 | % wt/wt |
| % Total monosaccharides Composition (HPAE-PAD) | 74.4 | DS/DS |
| XYLOSE | 16.14 (11.30) | DS/DS (w/w) |
| ARABINOSE | 6.89 (4.82) | DS/DS (w/w) |
| MANNOSE | 24.53 (17.15) | DS/DS (w/w) |
| GLUCOSE | 9.23 (6.46) | DS/DS (w/w) |
| GALACTOSE | 10.65 (4.26) | DS/DS (w/w) |
| FRUCTOSE | 10.82 (7.57) | DS/DS (w/w) |
| Impurities | | |
| Furfurals (UV) | 0.001 | % wt/wt |
| Phenols (UV) | 56.1 | ppm/DS |
| Metals & inorganics (ICP) | | |
| Ca | 1.1 | ppm/DS |
| Cu | ND** | ppm/DS |
| Fe | ND | ppm/DS |
| K | ND | ppm/DS |
| Mg | 0.1 | ppm/DS |
| Mn | ND | ppm/DS |
| Na | 6.8 | ppm/DS |
| S | 11.4 | ppm/DS |
| P | 7.4 | ppm/DS |

Example 18

Analysis of Hemicellulose Sugars from *Eucalyptus*

*Eucalyptus* wood chips were subject to hemicellulose sugar extraction as described in Examples 1 and 2. The hemicellulose sugar was purified as described in Examples 3 and 5. The compositions of the hemicellulose sugars were described in the table below.

Analysis of hemicellulose sugars from *Eucalyptus* is provided below:

| PARAMETER | RESULT | UNITS |
|---|---|---|
| APPEARANCE | Colorless | |
| pH | 3.13 | |
| Saccharides | | |
| DS (HPLC) | 72.37 | % wt/wt |
| % Total monosaccharides Composition (HPAE-PAD) | 91.71 | DS/DS (w/w) |
| XYLOSE | 67.23 (48.65) | DS/DS (w/w) |
| ARABINOSE | 3.09 (2.24) | DS/DS (w/w) |
| MANNOSE | 5.83 (4.22) | DS/DS (w/w) |
| GLUCOSE | 4.64 (3.36) | DS/DS (w/w) |
| GALACTOSE | 8.22 (5.95) | DS/DS (w/w) |
| FRUCTOSE | 3.40 (2.46) | DS/DS (w/w) |
| Impurities | | |
| Furfurals (UV) | 0.0005 | % wt/wt |
| Phenols (FC) | 0.047 | % wt/wt |

| PARAMETER | RESULT | UNITS |
|---|---|---|
| Metals & inorganics (ICP) | | |
| Ca | <2 | ppm |
| Cu | <2 | ppm |
| Fe | <2 | ppm |
| K | <2 | ppm |
| Mg | <2 | ppm |
| Mn | <2 | ppm |
| Na | 22 | ppm |
| S | 6.7 | ppm |
| P | 4.2 | ppm |

Example 19

Analysis of Sugar Stream

Bagasse is subject to hemicellulose sugar extraction as described in Examples 1 and 2. The hemicellulose sugar is purified as described in Examples 3 and 5. The resulting sugar solution is concentrated and fractionated as described in Example 6, to obtain a xylose rich solution containing more than 80% xylose, and a second stream containing oligomeric and monomeric sugars. The composition of the sugar mixture is given in the table below.

| Carbohydrate | % wt/DS (dissolved sugars) |
|---|---|
| Oligomers | 23.2% |
| Monomers composition out of total dissolved sugars: | |
| Glucose and fructose[1] | 27.6% |
| Mannose | 0.2% |
| Galactose | 2.9% |
| Xylose | 32.4% |
| Arabinose | 13.7% |

Example 20

Hydrolysis of Cellulose by Cellulase

Figure 42B:
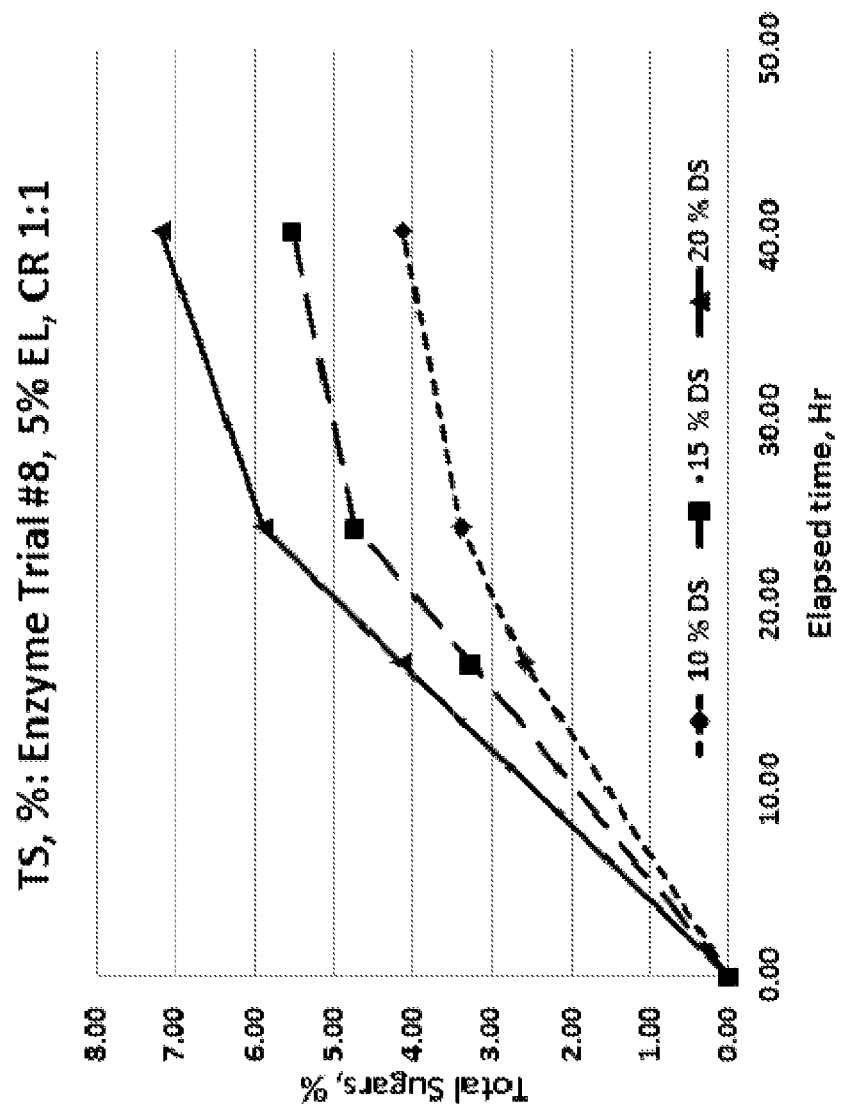
FIG. 42B shows glucose concentration in the solution at different starting cellulose pulp load in the reactor (10-20% wt dry solid)
Figure 42C:
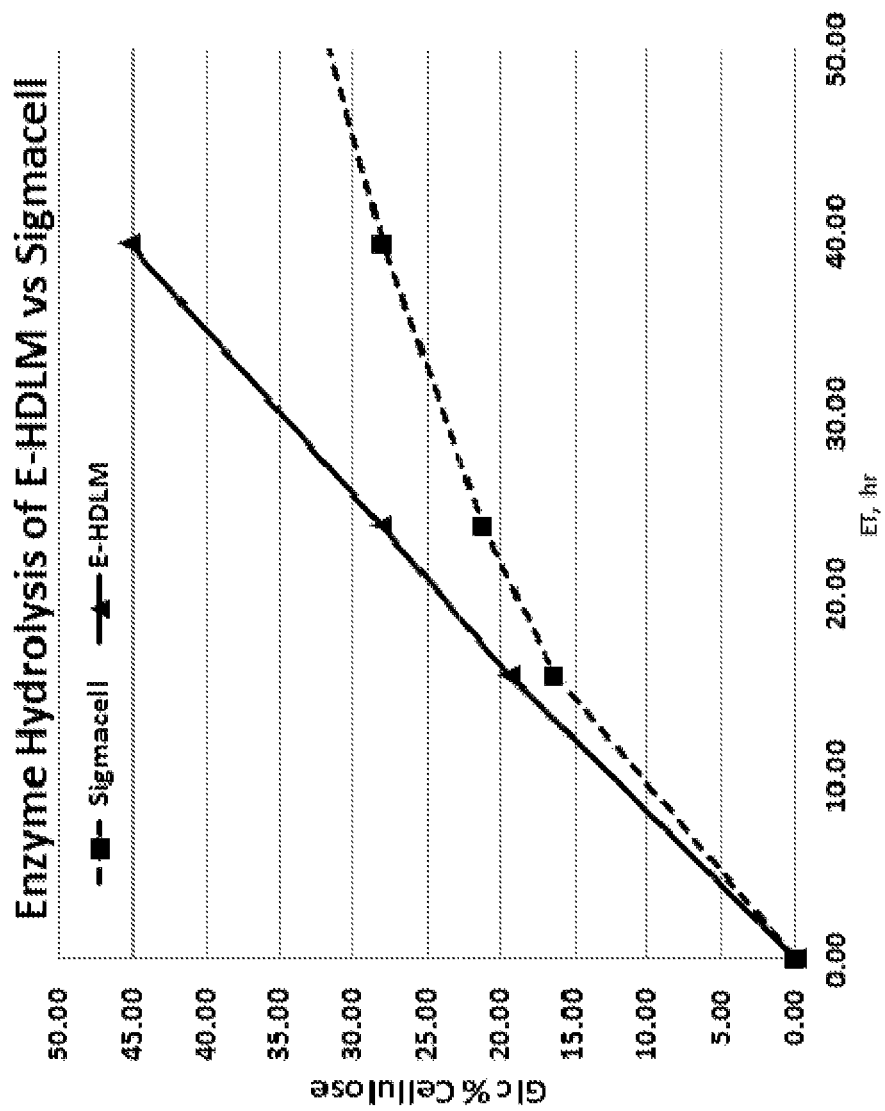
FIG. 42C illustrates comparative saccharification of cellulose pulp obtained by hemicelluloses axtraction followed by acid/solvent lignin extraction (E-HDLM), and a commercial Sigmacell cotton linters.

Cellulose pulp (*eucalyptus* pulp) was obtained as the remainder after the hemicellulose and lignin extraction. Cellulose pulp suspension having 10-20% solids in 0.05M acetate buffer, pH 4.55, 5%/cellulose, cellulase:cellobiase 1:1 was prepared. The suspension was stirred at 55° C. Samples of the liquor were taken periodically for analysis of the dissolved sugars. The dissolving sugars were mostly glucose, but can also include some residual hemicellulose sugars remaining in the pulp. The dissolved sugar contained 7.78% lignin and 94.22% holocellulose, (89.66% glucose). As % solids increased, overall yield decreased (so long as the enzyme loading is the same). However the yield was higher compared to a reference sample hydrolyzed under the same conditions using Sigmacell (Sigma # S5504 from cotton linters, type 50, 50 um), as seen in FIG. 42B. The cellulose pulp is well saccharified by the cellulase mix enzyme (although it still contains some residual lignin). The reaction rate of E-HDLM is higher than the reference material Example 21

Improvement to SSMB Sequence for Higher Product Recovery

Separation of xylose from the hemicellulose sugar mix was conducted on a purposely build, ProSep SSMB Operation model, 12 column carousel design SSMB system (hereinafter ProSep SSMB Operation 2.0). The improved sequence contained 6 stages, each of which has two columns. The columns were packed with Finex AS 510 GC, Type I, SBA, gel form, Styrene divinylbenzene copolymer, functional group trimethylamine, specific gravity 1.1-1.4 g/cm$^3$, mean bead size 280 millimicrons. The gel was in the sulfate form. It was pre-conditioned with 1.5 bed volume (BV) of 60 mM OH$^-$, adjusting the resin to 8-12% OH and leaving the remainder in the sulfate form. The table below compares common pulse sequence of the ProSep SSMB Operation 1.0 (original model) with the improved sequence of ProSep SSMB Operation 2.0.

| Step | ProSep SSMB Operation 1.0 | ProSep SSMB Operation 2.0 |
|---|---|---|
| Step 1 (Desorb to Extract; Feed to Raffinate) | | |
| Step 1 Time | 233 seconds | 331.5 seconds |
| Extract Flow | 77.0 ml/min | 80.4 ml/min |
| Raffinate Flow | 63.5 ml/min | 92.0 ml/min |
| Step 2 (Desorb to Raffinate; Desorb to Extract) | | |
| Step 2 Time | 345 seconds | 376.1 seconds |
| Raffinate Flow | 63.5 ml/min | 92.0 ml/min |
| Extract Flow | — | 33.5 ml/min |
| Step 3 (recycle) | | |
| Step 3 Time | 1028 seconds | 864 seconds |
| Recycle Flow | 63.5 ml/min | 60 ml/min |
| Results | | |
| Purity | 79% | 84.9% |
| Recovery | 81.7% | 84% |
| Desorb to Feed Ratio | 2.7 | 2.37 |
| Total Step Time | 26.76 minutes | 26.2 minutes |

Xylose was separated according to the improved sequence of ProSep SSMB Operation 2.0. A feed solution containing about 30% weight/weight sugars was provided. The feed solution contained about 65% weight/weight xylose out of total sugars. The product stream containing about 16.4% sugars was extracted. The product stream contained more than 80% weight/weight (e.g., in some cases, more 82%, 84%, 85% weight/weight) xylose out of total sugars. The recovery was greater than 80% weight/weight. The raffinate containing about 5% weight/weight total sugars was obtained. The raffinate contained only about 16.5% weight/weight out of total sugars.

What is claimed is:

1. A method of refining a sugar stream, comprising:
   (i) contacting the sugar stream with an amine extractant to form a mixture;
   (ii) separating from the mixture a first stream comprising the amine extractant and an acid or an impurity; and a second stream comprising one or more sugars; and
   (iii) contacting the first stream with a base to form a neutralized amine extractant.

2. The method of claim 1, wherein the first stream is an organic stream and the second stream is an aqueous stream.

3. The method of claim 1, wherein the first stream comprises less than 0.5% w/w sugars.

4. The method of claim 1, wherein the second stream comprises less than 0.5% w/w acid.

5. The method of claim 1, wherein the second stream comprises less than 0.5% w/w amine.

6. The method of claim 1, wherein the second stream comprises less than 0.5% w/w impurities.

7. The method of claim 1, wherein impurities are extracted from the sugar stream into the amine extractant.

8. The method of claim 1, further comprising, prior to step (i), contacting the sugar stream with a strong acid cation exchanger to remove residual cations.

9. The method of claim 1, wherein the amine extractant comprises an amine and a diluent.

10. The method of claim 9, wherein the ratio of the amine and the diluent is between 3:7 and 6:4.

11. The method of claim 9, wherein the diluent comprises a C6, C8, C10, C12, C14, or C16 alcohol or kerosene.

12. The method of claim 9, wherein the diluent comprises n-hexanol or 2-ethyl-hexanol.

13. The method of claim 9, wherein the amine is an amine comprising at least 20 carbon atoms.

14. The method of claim 1, further comprising:
   contacting the second stream with a strong acid cation exchanger to remove residual amines, thereby forming an amine-removed hydrolysate; and
   contacting the amine-removed hydrolysate with a weak base anion exchanger to form a neutralized hydrolysate.

15. The method of claim 1, further comprising:
   contacting the second stream with a strong acid cation exchanger to remove residual amines, thereby forming an amine-removed hydrolysate; and
   fractionating the amine-removed hydrolysate into a monomeric sugar stream and an oligomeric sugar stream.

16. The method of claim 1, prior to contacting the first stream with the base, further comprising washing the first stream with an aqueous stream to remove sugar from the first stream.

17. The method of claim 16, wherein the washed first stream comprises less than 0.1% weight/weight sugar.

18. The method of claim 1, further comprising washing at least a portion of the neutralized amine extractant with water and recycling the washed amine extractant.

19. The method of claim 1, wherein the first stream comprises the amine extractant, a mineral acid, an organic acid and furfural.

20. The method of claim 1, wherein the sugar stream is a lignocellulosic hydrolysate.

21. A method of refining a sugar stream, comprising:
(i) contacting the sugar stream with an amine extractant to form a mixture; and
(ii) separating from the mixture a first stream comprising the amine extractant and an acid or an impurity; and a second stream comprising one or more sugars, wherein the amine extractant comprises tri-laurylamine and a diluent.

22. The method of claim 21, wherein the first stream comprises less than 0.5% w/w sugars.

23. The method of claim 21, wherein the second stream comprises less than 0.5% w/w acid, less than 0.5% w/w amine, or less than 0.5 w/w impurities.

24. The method of claim 21, wherein the diluent comprises a C6, C8, C10, C12, C14, or C16 alcohol or kerosene.

25. The method of claim 21, wherein the diluent comprises n-hexanol or 2-ethyl-hexanol.

26. The method of claim 21, wherein the first stream comprises the amine extractant, a mineral acid, an organic acid and furfural.

27. A method of refining a sugar stream, comprising:
(i) contacting the sugar stream with an amine extractant to form a mixture;
(ii) separating from the mixture a first stream comprising the amine extractant and an acid or an impurity; and a second stream comprising one or more sugars; and
(iii) contacting the second stream with a strong acid cation exchanger to remove residual amines, thereby forming an amine-removed hydrolysate.

28. The method of claim 27, wherein the first stream comprises less than 0.5% w/w sugars.

29. The method of claim 27, wherein the second stream comprises less than 0.5% w/w acid, less than 0.5% w/w amine, or less than 0.5% w/w impurities.

30. The method of claim 27, wherein the amine extractant comprises an amine and a diluent.

31. The method of claim 30, wherein the diluent comprises n-hexanol or 2-ethyl-hexanol.

32. The method of claim 30, wherein the amine is tri-laurylamine.

33. The method of claim 27, wherein the first stream comprises the amine extractant, a mineral acid, an organic acid and furfural.

34. A method of refining a sugar stream, comprising:
(i) contacting the sugar stream with an amine extractant to form a mixture;
(ii) separating from the mixture a first stream comprising the amine extractant and an acid or an impurity; and a second stream comprising one or more sugars;
(iii) contacting the first stream with a base to form a neutralized amine extractant; and
(iv) contacting the second stream with a strong acid cation exchanger to remove residual amines, thereby forming an amine-removed hydrolysate,
wherein the amine extractant comprises tri-laurylamine and a diluent.

35. The method of claim 21, further comprising contacting the first stream with a base to form a neutralized amine extractant.

36. The method of claim 35, prior to contacting the first stream with the base, further comprising washing the first stream with an aqueous stream to remove sugar from the first stream.

37. The method of claim 36, wherein the washed first stream comprises less than 0.1% weight/weight sugar.

38. The method of claim 35, further comprising washing at least a portion of the neutralized amine extractant with water and recycling the washed amine extractant.

39. The method of claim 27, further comprising contacting the first stream with a base to form a neutralized amine extractant.

40. The method of claim 39, prior to contacting the first stream with the base, further comprising washing the first stream with an aqueous stream to remove sugar from the first stream.

41. The method of claim 40, wherein the washed first stream comprises less than 0.1% weight/weight sugar.

42. The method of claim 39, further comprising washing at least a portion of the neutralized amine extractant with water and recycling the washed amine extractant.

* * * * *

UNITED STATES PATENT AND TRADEMARK OFFICE
CERTIFICATE OF CORRECTION

PATENT NO. : 9,493,851 B2
APPLICATION NO. : 14/398444
DATED : November 15, 2016
INVENTOR(S) : Robert Jansen et al.

It is certified that error appears in the above-identified patent and that said Letters Patent is hereby corrected as shown below:

In the Specification

Column 1, Lines 26-31, please delete the header "STATEMENT AS TO FEDERALLY SPONSORED RESEARCH" and the paragraph "This invention was made with government support under Grant No. DE-EE0005003 awarded by the Department of Energy. The government has certain rights in the invention."

Signed and Sealed this
Eighth Day of May, 2018

Andrei Iancu
*Director of the United States Patent and Trademark Office*